US008324222B2

(12) United States Patent  
Lampe et al.

(10) Patent No.: US 8,324,222 B2
(45) Date of Patent: Dec. 4, 2012

(54) CYCLICALLY SUBSTITUTED FUROPYRIMIDINE DERIVATIVES AND USE THEREOF

(75) Inventors: Thomas Lampe, Düsseldorf (DE); Eva-Maria Becker, Wuppertal (DE); Raimund Kast, Wuppertal (DE); Hartmut Beck, Köln (DE); Mario Jeske, Solingen (DE); Joachim Schuhmacher, Wuppertal (DE); Friederike Stoll, Düsseldorf (DE); Martina Klein, Düsseldorf (DE); Metin Akbaba, Ratingen (DE); Andreas Knorr, Erkrath (DE); Johannes-Peter Stasch, Solingen (DE); Lars Bärfacker, Oberhausen (DE); Alexander Hillisch, Solingen (DE); Gunter Karig, Hofheim am Taunus (DE); Mark Meininghaus, Wuppertal (DE); Karl-Heinz Schlemmer, Wuppertal (DE); Rudolf Schohe-Loop, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 530 days.

(21) Appl. No.: 12/086,784

(22) PCT Filed: Dec. 8, 2006

(86) PCT No.: PCT/EP2006/011825
§ 371 (c)(1),
(2), (4) Date: May 24, 2010

(87) PCT Pub. No.: WO2007/079861
PCT Pub. Date: Jul. 19, 2007

(65) Prior Publication Data
US 2011/0124665 A1 May 26, 2011

(30) Foreign Application Priority Data

Dec. 21, 2005 (DE) .................... 10 2005 061 171

(51) Int. Cl.
*C07D 491/04* (2006.01)
*A61K 31/519* (2006.01)
*A61P 9/00* (2006.01)
(52) U.S. Cl. .................... 514/260.1; 544/278
(58) Field of Classification Search .................. 544/278; 514/260.1
See application file for complete search history.

(56) References Cited

U.S. PATENT DOCUMENTS 3,577,420 A   5/1971   Hess et al.
7,312,224 B2 12/2007   Eggenweiler et al.
2004/0259888 A1 12/2004 Bischoff et al.
2006/0040961 A1  2/2006 Buchanan et al.

FOREIGN PATENT DOCUMENTS

| DE | 1817146 A1 | 11/1969 |
|---|---|---|
| DE | 10148883 | 4/2003 |
| EP | 1018514 A1 | 7/2000 |
| EP | 1132093 A1 | 9/2001 |
| WO | WO-00/75145 A1 | 12/2000 |
| WO | WO-02/092603 A1 | 11/2002 |
| WO | WO 03/018589 | 3/2003 |
| WO | WO-03/022852 A2 | 3/2003 |
| WO | WO 2005/092896 A1 | 10/2005 |
| WO | WO-2005/121149 A1 | 12/2005 |
| WO | WO-2006/004658 A2 | 1/2006 |

OTHER PUBLICATIONS

G. J. Dusting et al.: "Prostacyclin and Vascular Function: Implications for Hypertension and Atherosclerosis," Pharmac. Ther., vol. 46, 1990, pp. 323-344.
J. Vane et al.: "Prostacyclin: a Vascular Mediator," Eur. J. Vasc. Endovasc. Surg., 26, 2003, pp. 571-578.
S. Narumiya et al.: "Prostanoid Receptors: Structures, Properties, and Functions," Physiological Review, vol. 79, No. 4, Oct. 1999, pp. 1183-1226.
K. Schrör et al.: "Roles of Vasodilatory Prostaglandins in Mitogenesis of Vascular Smooth Muscle Cells," Agents Action Supplement, vol. 48, 1997, pp. 63-91.
D. Kothapalli et al.: "Prostacyclin Receptor Activation Inhibits Proliferation of Aortic Smooth Muscle Cells by Regulating cAMP Response Element-Binding Protein- and Pocket Protein-Dependent Cyclin A Gene Expression," Molecular Pharmacology, vol. 64, No. 2, 2003, pp. 246-258.
P. Planchon et al.: "Evidence for Separate Mechanisms of Antiproliferative Action of Indomethacin and Prostaglandin on MCF-7 Breast Cancer Cells," Life Sciences, vol. 57, No. 12, 1995, pp. 1233-1240.
R. Daniel Rudic et al.: "COX-2-Derived Prostacyclin Modulates Vascular Remodeling," Circulation Research, vol. 96, 2005, pp. 1240-1247.
K. M. Egan et al.: "COX-2-Derived Prostacyclin Confers Atheroprotection on Female Mice," Science, vol. 306, Dec. 10, 2004, pp. 1954-1957.
M. R. Schneider et al.: "Prostacyclin and its Analogues: Antimetastatic Effects and Mechanisms of Action," Cancer and Metastasis Reviews, vol. 13, 1994, pp. 349-364.
H. Wise et al.: "Focus on Prostacyclin and its Novel Mimetics," TIPS, vol. 17, Jan. 1996, pp. 17-21.
D. B. Badesch et al.: "Prostanoid Therapy for Pulmonary Arterial Hypertension," Journal of the American College of Cardiology, vol. 43, No. 12, Supp. S, 2004, pp. 56-61.
S. C. Chattaraj: "Treprostinil Sodium Pharmacia," Current Opinion in Investigational Drugs, vol. 3, No. 4, 2002, pp. 582-586.

(Continued)

*Primary Examiner* — Susanna Moore
(74) *Attorney, Agent, or Firm* — Karen B. King; Thomas C. Blankinship

(57) ABSTRACT

The present application relates to novel, cyclically substituted furopyrimidine derivatives, methods for their production, their use for the treatment and/or prophylaxis of diseases and their use for the production of medicinal products for the treatment and/or prophylaxis of diseases, in particular for the treatment and/or prophylaxis of cardiovascular diseases.

8 Claims, No Drawings

OTHER PUBLICATIONS

R. J. Barst et al.: "Beraprost Therapy for Pulmonary Arterial Hypertension," Journal of the American College of Cardiology, vol. 41, No. 12, 2003, pp. 2119-2125.

F. Johannsen et al.: "Phosphorus Pentoxide in Organic Synthesis," Chemica Scripta, vol. 26, 1986, pp. 337-342.

H. Saikachi et al.: "Synthesis of the Furan Derivatives. XLVIII. On the Synthesis of Difurylfuro[2,3-d]pyrimidines and Difurylfuro[3,2-*d*]-s-triazolopyrimidines," Yakugaku Zasshi, vol. 10, 1969, pp. 1434-1439.

E. Hayashi et al.: "Anti-Tumor Activity of Eighty Four Synthesized N-Heteroaromatic Compounds," Yakugaku Zasshi, vol. 97, No. 9, 1977, pp. 1022-1033.

U.S. Appl. No. 12/086,783, 371(c) date Dec. 1, 2008.

U.S. Appl. No. 12/664,748, 371(c) date Mar. 28, 2011.

U.S. Appl. No. 12/743,227, 371(c) date Mayc. 14, 2010.

CYCLICALLY SUBSTITUTED FUROPYRIMIDINE DERIVATIVES AND USE THEREOF

The present application relates to novel, cyclically substituted furopyrimidine derivatives, methods of production thereof, and use thereof for the treatment and/or prophylaxis of diseases and use thereof for the production of medicinal products for the treatment and/or prophylaxis of diseases, in particular for the treatment and/or prophylaxis of cardiovascular diseases.

Prostacyclin ($PGI_2$) belongs to the class of bioactive prostaglandins, which are derivatives of arachidonic acid. $PGI_2$ is the main product of arachidonic acid metabolism in endothelial cells and is a potent vasodilator and inhibitor of platelet aggregation. $PGI_2$ is the physiological antagonist of thromboxane $A_2$ ($TxA_2$), a strong vasoconstrictor and stimulator of thrombocyte aggregation, and thus contributes to the maintenance of vascular homeostasis. A drop in $PGI_2$ levels is presumed to be partly responsible for the development of various cardiovascular diseases [Dusting, G. J. et al., Pharmac. Ther. 1990, 48: 323-344; Vane, J. et al., Eur. I Vasc. Endovasc. Surg. 2003, 26: 571-578].

After release of arachidonic acid from phospholipids via phospholipases $A_2$, $PGI_2$ is synthesized by cyclooxygenases and then by $PGI_2$-synthase. $PGI_2$ is not stored, but is released immediately after synthesis, exerting its effects locally. $PGI_2$ is an unstable molecule, which is transformed rapidly (half-life approx. 3 minutes) and non-enzymatically, to an inactive metabolite, 6-keto-prostaglandin-F1alpha [Dusting, G. J. et al., Pharmac. Ther. 1990, 48: 323-344].

The biological effects of $PGI_2$ occur through binding to a membrane-bound receptor, called the prostacyclin receptor or IP receptor [Narumiya, S. et al., Physiol. Rev. 1999, 79: 1193-1226]. The IP receptor is one of the G-protein-coupled receptors, which are characterized by seven transmembrane domains. In addition to the human IP receptor, prostacyclin receptors have also been cloned from rat and mouse [Vane, J. et al., Eur. J. Vasc. Endovasc. Surg. 2003, 26: 571-578]. In smooth muscle cells, activation of the IP receptor leads to stimulation of adenylate cyclase, which catalyses the formation of cAMP from ATP. Increase in the intracellular cAMP concentration is responsible for prostacyclin-induced vasodilation and for inhibition of platelet aggregation. In addition to the vasoactive properties, anti-proliferative effects [Schroer, K. et al., Agents Actions Suppl. 1997, 48: 63-91; Kothapalli, D. et al., Mol. Pharmacol. 2003, 64: 249-258; Planchon, P. et al., Life Sci. 1995, 57: 1233-1240] and anti-arteriosclerotic effects [Rudic, R. D. et al., Circ. Res. 2005, 96: 1240-1247; Egan K. M. et al., Science 2004, 114: 784-794] have also been described for $PGI_2$. Furthermore, $PGI_2$ also inhibits the formation of metastases [Schneider, M. R. et al., Cancer Metastasis Rev. 1994, 13: 349-64]. It is unclear whether these effects are due to stimulation of cAMP formation or to IP receptor-mediated activation of other signal transduction pathways in the respective target cell [Wise, H. et al. TIPS 1996, 17: 17-21], such as the phosphoinositide cascade, and of potassium channels.

Although the effects of $PGI_2$ are on the whole of benefit therapeutically, clinical application of $PGI_2$ is severely restricted by its chemical and metabolic instability. $PGI_2$ analogues that are more stable, for example iloprost [Badesch, D. B. et al., J. Am. Coll. Cardiol. 2004, 43: 56S-61S] and treprostinil [Chattaraj, S. C., Curr. Opion. Invest. Drugs 2002, 3: 582-586] have been made available, but these compounds still have a very short time of action. Moreover, the substances can only be administered to the patient via complicated routes of administration, e.g. by continuous infusion, subcutaneously or via repeated inhalations. These routes of administration can also have additional side-effects, for example infections or pains at the site of injection. The use of beraprost, which to date is the only $PGI_2$ derivative available for oral administration to the patient [Barst, R. J. et al., J. Am. Coll. Cardiol. 2003, 41: 2119-2125], is once again limited by its short time of action.

The compounds described in the present application are, compared with $PGI_2$, chemically and metabolically stable, non-prostanoid activators of the IP receptor, which imitate the biological action of $PGI_2$ and thus can be used for the treatment of diseases, in particular of cardiovascular diseases.

DE 1 817 146, EP 1 018 514, EP 1 132 093, WO 02/092603, WO 03/022852, WO 2005/092896, WO 2005/121149 and WO 2006/004658 describe various 4-oxy-, 4-thio- and/or 4-aminofuro[2,3-d]pyrimidine derivatives and their use for the treatment of diseases. WO 03/018589 discloses 4-aminofuropyrimidines as adenosine kinase inhibitors for the treatment of cardiovascular diseases. The production of certain 4-aminofuropyrimidine derivatives was announced in Chemica Scripta 1986, 26 (2): 337-342, Yakugaku Zasshi 1969, 89 (10): 1434-1439 and Yakugaku Zasshi 1977, 97 (9): 1022-1033. Compounds with a bicyclic heteroaryl nuclear structure are claimed as inhibitors of cellular adhesion in WO 00/75145.

The compounds claimed within the framework of the present application are characterized, in contrast to the compounds from the state of the art, by a 5,6-diphenylfuro[2,3-d]pyrimidine nuclear structure, which is coupled via position 4, at a certain spatial distance, to a carboxylic acid or carboxylic acid—like functionality.

The present invention relates to compounds of general formula (I)

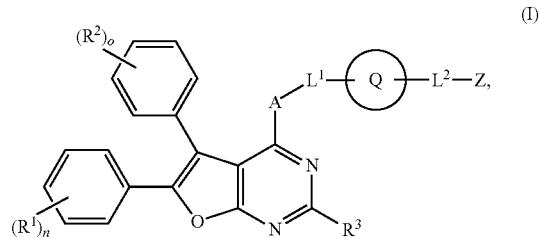

in which
A stands for O, S or N—$R^4$, where
   $R^4$ denotes hydrogen, ($C_1$-$C_6$)alkyl, ($C_3$-$C_7$)cycloalkyl or ($C_4$-$C_7$)cycloalkenyl,
$L^1$ stands for a bond or for ($C_1$-$C_4$)alkanediyl,
the Q ring stands for ($C_3$-$C_7$)cycloalkyl, ($C_4$-$C_7$)cycloalkenyl, a 5- to 7-membered heterocycle, phenyl or 5- or 6-membered heteroaryl, each of which may be up to disubstituted, identically or differently, by fluorine, chlorine, ($C_1$-$C_4$)alkyl, trifluoromethyl, hydroxyl, ($C_1$-$C_4$)alkoxy, trifluoromethoxy, amino, mono-($C_1$-$C_4$)alkylamino and/or di-($C_1$-$C_4$)alkylamino,
   where ($C_1$-$C_4$)alkyl may in turn be substituted by hydroxyl, ($C_1$-$C_4$)alkoxy, amino, mono- or di-($C_1$-$C_4$)alkylamino,
$L^2$ stands for ($C_1$-$C_4$)alkanediyl, which is mono- or disubstituted by fluorine and in which one methylene group may be exchanged for O or N—$R^5$ in which
   $R^5$ denotes hydrogen, ($C_1$-$C_6$)alkyl or ($C_3$-$C_7$)cycloalkyl, or stands for ($C_2$-$C_4$)alkenediyl, Z stands for a group of formula

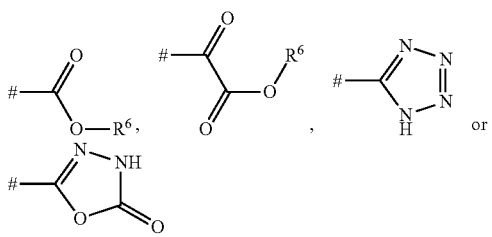

where
# denotes the point of linkage with group $L^2$
and
$R^6$ denotes hydrogen or $(C_1\text{-}C_4)$alkyl,
$R^1$ and $R^2$, independently of one another, stand for a substituent selected from the group comprising halogen, cyano, nitro, $(C_1\text{-}C_6)$alkyl, $(C_2\text{-}C_6)$alkenyl, $(C_2\text{-}C_4)$alkinyl, $(C_3\text{-}C_7)$ cycloalkyl, $(C_4\text{-}C_7)$cycloalkenyl, $(C_1\text{-}C_6)$alkoxy, trifluoromethyl, trifluoromethoxy, $(C_1\text{-}C_6)$alkylthio, $(C_1\text{-}C_6)$ acyl, amino, mono-$(C_1\text{-}C_6)$alkylamino, di-$(C_1\text{-}C_6)$alkylamino and $(C_1\text{-}C6)$acylamino,
and $(C_1\text{-}C_6)$alkyl and $(C_1\text{-}C_6)$alkoxy can in turn each be substituted with cyano, hydroxy, $(C_1\text{-}C_4)$alkoxy, $(C_1\text{-}C_4)$alkylthio, amino, mono- or di-$(C_1\text{-}C_4)$alkylamino, or
two residues $R^1$ and/or $R^2$ bound to adjacent carbon atoms of the respective phenyl ring, together form a group of formula —O—CH$_2$—O—, —O—CHF—O—, —O—CF$_2$—O—, —O—CH$_2$—CH$_2$—O— or —O—CF$_2$—CF$_2$—O—,
n and o, independently of one another, stand for the number 0, 1, 2 or 3,
and for the case when $R^1$ or $R^2$ occurs more than once, they can have the same or different meanings,
and
$R^3$ stands for hydrogen, $(C_1\text{-}C_4)$alkyl or cyclopropyl,
and their salts, solvates and solvates of the salts.

Compounds according to the invention are the compounds of formula (I) and their salts, solvates and solvates of the salts, the compounds covered by formula (I) of the formulae stated below and their salts, solvates and solvates of the salts and the compounds covered by formula (I), stated below as examples of application, and their salts, solvates and solvates of the salts, provided the compounds covered by formula (I), stated below, are not already salts, solvates and solvates of the salts.

The compounds according to the invention can, depending on their structure, exist in stereoisomeric forms (enantiomers, diastereomers). The invention therefore comprises the enantiomers or diastereomers and their respective mixtures. The stereoisomerically uniform constituents can be isolated in a known manner from such mixtures of enantiomers and/or diastereomers.

If the compounds according to the invention can occur in tautomeric forms, the present invention comprises all tautomeric forms.

Physiologically acceptable salts of the compounds according to the invention are preferred as salts within the scope of the present invention. Salts which in themselves are not suitable for pharmaceutical applications, but can be used for example for the isolation or purification of the compounds according to the invention, are also included.

Physiologically acceptable salts of the compounds according to the invention comprise salts of acid addition of inorganic acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also comprise salts of the usual bases, for example and preferably salts of alkali metals (e.g. sodium and potassium salts), salts of alkaline earths (e.g. calcium and magnesium salts) and ammonium salts, derived from ammonia or organic amines with 1 to 16 carbon atoms, for example and preferably ethylamine, diethylamine, triethylamine, ethyldiisopropylamine, monoethanolamine, diethanolamine, trisethanolamine, dicyclohexylamine, dimethylaminoethanol, procaine, dibenzylamine, N-methylmorpholine, arginine, lysine, ethylendiamine and N-methylpiperidine.

Within the framework of the invention, such forms of the compounds according to the invention that form a complex in the solid or liquid state by coordination with solvent molecules are termed solvates. Hydrates are a special form of solvates, in which coordination is accomplished with water. Hydrates are preferred as solvates within the scope of the present invention.

In addition, the present invention also comprises prodrugs of the compounds according to the invention. The term "prodrugs" comprises compounds which in themselves may be biologically active or inactive, but are converted (e.g. metabolically or by hydrolysis) to compounds according to the invention while they are in the body.

In particular, for the compounds of formula (I) in which Z stands for a group of formula

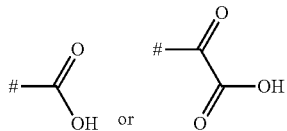

the present invention also comprises hydrolysable ester derivatives of these compounds. This comprises esters that can be hydrolysed to the free carboxylic acids, as the compounds that are mainly active biologically, in physiological media, in the conditions of the biological tests described later and in particular in vivo by enzymatic or chemical routes. $(C_1\text{-}C_4)$alkyl esters, in which the alkyl group can be linear or branched, are preferred as such esters. Methyl or ethyl esters are especially preferred (see also the corresponding definitions of the residue $R^6$).

Within the scope of the present invention, unless specified otherwise, the substituents have the following meanings:

Within the scope of the invention, $(C_1\text{-}C_6)$ alkyl, $(C_1\text{-}C_5)$ alkyl, $(C_1\text{-}C_4)$alkyl and $(C_1\text{-}C_3)$alkyl stand for a linear or branched alkyl residue with 1 to 6, 1 to 5, 1 to 4 or 1 to 3 carbon atoms. A linear or branched alkyl residue with 1 to 4 carbon atoms is preferred, and one with 1 to 3 carbon atoms is especially preferred. The following may be mentioned as preferred examples: methyl, ethyl, n-propyl, isopropyl, n-butyl, iso-butyl, sec.-butyl, tert.-butyl, 1-ethylpropyl, n-pentyl and n-hexyl.

Within the scope of the invention, $(C_2\text{-}C_6)$alkenyl and $(C_2\text{-}C_5)$alkenyl stand for a linear or branched alkenyl residue with 2 to 6 or 2 to 5 carbon atoms and one or two double bonds. A linear or branched alkenyl residue with 2 to 5 carbon atoms and one double bond is preferred. The following may be mentioned as preferred examples: vinyl, allyl, isopropenyl and n-but-2-en-1-yl.

Within the scope of the invention, $(C_2-C_4)$alkinyl stands for a linear or branched alkinyl residue with 2 to 4 carbon atoms and a triple bond. A linear alkinyl residue with 2 to 4 carbon atoms is preferred. The following may be mentioned as preferred examples: ethinyl, n-prop-1-in-1-yl, n-prop-2-in-1-yl, n-but-2-in-1-yl and n-but-3-in-1-yl.

Within the scope of the invention, $(C_1-C_4)$alkanediyl and $(C_1-C_3)$alkanediyl stand for a straight-chain or branched divalent alkyl radical with 1 to 4 or 1 to 3 carbon atoms. A straight-chain alkanediyl radical with 1 to 4 or 1 to 3 carbon atoms is preferred in each case. The following may be mentioned as preferred examples: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl and butan-2,3-diyl.

Within the scope of the invention, $(C_2-C_4)$alkenediyl and $(C_2-C_3)$ alkenediyl stand for a straight-chain or branched divalent alkenyl radical having 2 to 4 or 2 to 3 carbon atoms and up to 2 double bonds. A straight-chain alkenediyl radical with 2 to 4 or 2 to 3 carbon atoms and one double bond is preferred in each case. The following may be mentioned as preferred examples: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl and buta-1,3-diene-1,4-diyl.

Within the scope of the invention, $(C_1-C_6)$alkoxy and $(C_1-C_4)$alkoxy stand for a linear or branched alkoxy residue with 1 to 6 or 1 to 4 carbon atoms. A linear or branched alkoxy residue with 1 to 4 carbon atoms is preferred. The following may be mentioned as preferred examples: methoxy, ethoxy, n-propoxy, isopropoxy, n-butoxy, tert.-butoxy, n-pentoxy and n-hexoxy.

Within the scope of the invention, $(C_1-C_6)$alkylthio and $(C_1-C_4)$alkylthio stand for a linear or branched alkylthio residue with 1 to 6 or 1 to 4 carbon atoms. A linear or branched alkylthio residue with 1 to 4 carbon atoms is preferred. The following may be mentioned as preferred examples: methylthio, ethylthio, n-propylthio, isopropylthio, n-butylthio, tert.-butylthio, n-pentylthio and n-hexylthio.

Within the scope of the invention, $(C_1-C_6)$acyl [$(C_1-C_6)$alkanoyl], $(C_1-C_5)$ acyl [$(C_1-C_5)$-alkanoyl] and $(C_1-C_4)$acyl [$(C_1-C_4)$ alkanoyl] stand for a linear or branched alkyl residue with 1 to 6, 1 to 5 or 1 to 4 carbon atoms, which bears a double-bonded oxygen atom in position 1 and is linked via position 1. A linear or branched acyl residue with 1 to 4 carbon atoms is preferred. The following may be mentioned as preferred examples: formyl, acetyl, propionyl, n-butyryl, iso-butyryl and pivaloyl.

Within the scope of the invention, mono-$(C_1-C_6)$alkylamino and mono-$(C_1-C_4)$alkylamino stand for an amino group with a linear or branched alkyl substituent, which has 1 to 6 or 1 to 4 carbon atoms. A linear or branched monoalkylamino residue with 1 to 4 carbon atoms is preferred. The following may be mentioned as preferred examples: methylamino, ethylamino, n-propylamino, isopropylamino and tert.-butylamino.

Within the scope of the invention, di-$(C_1-C_6)$alkylamino and di-$(C_1-C_4)$alkylamino stand for an amino group with two identical or different linear or branched alkyl substituents, each having 1 to 6 or 1 to 4 carbon atoms. Linear or branched dialkylamino residues each with 1 to 4 carbon atoms are preferred. The following may be mentioned as preferred examples: N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Within the scope of the invention, $(C_1-C_6)$ acylamino and $(C_1-C_4)$acylamino stand for an amino group with a linear or branched acyl substituent, which has 1 to 6 or 1 to 4 carbon atoms and is linked via the carbonyl group. An acylamino residue with 1 to 4 carbon atoms is preferred. The following may be mentioned as preferred examples: formamido, acetamido, propionamido, n-butyramido and pivaloylamido.

Within the scope of the invention, $(C_3-C_7)$cycloalkyl and $(C_3-C_6)$ cycloalkyl stand for a mono-cyclic, saturated cycloalkyl group with 3 to 7 or 3 to 6 carbon atoms. A cycloalkyl residue with 3 to 6 carbon atoms is preferred. The following may be mentioned as preferred examples: cyclopropyl, cyclobutyl, cyclopentyl, cyclohexyl and cycloheptyl.

Within the scope of the invention, $(C_4-C_7)$cycloalkenyl, $(C_4-C_6)$cycloalkenyl and $(C_5-C_6)$ cycloalkenyl stand for a monocyclic cycloalkyl group with 4 to 7, 4 to 6 or 5 or 6 carbon atoms and a double bond. A cycloalkenyl residue with 4 to 6 carbon atoms is preferred or with 5 or 6 carbon atoms is particularly preferred. The following may be mentioned as preferred examples: cyclobutenyl, cyclopentenyl, cyclohexenyl and cycloheptenyl.

Within the scope of the invention, a 5- to 7-membered heterocycle stands for a saturated or partially unsaturated heterocycle with 5 to 7 ring atoms, which contains one or two ring heteroatoms from the group of N and/or O and is bonded via ring carbon atoms and/or, if appropriate, ring nitrogen atoms. Preference is given to a 5- or 6-membered saturated heterocycle with one or two ring heteroatoms from the group of N and/or O. Examples include: pyrrolidinyl, pyrrolinyl, pyrazolidinyl, tetrahydrofuranyl, piperidinyl, piperazinyl, tetrahydropyranyl, morpholinyl, hexahydroazepinyl and hexahydro-1,4-diazepinyl. Preference is given to pyrrolidinyl, tetrahydrofuranyl, piperidinyl, piperazinyl and tetrahydropyranyl.

Within the scope of the invention, 5- or 6-membered heteroaryl stands for an aromatic heterocycle (heteroaromatic) with 5 or 6 ring atoms, which contains one or two ring heteroatoms from the group of N, O and/or S and is bonded via ring carbon atoms and/or, if appropriate, a ring nitrogen atom. Examples include: furyl, pyrrolyl, thienyl, pyrazolyl, imidazolyl, thiazolyl, oxazolyl, isoxazolyl, isothiazolyl, pyridyl, pyrimidinyl, pyridazinyl and pyrazinyl. Preference is given to 6-membered heteroaryl radicals, for example pyridyl, pyrimidinyl, pyridazinyl and pyrazinyl.

Within the scope of the invention, halogen includes fluorine, chlorine, bromine and iodine. Chlorine or fluorine is preferred.

If residues are substituted in the compounds according to the invention, unless otherwise specified the residues can be singly or multiply substituted. Within the scope of the present invention, for all residues occurring more than once, their meanings are independent of one another. Substitution with one, two or three identical or different substituents is preferred. Substitution with one substituent is quite especially preferred.

Within the scope of the present invention, compounds of formula (I) are preferred in which A stands for O, S or N—$R^4$, where
$R^4$ denotes hydrogen, $(C_1-C_6)$alkyl, $(C_3-C_7)$cycloalkyl or $(C_4-C_7)$cycloalkenyl, $L^1$ stands for a bond or for $(C_1-C_4)$alkanediyl, the Q ring stands for $(C_3-C_7)$cycloalkyl, $(C_4-C_7)$cycloalkenyl, a 5- to 7-membered heterocycle, phenyl or 5- or 6-membered heteroaryl, each of which may be up to disubstituted, identically or differently, by fluorine, chlorine, ($C_1$-$C_4$)alkyl, trifluoromethyl, hydroxyl, ($C_1$-$C_4$)alkoxy, trifluoromethoxy, amino, mono-($C_1$-$C_4$)alkylamino and/or di-($C_1$-$C_4$)alkylamino, where ($C_1$-$C_4$)alkyl may in turn be substituted by hydroxyl, ($C_1$-$C_4$)alkoxy, amino, mono- or di-($C_1$-$C_4$)alkylamino, $L^2$ stands for ($C_1$-$C_4$)alkanediyl, which is mono- or disubstituted by fluorine and in which one methylene group may be exchanged for O or N—$R^5$ in which $R^5$ denotes hydrogen, ($C_1$-$C_6$)alkyl or ($C_3$-$C_7$)cycloalkyl, or stands for ($C_2$-$C_4$)alkenediyl, Z stands for a group of formula

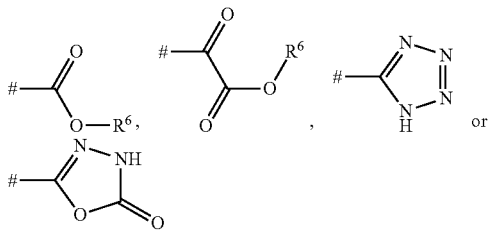

where
# denotes the point of linkage with group $L^2$
and
$R^6$ denotes hydrogen or ($C_1$-$C_4$)alkyl,
$R^1$ and $R^2$, independently of one another, stand for a substituent selected from the group comprising halogen, cyano, nitro, ($C_1$-$C_6$)alkyl, ($C_2$-$C_6$)alkenyl, ($C_2$-$C_4$)alkinyl, ($C_3$-$C_7$)cycloalkyl, ($C_4$-$C_7$)cycloalkenyl, ($C_1$-$C_6$)alkoxy, trifluoromethyl, trifluoromethoxy, ($C_1$-$C_6$)alkylthio, ($C_1$-$C_6$)acyl, amino, mono-($C_1$-$C_6$)alkylamino, di-($C_1$-$C_6$)alkylamino and ($C_1$-$C_6$)acylamino, and ($C_1$-$C_6$)alkyl and ($C_1$-$C_6$)alkoxy can in turn each be substituted with hydroxy, ($C_1$-$C_4$)alkoxy, amino, mono- or di-($C_1$-$C_4$)alkylamino, or
two residues $R^1$ and/or $R^2$ bound to adjacent carbon atoms of the respective phenyl ring together form a group of formula —O—$CH_2$—O—, —O—CHF—O—, —O—$CF_2$—O—, —O—$CH_2$—$CH_2$—O— or —O—$CF_2$—$CF_2$—O—, n and o, independently of one another, stand for the number 0, 1, 2 or 3,
and for the case when $R^1$ or $R^2$ occurs more than once, their meanings can each be identical or different,
and
$R^3$ stands for hydrogen, ($C_1$-$C_4$)alkyl or cyclopropyl,
and their salts, solvates and solvates of the salts.

Within the scope of the present invention, compounds of formula (I) are especially preferred in which
A stands for O or N—$R^4$, where
$R^4$ denotes hydrogen, ($C_1$-$C_4$)alkyl or ($C_3$-$C_6$)cycloalkyl,
$L^1$ stands for a bond or ($C_1$-$C_3$)alkanediyl,
the Q ring stands for ($C_3$-$C_6$)cycloalkyl, ($C_4$-$C_6$)cycloalkenyl, a 5- or 6-membered heterocycle, phenyl or 5- or 6-membered heteroaryl, each of which may be up to disubstituted, identically or differently, by fluorine, chlorine, ($C_1$-$C_3$)alkyl, trifluoromethyl, hydroxyl, methoxy, ethoxy, trifluoromethoxy, amino, methylamino, ethylamino, dimethylamino and/or diethylamino,
where ($C_1$-$C_3$)alkyl may in turn be substituted by hydroxyl, methoxy, ethoxy, amino, methylamino, ethylamino, dimethylamino or diethylamino, $L^2$ stands for ($C_1$-$C_3$)alkanediyl which may be mono- or disubstituted by fluorine, ($C_2$-$C_3$) alkenediyl or a group of the formula *-M-$CR^7R^8$—, *-M-$CH_2$—$CR^7R^8$— or *—$CH_2$-M-$CR^7R^8$—,
in which
* denotes the point of linkage with the Q ring,
M is O or N—$R^5$ in which
$R^5$ is hydrogen, ($C_1$-$C_3$)alkyl or cyclopropyl,
and
$R^7$ and $R^8$, independently of one another, are hydrogen or fluorine,
Z stands for a group of formula

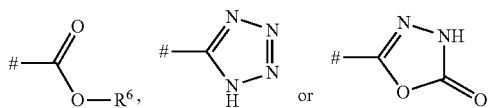

where
# denotes the point of linkage with group $L^2$
and
$R^6$ denotes hydrogen, methyl or ethyl,
$R^1$ and $R^2$, independently of one another, stand for a substituent selected from the group comprising fluorine, chlorine, cyano, ($C_1$-$C_5$)alkyl, ($C_2$-$C_5$)alkenyl, ($C_3$-$C_6$)cycloalkyl, ($C_4$-$C_6$)cycloalkenyl, ($C_1$-$C_4$)alkoxy, trifluoromethyl, trifluoromethoxy, ($C_1$-$C_4$)alkylthio, ($C_1$-$C_5$)acyl, amino, mono-($C_1$-$C_4$)alkylamino, di-($C_1$-$C_4$)alkylamino and ($C_1$-$C_4$)acyl-amino or
two residues $R^1$ and/or $R^2$ bound to adjacent carbon atoms of the respective phenyl ring, together form a group of formula —O—$CH_2$—O—, —O—CHF—O— or —O—$CF_2$—O—, n and o, independently of one another, stand for the number 0, 1, 2 or 3,
and for the case when $R^1$ or $R^2$ occurs more than once, their meanings can in each case be identical or different,
and
$R^3$ stands for hydrogen or ($C_1$-$C_3$)alkyl,
and their salts, solvates and solvates of the salts.

Within the scope of the present invention, compounds of formula (I) are quite especially preferred in which
A stands for O or N—$R^4$ in which
$R^4$ is hydrogen or ($C_1$-$C_4$)alkyl,
$L^1$ stands for a bond or ($C_1$-$C_3$)alkanediyl,
the Q ring stands for ($C_4$-$C_6$)cycloalkyl, ($C_5$-$C_6$)cycloalkenyl, a 5- or 6-membered heterocycle or phenyl, each of which may be up to disubstituted, identically or differently, by fluorine, chlorine, ($C_1$-$C_3$)alkyl, trifluoromethyl, hydroxyl, methoxy, ethoxy, trifluoromethoxy, amino, methylamino, ethylamino, dimethylamino and/or diethylamino,
$L^2$ stands for ($C_1$-$C_3$)alkanediyl which may be mono- or disubstituted by fluorine, ($C_2$-$C_3$)alkenediyl or a group of the formula *-M-$CR^7R^8$—, *-M-$CH_2$—$CR^7R^8$— or *—$CH_2$-M-$CR^7R^8$—,
in which
* denotes the point of linkage with the Q ring,
M is O or N—$R^5$ in which
$R^5$ is hydrogen or ($C_1$-$C_3$)alkyl,
and
$R^7$ and $R^8$, independently of one another, denote hydrogen or fluorine, Z stands for a group of formula

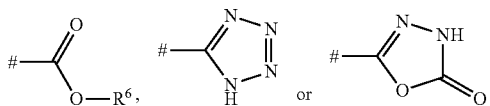

where
# denotes the point of linkage with group L² and
R⁶ denotes hydrogen, methyl or ethyl,
R¹ and R², independently of one another, stand for a substituent selected from the group comprising fluorine, chlorine, cyano, (C₁-C₅)alkyl, (C₂-C₅)alkenyl, (C₃-C₆)cycloalkyl, (C₄-C₆)cycloalkenyl, (C₁-C₄)alkoxy, trifluoromethyl, trifluoromethoxy, (C₁-C₄)alkylthio, (C₁-C₅)acyl, amino, mono-(C₁-C₄)alkylamino, di-(C₁-C₄)alkylamino and (C₁-C₄)acyl-amino
or
two residues R¹ and/or R², bound to adjacent carbon atoms of the respective phenyl ring, together form a group of formula —O—CH₂—O—, —O—CHF—O— or —O—CF₂—O—,
n and o, independently of one another, stand for the number 0, 1 or 2,
and for the case when R¹ or R² occurs twice, their meanings can in each case be identical or different,
and
R³ stands for hydrogen or (C₁-C₃)alkyl,
and their salts, solvates and solvates of the salts.

Of particular importance, within the scope of the present invention, are compounds of formula (I) in which
A stands for O or NH,
L¹ stands for a bond, methylene, ethane-1,1-diyl or ethane-1,2-diyl,
the Q ring stands for cyclobutyl, cyclopentyl, cyclopentenyl, cyclohexyl, pyrrolidinyl, piperidinyl, tetrahydrofuranyl, tetrahydropyranyl, morpholinyl or phenyl, each of which may be up to disubstituted, identically or differently, by fluorine, methyl, ethyl, trifluoromethyl, hydroxyl, methoxy, ethoxy, amino, methylamino and/or dimethylamino,
L² stands for (C₁-C₃)alkanediyl, (C₂-C₃)alkenediyl or a group of the formula *-M-CH₂— or *-M-CH₂—CH₂—, in which
* denotes the point of linkage to the Q ring
and
M denotes O or N—R⁵, in which
R⁵ is hydrogen or (C₁-C₃)alkyl,
Z stands for a group of formula

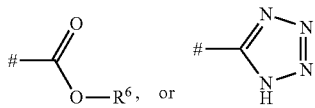

where
# denotes the point of linkage with group L² and
R⁶ denotes hydrogen, methyl or ethyl,
R¹ and R², independently of one another, stand for a substituent selected from the group comprising fluorine, chlorine, cyano, (C₁-C₅)alkyl, (C₂-C₅)alkenyl, (C₃-C₆)cycloalkyl, (C₄-C₆)cycloalkenyl, (C₁-C₄)alkoxy, trifluoromethyl, trifluoromethoxy, (C₁-C₄)alkylthio, (C₁-C₅)acyl, amino, mono-(C₁-C₄)alkylamino, di-(C₁-C₄)alkylamino and (C₁-C₄)acyl-amino
or
two residues R¹ and/or R², bound to adjacent carbon atoms of the respective phenyl ring, together form a group of formula —O—CH₂—O—, —O—CHF—O— or —O—CF₂—O—,
n and o, independently of one another, stand for the number 0, 1 or 2,
and for the case when R¹ or R² occurs twice, their meanings can in each case be identical or different,
and
R³ stands for hydrogen,
and their salts, solvates and solvates of the salts.

Of very particular importance, within the scope of the present invention, are compounds of formula (I) in which
A stands for O or NH,
L¹ stands for a bond, methylene or ethane-1,1-diyl,
the Q ring stands for cyclobutyl, cyclopentyl, cyclopentenyl, cyclohexyl, pyrrolidinyl, piperidinyl or phenyl, each of which may be up to disubstituted, identically or differently, by fluorine, methyl, hydroxyl and/or methoxy,
L² is (C₁-C₃)alkanediyl, (C₂-C₃)alkenediyl or a group of the formula *-M-CH₂— or *-M-CH₂—CH₂—,
in which
* denotes the point of linkage with the Q ring,
and
M denotes O or NH,
Z stands for a group of formula

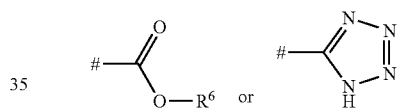

where
# denotes the point of linkage with group L² and
R⁶ denotes hydrogen, methyl or ethyl,
R¹ stands for a substituent selected from the group comprising fluorine, chlorine, methyl, ethyl, vinyl, trifluoromethyl and methoxy,
R² stands for a substituent selected from the group comprising fluorine, chlorine, cyano, methyl, ethyl, n-propyl, vinyl, trifluoromethyl, methoxy, ethoxy, trifluoromethoxy, methylthio, ethylthio, amino, methylamino and ethylamino,
n and o, independently of one another, stand for the number 0, 1 or 2,
and for the case when R¹ or R² occurs twice, their meanings can in each case be identical or different,
and
R³ stands for hydrogen,
and their salts, solvates and solvates of the salts.

The detailed definitions of residues given in the respective combinations and/or preferred combinations of residues are also replaced with any other definitions of residues of other combinations regardless of the respective combinations of residues stated.

Combinations of two or more of the aforementioned preferred ranges are quite especially preferred.

The invention further relates to a method of production of the compounds of formula (I) according to the invention, in which Z is —COOH or —C(=O)—COOH, characterized in that either

[A] compounds of formula (II)

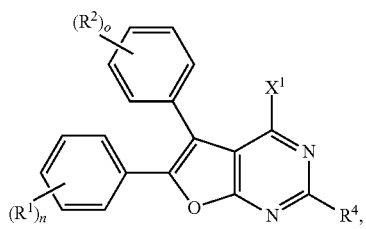

(II)

in which $R^1$, $R^2$, $R^3$, n and o have the respective meanings given above
and
$X^1$ stands for a leaving group, for example halogen, and especially chlorine,
in the presence of a base and if necessary in an inert solvent with a compound of formula (III)

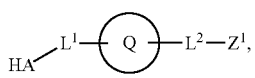

(III)

in which A, $L^1$, $L^2$ and Q have the respective meanings given above
and
$Z^1$ stands for cyano or a group of formula —[C(O)]$_y$—COOR$^{6A}$, where
y denotes the number 0 or 1
and
$R^{6A}$ denotes (C$_1$-C$_4$)alkyl,
are reacted to compounds of formula (IV)

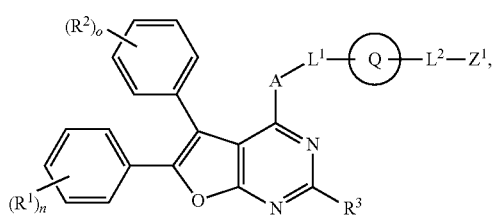

(IV)

in which A, $L^1$, $L^2$, Q, $Z^1$, $R^1$, $R^2$, $R^3$, n and o have the respective meanings given above,
or
[B] compounds of formula (V-1)

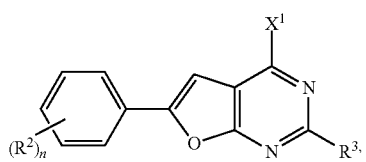

(V-1)

in which $R^1$, $R^3$, $X^1$ and n have the respective meanings given above,
are reacted, in the presence of a base and if necessary in an inert solvent, with a compound of formula (III) to compounds of formula (VI-1)

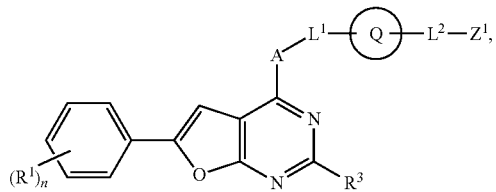

(VI-1)

in which A, $L^1$, $L^2$, Q, $Z^1$, $R^1$, $R^3$ and n have the respective meanings given above,
and are then brominated, in an inert solvent, for example with N-bromosuccinimide to compounds of formula (VII-1)

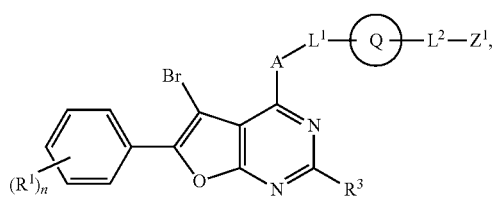

(VII-1)

in which A, $L^1$, $L^2$, Q, $Z^1$, $R^1$, $R^3$ and n have the respective meanings given above,
and these are then coupled, in an inert solvent in the presence of a base and a suitable palladium catalyst, with a phenylboronic acid of formula (VIII-1)

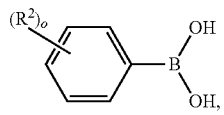

(VIII-1)

in which $R^2$ and o have the meanings given above,
to compounds of formula (IV)
or
[C] compounds of formula (V-2)

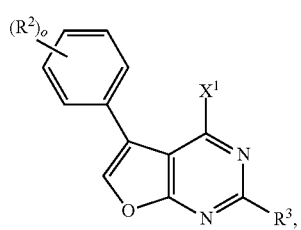

(V-2)

in which $R^2$, $R^3$, $X^1$ and o have the respective meanings given above,
are reacted in the presence of a base and if necessary in an inert solvent, with a compound of formula (III) to compounds of formula (VI-2)

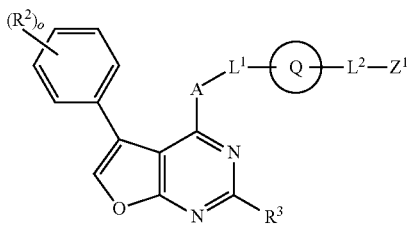
(VI-2)

in which A, L$^1$, L$^2$, Q, Z$^1$, R$^2$, R$^3$ and o have the respective meanings given above,
then brominated in an inert solvent for example with N-bromosuccinimide to compounds of formula (VII-2)

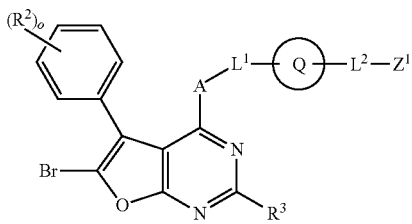
(VII-2)

in which A, L$^1$, L$^2$, Q, Z$^1$, R$^2$, R$^3$ and o have the respective meanings given above,
and these are then coupled, in an inert solvent in the presence of a base and a suitable palladium catalyst, with a phenylboronic acid of formula (VIII-2)

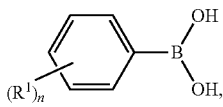
(VIII-2)

in which R$^1$ and n have the meanings given above,
to compounds of formula (IV),
and in each case the resultant compounds of formula (IV) are then transformed by hydrolysis of the ester- or cyano group Z$^1$ to the carboxylic acids of formula (I-A)

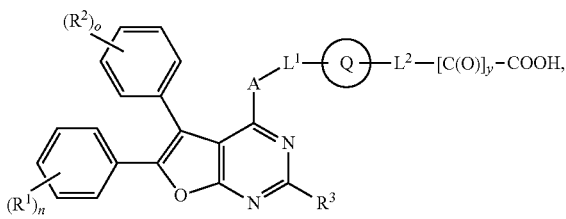
(I-A)

in which A, L$^1$, L$^2$, Q, R$^1$, R$^2$, R$^3$, n, o and y have the respective meanings given above,
and these are converted if necessary with the corresponding (i) solvents and/or (ii) bases or acids to their solvates, salts and/or solvates of the salts.

Inert solvents for steps (II)+(III)→(IV), (V-1)+(III)→(VI-1) and (V-2)+(III)→(VI-2) are for example ethers such as diethyl ether, methyl-tert.-butyl ether, dioxan, tetrahydrofuran, glycol dimethyl ether or diethyleneglycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichlorethane, trichlorethane, tetrachloroethane, trichloroethylene, chlorobenzene or chlorotoluene, or other solvents such as dimethylformamide (DMF), dimethylsulphoxide (DMSO), N,N'-dimethylpropyleneurea (DMPU), N-methylpyrrolidone (NMP) or acetonitrile. It is also possible to use mixtures of the aforementioned solvents. Tetrahydrofuran, dimethylformamide, dimethylsulphoxide or mixtures thereof are preferably used.

However, steps (II)+(III)→(IV), (V-1)+(III)→(VI-1) and (V-2)+(III)→(VI-2) can if necessary also be carried out without solvents.

Usual inorganic or organic bases are suitable as bases for steps (II)+(III)→(IV), (V-1)+(III)→(VI-1) and (V-2)+(III)→(VI-2). Preferably these include alkali hydroxides, for example lithium, sodium or potassium hydroxide, alkali or alkaline-earth carbonates such as lithium, sodium, potassium, calcium or caesium carbonate, alkali-alcoholates such as sodium or potassium tert.-butylate, alkali hydrides such as sodium or potassium hydride, amides such as lithium or potassium bis(trimethylsilyl)amide or lithium diisopropylamide, organometallic compounds such as butyllithium or phenyllithium, or organic amines such as triethylamine, N-methylmorpholine, N-methylpiperidine, N,N-diisopropylethylamine or pyridine.

In the case of reaction with alcohol derivatives [A in (III)=O], phosphazene bases (so-called "Schwesinger bases"), for example P2-t-Bu or P4-t-Bu, are also suitable [cf. e.g. R. Schwesinger, H. Schlemper, Angew. Chem. Int. Ed. Engl. 26, 1167 (1987); T. Pietzonka, D. Seebach, Chem. Ber. 124, 1837 (1991)].

For reaction with amine derivatives [A in (III)=N], tertiary amines, such as in particular N,N-diisopropylethylamine, are preferably used as the base. If necessary, however, these reactions can also be carried out—using an excess of the amine component (III)—without addition of an auxiliary base. For reaction with alcohol derivatives [A in (III)=O], potassium or caesium carbonate or the phosphazene bases P2-t-Bu and P4-t-Bu are preferred.

Steps (II)+(III)→(IV), (V-1)+(III)→(VI-1) and (V-2)+(III)→(VI-2) can if carried out advantageously with addition of a crown ether.

In a variant of the process, reactions (II)+(III)→(IV), (V-1)+(III)→(VI-1) and (V-2)+(III)→(VI-2) can also be carried out in a two-phase mixture, comprising an aqueous alkali hydroxide solution as base and one of the aforementioned hydrocarbons or halohydrocarbons as additional solvent, using a phase-transfer catalyst such as tetrabutylammonium hydrogensulphate or tetrabutylammonium bromide.

Steps (II)+(III)→(IV), (V-1)+(III)→(VI-1) and (V-2)+(III)→(VI-2) are carried out, in the case of reaction with amine derivatives [A in (HI) =N], generally in a temperature range from +50° C. to +150° C. For reaction with alcohol derivatives [A in (III)=O], the reactions are generally carried out in a temperature range from −20° C. to +120° C., and preferably at 0° C. to +60° C.

The bromination in steps (VI-1)→(VII-1) or (VI-2)→(VII-2) is preferably carried out in a halohydrocarbon as solvent, especially in tetrachloromethane, in a temperature range from +50° C. to +100° C. Suitable brominating agents are elemental bromine and especially N-bromosuccinimide (NBS), if necessary with addition of α,α'-azobis(isobutyronitrile) (AIBN) as initiator.

Inert solvents for steps (VII-1)+(VIII-1)→(IV) and (VII-2)+(VIII-2)→(IV) are for example alcohols such as methanol, ethanol, n-propanol, isopropanol, n-butanol or tert.-butanol, ethers such as diethyl ether, dioxan, tetrahydrofuran, glycol dimethyl ether or diethyleneglycol dimethyl ether, hydrocarbons such as benzene, xylene, toluene, hexane, cyclohexane or petroleum fractions, or other solvents such as dimethylformamide, dimethylsulphoxide, N,N'-dimethylpropyleneurea (DMPU), N-methylpyrrolidone (NMP), pyridine, acetonitrile or even water. It is also possible to use mixtures of the aforementioned solvents. A mixture of dimethylsulphoxide and water is preferred.

Usual inorganic bases are suitable as bases for steps (VII-1)+(VIII-1)→(N) and (VII-2)+(VIII-2)→(IV). These include in particular alkali hydroxides such as lithium, sodium or potassium hydroxide, alkali hydrogencarbonates such as sodium or potassium hydrogencarbonate, alkali or alkaline-earth carbonates such as lithium, sodium, potassium, calcium or caesium carbonate, or alkali hydrogenphosphates such as disodium or dipotassium hydrogenphosphate. Sodium or potassium carbonate is preferably used.

Suitable palladium catalysts for steps (VII-1)+(VIII-1)→(N) and (VII-2)+(VIII-2)→(IV) ["Suzuki coupling"] are for example palladium on activated charcoal, palladium(II) acetate, tetrakis-(triphenylphosphine)-palladium(0), bis-(triphenylphosphine)-palladium(II) chloride, bis-(acetonitrile)-palladium(II) chloride and [1,1'-bis(diphenylphosphino)ferrocene]dichloropalladium-(II)-dichloromethane complex [cf. e.g. J. Hassan et al., Chem. Rev. 102, 1359-1469 (2002)].

Reactions (VII-1)+(VIII-1)→(IV) and (VII-2)+(VIII-2)→(IV) are generally carried out in a temperature range from +20° C. to +150° C., preferably at +50° C. to +100° C.

Hydrolysis of the ester or nitrile group $Z^1$ in step (IV)→(I-A) is carried out by usual methods, by treating the esters or nitriles in inert solvents with acids or bases, and in the latter case the salts that are formed initially are converted to the free carboxylic acids by treatment with acid. In the case of the tert.-butyl esters, ester cleavage is preferably carried out with acids.

Water or the usual organic solvents for ester cleavage are suitable as inert solvents for these reactions. These preferably include alcohols such as methanol, ethanol, n-propanol, isopropanol, n-butanol or tert.-butanol, or ethers such as diethyl ether, tetrahydrofuran, dioxan or glycoldimethyl ether, or other solvents such as acetone, dichloromethane, dimethylformamide or dimethylsulphoxide. It is also possible to use mixtures of the aforementioned solvents. In the case of basic ester hydrolysis, the use of mixtures of water with dioxan, tetrahydrofuran, methanol and/or ethanol is preferred, and for nitrile hydrolysis it is preferable to use water and/or n-propanol. The use of dichloromethane is preferred in the case of reaction with trifluoroacetic acid, and in the case of reaction with hydrogen chloride it is preferable to use tetrahydrofuran, diethyl ether, dioxan or water.

The usual inorganic bases are suitable as bases. These preferably include alkali or alkaline-earth hydroxides such as sodium, lithium, potassium or barium hydroxide, or alkali or alkaline-earth carbonates such as sodium, potassium or calcium carbonate. Sodium or lithium hydroxide is especially preferred.

Sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid or mixtures thereof are generally suitable as acids for ester cleavage, if necessary with addition of water. Hydrogen chloride or trifluoroacetic acid is preferred in the case of the tert.-butyl esters and hydrochloric acid in the case of the methyl esters.

Ester cleavage is generally carried out in a temperature range from 0° C. to +100° C., preferably at +0° C. to +50° C. Nitrile hydrolysis is generally carried out in a temperature range from +50° C. to +150° C., preferably at +80° C. to +120° C.

The aforementioned reactions can be carried out at normal, at increased or at reduced pressure (e.g. from 0.5 to 5 bar). Normal pressure is generally used in each case.

The compounds according to the invention of formula (I), in which Z stands for a group of formula

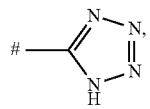

can be produced by reacting compounds of formula (IV), in which $Z^1$ stands for cyano, in an inert solvent with an alkali azide in the presence of ammonium chloride or with trimethylsilylazide if necessary in the presence of a catalyst.

Inert solvents for this reaction are for example ethers such as diethyl ether, dioxan, tetra-hydrofuran, glycol dimethyl ether or diethyleneglycol dimethyl ether, hydrocarbons such as benzene, toluene, xylene, hexane, cyclohexane or petroleum fractions, or other solvents such as dimethylsulphoxide, dimethylformamide, N,N'-dimethylpropyleneurea (DMPU) or N-methyl-pyrrolidone (NMP). It is also possible to use mixtures of the aforementioned solvents. Use of toluene is preferred.

In particular sodium azide is suitable as azide reagent, in the presence of ammonium chloride or trimethylsilylazide. The latter reaction can be carried out more advantageously in the presence of a catalyst. Compounds such as di-n-butyltin oxide, trimethylaluminium or zinc bromide are especially suitable for this. It is preferable to use trimethylsilylazide in combination with di-n-butyltin oxide.

The reaction is generally carried out in a temperature range from +50° C. to +150° C., preferably at +60° C. to +110° C. The reaction can be carried out at normal, increased or reduced pressure (e.g. from 0.5 to 5 bar). It is generally carried out at normal pressure.

The compounds according to the invention of formula (I), in which Z stands for a group of formula

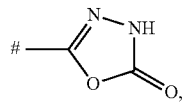

can be produced by converting compounds of formula (IV), in which $Z^1$ stands for methoxy- or ethoxycarbonyl, first in an inert solvent with hydrazine to compounds of formula (IX)

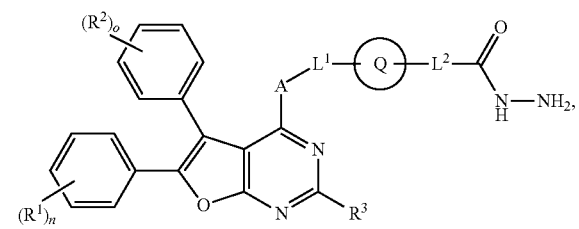

(IX)

in which A, $L^1$, $L^2$, Q, $R^2$, $R^3$, n and o have the respective meanings given above,
and then reacting them in an inert solvent with phosgene or a phosgene equivalent, such as N,N'-carbonyl diimidazole.

Suitable inert solvents for the first step of this reaction sequence are in particular alcohols such as methanol, ethanol, n-propanol, isopropanol, n-butanol or tert.-butanol, or ethers such as diethyl ether, dioxan, tetrahydrofuran, glycol dimethyl ether or diethyleneglycol dimethyl ether. It is also possible to use mixtures of these solvents. A mixture of methanol and tetrahydrofuran is preferably used. The second reaction step is preferably carried out in an ether, in particular in tetrahydrofuran. The reactions are generally carried out in a temperature range from 0° C. to +70° C. at normal pressure.

The compounds according to the invention of formula (I), in which $L^2$ stands for a group of formula *-M-CR$^7$R$^8$— or *-M-CH$_2$—CR$^7$R$^8$—, in which M, R$^7$ and R$^8$ have the meanings given above, can alternatively also be produced by converting compounds of the formula (X)

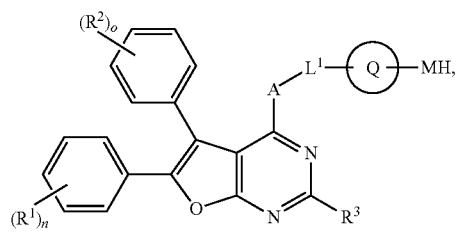

(X)

in which A, L$^1$, M, Q, R$^1$, R$^2$, R$^3$, n and o have the respective meanings given above,
in the presence of a base and if necessary in an inert solvent with a compound of the formula (XI)

(XI)

in which R$^7$, R$^8$ and Z$^1$ have the respective meanings given above,
m stands for the number 0 or 1,
and
X$^2$ stands for a leaving group, such as halogen, mesylate or tosylate,
or in the case when L$^2$ stands for *-M-CH$_2$CH$_2$—, with a compound of formula (XII)

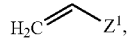

(XII)

in which Z$^1$ has the meaning given above,
to compounds of formula (IV-A)

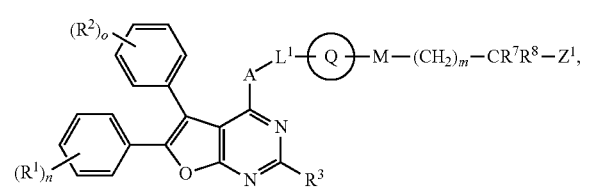

(IV-A)

in which A, L$^1$, M, Q, Z$^1$, R$^1$, R$^2$, R$^3$, R$^7$, R$^8$, m, n and o have the respective meanings given above,
and these are then processed further in accordance with the method described previously.

The compounds of formula (X) can be obtained starting from a compound of formula (II), (V-1) or (V-2) by base-catalysed reaction with a compound of formula (XIII)

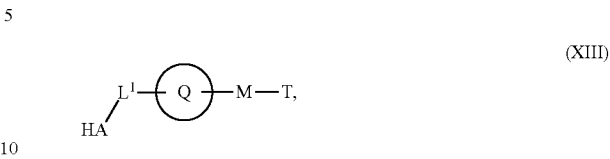

(XIII)

in which A, L$^1$, M and Q have the respective meanings given above
and
T stands for hydrogen or a temporary O- or N-protecting group,
and correspondingly by further reaction similar to the process variants [B] or [C] described previously, and in the case of the reaction sequence (V-1) or (V-2)→(IV-A), the order of the individual process steps can also be varied if that is desirable (cf. the reaction schemes 2-9 given below).

For steps (X)+(XI) or (XII)→(IV-A) and (II)+(XIII)→(X), the reaction parameters such as solvents, bases and reaction temperatures described for reactions (II)+(III)→(IV), (V-1)+(III)→(VI-1) or (V-2)+(III)→(VI-2) are used similarly.

The compounds of formulae (II), (III), (V-1), (VIII-1), (V-2), (VIII-2), (XI), (XII) and (XIII) are commercially available, known from the literature or can be produced by analogy with methods known in the literature (cf. e.g. WO 03/018589; see also Reaction Scheme 1).

Production of the compounds according to the invention can be illustrated by the following synthesis schemes:

Scheme 1

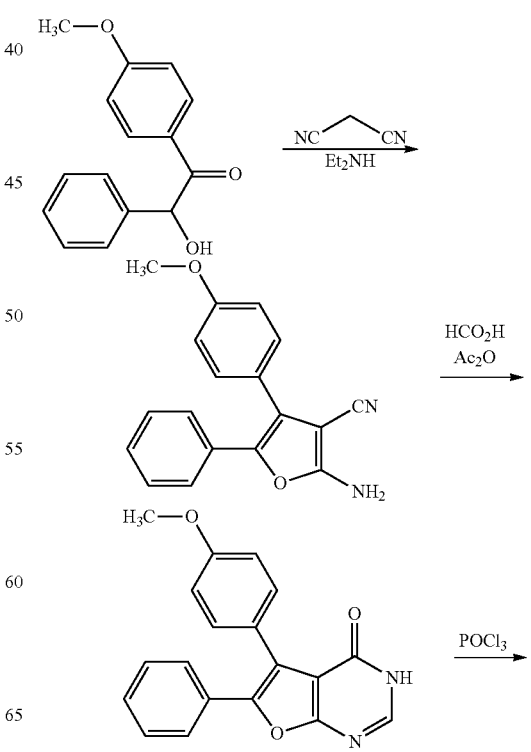

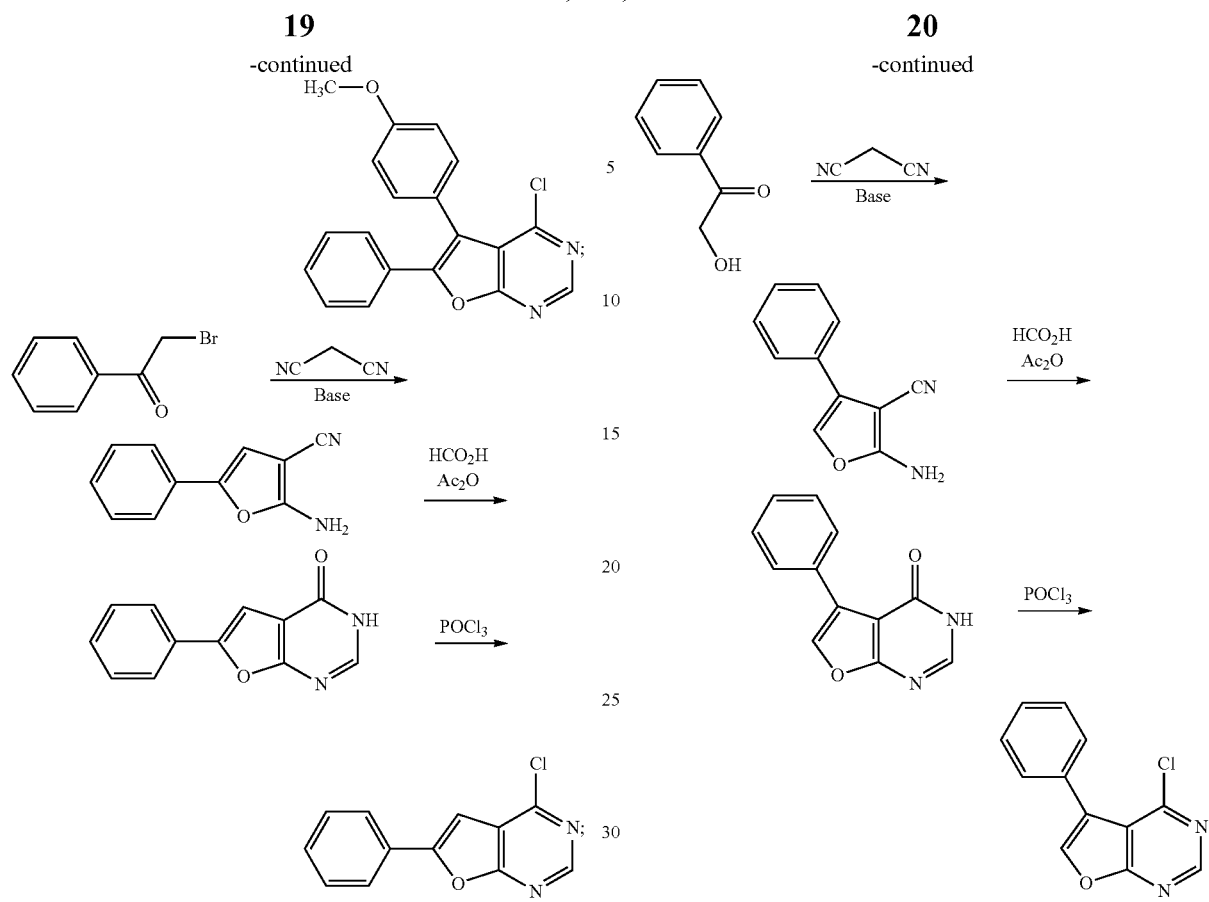
Scheme 2
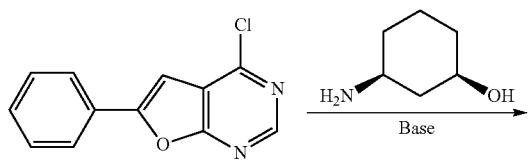
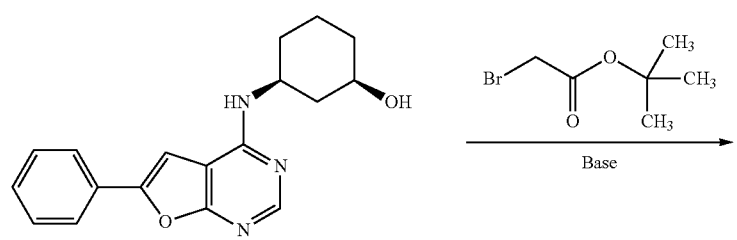
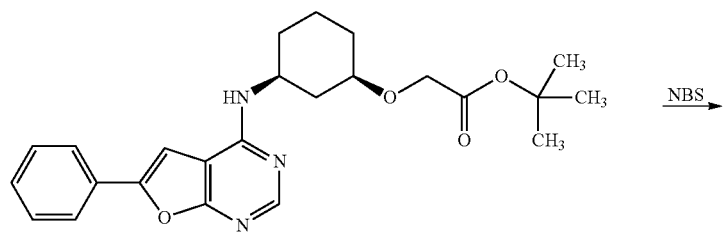

-continued
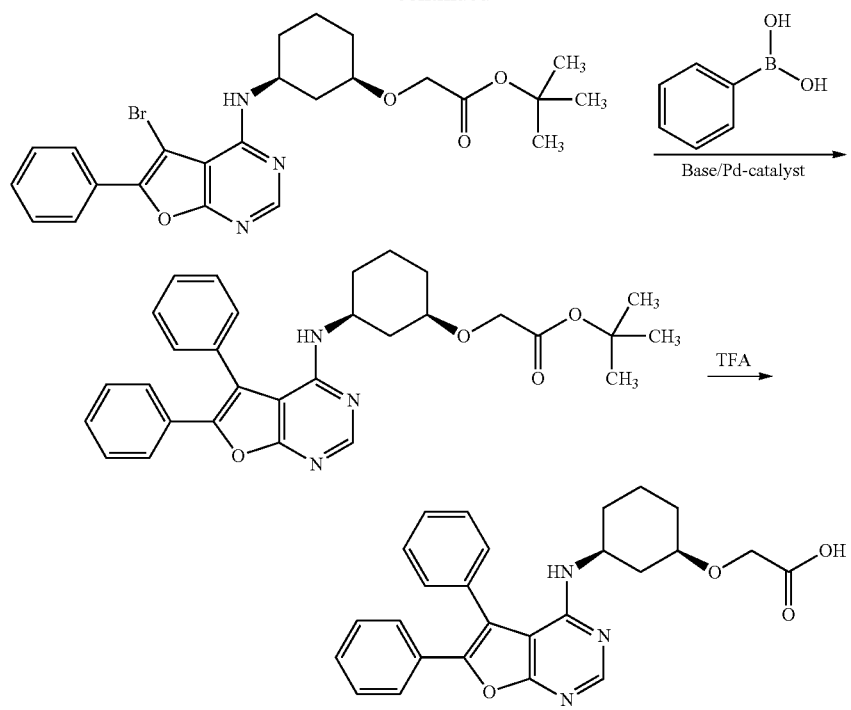
Scheme 3
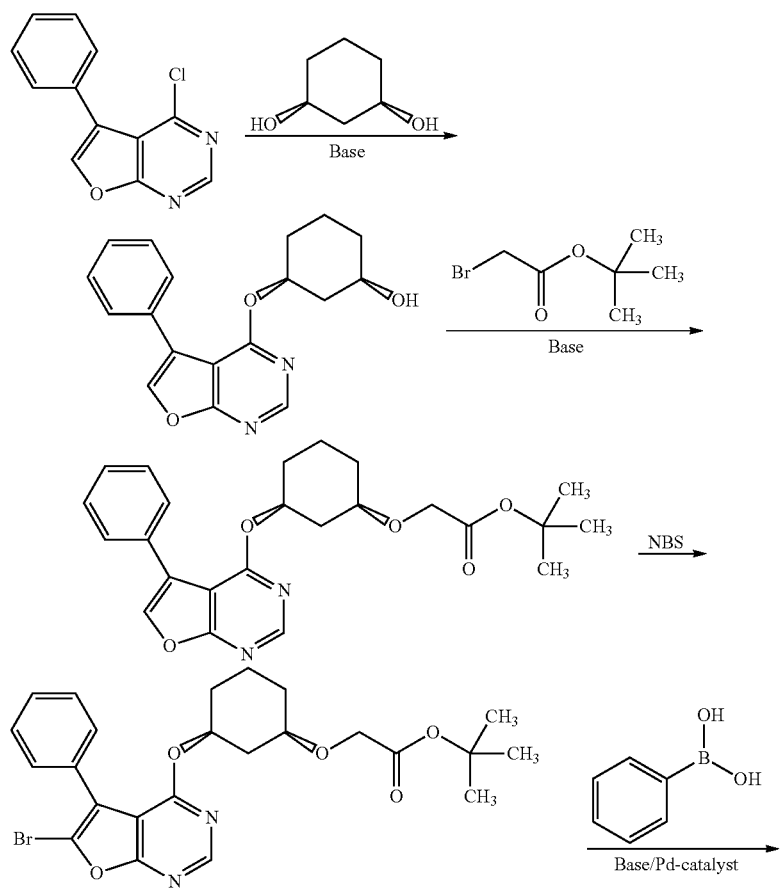

23  24
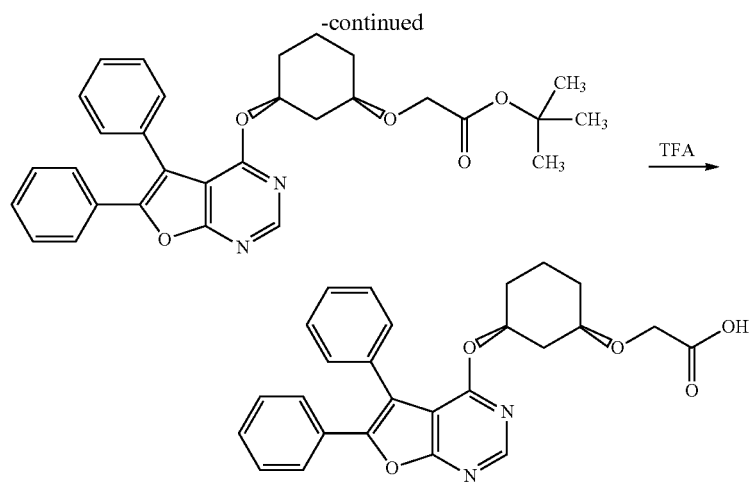
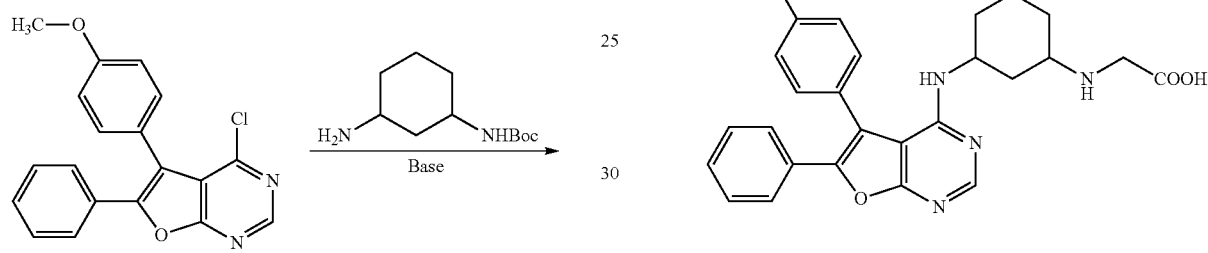
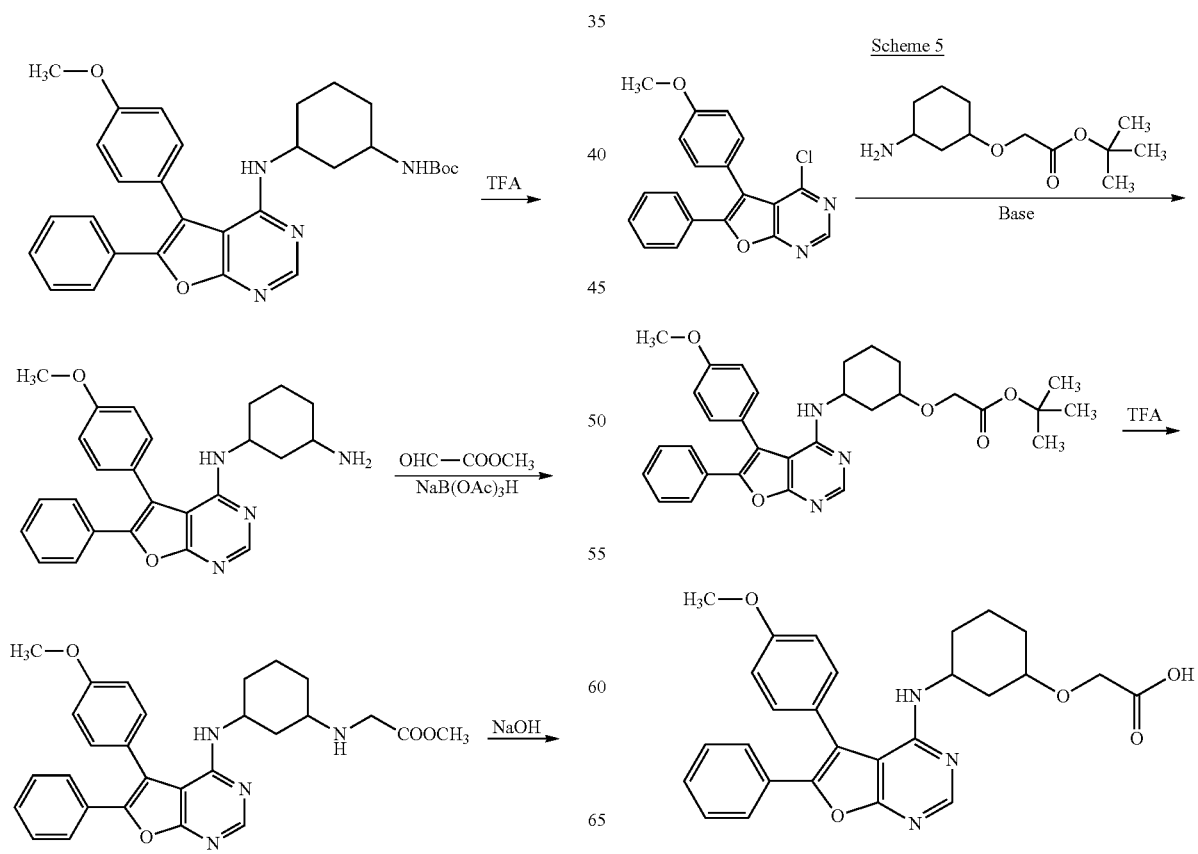

Scheme 6
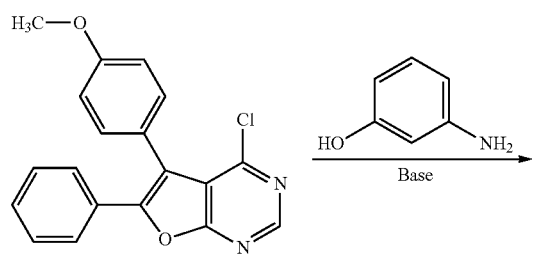
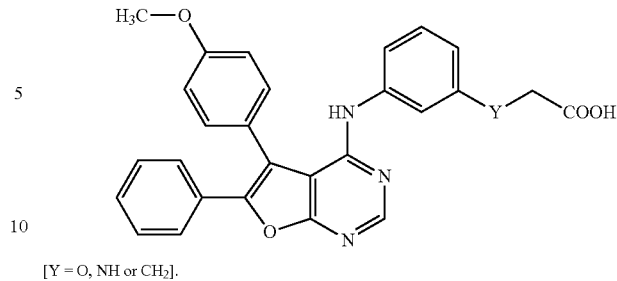
[Y = O, NH or CH₂].
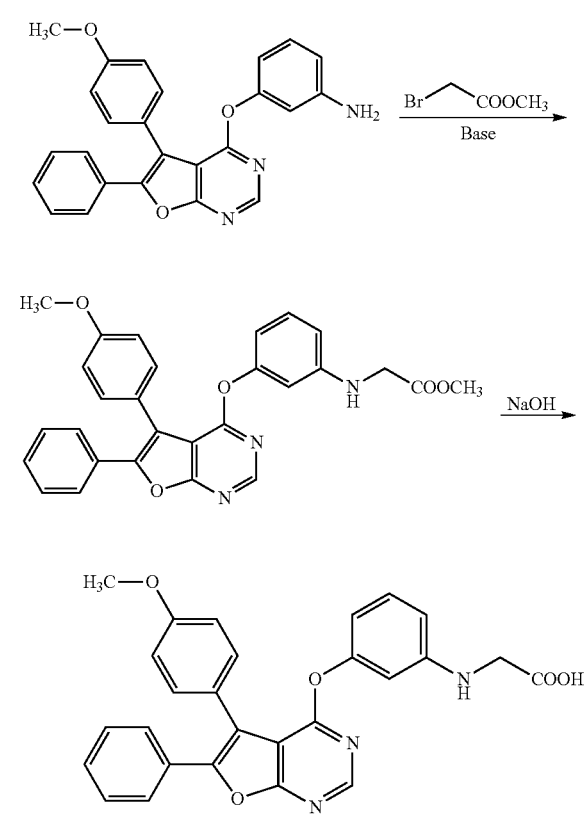
Scheme 8
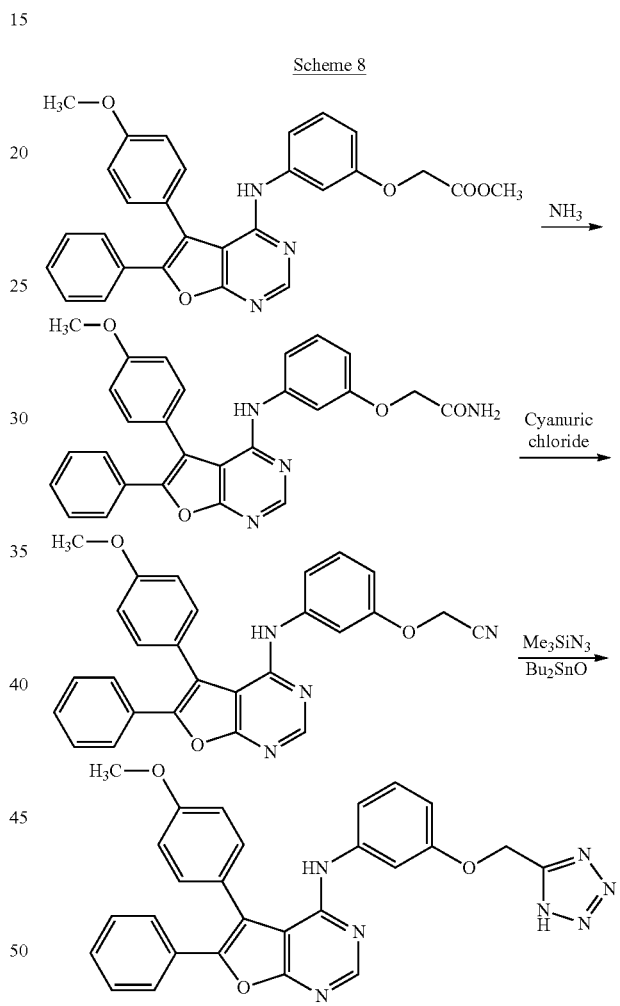
Scheme 7
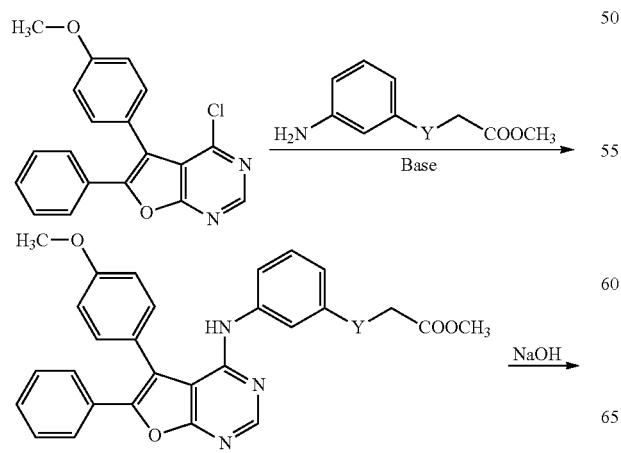
Scheme 9
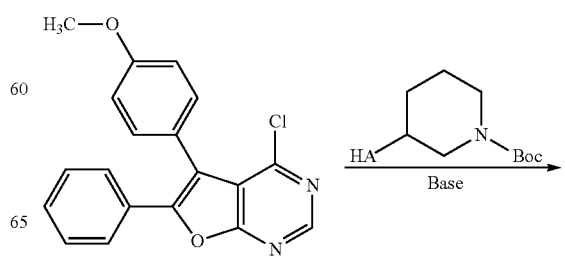

-continued

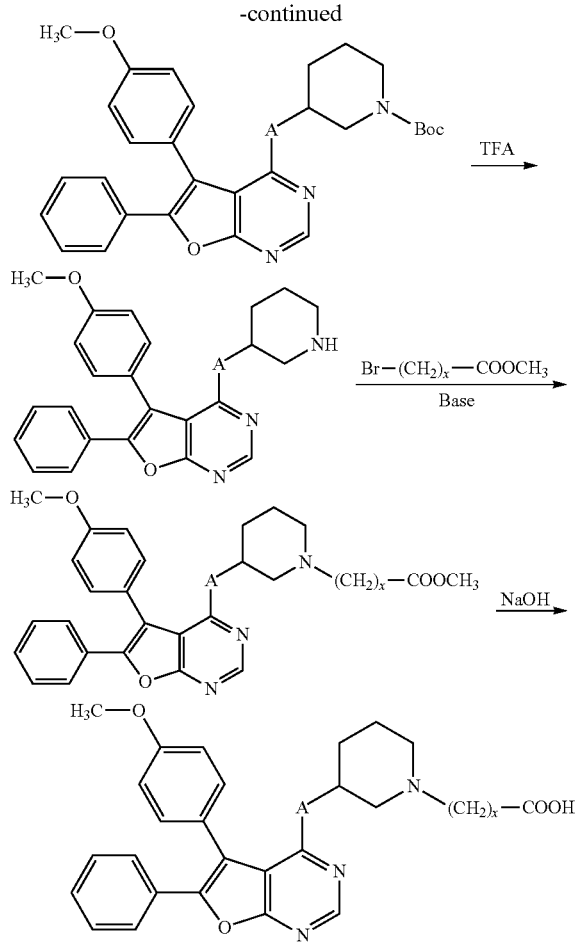

[A = O or NH; x = 1-3].

The compounds according to the invention possess valuable pharmacological properties and can be used for the prevention and treatment of diseases in humans and animals.

They are suitable in particular for the prophylaxis and/or treatment of cardiovascular diseases such as stable and unstable angina pectoris, of peripheral and cardiac vascular diseases, of hypertension and heart failure, pulmonary hypertension, peripheral circulatory disturbances, for the prophylaxis and/or treatment of thromboembolic diseases and ischaemias such as myocardial infarction, stroke, transient and ischaemic attacks and subarachnoid haemorrhage, and for the prevention of restenosis such as after thrombolytic treatments, percutaneous transluminal angioplasty (PTA), coronary angioplasty (PTCA) and bypass surgery.

Furthermore, the compounds according to the invention can be used for the treatment of arterio-sclerosis, hepatitis, asthmatic diseases, chronic obstructive pulmonary diseases (COPD), fibrosing lung diseases such as idiopathic pulmonary fibrosis (IPF) and ARDS, inflammatory vascular diseases such as scleroderma and lupus erythematosus, renal failure, arthritis and osteoporosis.

In addition, the compounds according to the invention can be used for the prophylaxis and/or treatment of cancers, especially of metastasizing tumours.

Moreover, the compounds according to the invention can also be used as an addition to the preserving medium of an organ transplant, e.g. kidneys, lungs, heart or islet cells.

The present invention further relates to the use of the compounds according to the invention for the treatment and/or prevention of diseases, and especially of the aforementioned diseases.

The present invention further relates to the use of the compounds according to the invention for the production of a medicinal product for the treatment and/or prevention of diseases, and especially of the aforementioned diseases.

The present invention further relates to a method for the treatment and/or prevention of diseases, especially of the aforementioned diseases, using an effective amount of at least one of the compounds according to the invention.

The compounds according to the invention can be used alone or if necessary in combination with other active substances. The present invention further relates to medicinal products containing at least one of the compounds according to the invention and one or more additional active substances, in particular for the treatment and/or prevention of the aforementioned diseases. The following may be mentioned as preferred examples of suitable combination active substances:

organic nitrates and NO-donors, such as sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil;

NO-independent, but haem-dependent stimulators of guanylate cyclase, such as in particular the compounds described in WO 00/06568, WO 00/06569, WO 02/42301 and WO 03/095451;

NO- and haem-independent activators of guanylate cyclase, such as in particular the compounds described in WO 01/19355, WO 01/19776, WO 01/19778, WO 01/19780, WO 02/070462 and WO 02/070510;

compounds which inhibit human neutrophilic elastase, such as sivelestat or DX-890 (Reltran);

compounds inhibiting the signal transduction cascade, such as tyrosine kinase and/or serine/threonine kinase inhibitors, in particular imatinib, gefitinib, erlotinib, sorafenib and sunitinib;

compounds influencing the energy metabolism of the heart, for example and preferably etomoxir, dichloroacetate, ranolazine or trimetazidine;

antithrombotic agents, for example and preferably from the group comprising platelet aggregation inhibitors, anticoagulants or profibrinolytic substances;

active substances for lowering blood pressure, for example and preferably from the group comprising calcium antagonists, angiotensin AII antagonists, ACE inhibitors, endothelin antagonists, renin inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

"Agents with antithrombotic action" preferably means compounds from the group comprising inhibitors of platelet aggregation, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, melagatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably BAY 59-7939, DU-176b, Fidexaban, Razaxaban, Fondaparinux, Idraparinux, PMD-3112, YM-150, KFA-1982, EMD-503982, MCM-17, m1N-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

"Agents for lowering blood pressure" are preferably understood to be compounds from the group comprising calcium antagonists, angiotensin AII antagonists, ACE inhibitors, endothelin antagonists, renin inhibitors, alpha receptor blockers, beta receptor blockers, mineralocorticoid receptor antagonists, Rho-kinase inhibitors and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1 receptor blocker, for example and preferably prazosin.

In a preferred embodiment of the invention, the compounds according to the invention are administered in combination with a beta receptor blocker, for example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embusartan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid receptor antagonist, for example and preferably spironolactone or eplerenone.

In a preferred embodiment of the invention, the compounds according to the invention are administered in combination with a Rho-kinase inhibitor, for example and preferably fasudil, Y-27632, SLx-2119, BF-66851, BF-66852, BF-66853, KI-23095 or BA-1049.

In a preferred embodiment of the invention, the compounds according to the invention are administered in combination with a diuretic, for example and preferably furosemide.

"Agents modifying lipid metabolism" are preferably understood to be compounds from the group comprising CETP inhibitors, thyroid receptor agonists, inhibitors of cholesterol synthesis such as HMG-CoA-reductase or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds according to the invention are administered in combination with a CETP inhibitor, for example and preferably torcetrapib (CP-529 414), HT-705 or CETP-vaccine (Avant).

In a preferred embodiment of the invention, the compounds according to the invention are administered in combination with a thyroid receptor agonist, for example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA-reductase inhibitor from the class of the statins, for example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, Colesolvam, CholestaGel or Colestimid.

In a preferred embodiment of the invention, the compounds according to the invention are administered in combination with a bile acid reabsorption inhibitor, for example and preferably ASBT (=IBAT) inhibitors such as AZD-7806, S-8921, AK-105, BARI-1741, SC-435 or SC-635.

In a preferred embodiment of the invention, the compounds according to the invention are administered in combination with a lipoprotein(a) antagonist, for example and preferably Gemcabene calcium (CI-1027) or nicotinic acid.

The present invention further relates to medicinal products that contain at least one compound according to the invention, usually together with one or more inert, nontoxic, pharmaceutically acceptable excipients, and use thereof for the purposes mentioned previously.

The compounds according to the invention can have systemic and/or local action. For this purpose they can be applied by a suitable route, e.g. oral, parenteral, pulmonary, nasal, sublingual, lingual, buccal, rectal, dermal, transdermal, conjunctival, otic or as implant or stent.

For these routes of administration, the compounds according to the invention can be administered in suitable dosage forms.

Dosage forms suitable for oral administration are those that function according to the state of the art, which provide rapid and/or modified release of the compounds according to the invention, and which contain the compounds according to the invention in crystalline and/or amorphized and/or dissolved form, for example tablets (uncoated or coated tablets, e.g. with enteric coatings or with insoluble coatings or coatings with delayed dissolution, which control the release of the compound according to the invention), tablets that disintegrate rapidly in the oral cavity or films/wafers, films/lyophilizates, capsules (e.g. hard-gelatin or soft-gelating capsules), sugar-coated tablets, granules, pellets, powders, emulsions, suspensions, aerosols or solutions.

Parenteral administration can take place with avoidance of an absorption step (e.g. intravenous, intra-arterial, intracardial, intraspinal or intralumbal) or with inclusion of absorption (e.g. intramuscular, subcutaneous, intracutaneous, percutaneous or intraperitoneal). Suitable dosage forms for parenteral administration include injection and infusion preparations in the form of solutions, suspensions, emulsions, lyophilizates or sterile powders.

The following are examples of forms that are suitable for other routes of administration: pharmaceutical forms for inhalation (including powder inhalers, nebulizers), nasal drops, solutions or sprays, tablets for lingual, sublingual or buccal application, films/wafers or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral application, and especially oral application, are preferred.

The compounds according to the invention can be converted to the aforementioned dosage forms. This can be done in a known manner by mixing with inert, nontoxic, pharmaceutically acceptable excipients. These -excipients include, among others: vehicles (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinyl pyrrolidone), synthetic and natural polymers (for example albumin), stabilizers (e.g. antioxidants such as ascorbic acid), colorants (e.g. inorganic pigments such as iron oxides) and agents for correcting taste and/or odour.

Generally it has proved advantageous, in the case of parenteral application, to administer amounts from about 0.001 to 1 mg/kg, preferably about 0.01 to 0.5 mg/kg body weight, for achieving effective results. For oral application the dosage is about 0.01 to 100 mg/kg, preferably about 0.01 to 20 mg/kg and quite especially preferred, 0.1 to 10 mg/kg of body weight.

In certain circumstances it may, however, be necessary to deviate from the stated amounts, depending on body weight, route of administration, individual response to the active substance, type of preparation and point of time or time interval for administration. Thus, in some cases a smaller amount than the minimum amount stated above may prove sufficient, whereas in other cases the stated upper limit must be exceeded. If larger amounts are administered, it may be advisable to distribute these in several divided doses over the day.

The following examples of application explain the invention. The invention is not limited to the examples.

Unless stated otherwise, the percentages in the following tests and examples are percentages by weight; parts are parts by weight. Proportions of solvents, dilution ratios and concentration data for liquid/liquid solutions always relate to the volume.

A. Examples

Abbreviations:

abs. absolute
Ac acetyl
$Ac_2O$ acetic anhydride
Boc tert.-butoxycarbonyl
Bu butyl
c concentration
DCI direct chemical ionization (in MS)
DIEA diisopropylethylamine ("Hünig base")
DMF N,N-dimethylformamide
DMSO dimethylsulphoxide
of theor. of theoretical (for Percentage Yield)
EI electron impact ionization (in MS)
eq equivalent(s)
ESI electrospray ionization (in MS)
Et ethyl
m.p. melting point
GC-MS gas chromatography-coupled mass spectrometry
satd. saturated
h hour(s)
HPLC high-performance liquid chromatography
conc. concentrated
LC-MS liquid chromatography-coupled mass spectrometry
Me methyl
min minute(s)
Ms methanesulphonyl (mesyl)
MS mass spectrometry
NBS N-bromosuccinimide
NMR nuclear magnetic resonance spectrometry
Pd/C palladium on activated charcoal
rac. racemic
RP reverse phase (in HPLC)
RT room temperature
$R_t$ retention time (in HPLC)
TFA trifluoroacetic acid
THF tetrahydrofuran LC-MS, GC-MS and HPLC Methods:

Method 1 (HPLC):

Instrument: HP 1100 with DAD detection; column: Kromasil 100 RP-18, 60 mm×2.1 mm, 3.5 µm; eluent A: 5 ml HClO$_4$ (70%)/1 water, eluent B: acetonitrile; gradient: 0 min 2% B→0.5 min 2% B→4.5 min 90% B→9 min 90% B→9.2 min 2% B→10 min 2% B; flow: 0.75 ml/min; column temperature: 30° C.; UV detection: 210 nm.

Method 2 (HPLC):

Instrument: HP 1100 with DAD detection; column: Kromasil 100 RP-18, 60 mm×2.1 mm, 3.5 µm; eluent A: 5 ml HClO$_4$ (70%)/1 water, eluent B: acetonitrile; gradient: 0 min 2% B→0.5 min 2% B→4.5 min 90% B→6.5 min 90% B→6.7 min 2% B→7.5 min 2% B; flow: 0.75 ml/min; column temperature: 30° C.; UV detection: 210 nm.

Method 3 (LC-MS):

Equipment type MS: Micromass ZQ; equipment type HPLC: Waters Alliance 2795; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 210 nm.

Method 4 (LC-MS):

Instrument: Micromass Platform LCZ with HPLC Agilent Series 1100; column: Thermo Hypersil GOLD 3µ 20 mm×4 mm; eluent A: 1 l water+0.5 ml 50% formic acid, eluent B: 1 l acetonitrile+0.5 ml 50% formic acid; gradient: 0.0 min 100% A→0.2 min 100% A→2.9 min 30% A→3.1 min 10% A→5.5 min 10% A; furnace: 50° C.; flow: 0.8 ml/min; UV detection: 210 nm.

Method 5 (LC-MS):

Equipment type MS: Micromass ZQ; equipment type HPLC: HP 1100 Series; UV DAD; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 210 nm.

Method 6 (LC-MS):

Instrument: Micromass Quattro LCZ with HPLC Agilent Series 1100; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 208-400 nm.

Method 7 (LC-MS):

Equipment type MS: Micromass ZQ; equipment type HPLC: Waters Alliance 2795; column: Merck Chromolith SpeedROD RP-18e 100×4.6 mm; eluent A: water+500 µl 50% formic acid/l, eluent B: acetonitrile+500 µl 50% formic acid/l; gradient: 0.0 min 10% B→7.0 min 95% B→9.0 min 95% B; furnace: 35° C.; flow: 0.0 min 1.0 ml/min→7.0 min 2.0 ml/min→9.0 min 2.0 ml/min; UV detection: 210 nm.

Method 8 (LC-MS):

Equipment type MS: Micromass ZQ; equipment type HPLC: HP 1100 series; UV DAD; column: Phenomenex Gemini 3µ 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 210 nm.

Method 9 (GC-MS):

Instrument: Micromass GCT, GC 6890; column: Restek RTX-35, 15 m×200 µm×0.33 µm; constant flow with helium: 0.88 ml/min; furnace: 70° C.; inlet: 250° C.; gradient: 70° C.; 30° C./min→310° C. (hold 3 min).

Method 10 (GC-MS):

Instrument: Micromass GCT, GC6890; column: Restek RTX-35MS, 30 m×250 µm×0.25 µm; constant flow with helium: 0.88 ml/min; furnace: 60° C.; inlet: 250° C.; gradient: 60° C. (hold for 0.30 min), 50° C./min→120° C., 16° C./min→250° C., 30° C./min→300° C. (hold for 1.7 min).

Method 11 (GC-MS):

Instrument: Micromass GCT, GC6890; column: Restek RTX-35, 15 m×200 µm×0.33 µm; constant flow with helium: 0.88 ml/min; furnace: 70° C.; inlet: 250° C.; gradient: 70° C., 30° C./min→310° C. (hold for 12 min).

Method 12 (LC-MS):

Instrument: Micromass Quattro LCZ with HPLC Agilent Series 1100; column: Phenomenex Gemini 3µ, 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 208-400 nm.

Method 13 (LC-MS):

Instrument: Micromass Quattro LCZ with HPLC Agilent Series 1100; column: Phenomenex Onyx Monolithic C18, 100 mm×3 mm; eluent A: 1 l water+0.5 ml 50% formic acid, eluent B: 1 l acetonitrile+0.5 ml 50% formic acid; gradient: 0.0 min 90% A→2 min 65% A→4.5 min 5% A→6 min 5% A; flow: 2 ml/min; furnace: 40° C.; UV detection: 208-400 nm.

Starting Compounds and Intermediates:

Example 1A

3-Nitrophenoxyacetic acid methyl ester

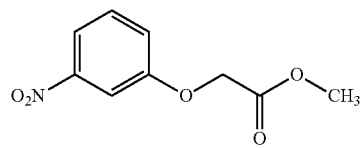

Initially charge 50 g (359.4 mmol) of 3-nitrophenol and 175.67 g (539 mmol) of caesium carbonate in 1.0 liter of acetone and add 71.5 g (467.3 mmol) of bromoacetic acid methyl ester. Stir the mixture at 50° C. for 1 h and, after cooling, pour onto 7.5 liters of water. Stir the suspension for 30 min, then filter off with suction and wash the filter residue with water. Dry the solid in a drying cabinet at 50° C. and 100 mbar. 64.3 g (84.7% of theory) of the target compound are obtained.

HPLC (Method 1): $R_t$=4.07 min

MS (DCI): m/z=229 (M+NH$_4$)$^+$ $^1$H-NMR (300 MHz, CDCl$_3$): δ=7.90 (dd, 1H), 7.43 (t, 1H), 7.48 (t, 1H), 7.28 (dd, 1H), 4.75 (s, 2H), 3.86 (s, 3H).

Example 2A

3-Aminophenoxyacetic acid methyl ester

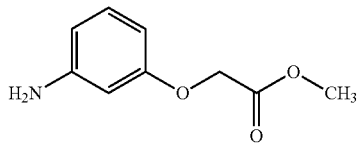

Add 1.3 g of palladium on activated carbon (10%) to 13 g (61.6 mmol) of 3-nitrophenoxyacetic acid methyl ester in 150 ml of methanol under argon. Stir the mixture at RT under a hydrogen atmosphere (standard pressure) for 18 h. Filter the catalyst off through kieselguhr and concentrate the filtrate under reduced pressure. After drying under high vacuum, 10.7 g (95.9% of theory) of the target compound are obtained.

HPLC (Method 2): $R_t$=2.81 min
MS (DCI): m/z=199 $(M+NH_4)^+$, 182 $(M+H)^+$
$^1$H-NMR (400 MHz, CDCl$_3$): δ=7.10-7.02 (m, 1H), 6.35-6.23 (m, 2H), 4.58 (s, 2H), 3.79 (s, 3H), 3.65 (br. s, 2H).

Example 3A

2-Amino-4,5-diphenyl-3-furonitrile

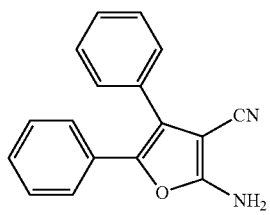

Stir 100 g (470 mmol) of benzoin, 62.25 g (940 mmol) of malononitrile and 47.68 g (470 mmol) of triethylamine at RT in 1345 ml of DMF overnight. Add a further 41 g (620 mmol) of malononitrile and stir the mixture at RT for another 24 h. Then add ethyl acetate and water and extract the aqueous phase twice with ethyl acetate. Dry the combined organic phases over magnesium sulphate and concentrate them under reduced pressure. After column chromatography on silica gel (eluent: dichloromethane→dichloromethane/methanol 98:2), 120 g (97.9% of theory) of the title compound are obtained as yellowish solid.

HPLC (Method 2): $R_t$=4.68 min
MS (DCI): m/z=278 $(M+NH_4)^+$, 261 $(M+H)^+$.

Example 4A 5,6-Diphenylfuro[2,3-d]pyrimidin-4(3H)-one

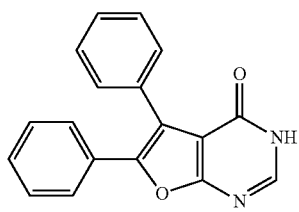

Add 28.5 ml of formic acid dropwise at 0° C. to 57 ml of acetic anhydride. Stir the mixture at 0° C. for 30 min and then add 10.0 g (40 mmol) of 2-amino-4,5-diphenyl-3-furonitrile. Remove the cooling and heat the mixture under reflux overnight. After cooling, add a little diethyl ether and filter off the percipitated solid with suction. Wash the residue with diethyl ether and dry it under reduced pressure. 6 g (52.2% of theory) of the target product are obtained.

HPLC (Method 2): $R_t$=4.40 min
MS (DCI): m/z=306 $(M+NH_4)^+$, 289 $(M+H)^+$.

Example 5A

4-Chloro-5,6-diphenylfuro[2,3-d]pyrimidine

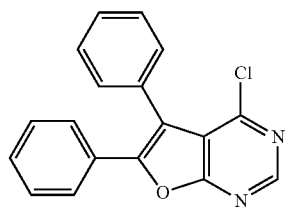

Add 570 ml of phosphorus oxychloride to 57 g (200 mmol) of 5,6-diphenylfuro[2,3-d]pyrimidin-4(3H)-one. Stir the mixture under reflux for 3 h, then cool it and concentrate it under reduced pressure. Stir the residue with ice-water for 30 min and then admix it with dichloromethane. Wash the resulting organic phase three times with water, dry it over sodium sulphate and concentrate it under reduced pressure. 58 g (93.2% of theory) of the target product are obtained.

HPLC (Method 1): $R_t$=5.26 min
MS (DCI): m/z=324 $(M+NH_4)^+$, 307 $(M+H)^+$
$^1$H-NMR (400 MHz, CDCl$_3$): δ=8.78 (s, 1H), 7.62-7.58 (m, 2H), 7.55-7.42 (m, 5H), 7.38-7.30 (m, 3H).

Example 6A (4-Methoxyphenyl)[(trimethylsilyl)oxy]acetonitrile

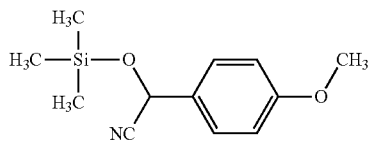

As in the published procedure [*J. Chem. Soc. Perkin Trans. I*, 1992, 2409-2417], add a solution of 221.88 g (2236 mmol) trimethylsilyl cyanide in 25 liter benzene to a mixture of 290.0 g (2130 mmol) 4-methoxybenzaldehyde and 1.156 g (3.622 mmol) zinc iodide in 37.5 liter benzene at RT with cooling in the space of approx. 5 min. Stir the mixture for 90 min at RT and then concentrate by vacuum evaporation. Purify the residue by column filtration on silica gel (solvent: cyclohexane/ethyl acetate 4:1). 442.4 g (88.3% of theor.) of the target compound is obtained.

HPLC (Method 2): $R_t$=3.76 min
MS (DCI): m/z=253 $(M+NH_4)^+$
$^1$H-NMR (400 MHz, CDCl$_3$): δ=7.49 (d, 2H), 6.92 (d, 2H), 5.42 (s, 1H), 3.81 (s, 3H).

Example 7A

2-Hydroxy-1-(4-methoxyphenyl)-2-phenylethanone

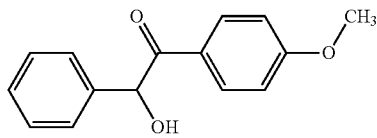

According to the procedure in the literature [*J. Chem. Soc. Perkin Trans. I*, 1992, 2409-2417], dissolve 292 ml (2.08 mol) diisopropylamine in 3.6 liter 1,2-dimethoxyethane and cool to −78° C. Add 826 ml n-butyllithium solution (2.5 M in n-hexane, 2.066 mol) at a temperature below −60° C. Stir the mixture for a further 15 min at <−60° C. and then add a solution of 442 g (1.877 mol) (4-methoxyphenyl)[(trimethylsilyl)oxy]acetonitrile in 1.41 liter 1,2-dimethoxyethane dropwise at <−60° C. After further stirring for 30 min at −60° C., add a solution of 199.3 g (1.878 mol) benzaldehyde in 1.4 liter 1,2-dimethoxyethane in the space of 20 min at −60° C. Next, heat the reaction mixture slowly to RT in 4 h. Add 7 liter saturated ammonium chloride solution and extract with ethyl acetate. Wash the organic phase with saturated ammonium chloride solution, dry, and concentrate under vacuum. Take up the residue in 7 liter dioxan and 5 liter methanol, and add 6 liter 1 N hydrochloric acid. Stir the mixture for 3 h at RT, then add 3 liter saturated sodium chloride solution and extract the mixture with 6.5 liter ethyl acetate. Wash the organic phase with 1.0 liter 1 N sodium hydroxide solution and with saturated sodium chloride solution, dry, and concentrate under vacuum. Take up the residue in 2 liter diisopropyl ether, decant from the insoluble matter and seed with crystals. Stir the resultant suspension for 2 h at RT and then filter off the crystals with suction. Wash with 300 ml diisopropyl ether and petroleum ether and dry under vacuum. 236.8 g (47.8% of theor.) of the target compound is obtained.

HPLC (Method 2): $R_t$=4.23 min
MS (DCI): m/z=260 (M+NH$_4$)$^+$, 243 (M+H)$^+$
$^1$H-NMR (400 MHz, CDCl$_3$): δ=7.92 (d, 2H), 7.38-7.28 (m, 5H), 6.88 (d, 2H), 5.90 (d, 1H), 4.64 (d, 1H), 3.82 (s, 3H).

Example 8A

2-Amino-4-(4-methoxyphenyl)-5-phenyl-3-furonitrile

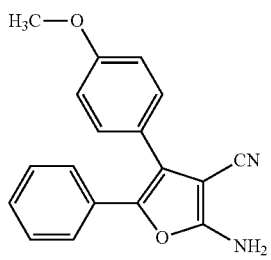

Dissolve 236 g (974 mmol) 2-hydroxy-1-(4-methoxyphenyl)-2-phenylethanone and 83.66 g (1266 mmol) malononitrile in 470 ml DMF and, with cooling on an ice bath, add 86.6 ml (836.7 mmol) diethylamine. After 1 h, heat the mixture to RT and continue stirring for 4 h at RT, before adding 2.5 liter water and a few seed crystals. After 30 min, decant the supernatant water and replace with 1.25 liter of fresh water. Stir the suspension thoroughly and again decant the supernatant water. Take up the sticky crystalline residue in ethyl acetate and then concentrate under vacuum almost completely. Stir the residue with 730 ml diisopropyl ether and leave the suspension to stand overnight at RT. Then filter off the solid matter with suction and dry under vacuum. 211.5 g (57.6% of theor.) of the title compound is obtained.

HPLC (Method 2): $R_t$=4.60 min
MS (DCI): m/z=308 (M+NH$_4$)$^+$, 291 (M+H)$^+$
$^1$H-NMR (400 MHz, CDCl$_3$): δ=7.39-7.33 (m, 5H), 7.28-7.18 (m, 3H), 6.93 (d, 2H), 5.02 (s, 2H), 3.85 (s, 3H).

Example 9A 5-(4-Methoxyphenyl)-6-phenylfuro[2,3-d]pyrimidin-4(3H)-one

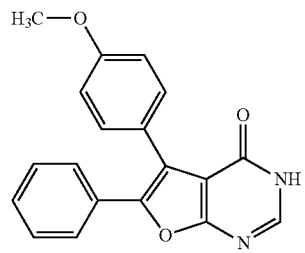

Add 800 ml (21.21 mol) formic acid dropwise to 1600 ml (16.96 mol) acetic anhydride at 0° C. Stir the mixture for 30 min at 0° C. and then add 211 g (727 mmol) 2-amino-4-(4-methoxyphenyl)-5-phenyl-3-furonitrile. Remove the cooling and heat the mixture; evolution of gas begins at approx. 80° C., and ceases after approx. 3 h. Stir for a total of 24 h under reflux (bath temperature approx. 130° C.). After cooling to RT, stir for 2 h at 10° C. and filter off the solid matter that forms. Wash the residue with diethyl ether and dry at high vacuum. 135.6 g (58.6% of theor.) of the title compound is obtained.

HPLC (Method 2): $R_t$=4.38 min
MS (DCI): m/z=336 (M+NH$_4$)$^+$, 319 (M+H)$^+$
$^1$H-NMR (400 MHz, CDCl$_3$): δ=10.3 (br. s, 1H), 7.95 (s, 1H), 7.58-7.53 (m, 2H), 7.47 (d, 2H), 7.33-7.27 (m, 3H), 6.95 (d, 2H), 3.86 (s, 3H).

Example 10A

4-Chloro-5-(4-methoxyphenyl)-6-phenylfuro[2,3-d]pyrimidine

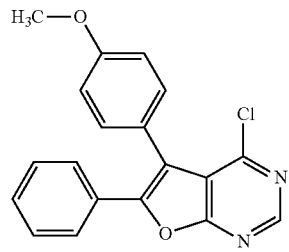

Suspend 135 g (424 mmol) 5-(4-methoxyphenyl)-6-phenylfuro[2,3-d]pyrimidin-4(3H)-one at RT in 675 ml (7241 mmol) phosphoryl chloride and heat the mixture to boiling (evolution of HCl). After 1 h, cool the dark solution to RT and add dropwise to a vigorously stirred mixture of 2.25 liter water and 4.05 liter conc. ammonia solution (25 wt. %) (heating to 55-75° C., pH>9). At the end of addition, cool to RT and extract the mixture three times with 1.0 liter dichloromethane each time. Combine the organic phases, dry, and concentrate by vacuum evaporation. Stir the residue with diethyl ether, filter with suction and dry at high vacuum. 134.4 g (94.1% of theor.) of the title compound is obtained.

HPLC (Method 2): $R_t$=4.96 min

MS (DCI): m/z=354 $(M+NH_4)^+$, 337 $(M+H)^+$ $^1$H-NMR (400 MHz, CDCl$_3$): δ=8.76 (s, 1H), 7.62 (d, 2H), 7.40-7.30 (m, 5H), 7.03 (d, 2H), 3.90 (s, 3H).

Example 11A

2-Amino-5-phenyl-3-furonitrile

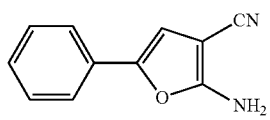

Add 68.6 ml (663 mmol) diethylamine dropwise to a mixture of 60.0 g (301 mmol) bromoacetophenone and 25.89 g (391.86 mmol) malononitrile in 130 ml DMF at RT (cooling is required to maintain the temperature). Towards the end of addition, remove the cooling, stir the mixture for 1 h at RT and then add water to 385 ml. Dilute with a further 125 ml water and stir for 20 min at RT. Filter off the precipitated solids with suction, wash twice with 125 ml water each time, dry under suction and wash with petroleum ether. Dry the residue at high vacuum. 33.3 g (50.1% of theor.) of the target compound is obtained as yellowish-brown crystals.

HPLC (Method 2): $R_t$=4.27 min

MS (DCI): m/z=202 $(M+NH_4)^+$, 185 $(M+H)^+$ $^1$H-NMR (400 MHz, CDCl$_3$): δ=7.51-7.45 (m, 2H), 7.39-7.32 (m, 3H), 6.54 (s, 1H), 4.89 (br. s, 1H).

Example 12A

6-Phenylfuro[2,3-d]pyrimidin-4(3H)-one

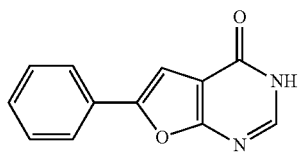

Add 424.5 ml (11.25 mol) formic acid dropwise to 884.9 ml (9.378 mol) acetic anhydride at 0° C. Stir the mixture for 30 min at 0° C. and then add 69.1 g (0.375 mol) 2-amino-5-phenyl-3-furonitrile. Remove the cooling and heat the mixture; evolution of gas begins at approx. 80° C., and stops after approx. 3 h. Stir for a total of 24 h under reflux (bath temperature approx. 130° C.). After cooling the suspension to RT, add 750 ml diisopropyl ether, cool to 0° C. and filter. Wash the residue with diisopropyl ether and dry at high vacuum. 50.83 g (58.7% of theor.) of the target compound is obtained as a brown solid.

HPLC (Method 2): $R_t$=3.92 min

MS: m/z=213 $(M+H)^+$ $^1$H-NMR (400 MHz, DMSO-d$_6$): δ=12.68 (br. s, 1H), 8.17 (s, 1H), 7.88 (d, 2H), 7.52-7.48 (m, 3H), 7.42-7.38 (m, 1H).

Example 13A

4-Chloro-6-phenylfuro[2,3-d]pyrimidine

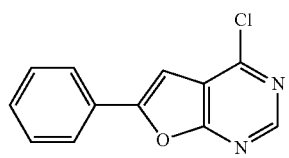

Suspend 50 g (235.6 mmol) 6-phenylfuro[2,3-d]pyrimidin-4(3H)-one at RT in 375 ml (4023 mmol) phosphoryl chloride and heat the mixture to boiling (evolution of HCl). After 1 h, cool the dark solution to RT and add dropwise to a vigorously stirred mixture of 1.25 liter water and 2.25 liter conc. ammonia solution (25 wt. %) (heating to 55-75° C., pH >9). At the end of addition, cool to RT and extract the mixture three times with 1.6 liter dichloromethane each time. Combine the organic phases, dry, and concentrate by vacuum evaporation. Stir the residue with diethyl ether, filter with suction, and dry at high vacuum. 47.3 g (87% of theor.) of the target compound is obtained.

HPLC (Method 2): $R_t$=4.67 min

MS: m/z=231 $(M+H)^+$ $^1$H-NMR (300 MHz, DMSO-d$_6$): δ=8.84 (s, 1H), 8.05 (m, 2H), 7.77 (s, 1H), 7.61-7.50 (m, 3H).

Example 14A

2-Amino-4-phenyl-3-furonitrile

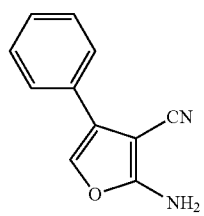

Add 3.78 ml (36.7 mmol) diethylamine dropwise to a mixture of 10 g (73.4 mmol) hydroxyacetophenone and 4.852 g (73.4 mmol) malononitrile in 24 ml DMF with cooling at RT. Stir the dark mixture for 2 h at RT and then add slowly to water (200 ml), with stirring and cooling. Continue stirring the precipitate for 30 min at approx. 10° C., filter with suction, suspend in water twice more, and filter with suction again. Dry the residue at high vacuum to constant weight. 10.99 g (81.2% of theor.) of the target compound is obtained as a yellowish-brown solid.

LC-MS (Method 3): $R_t$=1.81 min; m/z=185 $(M+H)^+$ $^1$H-NMR (400 MHz, DMSO-d$_6$): δ=7.54 (d, 2H), 7.50 (s, 2H), 7.45-7.32 (m, 4H).

Example 15A

5-Phenylfuro[2,3-d]pyrimidin-4(3H)-one

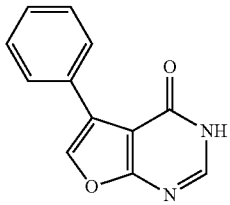

Cool 108.5 ml (1154 mmol) acetic anhydride to 0° C. and, under argon, add 52.2 ml (1384 mmol) formic acid. Stir the mixture for approx. 45 min at 0° C. and then add 8.5 g (46.2 mmol) 2-amino-4-phenyl-3-furonitrile in portions. A dark mixture is formed, and it turns violet after 15 min at 0° C. Remove the cooling and heat the suspension, which is now blue, to RT. After 15 min, heat the mixture to reflux (bath temperature 125-130° C.), whereupon gas begins to be evolved. Stir the mixture overnight under reflux. After cooling, concentrate the mixture under vacuum and dry the residue at high vacuum. Approx. 3 g of a deep dark red to black solid is obtained from the raw product by column filtration on silica gel (solvent gradient: dichloromethane→dichloromethane/methanol 50:1). Dissolve this in approx. 8 ml dichloromethane, precipitate with diisopropyl ether, filter with suction, and dry at high vacuum. 1.81 g (purity approx. 84%, yield approx. 15% of theor.) of the target compound is obtained as a dark red solid.

LC-MS (Method 4): $R_t$=3.2 min; m/z=211 (M−H)$^+$ $^1$H-NMR (400 MHz, DMSO-d$_6$): δ=12.7 (s, 1H), 8.26 (s, 1H), 8.19 (s, 1H), 7.98 (d, 2H), 7.50-7.30 (m, 3H).

Example 16A

4-Chloro-5-phenylfuro[2,3-d]pyrimidine

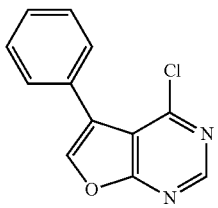

Add 9.5 ml (101.8 mmol) phosphoryl chloride to 1.8 g (approx. 6.8 mmol) 5-phenylfuro[2,3-d]pyrimidin-4(3H)-one at RT and heat the mixture for 1 h under reflux. Cool the resultant black mixture to RT and carefully add dropwise at <10° C. to a well-stirred solution of 70 ml conc. ammonia solution and 50 ml water cooled to 0° C. (pH>9). At the end of addition, heat the black suspension to RT and stir for a further 15 min. Filter off the black solid with suction, resuspend with water three times, filter with suction again, and dry at high vacuum. Dissolve the solid in dichloromethane and column-filter on silica gel (solvent: dichloromethane). 1371 mg (80.6% of theor.) of the target compound is obtained as a yellow solid.

LC-MS (Method 5): $R_t$=2.47 min; m/z=231 (M+H)$^+$ $^1$H-NMR (400 MHz, DMSO-d$_6$): δ=8.90 (s, 1H), 8.49 (s, 1H), 7.64-7.58 (m, 2H), 7.52-7.45 (m, 3H).

Example 17A

3-{[5-(4-Methoxyphenyl)-6-phenylfuro[2,3-d]pyrimidin-4-yl]oxy}phenol

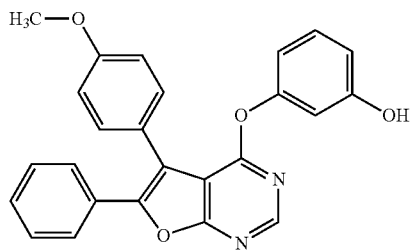

Heat 500 mg (1.49 mmol) of 4-chloro-5-(4-methoxyphenyl)-6-phenylfuro[2,3-d]pyrimidine, 654 mg (5.94 mmol) of resorcinol and 726 mg (2.23 mmol) of caesium carbonate in 10 ml of DMF to 120° C. for 2 h. After cooling, filter and purify the filtrate directly by means of preparative HPLC. Stir the resulting product with dichloromethane, filter with suction, wash with dichloromethane and dry under reduced pressure. 171.4 mg (27% of theory) of the target product are obtained as a beige solid.

LC-MS (Method 5): $R_t$=2.78 min; m/z=411 (M+H)$^+$.

Example 18A

3-{[5-(4-Methoxyphenyl)-6-phenylfuro[2,3-d]pyrimidin-4-yl]oxy}aniline

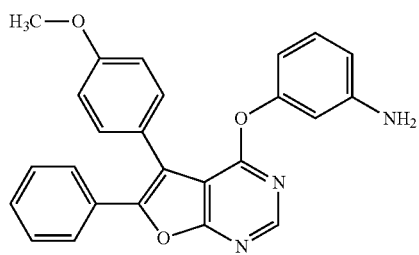

Stir 1000 mg (2.97 mmol) of 4-chloro-5-(4-methoxyphenyl)-6-phenylfuro[2,3-d]pyrimidine, 1296 mg (11.9 mmol) of 3-aminophenol and 615.6 mg (4.45 mmol) of potassium carbonate in 10 ml of DMF at 80° C. for 8 h. After cooling, concentrate under reduced pressure and take up the residue in water. Filter off the precipitated solid, wash the filter residue repeatedly with water and dry the solid at 50° C. under high vacuum. 1195 mg (98.3% of theory) of the target compound are obtained as a brownish solid.

LC-MS (Method 3): $R_t$=2.53 min; m/z=410 (M+H)$^+$ $^1$H-NMR (300 MHz, DMSO-d$_6$): δ=8.53 (s, 1H), 7.60-7.40 (m, 7H), 7.06-6.99 (dd, 1H), 6.34-6.27 (m, 2H), 6.25 (br. s, 2H), 3.80 (s, 3H).

Example 19A 2-(3-{[5-(4-Methoxyphenyl)-6-phenylfuro[2,3-d]pyrimidin-4-yl]amino}phenoxy)acetamide

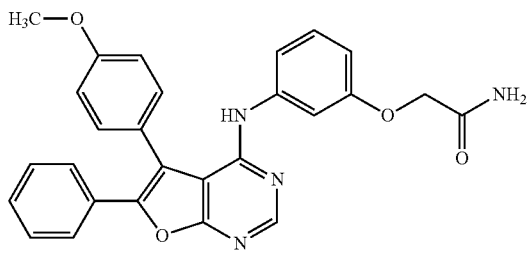

Add ammonia in methanol (14.2 ml of an approx. 7 M solution) to 800 mg (1.66 mmol) of 3-{[5-(4-methoxyphenyl)-6-phenylfuro[2,3-d]pyrimidin-4-yl]amino}phenoxyacetic acid methyl ester (Example 9) at RT and stir overnight. Concentrate the mixture under reduced pressure, stir it with a little methanol and filter with suction. Wash the filter residue with diisopropyl ether and dry it at 50° C. under high vacuum overnight. 663 mg (86.5% of theory) of the target product are obtained as a virtually white solid.

LC-MS (Method 3): $R_t$=2.40 min; m/z=467 (M+H)$^+$ $^1$H-NMR (300 MHz, DMSO-d$_6$): δ=8.54 (s, 1H), 7.63-7.50 (m, 5H), 7.45-7.20 (m, 9H), 6.90 (s, 1H), 6.81 (dd, 1H), 6.64 (dd, 1H), 4.41 (s, 2H), 3.90 (s, 3H).

Example 20A (3-{[5-(4-Methoxyphenyl)-6-phenylfuro[2,3-d]pyrimidin-4-yl]amino}phenoxy)acetonitrile

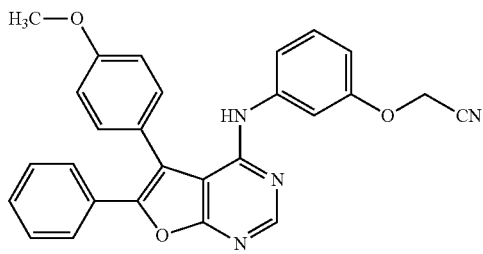

Dissolve 800 mg (1.72 mmol) of 2-(3-{[5-(4-methoxyphenyl)-6-phenylfuro[2,3-d]pyrimidin-4-yl]amino}phenoxy)acetamide in 5 ml of DMF, cool to 0° C. and add 316 mg (1.72 mmol) of cyanuric chloride. Stir the mixture at 0° C. for 2 h. Then add water and ethyl acetate. After phase separation, extract the aqueous phase twice with ethyl acetate. Wash the combined organic phases three times with buffer solution (pH 7), dry them over magnesium sulphate and concentrate them under reduced pressure. The crude product is purified by chromatography on silica gel (eluent: dichloromethane/ethyl acetate 20:1). 179 mg (22.3% of theory) of the target product are obtained as a white solid.

LC-MS (Method 3): $R_t$=2.84 min; m/z=449 (M+H)$^+$ $^1$H-NMR (300 MHz, DMSO-d$_6$): δ=8.57 (s, 1H), 7.63-7.51 (m, 4H), 7.45-7.20 (m, 7H), 6.99 (s, 1H), 6.89 (dd, 1H), 6.28 (dd, 1H), 5.65 (s, 2H), 3.90 (s, 3H).

Example 21A 3-(3-Aminophenyl)propanoic acid methyl ester hydrochloride

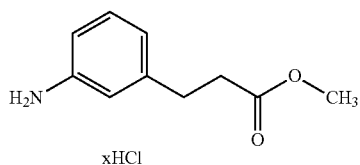

Initially charge 2000 mg (12.1 mmol) of 3-(3-aminophenyl)propanoic acid in 30 ml of methanol, cool to 0° C. and add 0.93 ml (12.7 mmol) of thionyl chloride dropwise. Warm the mixture slowly to RT and stir it overnight. After concentration under reduced pressure, take up the residue in a little methanol. After adding diisopropyl ether, filter off the precipitated solid with suction. 2450 mg (93.8% of theory) of the target product are obtained as a white solid.

LC-MS (Method 4): $R_t$=2.30 min; m/z=180 (M-Cl+H)$^+$ $^1$H-NMR (300 MHz, DMSO-d$_6$): δ=10.15 (br. s, ca. 3H), 7.42-7.38 (m, 1H), 7.28-7.17 (m, 3H), 3.60 (s, 3H), 2.38 (t, 2H), 2.68 (t, 2H).

The free aniline is obtained by washing a solution (or suspension) of the hydrochloride in dichloromethane with saturated sodium hydrogencarbonate solution and concentrating under reduced pressure.

Example 22A 4-(4-Aminophenyl)butanoic acid methyl ester hydrochloride

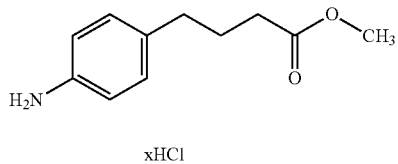

Initially charge 700 mg (3.91 mmol) of 4-(4-aminophenyl)butanoic acid in 7 ml of methanol, cool to 0° C. and add 0.3 ml (4.1 mmol) of thionyl chloride dropwise. Warm the mixture slowly to RT and stir overnight. After concentrating under reduced pressure, stir the residue in a little methanol and filter off the resulting solid with suction. 800.6 mg (89.2% of theory) of the target product are obtained as a white solid.

LC-MS (Method 5): $R_t$=1.10 min; m/z=194 (M-Cl+H)$^+$.

The free aniline is obtained by washing a solution (or suspension) of the hydrochloride in dichloromethane with saturated sodium hydrogencarbonate solution and concentrating under reduced pressure.

Example 23A

4-(2-Nitrophenyl)butanoic acid methyl ester

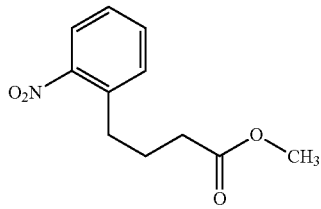

Initially charge 705 mg (3.37 mmol) of 4-(2-nitrophenyl)butanoic acid in 7 ml of methanol, cool to 0° C. and add 0.26 ml (3.54 mmol) of thionyl chloride dropwise. Warm the mixture slowly to RT and stir overnight. To complete the reaction, add an approx. 20% excess of thionyl chloride and stir the mixture at RT for a further 5 h. After concentration under reduced pressure, stir the residue in a little methanol and filter off the resulting solid. 700 mg (95.5% of theory) of the target product are obtained as a white solid.

LC-MS (Method 5): $R_t$=2.34 min; m/z=224 $(M+H)^+$.

Example 24A

4-(2-Aminophenyl)butanoic acid methyl ester

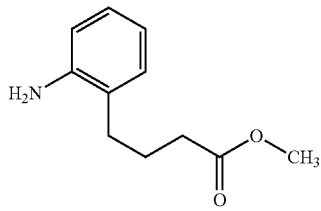

Initially charge 715 mg (3.2 mmol) of 4-(2-nitrophenyl)butanoic acid methyl ester in 1.5 ml of ethanol, add 34 mg of palladium on activated carbon (10%) under argon and stir under a hydrogen atmosphere (standard pressure) at RT overnight. In order to complete the reaction, add more palladium on activated carbon and stir at RT under a hydrogen atmosphere for a further 24 h. Filter the catalyst off and concentrate the solution under reduced pressure. 229 mg (37.1% of theory) of the target product are obtained.

LC-MS (Method 5): $R_t$=1.67 min; m/z=194 $(M+H)^+$.

Example 25A

2-(3-{[5-(4-Methoxyphenyl)-6-phenylfuro[2,3-d]pyrimidin-4-yl]amino}phenyl)acetic hydrazide

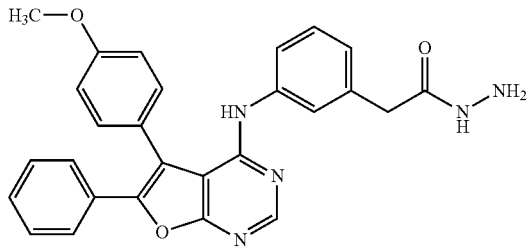

Add 215 mg (4.3 mmol) of hydrazine hydrate at RT to 100 mg (0.215 mmol) of 3-{[5-(4-methoxy-phenyl)-6-phenyl-furo[2,3-d]pyrimidin-4-yl]amino}phenylacetic acid methyl ester (Example 28), dissolved in 1.5 ml of THF and 2 ml of methanol. Stir the mixture at 65° C. for 1 h and at RT overnight and then concentrate under reduced pressure. After stirring with diisopropyl ether, filter off the solid with suction and dry under reduced pressure. 89.3 mg (89.3% of theory) of the target product are obtained.

LC-MS (Method 3): $R_t$=2.16 min; m/z=466 $(M+H)^+$ $^1$H-NMR (400 MHz, DMSO-$d_6$): δ=9.20 (s, 1H), 8.51 (s, 1H), 7.62-7.51 (m, 4H), 7.43-7.36 (m, 3H), 7.30-7.20 (m, 5H), 6.95 (d, 1H), 6.89 (s, 1H), 4.24 (br. s, 2H), 3.89 (s, 3H).

General Method A: Reaction of amines with 4-chlorofuro[2,3-d]pyrimidine derivatives Stir a mixture of 1.0 eq. of 4-chloro-5-(4-methoxyphenyl)-6-phenylfuro[2,3-d]pyrimidine, 1.0 to 1.4 eq. of amine component and 1.5 to 3.0 eq. of DIEA in DMF (concentration 0.5 to 1.5 mol/l) at 80-140° C. for 1-24 h. After cooling, remove the DMF under reduced pressure and treat the residue with water. Extract with dichloromethane, wash the organic phase with saturated sodium hydrogencarbonate solution and sodium chloride solution, dry over magnesium sulphate and concentrate under reduced pressure. The target compound can be isolated from the crude product and purified by crystallization from alcoholic solvents (e.g. methanol), by chromatography on silica gel (preferred eluent systems are dichloromethane/methanol and cyclohexane/ethyl acetate), by preparative RP-HPLC (eluent: water/acetonitrile) or by a combination of these methods.

General method B: Reaction of alcohols with 4-chlorofuro[2,3-d]pyrimidine derivatives Add a solution of 1.0 to 1.5 eq. of phosphazene base P2-t-Bu in THF (approx. 2 mol/l) [from Fluka, Art. No. 79416] or phosphazene base P4-t-Bu in cyclohexane (approx. 1 mol/l) [from Fluka, Art. No. 79421] dropwise at 0° C. to RT to a mixture of 1.0 eq. of 4-chloro-5-(4-methoxyphenyl)-6-phenylfuro[2,3-d]pyrimidine and 1.0 to 1.5 eq. of alcohol components in THF or DMF (or mixtures thereof; concentration 0.2 to 1.0 mol/l). Stir the mixture at RT for 30 min to 6 h. Then dilute with dichloromethane or ethyl acetate and work up under aqueous conditions. Wash the organic phase with 1N hydrochloric acid, saturated sodium hydrogencarbonate solution and/or sodium chloride solution, dry over magnesium sulphate and concentrate under reduced pressure. The target compound can be isolated from the crude product and purified by crystallization from alcoholic solvents (e.g. methanol), by chromatography on silica gel (preferred eluent systems are dichloromethane/methanol and cyclohexane/ethyl acetate), by preparative RP-HPLC (eluent: water/acetonitrile) or by a combination of these methods.

The following compounds are prepared by general method A or B proceeding from 4-chloro-5-(4-methoxyphenyl)-6-phenylfuro[2,3-d]pyrimidine and the appropriate amines or alcohols:

| Example | Structure | Analytical data |
|---|---|---|
| 26A | (+/-)-cis/trans | LC-MS (Method 6): $R_t$ = 3.10 min; m/z = 515 (M + H)+. |
| 27A | (rac.) | LC-MS (Method 6): $R_t$ = 3.22 min; m/z = 502 (M + H)+ <br> 1H-NMR (400 MHz, DMSO-$d_6$): δ = 8.61 (s, 1H), 7.52 (d, 2H), 7.45-7.31 (m, 5H), 7.0 (d, 2H), 5.20 (br. s, 1H), 4.34 (br. d, 1H), 3.90-3.80 (m, 4H), 3.14 (br. d, 1H), 2.28 (br. t, 1H), 1.85-1.68 (m, 2H), 1.45-1.25 (m, 5H), 0.97 (s, 9H). |
| 28A | (rac.) | LC-MS (Method 6): $R_t$ = 3.27 min; m/z = 502 (M + H)+ <br> 1H-NMR (400 MHz, DMSO-$d_6$): δ = 8.58 (s, 1H), 7.52 (d, 2H), 7.42-7.37 (m, 5H), 7.03 (d, 2H), 4.58-4.40 (m, 2H), 3.90-3.81 (m, 4H), 3.22-3.13 (m, 1H), 2.95-2.80 (m, 1H), 1.88-1.75 (m, 1H), 1.64-1.45 (m, 3H), 1.35 (s, 9H). |
| 29A | (rac.) | LC-MS (Method 6): $R_t$ = 3.06 min; m/z = 502 (M + H)+ <br> 1H-NMR (400 MHz, DMSO-$d_6$): δ = 8.39 (s, 1H), 7.49 (d, 2H), 7.47-7.33 (m, 5H), 7.15 (d, 2H), 4.92 (d, 1H), 4.05 (br. s, 1H), 3.86 (s, 3H), 3.60 (br. s, 1H), 3.17 (br. s, 1H), 2.89 (br. s, 1H), 1.75 (br. t, 1H), 1.45-1.0 (m, 12H). |
| 30A | (R-Enantiomer) | LC-MS (Method 6): $R_t$ = 3.32 min; m/z = 502 (M + H)+ <br> 1H-NMR (400 MHz, DMSO-$d_6$): δ = 8.58 (s, 1H), 7.52 (d, 2H), 7.42-7.37 (m, 5H), 7.03 (d, 2H), 4.59-4.40 (m, 2H), 3.87 (m, 1H), 3.81 (s, 3H), 3.22-3.13 (m, 1H), 2.95-2.80 (m, 1H), 1.88-1.75 (m, 1H), 1.64-1.45 (m, 3H), 1.35 (s, 9H). |

-continued

| Example | Structure | Analytical data |
|---|---|---|
| 31A | (S-Enantiomer) | LC-MS (Method 3): $R_t$ = 3.14 min; m/z = 502 (M + H)$^+$<br>$^1$H-NMR (400 MHz, DMSO-d$_6$):<br>δ = 8.58 (s, 1H), 7.52 (d, 2H), 7.42-7.37 (m, 5H), 7.03 (d, 2H), 4.59-4.40 (m, 2H), 3.87 (m, 1H), 3.81 (s, 3H), 3.22-3.13 (m, 1H), 2.95-2.80 (m, 1H), 1.88-1.75 (m, 1H), 1.64-1.45 (m, 3H), 1.35 (s, 9H). |

Example 32A (+/−)-cis/trans-3-{[5-(4-Methoxyphenyl)-6-phenyl-furo[2,3-d]pyrimidin-4-yl]oxy}cyclohexanol

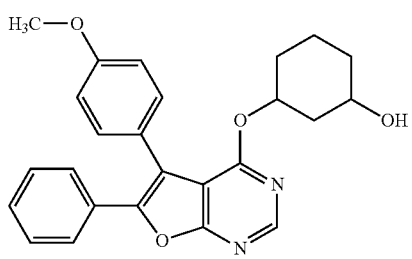

Dissolve 1.552 g (13.36 mmol) of 1,3-cyclohexanediol (cis/trans mixture) in 12 ml of absolute THF, cool to 0° C. and add 13.36 ml of phosphazene base P2-t-Bu in THF (approx. 2 M solution). After the addition has ended, continue to stir at RT for approx. 10 min, then cool again to 0° C. and add 3.0 g (8.91 mmol) of 4-chloro-5-(4-methoxyphenyl)-6-phenylfuro[2,3-d]pyrimidine in portions. Stir the reaction mixture at RT for 1 h, add to water and extract three times with ethyl acetate. Wash the combined organic phases with saturated sodium chloride solution, dry over magnesium sulphate and concentrate under reduced pressure. The residue is purified by chromatography on silica gel (eluent: cyclohexane/ethyl acetate 5:1→1:1). 3.02 g (81% of theory) of the target compound are obtained.

LC-MS (Method 3):
Isomer 1. $R_t$=2.52 min; m/z=417 (M+H)$^+$,
Isomer 2 $R_t$=2.55 min; m/z=417 (M+H)$^+$.

The cis/trans isomer mixture thus obtained is separated by means of HPLC [eluent: water/acetonitrile 1:1; Kromasil column 100 C 18, 250 mm×20 mm; flow rate: 25 ml/min; UV detection: 210 nm; temperature: 30° C.]. 2.0 g of isomer mixture are applied, dissolved in 35 ml of THF and approx. 15 ml of water, in several injections (injection volume approx. 1 ml). 750 mg of (+/−)-cis-3-{[5-(4-methoxyphenyl)-6-phenylfuro[2,3-d]pyrimidin-4-yl]oxy}cyclohexanol (Example 33A) are obtained, as are 640 mg of (+/−)-trans-3-{[5-(4-methoxyphenyl)-6-phenylfuro[2,3-d]pyrimidin-4-yl]oxy}cyclohexanol (Example 34A).

Example 33A (+/−)-cis-3-{[5-(4-Methoxyphenyl)-6-phenylfuro[2,3-d]pyrimidin-4-yl]oxy}cyclohexanol

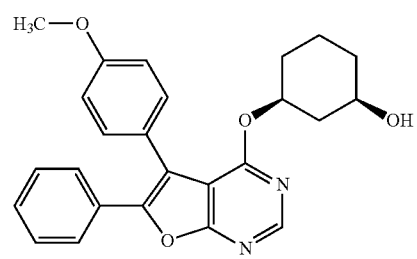

LC-MS (Method 5): $R_t$=2.86 min; m/z=417 (M+H)$^+$
$^1$H-NMR (400 MHz, DMSO-d$_6$): δ=8.57 (s, 1H), 7.53 (m, 2H), 7.42-7.37 (m, 5H), 7.0 (d, 2H), 5.11 (m, 1H), 4.69 (d, 1H), 3.83 (s, 3H), 2.27 (d, 1H), 2.01 (d, 1H), 1.79 (d, 1H), 1.62-1.68 (m, 1H), 1.30-1.05 (m, 4H).

Example 34A (+/−)-trans-3-{[5-(4-Methoxyphenyl)-6-phenylfuro[2,3-d]pyrimidin-4-yl]oxy}cyclohexanol

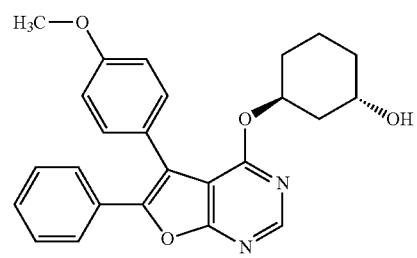

LC-MS (Method 5): $R_t$=2.88 min; m/z=417 (M+H)$^+$
$^1$-NMR (400 MHz, DMSO-d$_6$): δ=8.58 (s, 1H), 7.54 (d, 2H), 7.42-7.39 (m, 5H), 7.04 (d, 2H), 5.59 (m, 1H), 4.42 (d, 1H), 3.82 (s, 3H), 3.48 (m, 1H), 1.90-1.82 (m, 1H), 1.62-1.45 (m, 5H), 1.25-1.15 (m, 2H).

Example 35A (+/−)-all-cis-5-{[5-(4-Methoxyphenyl)-6-phenylfuro[2,3-d]pyrimidin-4-yl]oxy}cyclohexane-1,3-diol

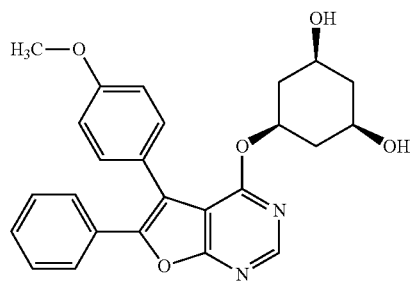

Dehydration of all-cis-1,3,5-cyclohexanetriol dihydrate: Dissolve all-cis-1,3,5-cyclohexanetriol dihydrate in DMF at 70° C. Remove the volatile components under reduced pressure and dry the residue under high vacuum.

Dissolve 0.81 g (6.12 mmol) of all-cis-1,3,5-cyclohexanetriol in 15 ml of DMF, cool to 0° C. and add 245 mg of sodium hydride (approx. 60% dispersion in oil, approx. 6.12 mmol) in portions. Stir the suspension at RT for 1 h and at 40-50° C. for approx. 2.5 h. After cooling to RT, add 1.376 g (4.09 mmol) of 4-chloro-5-(4-methoxyphenyl)-6-phenylfuro[2,3-d]pyrimidine and stir the mixture at RT overnight. Add the reaction mixture cautiously to water. After saturating with sodium chloride, extract three times with ethyl acetate. Dry the combined organic phases over magnesium sulphate and concentrate under reduced pressure. Chromatograph the residue on silica gel (eluent: dichloromethane/methanol 30:1→4:1). 1.38 g (77.8% of theory) of the target compound are obtained.

LC-MS (Method 3): $R_t$=2.04 min; m/z=433 (M+H)$^+$ $^1$H-NMR (400 MHz, DMSO-d$_6$): δ=8.59 (s, 1H), 7.55 (m, 2H), 7.46-7.40 (m, 5H), 7.02 (d, 2H), 5.61 (m, 1H), 4.74 (d, 2H), 3.84 (s, 3H), 3.58-3.49 (m, 2H), 2.27-2.20 (m, 2H), 2.05 (d, 1H), 1.06 (q, 3H).

General Method Step C: Detachment of Boc Protecting Groups

Add 0.5-1.0 part by volume of TFA at RT dropwise to a solution of Boc-protected amine in dichloromethane (concentration 0.1 to 1.5 mol/l, possibly with a few drops of water) (this results in a dichloromethan/TFA ratio of approx. 2:1 to 1:1). Stir the mixture at RT for a period of 30 min to 18 h. After diluting with dichloromethane, wash with saturated sodium carbonate or sodium hydrogencarbonate solution. Dry the organic phase over magnesium sulphate or sodium sulphate and concentrate under reduced pressure. If appropriate, the amine can be purified further by preparative HPLC or chromatography on silica gel (eluent: dichloromethane/methanol).

The following compounds are prepared according to general method C proceeding from compounds 26A-31A:

| Example | Structure | Analytical data |
|---|---|---|
| 36A | H$_3$C—O—...—NH—cyclohexane—NH$_2$ (furo[2,3-d]pyrimidine, 4-methoxyphenyl, phenyl) (+/−)-cis/trans | LC-MS (Method 3): $R_t$ = 1.56 min; m/z = 415 (M + H)$^+$. |
| 37A | H$_3$C—O—...—O—piperidine (furo[2,3-d]pyrimidine, 4-methoxyphenyl, phenyl) (rac.) | LC-MS (Method 5): $R_t$ = 1.81 min; m/z = 402 (M + H)$^+$<br>$^1$H-NMR (400 MHz, DMSO-d$_6$): δ = 8.68 (s, 1H), 7.56 (d, 2H), 7.49-7.39 (m, 5H), 7.03 (d, 2H), 5.15 (m, 1H), 3.83 (s, 3H), 3.02 (dd, 1H), 2.72-2.55 (m, 3H), 1.97-1.90 (m, 1H), 1.56-1.32 (m, 3H). |

-continued

| Example | Structure | Analytical data |
|---|---|---|
| 38A | 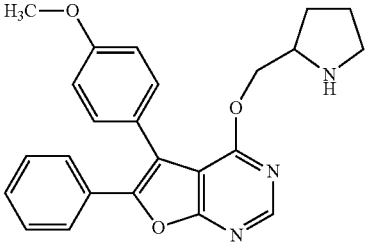<br>(rac.) | LC-MS (Method 3): $R_t$ = 1.54 min; m/z = 402 (M + H)$^+$<br>$^1$H-NMR (400 MHz, DMSO-d$_6$): δ = 8.59 (s, 1H), 7.55 (d, 2H), 7.46-7.39 (m, 5H), 7.03 (d, 2H), 4.31 (q, 2H), 3.82 (s, 3H), 3.5-3.30 (m, 2H), 2.80-2.72 (m, 1H), 2.20-2.12 (m, 1H), 1.78-1.70 (m, 1H), 1.60-1.55 (m, 2H), 1.40-1.30 (m, 1H). |
| 39A | 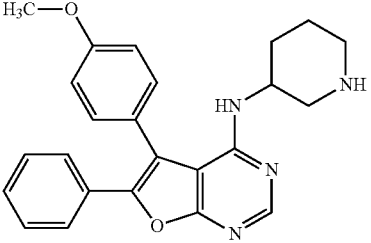<br>(rac.) | LC-MS (Method 3): $R_t$ = 1.52 min; m/z = 401 (M + H)$^+$<br>$^1$H-NMR (400 MHz, DMSO-d$_6$): δ = 8.35 (s, 1H), 7.50-7.47 (m, 4H), 7.40-7.31 (m, 4H), 7.15 (d, 2H), 5.29 (d, 1H), 4.19 (m, 1H), 3.86 (s, 3H), 2.95 (d, 1H), 2.75-2.69 (m, 1H), 2.62-2.58 (m, 1H), 2.50-2.47 (m, 2H), 1.73-1.68 (m, 1H), 1.47-1.32 (m, 3H). |
| 40A | 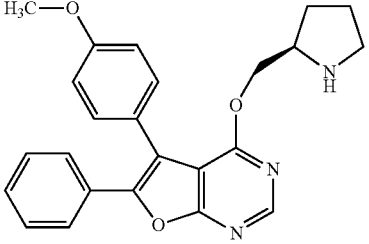<br>(R-Enantiomer) | LC-MS (Method 6): $R_t$ = 1.66 min; m/z = 402 (M + H)$^+$<br>$^1$H-NMR (400 MHz, DMSO-d$_6$): δ = 8.58 (s, 1H), 7.55 (d, 2H), 7.46-7.39 (m, 5H), 7.03 (d, 2H), 4.30 (dd, 1H), 4.20 (dd, 1H), 3.82 (s, 3H), 3.20 (m, 1H), 2.70 (m, 2H), 1.69-1.52 (m, 3H), 1.30-1.20 (m, 2H). |
| 41A | 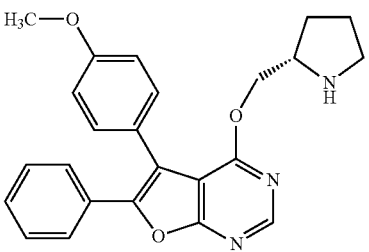<br>(S-Enantiomer) | LC-MS (Method 6): $R_t$ = 1.66 min; m/z = 402 (M + H)$^+$<br>$^1$H-NMR (400 MHz, DMSO-d$_6$): δ = 8.58 (s, 1H), 7.55 (d, 2H), 7.46-7.39 (m, 5H), 7.03 (d, 2H), 4.30 (dd, 1H), 4.20 (dd, 1H), 3.82 (s, 3H), 3.20 (m, 1H), 2.70 (m, 2H), 1.69-1.52 (m, 3H), 1.30-1.20 (m, 2H). |

Example 42A (+/−)-cis-{[3-Hydroxycyclohexyl]oxy}acetic acid tert-butyl ester

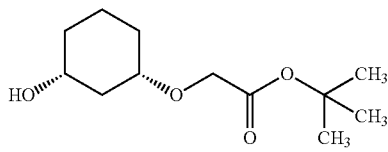

Dissolve 5.0 g (43 mmol) of cis/trans-1,3-cyclohexanediol (approx. 1.2:1 cis/trans mixture) in 20 ml of absolute THF and, at RT, add 24.8 ml (approx. 49.5 mmol) of phosphazene base P2-t-Bu in THF (approx. 2 M solution) dropwise. Stir the solution at RT for a further 30 min and then add dropwise to a mixture of 9.5 ml (64.6 mmol) of bromoacetic acid tert-butyl ester and add 10 ml of THF dropwise. Stir the mixture at RT overnight, then dilute with dichloromethane, and wash the organic phase successively with 1N hydrochloric acid, buffer solution (pH 7) and sodium chloride solution, dry over sodium sulphate and concentrate under reduced pressure. Separate the crude product by means of chromatography on silica gel (eluent: cyclohexane/ethyl acetate 5:1→1:1). 2.73 g (27.6% of theory) of the cis-configured target compound are isolated as a pure fraction.

MS (DCI): m/z=248 (M+NH$_4$)$^+$ $^1$H-NMR (400 MHz, DMSO-d$_6$): δ=4.59 (d, 1H), 3.95 (s, 2H), 3.38-3.21 (m, 2H), 2.20-2.12 (m, 1H), 1.89 (d, 1H), 1.74 (d, 1H), 1.66-1.60 (m, 1H), 1.41 (s, 9H), 1.14-0.95 (m, 4H).

Example 43A (+/−)-trans-{[3-Aminocyclohexyl]oxy}acetic acid tert-butyl ester

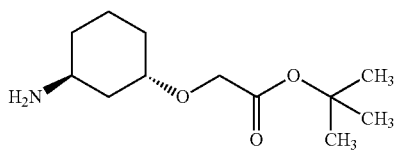

Stage a):

Dissolve 500 mg (2.17 mmol) of (+/−)-cis-{[3-hydroxycyclohexyl]oxy}acetic acid tert-butyl ester and 0.907 ml (6.51 mmol) of triethylamine in 2 ml of dichloromethane and cool to 0° C. Add 0.20 ml (2.61 mmol) of methanesulphonyl chloride dropwise. Stir the mixture at 0° C. for a further 1 h and then add to water. Remove the organic phase and extract the aqueous phase with dichloromethane. Wash the combined organic phases with saturated sodium chloride solution, dry over magnesium sulphate and concentrate under reduced pressure. 690 mg of the mesylate are obtained, which are reacted further directly.

Stage b):

Dissolve 690 mg of the mesylate obtained above in 2 ml of DMF at RT and add 873 mg (13.4 mmol) of sodium azide. Stir the suspension vigorously at 60° C. overnight and then add to water with cooling. Extract three times with ethyl acetate, wash the combined organic phases with saturated sodium chloride solution, dry over magnesium sulphate and concentrate under reduced pressure. 416 mg of the azide are obtained as a yellowish oil, which is reacted further directly.

Stage c):

Dissolve 418 mg of the azide obtained above in 1.8 ml of ethanol and 0.2 ml of water, add palladium on activated carbon and stir at RT under a hydrogen atmosphere (standard pressure) for 2 h. Remove the catalyst by filtration through kieselguhr, concentrate the filtrate under reduced pressure and dry the residue under high vacuum. 456 mg of the title compound are obtained, which are used without further purification.

Example 44A (+/−)-cis/trans-3-{[5-(4-Methoxyphenyl)-6-phenyl-furo[2,3-d]pyrimidin-4-yl]amino}cyclohexanol

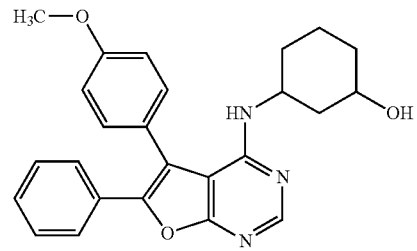

Initially charge 1.0 g (2.97 mmol) of 4-chloro-5-(4-methoxyphenyl)-6-phenylfuro[2,3-d]pyrimidine and 513 mg (approx. 4.5 mmol) of (+/−)-cis/trans-3-aminocyclohexanol (approx. 3:1 cis/trans mixture; prepared according to *J. Chem. Soc. Perkin Trans. I,* 1994, 537) in 2.7 ml of DMF. After adding 1.03 ml (5.94 mmol) of DIEA, heat the mixture to 120° C. for 2 h. After cooling, add to ice-water. Filter off the precipitated solid with suction, wash with water and dry under reduced pressure. Purify the crude product by chromatography on silica gel (eluent: cyclohexane/ethyl acetate 2:1→1:2). 1.05 g (85.1% of theory) of the target product are obtained as a cis/trans mixture.

LC-MS (Method 6): R$_t$=2.53 min; m/z=416 (M+H)$^+$.

Example 45A (+/−)-cis-3-[(6-Phenylfuro[2,3-d]pyrimidin-4-yl)amino]cyclohexanol

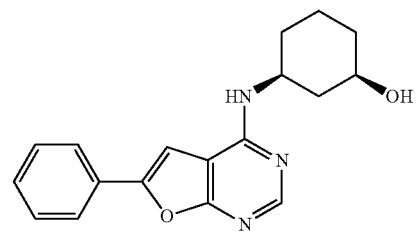

Heat a mixture of 4.0 g (17.34 mmol) of 4-chloro-6-phenylfuro[2,3-d]pyrimidine, 4.5 ml (26 mmol) of DIEA and 2.8 g of (+/−)-cis/trans-3-aminocyclohexanol (approx. 85% strength, approx. 20.8 mmol; approx. 3:1 cis/trans mixture; prepared according to *J. Chem. Soc. Perkin Trans. I,* 1994, 537) in 15 ml of DMF is heated to 120° C. overnight. After cooling, add the reaction mixture to water and extract three times with ethyl acetate. Wash the combined organic phases with saturated sodium chloride solution, dry over magnesium sulphate and concentrate under reduced pressure. Repeated stirring of the crude product with a mixture of methyl tert-butyl ether and dichloromethane enriches the product in the mother liquor. After concentrating the mother liquor, filter off the product with suction after crystallization from dichloromethane/methanol (10:1) and dry it under reduced pressure. 1.11 g (20.7% of theory) of the target product are obtained.

LC-MS (Method 6): $R_t$=1.95 min; m/z=310 (M+H)$^+$ $^1$-NMR (400 MHz, DMSO-d$_6$): δ=8.25 (s, 1H), 7.88-7.72 (m, 3H), 7.55-7.47 (m, 2H), 7.46-7.38 (m, 2H), 4.71 (d, 1H), 4.11-4.01 (m, 1H), 3.59-3.47 (m, 1H), 2.19 (d, 1H), 1.96-1.19 (m, 3H), 1.36-1.05 (m, 4H).

Example 46A (+/−)-cis-({3-[(6-Phenylfuro[2,3-d]pyrimidin-4-yl) amino]cyclohexyl}oxy)acetic acid tert-butyl ester

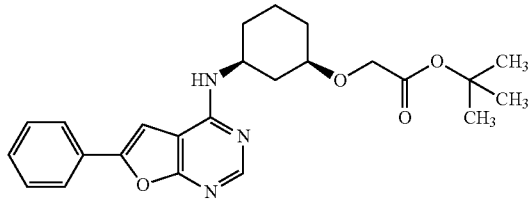

At 40° C., add approx. 0.06 mmol of tetrabutylammonium hydrogensulphate and a solution of 200 mg (0.646 mmol) of (+/−)-cis-3-[(6-phenylfuro[2,3-d]pyrimidin-4-yl)amino]cyclohexanol in 0.5 ml of toluene and 0.1 ml of THF to a mixture of 517 mg of 50% sodium hydroxide solution (6.5 mmol) and 0.5 ml of toluene. Admix the resulting mixture with 0.19 ml (1.29 mmol) of bromoacetic acid tert-butyl ester with vigorous stirring and heat it to 70° C. After 2 h, cool the mixture and add it to water. Extract three times with dichloromethane, wash the combined organic phases with saturated sodium chloride solution and concentrate under reduced pressure. After preparative RP-HPLC (eluent: acetonitrile/water), 152 mg (55.5% of theory) of the target product are isolated from the crude product.

LC-MS (Method 6): $R_t$=2.87 min; m/z=424 (M+H)$^+$.

$^1$H-NMR (400 MHz, DMSO-d$_6$): δ=8.26 (s, 1H), 7.89-7.78 (m, 3H), 7.51 (t, 2H), 7.45-7.39 (m, 2H), 4.17-4.05 (m, 1H), 4.01 (s, 2H), 3.49-3.40 (m, 1H), 2.33 (br. d, 1H), 2.01 (br. d, 1H), 1.91 (br. d, 1H), 1.81-1.75 (m, 1H), 1.42 (s, 9H), 1.34-1.10 (m, 4H).

Example 47A (+/−)-cis-({3-[(5-Bromo-6-phenylfuro[2,3-d]pyrimidin-4-yl)amino]cyclohexyl}oxy)acetic acid tert-butyl ester

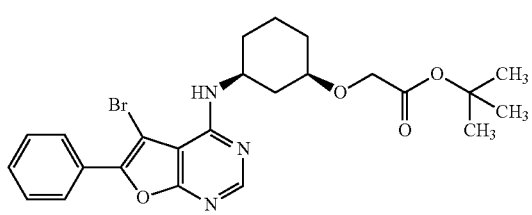

Suspend 132 mg (0.312 mmol) of (+/−)-cis-({3-[(6-phenylfuro[2,3-d]pyrimidin-4-yl)amino]cyclo-hexyl}oxy)acetic acid tert-butyl ester in 0.3 ml of tetrachloromethane, add 61 mg (0.343 mmol) of NBS and heat to reflux. On completion of conversion (approx. 1 h), cool the reaction mixture and isolate the product directly by preparative RP-HPLC. 104 mg (66.4% of theory) of the target compound are obtained.

LC-MS (Method 5): $R_t$=3.36 min; m/z=502, 504 (M+H)$^+$ $^1$H-NMR (400 MHz, DMSO-d$_6$): δ=8.34 (s, 1H), 8.01 (d, 2H), 7.60-7.49 (m, 3H), 7.08 (br. d, 1H), 4.42-4.25 (m, 1H), 4.09 (s, 2H), 3.65-3.58 (m, 1H), 2.11 (br. d, 1H), 1.81-1.68 (m, 4H), 1.65-1.47 (m, 2H), 1.43 (s, 9H), 1.41-1.30 (m, 1H).

Example 48A (+/−)-cis-({3-[(5-Phenylfuro[2,3-d]pyrimidin-4-yl) oxy]cyclohexyl}oxy)acetic acid tert-butyl ester

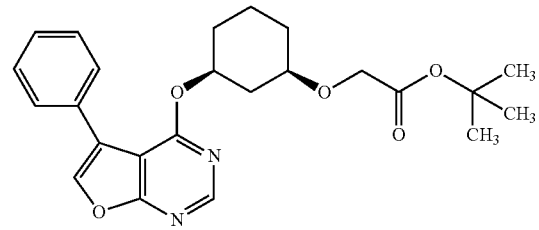

Dissolve 500 mg (2.17 mmol) of (+/−)-cis-{[3-hydroxycyclohexyl]oxy}acetic acid tert-butyl ester in 2.0 ml of dry THF, cool to 0° C. and add 1.24 ml (approx. 2.5 mmol) of a 2N solution of phosphazene base P2-t-Bu in THF. After removing the cooling, stir the mixture at RT for a further 30 min, before adding 500.7 mg (2.17 mmol) of 4-chloro-5-phenylfuro[2,3-d]pyrimidine at RT. Stir the mixture at RT overnight and then concentrate under reduced pressure. Purify the residue by chromatography on silica gel (eluent: cyclohexane/ethyl acetate 10:1→8:1). The target product is obtained after further purification by means of RP-HPLC (eluent: acetonitrile/water). 380 mg (41.2% of theory) are isolated.

LC-MS (Method 3): $R_t$=2.89 min; m/z=425 (M+H)$^+$ $^1$H-NMR (400 MHz, DMSO-d$_6$): δ=8.61 (s, 1H), 8.35 (s, 1H), 7.27 (d, 2H), 7.49-7.39 (m, 3H), 5.25 (m, 1H), 3.99 (s, 2H), 3.47 (m, 1H), 2.12 (br. s, 1H), 1.99 (br. d, 1H), 1.32-1.26 (m, 1H), 1.41 (s, 9H), 1.40-1.12 (m, 5H).

Example 49A (+/−)-cis-({3-[(6-Bromo-5-phenylfuro[2,3-d]pyrimidin-4-yl)oxy]cyclohexyl}oxy)acetic acid tert-butyl ester

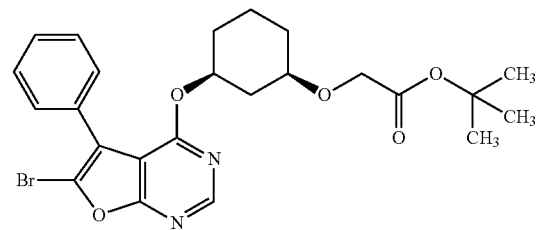

Suspend 100 mg (0.236 mmol) of (+/−)-cis-({3-[(5-phenylfuro[2,3-d]pyrimidin-4-yl)oxy]cyclohexyl}oxy)acetic acid tert-butyl ester in 0.2 ml of tetrachloromethane and add 46.1 mg (0.259 mmol) of NBS. Stir the reaction mixture at 60° C. for a total of 2 h, and add a further 23 mg of NBS after 1 h. After cooling, remove the tetrachloromethane under reduced pressure and purify the residue by preparative RP-HPLC (eluent: acetonitrile/water). 43.6 mg (36.8% of theory) of the target product are obtained.

LC-MS (Method 5): $R_t$=3.31 min; m/z=503, 505 (M+H)$^+$ $^1$H-NMR (400 MHz, DMSO-d$_6$): δ=8.59 (s, 1H), 7.62 (d, 2H), 7.53-7.43 (m, 3H), 5.15 (m, 1H), 3.98 (s, 2H), 3.41 (m, 1H), 2.45 (br. d, 1H), 2.04 (br. d, 1H), 1.95 (br. d, 1H), 1.41 (s, 9H), 1.30-1.06 (m, 5H).

Example 50A (4-Ethylphenyl)[(trimethylsilyl)oxy]acetonitrile

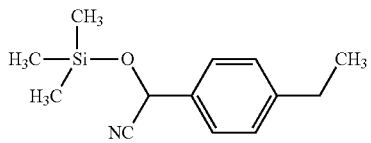

Mix 600 g (4.47 mol) 4-ethylbenzaldehyde in 5.3 liters toluene with 2.4 g (7.5 mmol) zinc iodide. At RT, with gentle cooling, add 587.4 ml (4.7 mol) trimethylsilyl cyanide, dissolved in 3.6 liters toluene, over a period of approx. 5 min Stir the mixture for 90 min at RT, before removal of volatile components under vacuum and quick chromatography of the residue on silica gel (eluent: petroleum ether/ethyl acetate 9:1). 990 g (94.9% of theor.) of the title compound is obtained as a colourless oil.

$^1$H-NMR (400 MHz, CDCl$_3$): δ=7.38 (d, 2H), 7.23 (d, 2H), 4.97 (s, 1H), 2.68 (q, 2H), 1.25 (t, 3H), 0.23 (s, 9H).

Example 51A 1-(4-Ethylphenyl)-2-hydroxy-2-phenylethanone

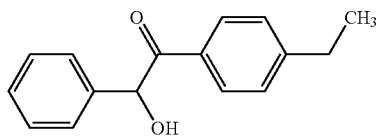

Dissolve 290 ml (2.069 mol) diisopropylamine in 3.6 liters DME and precool to −78° C. Add 820 ml (2.05 mol) n-butyllithium (2.5 M solution in hexane) dropwise in the space of approx. 20 min (temperature<−60° C.). After 15 min at −60° C., add a solution of 435 g (1.864 mol) (4-ethylphenyl)[(trimethylsilyl)oxy]acetonitrile in 1.4 liters DME dropwise (temperature<−60° C.). Stir the mixture for a further 30 min at −60° C., before adding a solution of 189.5 ml (1.864 mol) benzaldehyde in 1.4 liters DME (time approx. 20 min, temperature −60° C.). Heat the mixture over a period of 4 h to RT, before adding 7 liter satd. ammonium chloride solution. Extract the reaction mixture with ethyl acetate. After phase separation, wash the organic phase with satd. ammonium chloride solution, dry, and concentrate by vacuum evaporation. Dissolve the residue in 7 liters dioxan and 5 liters methanol, and add 6 liters 1 N hydrochloric acid. Stir the mixture overnight at RT, then, after adding 11 liters satd. sodium chloride solution, extract with 6.5 liters ethyl acetate. Wash the organic phase with water and with satd. sodium chloride solution, dry, and concentrate by vacuum evaporation. Dissolve the residue in 2 liters diisopropyl ether, add seed crystals and stir for 2 h. The precipitated solid is filtered with suction, washed with 300 ml diisopropyl ether and petroleum ether and dried under vacuum. Concentrate the mother liquor, and after storing for 2 days at 4° C., again filter off the precipitated solid with suction, wash with approx. 100 ml diisopropyl ether and petroleum ether and dry under vacuum. On combining the two solids, 154.9 g (34% of theor.) of the target product is obtained.

HPLC (Method 1): $R_t$=4.55 min

MS (DCI): m/z=258 (M+NH$_4$)$^+$ $^1$H-NMR (400 MHz, CDCl$_3$): δ=7.85 (d, 2H), 7.48-7.35 (m, 5H), 7.21 (d, 2H), 5.92 (d, 1H), 4.59 (d, 1H), 2.65 (q, 2H), 1.20 (t, 3H).

Example 52A

2-Amino-4-(4-ethylphenyl)-5-phenyl-3-furonitrile

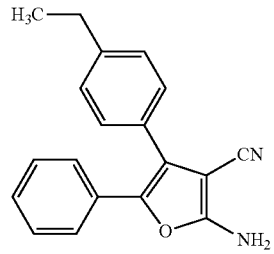

Cool a mixture of 145 g (603 mmol) 1-(4-ethylphenyl)-2-hydroxy-2-phenylethanone and 51.8 g (784.4 mmol) malononitrile in 2.23 liters DMF to 0° C. and add 53.7 ml (518 mmol) diethylamine, with cooling. After 1 h, heat the reaction mixture to RT and stir for a further 4 h, before adding 1.5 liter water. After 30 min, pour off a large proportion of the water and replace with 750 ml of fresh water. Stir the mixture vigorously, before decanting from the sticky organic residue. Dissolve the residue in ethyl acetate, dry, and concentrate under vacuum, until the product begins to crystallize. Add 450 ml diisopropyl ether, stir and then leave to stand overnight. Filter off the crystalline precipitate with suction, wash twice with 50 ml diisopropyl ether and dry under vacuum. 98.5 g (56.6% of theor.) of the target product is obtained.

HPLC (Method 1): $R_t$=5.10 min

MS (DCI): m/z=306 (M+NH$_4$)$^+$ $^1$H-NMR (400 MHz, CDCl$_3$): δ=7.90-7.82 (m, 4H), 7.28-7.18 (m, 5H), 4.98 (s, 2H), 2.69 (q, 2H), 1.28 (t, 3H).

Example 53A 5-(4-Ethylphenyl)-6-phenylfuro[2,3-d]pyrimidin-4(3H)-one

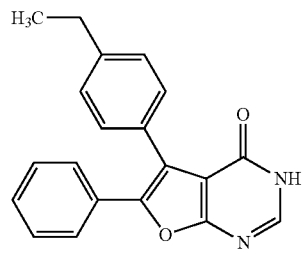

Cool 770 ml (8.16 mol) acetic anhydride to 0° C. and, with cooling, add 372 ml (10.4 mol) formic acid. Stir the mixture for 30 min at 0° C., before adding 98 g (340 mmol) 2-amino-4-(4-ethylphenyl)-5-phenyl-3-furonitrile. Heat the mixture to reflux (with increasing intensity of evolution of gas) and stir for 24 h under reflux. After cooling, stir for about 2 h at 10° C. and then suction-filter the precipitated solid, wash with diisopropyl ether and dry at high vacuum. 69.3 g (64.5% of theor.) of the target product is obtained.

HPLC (Method 1): $R_t$=4.77 min

MS (DCI): m/z=334 (M+NH$_4$)$^+$, 317 (M+H)$^+$ $^1$-NMR (400 MHz, DMSO-d$_6$): δ=12.63 (br. s, 1H), 8.19 (s, 1H), 7.43 (d, 2H), 7.40-7.30 (m, 5H), 7.25 (m, 2H), 3.35 (s, 2H), 2.68 (d, 2H), 1.25 (t, 3H).

Example 54A

4-Chloro-5-(4-ethylphenyl)-6-phenylfuro[2,3-d]pyrimidine

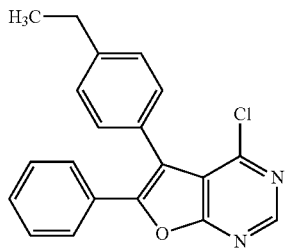

Put 72 g (227.6 mmol) 5-(4-ethylphenyl)-6-phenylfuro[2,3-d]pyrimidin-4(3H)-one in 360 ml (4.6 mol) phosphoryl chloride and heat to reflux. Stir the mixture for approx. 1 h at 120° C., before adding the reaction mixture dropwise, after cooling to RT, at controlled dose and with vigorous stirring, to a mixture of 2.2 liters of 25% ammonia solution and 1.2 liters water (pH>9, temperature 55-75° C.). Extract the aqueous mixture three times with dichloromethane, combine the organic phases, dry over sodium sulphate and concentrate by vacuum evaporation. Wash the residue with a little diisopropyl ether, and after filtration and drying at high vacuum, 66.1 g (85.2% of theor.) of the target product is obtained.

HPLC (Method 1): $R_t$=5.68 min

MS (DCI): m/z=335 (M+H)$^+$ $^1$-NMR (400 MHz, CDCl$_3$): δ=8.76 (s, 1H), 7.61 (d, 2H), 7.48-7.30 (m, 7H), 2.78 (q, 2H), 1.36 (t, 3H).

Example 55A

6-Phenylfuro[2,3-d]pyrimidine-4-amine

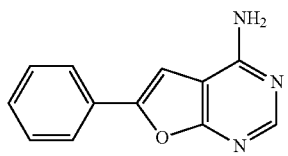

Suspend 110 g (597 mmol) 2-amino-5-phenyl-3-furonitrile in 355 ml (9 mol) formamide and heat for 1.5 h (bath temperature approx. 210° C.). Then cool the mixture to RT and stir into water. Filter off the precipitated solid with suction, and wash with water. Stir the still moist product in dichloromethane, filter with suction again and dry under vacuum. 106 g (80% of theor.) of the target compound is obtained.

LC-MS (Method 4): $R_t$=3.1 min; m/z=212 (M+H)$^+$

HPLC (Method 1): $R_t$=3.63 min $^1$H-NMR (400 MHz, DMSO-d$_6$): δ=8.20 (s, 1H), 7.8 (d, 2H), 7.55-7.32 (m, 6H).

Example 56A

5-Bromo-6-phenylfuro[2,3-d]pyrimidine-4-amine

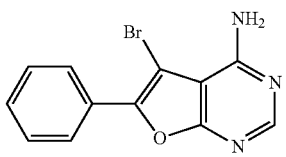

Heat 80 g (378.7 mmol) 6-phenylfuro[2,3-d]pyrimidine-4-amine in 770 ml carbon tetrachloride to 60° C. Add 84.3 g (473.4 mmol) N-bromosuccinimide, and stir the mixture overnight under reflux. After cooling, filter, mix the filter cake successively with dichloromethane and acetonitrile, and filter again. Then dry the filter cake under vacuum. 86 g of the target product (78.2% of theor.) is obtained.

MS (DCI): m/z=290/292 (M+H)$^+$ $^1$H-NMR (400 MHz, DMSO-d$_6$): δ=8.28 (s, 1H), 8.03 (d, 2H), 7.60-7.50 (m, 5H).

Example 57A

5-Bromo-4-chloro-6-phenylfuro[2,3-d]pyrimidine

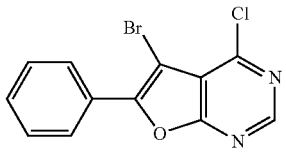

Put 54 g (186 mmol) 5-bromo-6-phenylfuro[2,3-d]pyrimidine-4-amine in 135 ml chloroform, add 70 ml 4 N hydrogen chloride in dioxan (280 mmol) and heat to reflux. Add 50 ml (372 mmol) isoamyl nitrite dropwise (evolution of gas). At the end of addition, stir for 3 h under reflux, before adding the cooled reaction mixture to water and extracting it with dichloromethane. Wash the organic phase with satd. sodium hydrogencarbonate solution, dry over sodium sulphate and concentrate by vacuum evaporation. Purify the raw product by chromatography on silica gel (eluent: dichloromethane). For further purification, mix the product in methanol, filter with suction, and dry at high vacuum. 32 g of the target product (55.5% of theor.) is obtained.

LC-MS (Method 3): $R_t$=2.54 min; m/z=309/310 (M+H)$^+$

HPLC (Method 1): $R_t$=5.08 min $^1$H-NMR (400 MHz, CDCl$_3$): δ=8.79 (s, 1H), 8.23-8.20 (m, 2H), 7.58-7.51 (m, 3H).

Example 58A and Example 59A (+/−)-trans- and (+/−)-cis-3-{[5-(4-methoxyphenyl)-6-phenylfuro[2,3-d]pyrimidin-4-yl]amino}-cyclohexanol

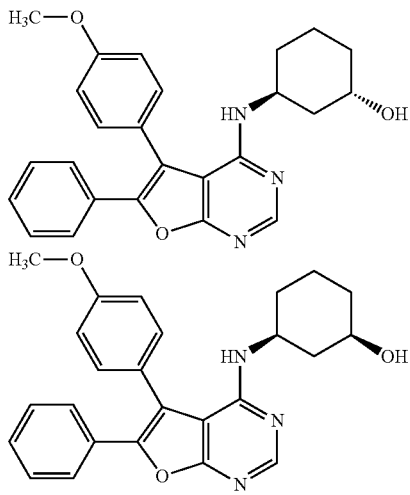

Separate 300 mg (0.72 mmol) of (+/−)-3-{[5-(4-methoxyphenyl)-6-phenylfuro[2,3-d]pyrimidin-4-yl]amino}cyclohexanol (cis/trans mixture) by preparative HPLC into the pure cis- and trans isomers [column: Phenomenex Gemini, C-18, 5 μm, 250 mm×21.2 mm; flow rate: 20 ml/min; temperature: 25° C.; eluent: water/THF 60:40]. 43 mg (14.3% of theory) of (+/−)-trans-3-{[5-(4-methoxyphenyl)-6-phenylfuro[2,3-d]pyrimidin-4-yl]amino}cyclohexanol (Example 58A) and 150 mg (50.0% of theory) of (+/−)-cis-3-{[5-(4-methoxyphenyl)-6-phenylfuro[2,3-d]pyrimidin-4-yl]amino}cyclohexanol (Example 59A) are obtained.

Example 58A

LC-MS (Method 6): $R_t$=2.49 min; m/z=416 (M+H)$^+$
$^1$-NMR (400 MHz, DMSO-d$_6$): δ=8.32 (s, 1H), 7.50 (d, 4H), 7.40-7.30 (m, 3H), 7.19 (d, 2H), 4.75 (d, 1H), 4.49 (s, 1H), 4.40-4.30 (m, 1H), 3.86 (s, 3H), 3.48 (s, 1H), 1.67-1.01 (m, 8H).

Example 59A

LC-MS (Method 6): $R_t$=2.51 min; m/z=416 (M+H)$^+$
$^1$-NMR (400 MHz, DMSO-d$_6$): δ=8.32 (s, 1H), 7.49-7.41 (m, 4H), 7.40-7.30 (m, 3H), 7.13 (d, 2H), 5.15 (s, 1H), 4.52 (s, 1H), 4.10-4.00 (m, 1H), 3.88 (s, 3H), 3.53-3.48 (m, 1H), 1.80-0.89 (m, 8H).

Example 60A (+/−)-4-(3-{[5-(4-Methoxyphenyl)-6-phenylfuro[2,3-d]pyrimidin-4-yl]oxy}piperidin-1-yl)butanenitrile

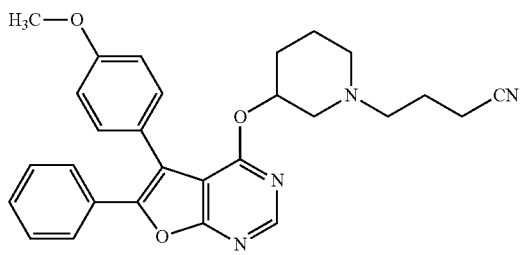

Add 147.5 mg (0.996 mmol) of 4-bromobutyronitrile at RT to a mixture of 200 mg (0.498 mmol) of (+/−)-5-(4-methoxyphenyl)-6-phenyl-4-(piperidin-3-yloxy)furo[2,3-d]pyrimidine, 0.25 ml (1.5 mmol) of diisopropylethylamine and 8.3 mg of potassium iodide in 2 ml of THF. The mixture is stirred under reflux for 10 h. After adding a further 0.25 ml (1.5 mmol) of diisopropylethylamine and 147.5 mg (0.996 mmol) of 4-bromobutyronitrile, continue to stir under reflux overnight. After cooling to RT, dilute with dichloromethane, wash with satd. sodium hydrogencarbonate solution, remove the organic phase, dry over sodium sulphate and concentrate under reduced pressure. After purifying the residue by means of preparative RP-HPLC (eluent: acetonitrile/water gradient) 189 mg of the target product are obtained (81.1% of theory).

LC-MS (Method 6): $R_t$=1.80 min; m/z=469 (M+H)$^+$
$^1$H-NMR (400 MHz, DMSO-d$_6$): δ=8.59 (s, 1H), 7.55 (d, 2H), 7.45-7.35 (m, 5H), 7.00 (d, 2H), 5.31-5.23 (m, 1H), 3.81 (s, 3H), 2.82-2.76 (m, 1H), 2.40 (t, 3H), 2.31 (t, 2H), 2.29-2.12 (m, 2H), 1.93-1.85 (m, 1H), 1.67 (t, 3H), 1.50-1.30 (m, 2H).

Example 61A (+/−)-cis-3-{[3-{[5-(4-Methoxyphenyl)-6-phenylfuro[2,3-d]pyrimidin-4-yl]oxy}cyclohexyl]oxy}-propanenitrile

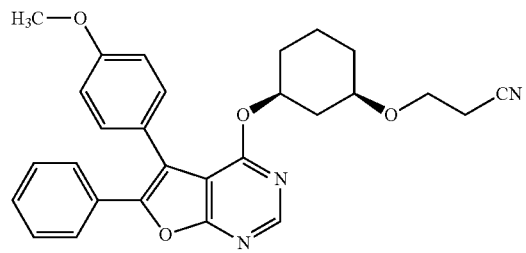

Add a solution of 10 mg of potassium tert-butoxide in 0.5 ml of THF dropwise to a solution of 150 mg (0.36 mmol) of (+/−)-cis-3-{[5-(4-methoxyphenyl)-6-phenylfuro[2,3-d]pyrimidin-4-yl]oxy}cyclohexanol in 1 ml of acrylonitrile. Stir the reaction mixture with exclusion of light at RT for approx. 2 h. After dilution with dichloromethane, wash successively with 1N hydrochloric acid, satd. sodium hydrogencarbonate solution and satd. sodium chloride solution, and concentrate the organic phase under reduced pressure. After purification of the residue by means of preparative RP-HPLC (eluent: acetonitrile/water gradient), 136.9 mg of the target product are obtained (81% of theory).

LC-MS (Method 3): $R_t$=2.88 min; m/z=470 (M+H)$^+$
$^1$H-NMR (400 MHz, DMSO-d$_6$): δ=8.60 (s, 1H), 7.55 (d, 2H), 7.43-7.34 (m, 5H), 7.00 (d, 2H), 5.20-5.10 (m, 1H), 3.81 (s, 3H), 3.63-3.55 (m, 2H), 3.50-3.40 (m, 1H), 2.70 (t, 2H), 2.48-1.40 (m, 1H), 2.19-1.90 (m, 2H), 1.80-1.70 (m, 1H), 1.38-1.02 (m, 4H).

Example 62A (+/−)-trans-3-{[3-{[5-(4-Methoxyphenyl)-6-phenyl-furo[2,3-d]pyrimidin-4-yl]amino}cyclohexyl]-oxy}propanenitrile

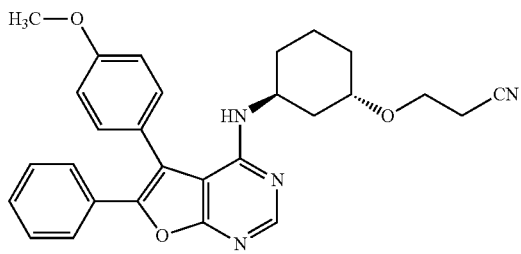

Add a solution of approx. 2 mg of potassium tert-butoxide in 0.2 ml of THF dropwise to a solution of 34.4 mg (0.059 mmol) of (+/−)-trans-3-{[5-(4-methoxyphenyl)-6-phenyl-furo[2,3-d]pyrimidin-4-yl]amino}cyclohexanol in 0.23 ml of acrylonitrile. Stir the reaction mixture with exclusion of light at RT for approx. 2 h. After diluting with dichloromethane, wash successively with 1N hydrochloric acid, satd. sodium hydrogencarbonate solution and satd. sodium chloride solution, and concentrate the organic phase under reduced pressure. After the residue has been purified by means of preparative RP-HPLC (eluent: acetonitrile/water gradient), 33.6 mg of the target product are obtained (86.6% of theory).

LC-MS (Method 6): $R_t$=2.86 min; m/z=469 (M+H)$^+$
$^1$H-NMR (400 MHz, DMSO-d$_6$): δ=8.32 (s, 1H), 7.52-7.49 (m, 3H), 7.19 (d, 2H), 4.73 (d, 1H), 4.85-4.25 (m, 1H), 3.88 (s, 3H), 3.60-3.50 (m, 2H), 2.78-2.70 (m, 2H), 1.80-1.62 (m, 2H), 1.60-1.49 (m, 4H), 1.27-1.12 (m, 3H).

Example 63A (+/−)-4-[2-({[5-(4-Methoxyphenyl)-6-phenylfuro[2,3-d]pyrimidin-4-yl]oxy}methyl)pyrrolidin-1-yl]butanenitrile

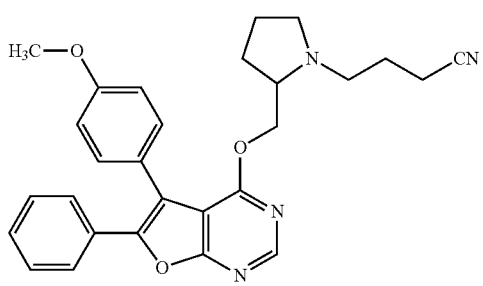

Add 221.2 mg (0.996 mmol) of 4-bromobutyronitrile at RT to a solution of 300 mg (0.747 mmol) of (+/−)-5-(4-methoxyphenyl)-6-phenyl-4-(pyrrolidin-2-ylmethoxy)furo[2,3-d]pyrimidine, 0.37 ml (2.24 mmol) of diisopropylethylamine and 12.4 mg of potassium iodide in 3 ml of THF. Stir the mixture under reflux for 6 h. After cooling to RT, dilute with dichloromethane, wash with satd. sodium hydrogencarbonate solution, remove the organic phase, dry over sodium sulphate and concentrate under reduced pressure. After drying the residue by means of preparative RP-HPLC (eluent: acetonitrile/water gradient), 178.1 mg of the target product are obtained (50.9% of theory).

LC-MS (Method 3): $R_t$=1.59 min; m/z=469 (M+H)$^+$
$^1$H-NMR (400 MHz, DMSO-d$_6$): δ=8.49 (s, 1H), 7.57-7.50 (m, 2H), 7.43-7.36 (m, 5H), 7.01 (d, 2H), 4.36 (dd, 1H), 4.24 (dd, 1H), 3.81 (s, 3H), 2.99-2.90 (m, 1H), 2.69-2.60 (m, 2H), 2.41-2.01 (m, 4H), 1.79-1.70 (m, 1H), 1.61-1.40 (m, 5H).

Example 64A (+/−)-3-(3-{[5-(4-methoxyphenyl)-6-phenylfuro[2,3-d]pyrimidin-4-yl]oxy}piperidin-1-yl)propanenitrile

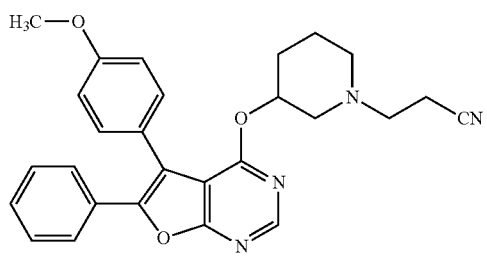

Stir a mixture of 900 mg (2.24 mmol) of (+/−)-5-(4-methoxyphenyl)-6-phenyl-4-(piperidin-3-yloxy)furo[2,3-d]pyrimidine and 1.5 ml (22.4 mmol) of acrylonitrile under reflux for 3 h. After cooling to RT, concentrate under reduced pressure and dry the residue under high vacuum. 1000 mg (98.1% of theory) of the target compound are obtained.

LC-MS (Method 3): $R_t$=1.97 min; m/z=455 (M+H)$^+$.

Separate 1.0 g (2.2 mmol) of (+/−)-3-(3-{[5-(4-methoxyphenyl)-6-phenylfuro[2,3-d]pyrimidin-4-yl]oxy}piperidin-1-yl)propanenitrile thus obtained into the enantiomers by chromatography on chiral phase (see Examples 65A and 66A) [column: Daicel Chiralpak AS-H, 5 µm, 250 mm×20 mm; flow rate: 15 ml/min; temperature: 30° C.; eluent: isohexane/THF 50:50].

Example 65A (−)-3-(3-{[5-(4-methoxyphenyl)-6-phenylfuro [2,3-d]pyrimidin-4-yl]oxy}piperidin-1-yl)propanenitrile (Enantiomer 1)

Yield: 459 mg (45.1% of theory)
$[α]_D^{20}$=−60.5°, c=0.545, CHCl$_3$
LC-MS (Method 6): $R^t$=2.05 min.; m/z=455 (M+H)$^+$
$^1$H-NMR (400 MHz, DMSO-d$_6$): δ=8.60 (s, 1H), 7.54 (d, 2H), 7.48-7.37 (m, 5H), 7.01 (d, 2H), 5.31-5.23 (m, 1H), 3.81 (s, 3H), 2.91-2.82 (m, 1H), 2.68-2.58 (m, 3H), 2.55 (s, 2H), 2.38-2.22 (m, 2H), 1.93-1.82 (m, 1H), 1.69-1.58 (m, 1H), 1.50-1.29 (m, 2H).

Example 66A (+)-3-(3-{[5-(4-Methoxyphenyl)-6-phenylfuro[2,3-d]pyrimidin-4-yl]oxy}piperidin-1-yl)propanenitrile (Enantiomer 2)

Yield: 479 mg (47.0% of theory)
$[α]_D^{20}$=+59.1°, c=0.545, CHCl$_3$
LC-MS (Method 6): $R_t$=2.05 min; m/z=455 (M+H)$^+$
$^1$H-NMR (400 MHz, DMSO-d$_6$): δ=8.60 (s, 1H), 7.54 (d, 2H), 7.48-7.37 (m, 5H), 7.01 (d, 2H), 5.31-5.23 (m, 1H), 3.81

(s, 3H), 2.91-2.82 (m, 1H), 2.68-2.58 (m, 3H), 2.55 (s, 2H), 2.38-2.22 (m, 2H), 1.93-1.82 (m, 1H), 1.69-1:58 (m, 1H), 1.50-1.29 (m, 2H).

Example 67A (2E)-3-{(2S,4R)-4-Hydroxy-1-[(1R)-1-phenylethyl]piperidin-2-yl}acrylic acid methyl ester

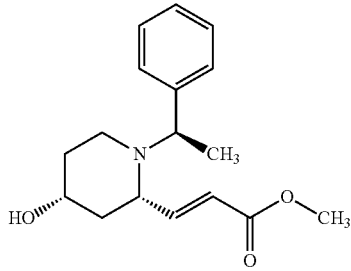

Dissolve 2.0 g (8.647 mmol) of (1S,5R)-2-[(1R)-1-phenylethyl]-6-oxa-2-azabicyclo[3.2.1]octan-7-one [prepared from N-[(1R)-1-phenylethyl]but-3-en-1-amine according to Bioorg. Med. Chem. Lett. 6 (8), 964 (1996)] in 8 ml of abs. THF, cool to −78° C. and add 9.5 ml (9.5 mmol) of a 1M solution of L-Selectride in THF. After the end of the addition, continue stirring at −78° C. for 1 h, then warm to −20° C. and add 2.1 ml (13 mmol) of phosphonoacetic acid trimethyl ester. Then warm the reaction mixture to 0° C. and stir for 1 h. Water is then added and 1N hydrochloric acid is used to set a pH of approx. 7-8. Extract the mixture with dichloromethane three times, and combine the organic phases, dry over magnesium sulphate and concentrate under reduced pressure. 4.32 g of crude product are obtained, which are used without further purification in the next stage.

LC-MS (Method 4): $R_t$=2.48 min; m/z=290 (M+H)$^+$.

Example 68A tert-Butyl(2R,4R)-4-hydroxy-2-(3-methoxy-3-oxopropyl)piperidine-1-carboxylate

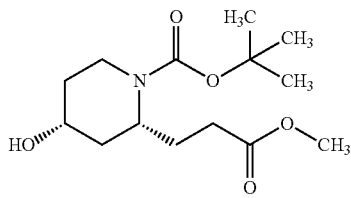

Dissolve 3.8 g of (2E)-3-{(2S,4R)-4-hydroxy-1-[(1R)-1-phenylethyl]piperidin-2-yl}acrylic acid methyl ester (as the crude product) in 50 ml of isopropanol and add 4.3 g of di-tert-butyl dicarbonate and a catalytic amount of 10% Pd/C. Stir the mixture at RT overnight and standard pressure under a hydrogen atmosphere. Filter through kieselguhr and concentrate the filtrate under reduced pressure. From the residue, after purification by chromatography on silica gel (eluent: cyclohexane/ethyl acetate 5:1→1:1), 0.98 g of the target product is obtained.

LC-MS (Method 8): $R_t$=1.87 min; m/z=288 (M+H)$^+$ $^1$H-NMR (400 MHz, DMSO-$d_6$): δ=4.64 (d, 1H), 4.08-3.99 (m, 1H), 3.91 (d, 1H), 3.69 (d, 1H), 3.58 (s, 3H), 3.05 (dt, 1H), 2.36-2.12 (m, 3H), 1.82-1.71 (m, 1H), 1.60 (s, 2H), 1.55-1.41 (m, 2H), 1.38 (s, 9H).

Example 69A (+/−)-({3-[(6-Phenylfuro[2,3-d]pyrimidin-4-yl)amino]cyclohexyl}oxy)acetic acid tert-butyl ester

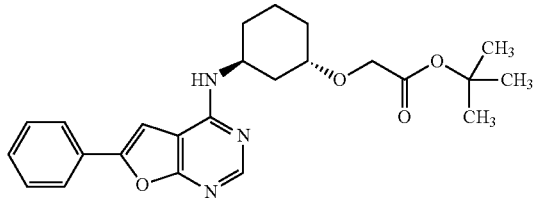

Initially charge 1.61 g (6.98 mmol) of 4-chloro-6-phenylfuro[2,3-d]pyridine and 1.60 g (6.98 mmol) of (+/−)-trans-{[3-aminocyclohexyl]oxy}acetic acid tert-butyl ester in 6.0 ml of DMF and add 1.8 ml (10.5 mmol) of N,N-diisopropylethylamine. Heat the reaction mixture to 120° C. for 3 h, then cool to RT and add to water. Extract three times with ethyl acetate, combine the organic phases, wash with satd. sodium chloride solution and concentrate under reduced pressure. From the residue, after purification by chromatography on silica gel (eluent: cyclohexane/ethyl acetate 20:1→2:1), 1.67 g of the target product are isolated (56.5% of theory).

LC-MS (Method 3): $R_t$=2.62 min; m/z=424 (M+H)$^+$ $^1$H-NMR (400 MHz, DMSO-$d_6$): δ=8.27 (s, 1H), 7.88-7.68 (m, 3H), 7.50 (t, 2H), 7.47-7.39 (m, 1H), 4.40 (s, 1H), 4.03 (s, 2H), 3.80 (s, 1H), 2.15-1.50 (m, 8H), 1.50-1.30 (m, 9H).

Example 70A (+/−)-({3-[(5-Bromo-6-phenylfuro[2,3-d]pyrimidin-4-yl)amino]cyclohexyl}oxy)acetic acid tert-butyl ester

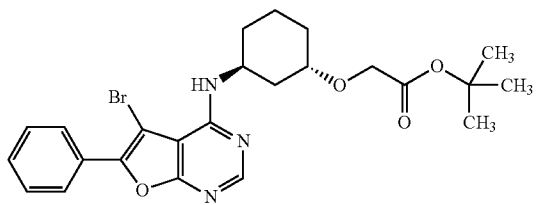

Suspend 1.65 g (3.9 mmol) of (+/−)-({3-[(6-phenylfuro[2,3-d]pyrimidin-4-yl)amino]cyclohexyl}-oxy)acetic acid tert-butyl ester in 4 ml of carbon tetrachloride and add 762 mg (4.3 mmol) of N-bromosuccinimide. Heat the reaction mixture under reflux for 1 h. After cooling to RT, add a further 350 mg of N-bromosuccinimide. Stir the reaction mixture under reflux again for 1 h, then cool and concentrate under reduced pressure. From the residue, after purification by chromatography on silica gel (eluent: cyclohexane/ethyl acetate 5:1), 0.99 g of the target product is isolated (50.6% of theory).

LC-MS (Method 3): $R_t$=3.09 min; m/z=502 (M+H)$^+$ $^1$H-NMR (400 MHz, DMSO-d$_6$): δ=8.38 (s, 1H), 8.00 (d, 2H), 7.61-7.49 (m, 3H), 6.39 (d, 1H), 4.53-4.42 (m, 1H), 4.03 (s, 2H), 3.78 (s, 1H), 2.09-1.42 (m, 8H), 1.40 (s, 9H).

Example 71A and Example 72A (+)-cis-{[3-Hydroxycyclohexyl]oxy}acetic acid tert-butyl ester (Enantiomer 1)

and (−)-cis-{[3-Hydroxycyclohexyl]oxy}acetic acid tert-butyl ester (Enantiomer 2)

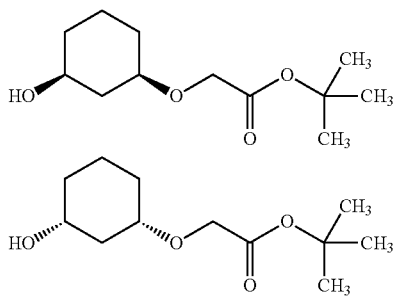

Separate 500 mg (2.17 mmol) of (+/−)-cis-{[3-hydroxycyclohexyl]oxy}acetic acid tert-butyl ester by chromatography on chiral phase into the enantiomers [column: Daicel Chiralpak AS-H, 5 μm, 250 mm×20 mm; flow rate: 15 ml/min; temperature: 30° C.; eluent: isohexane/ethanol 75:25].
Enantiomer 1:
  Yield: 124 mg (24.8% of theory)
  [α]$_D^{20}$=+2.4°, c=0.50, CHCl$_3$
  $^1$H-NMR (400 MHz, DMSO-d$_6$): δ=4.60 (d, 1H), 3.97 (s, 2H), 3.39-3.29 (m, 1H), 3.28-3.19 (m, 1H), 2.20-2.12 (m, 1H), 1.90 (d, 1H), 1.74 (d, 1H), 1.69-1.59 (m, 1H), 1.41 (s, 9H), 1.17-0.90 (m, 4H).
Enantiomer 2:
  Yield: 121 mg (24.2% of theory)
  [α]$_D^{20}$=−3.4°, c=0.50, CHCl$_3$
  $^1$H-NMR (400 MHz, DMSO-d$_6$): δ=4.60 (d, 1H), 3.97 (s, 2H), 3.39-3.29 (m, 1H), 3.28-3.19 (m, 1H), 2.20-2.12 (m, 1H), 1.90 (d, 1H), 1.74 (d, 1H), 1.69-1.59 (m, 1H), 1.41 (s, 9H), 1.17-0.90 (m, 4H).

Example 73A tert-Butyl(+/−)-3-(benzyloxy)piperidinecarbamate

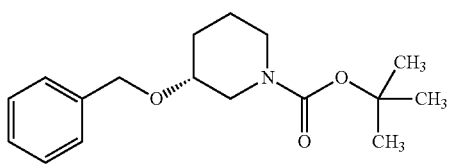

Dissolve 15 g (74.5 mmol) of tert-butyl(+/−)-3-hydroxypiperidinecarbamate while heating in 86.5 ml of toluene and successively add 11.9 ml of 50% sodium hydroxide solution (447 mmol), 2.53 g (7.5 mmol) of tetra-n-butylammonium hydrogen sulphate and 11.5 ml (96.9 mmol) of benzyl bromide. Stir the biphasic reaction mixture vigorously at 70° C. for 4 h. After cooling, add water and neutralize with conc. hydrochloric acid. Remove the organic phase, dry it over sodium sulphate and concentrate it under reduced pressure. Purify the crude product by chromatography on silica gel (eluent: cyclohexane/ethyl acetate 30:1→10:1). 16.21 g of the target product are obtained (74.6% of theory).
  LC-MS (Method 3): R$_f$=2.64 min.; m/z=293 (M+H)$^+$
  $^1$H-NMR (400 MHz, DMSO-d$_6$): δ=7.38-7.24 (m, 5H), 4.53 (dd, 2H), 3.43-3.35 (m, 2H), 3.30-3.18 (m, 2H), 1.84 (br. s, 1H), 1.71-1.48 (m, 4H), 1.36 (s, 9H).

Example 74A and Example 75A tert-Butyl(−)-(3R)-3-(benzyloxy)piperidinecarbamate (Enantiomer 1)

and tert-Butyl(+)-(3S)-3-(benzyloxy)piperidinecarbamate (Enantiomer 2)

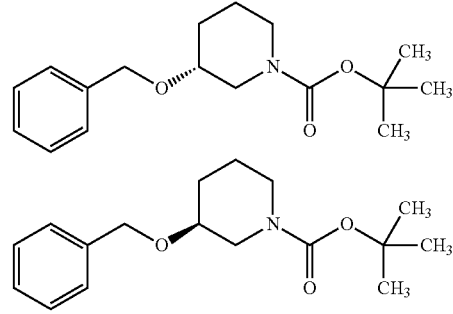

Separate 16.0 g (54.9 mmol) of tert-butyl(+/−)-3-(benzyloxy)piperidinecarbamate into the enantiomers by chromatography on chiral phase [column: Daicel Chiralpak AS-H, 5 μm, 250 mm×20 mm; flow rate: 15 ml/min; temperature: 28° C.; eluent: isohexane/2-propanol 95:5].
Enantiomer 1:
  Yield: 7.40 g (49.3% of theory)
  [α]$_D^{20}$=−5.8°, c=0.635, CHCl$_3$
  LC-MS (Method 3): R$^t$=2.65 min; m/z=292 (M+H)$^+$
  $^1$H-NMR (400 MHz, DMSO-d$_6$): δ=7.49-7.23 (m, 5H), 4.60-4.45 (m, 2H), 3.42-3.38 (m, 2H), 1.82 (br. s, 1H), 1.70-1.48 (m, 2H), 1.34 (s, 9H), 1.40-1.26 (m, 4H).
Enantiomer 2:
  Yield: 6.50 g (43.3% of theory)
  [α]$_D^{20}$=+6.0°, c=1.045, CHCl$_3$
  LC-MS (Method 3): R$^t$=2.65 min; m/z=292 (M+H)$^+$
  $^1$H-NMR (400 MHz, DMSO-d$_6$): δ=7.49-7.23 (m, 5H), 4.60-4.45 (m, 2H), 3.42-3.38 (m, 2H), 1.82 (br. s, 1H), 1.70-1.48 (m, 2H), 1.34 (s, 9H), 1.40-1.26 (m, 4H).

Example 76A (+)-4-[(3R)-3-(Benzyloxy)piperidin-1-yl]butanoic acid methyl ester

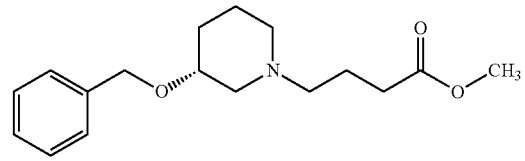

At RT, add one drop of water and 7.7 ml of trifluoroacetic acid to a solution of 3.025 g (10.38 mmol) of tert-butyl(+)-(3S)-3-(benzyloxy)piperidinecarbamate in 14.4 ml of dichloromethane. Stir the mixture for 1 h and then dilute with water and dichloromethane. After phase separation, wash the organic phase with satd. sodium chloride solution and satd. sodium hydrogencarbonate solution, dry over sodium sulphate and concentrate under reduced pressure. 2.12 g of crude product are obtained. Dissolve this without further purification in 37 ml of THF and successively add 5.7 ml (32.9 mmol) of N,N-diisopropylethylamine, 182 mg (1.1 mmol) of potassium iodide and 3.98 g (22 mmol) of 4-bromobutyric acid methyl ester. Then stir the mixture under reflux for 3 h. After cooling, dilute with dichloromethane, wash successively with water, satd. ammonium chloride solution and satd. sodium chloride solution, dry the organic phase over sodium sulphate and concentrate under reduced pressure. After purification by preparative RP-HPLC (eluent: acetonitrile/water), 2.0 g of the target product are isolated from the residue (62.6% of theory over the two stages).

$[\alpha]_D^{20}$=+1.3°, c=0.51, CHCl$_3$

LC-MS (Method 8): R$_t$=0.89 min; m/z=292 (M+H)$^+$ $^1$H-NMR (400 MHz, DMSO-d$_6$): δ=7.38-7.23 (m, 5H), 4.51 (s, 2H), 3.59 (s, 2H), 3.45-3.31 (m, 1H), 3.00-2.90 (m, 1H), 2.69-2.56 (m, 1H), 2.37-2.19 (m, 5H), 1.99-1.80 (m, 3H), 1.70-1.60 (m, 3H), 1.44-1.30 (m, 1H), 1.22-1.10 (m, 1H).

Example 77A (−)-4-[(3R)-3-Hydroxypiperidin-1-yl]butanoic acid methyl ester

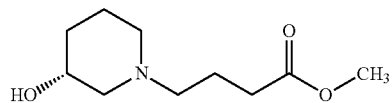

Add approx. 200 mg of 10% Pd/C at RT to a solution of 2.0 g (6.86 mmol) of (+)-4-[(3R)-3-(benzyloxy)piperidin-1-yl]butanoic acid methyl ester in 15 ml of acetic acid. The suspension is stirred vigorously at RT overnight under a hydrogen atmosphere (standard pressure). The reaction mixture is then filtered through Celite, the filter residue is washed with dichloromethane and the filtrate is concentrated under reduced pressure. The residue is taken up in dichloromethane, washed with satd. sodium hydrogencarbonate solution, dried over sodium sulphate and concentrated under reduced pressure. 833.9 mg (60.4% of theory) of the target compound are obtained.

$[\alpha]_D^{20}$=+6.9°, c=0.57, CHCl$_3$

GC-MS (Method 9): R$_t$=5.20 min; m/z=202 (M+H)$^+$ $^1$H-NMR (400 MHz, DMSO-d$_6$): δ=4.54 (br. s, 1H), 3.60 (s, 3H), 3.48-3.38 (m, 1H), 2.81-2.71 (m, 1H), 2.65-2.56 (m, 1H), 2.32-2.15 (m, 4H), 1.81-1.70 (m, 2H), 1.70-1.52 (m, 4H), 1.42-1.30 (m, 1H), 1.10-0.98 (m, 1H).

Example 78A tert-Butyl rac-3-[(5-bromo-6-phenylfuro[2,3-d]pyrimidin-4-yl)oxy]-1-piperidinecarbamate

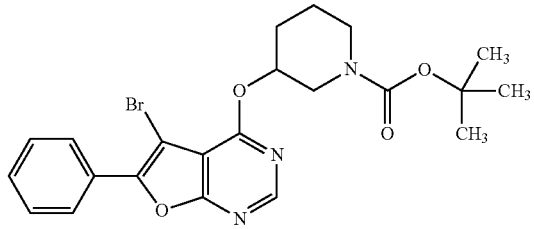

Dissolve 1.1 g (3.55 mmol) of 5-bromo-4-chloro-6-phenylfuro[2,3-d]pyrimidine at 70° C. in 20 ml of toluene and 10 ml of 1,2-dimethoxyethane. Add 2.84 g of 50% sodium hydroxide solution (35.5 mmol), 120.6 mg (0.26 mmol) of tetra-n-butylammonium hydrogen sulphate and 1.79 g (8.88 mmol) of 1-tert-butoxycarbonyl-3-hydroxypiperidine, and then stir the reaction mixture vigorously at 70° C. for 1 h. After cooling, add the mixture to water and adjust it to pH approx. 7 with conc. hydrochloric acid. Extract the aqueous phase three times with ethyl acetate, wash the combined organic phases with satd. sodium chloride solution, dry over magnesium sulphate and concentrate under reduced pressure. After purification by chromatography on silica gel (eluent: cyclohexane/ethyl acetate 5:1), 1.06 g of the target compound are isolated from the residue (62.9% of theory).

LC-MS (Method 3): R$_t$=3.03 min; m/z=474 (M+H)$^+$ $^1$H-NMR (400 MHz, DMSO-d$_6$): δ=8.66 (s, 1H), 8.07 (d, 2H), 7.63-7.51 (m, 3H), 5.33 (br. s, 1H), 4.30 (br. d, 1H), 4.02-3.92 (m, 1H), 2.10-1.90 (m, 3H), 1.60-1.50 (m, 1H), 1.34 (s, 2H), 0.92 (s, 9H).

Example 79A rac-5-Bromo-6-phenyl-4-(piperidin-3-yloxy)furo[2,3-d]pyrimidine

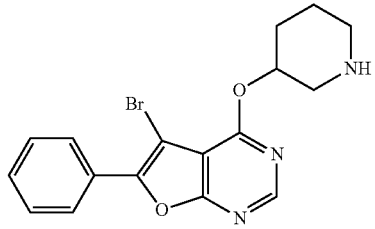

Add a total of 3.4 ml of TFA in several portions at RT to a solution of 1.05 g (2.21 mmol) of tert-butyl rac-3-[(5-bromo-6-phenylfuro[2,3-d]pyrimidin-4-yl)oxy]-1-piperidinecarbamate in 2 ml of dichloromethane, and stir at RT for 2 h. Then dilute with dichloromethane, add satd. sodium hydrogencarbonate solution cautiously to the solution and then wash twice with satd. sodium hydrogencarbonate solution. Dry the organic phase over magnesium sulphate and concentrate under reduced pressure. Stir the oily residue with methanol, filter off the precipitated solid with suction and wash with methanol. Combine mother liquor and wash solution, concentrate under reduced pressure and stir again with a little methanol. Filter off the resulting crystals with suction, wash with methanol and combine with the first crystal fraction. A total of 550 mg (66.4% of theory) of the target compound are obtained.

LC-MS (Method 6): R$_t$=1.61 min; m/z=374 (M+H)$^+$ $^1$H-NMR (400 MHz, DMSO-d$_6$): δ=8.60 (s, 1H), 8.09 (d, 2H), 7.64-7.51 (m, 3H), 5.29-5.20 (m, 1H), 3.15 (dd, 1H), 2.80-2.70 (m, 2H), 2.65-2.57 (m, 1H), 2.21-2.08 (m, 2H), 1.82-1.68 (m, 2H), 1.56-1.43 (m, 1H).

Example 80A (+/−)-4-{3-[(5-Bromo-6-phenylfuro[2,3-d]pyrimidin-4-yl)oxy]piperidin-1-yl}butanoic acid methyl ester

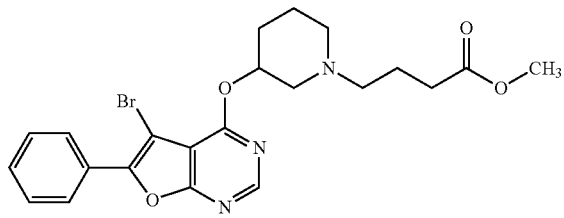

Heat a mixture of 550 mg (1.47 mmol) of rac-5-bromo-6-phenyl-4-(piperidin-3-yloxy)furo[2,3-d]-pyrimidine, 532 mg (2.94 mmol) of 4-bromobutyric acid methyl ester, 24.4 mg (0.147 mmol) of potassium iodide and 0.77 ml (4.41 mmol) of N,N-diisopropylethylamine in 1.5 ml of THF under reflux for 2 h. After cooling, dilute with dichloromethane and add to water. After phase separation, extract the aqueous phase with dichloromethane. Combine the organic phases, wash with satd. sodium hydrogencarbonate solution, dry over magnesium sulphate and concentrate under reduced pressure. From the residue, after purification by preparative RP-HPLC (eluent: acetonitrile/water), 780 mg of the target product are isolated, which are used without further purification.

LC-MS (Method 3): $R^t$=1.62 min; m/z=474 (M+H)$^+$ $^1$H-NMR (400 MHz, DMSO-$d_6$): δ=8.61 (s, 1H), 8.09 (d, 2H), 7.62-7.51 (m, 3H), 5.39-5.30 (m, 1H), 3.52 (s, 3H), 2.90 (d, 1H), 2.60-2.52 (m, 1H), 2.47-2.39 (m, 1H), 2.38-2.28 (m, 4H), 2.26-2.19 (m, 1H), 2.19-2.00 (m, 1H), 1.90-1.80 (m, 1H), 1.70-1.51 (m, 4H).

Example 81A and Example 82A (−)-4-{(3R)-3-[(5-Bromo-6-phenylfuro[2,3-d]pyrimidin-4-yl)oxy]piperidin-1-yl}butanoic acid methyl ester (Enantiomer 1)

and (+)-4-{(3S)-3-[(5-Bromo-6-phenylfuro[2,3-d]pyrimidin-4-yl)oxy]piperidin-1-yl}butanoic acid methyl ester (Enantiomer 2)

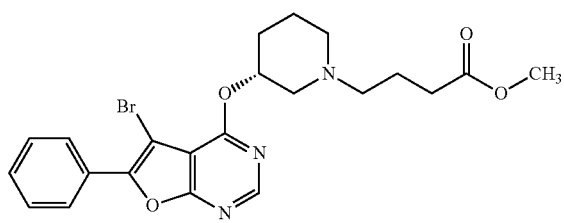

-continued

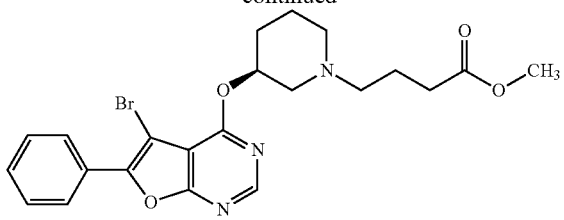

Separate 780 mg (1.64 mmol) of (+/−)-3-[(5-bromo-6-phenylfuro[2,3-d]pyrimidin-4-yl)oxy]-piperidin-1-yl}butanoic acid methyl ester into the enantiomers by chromatography on chiral phase [column: Daicel Chiralpak AS-H, 5 μm, 250 mm×20 mm; flow rate: 15 ml/min; temperature: 28° C.; eluent: isohexane/2-propanol (+0.2% diethylamine) 80:20].

Enantiomer 1:
Yield: 350 mg (44.8% of theory)
[α]$_D^{20}$=−43.1°, c=0.505, CHCl$_3$
LC-MS (Method 3): $R_t$=1.59 min.; m/z=475 (M+H)$^+$
$^1$H-NMR (400 MHz, DMSO-$d_6$): δ=8.62 (s, 1H), 8.08 (d, 2H), 7.64-7.51 (m, 3H), 5.38-5.30 (m, 1H), 3.53 (s, 3H), 2.94-2.88 (m, 1H), 2.47-2.40 (m, 1H), 2.38-2.29 (m, 4H), 2.25-2.19 (m, 1H), 2.10-2.00 (m, 1H), 1.90-1.80 (m, 1H), 1.70-1.52 (m, 4H), 0.90-0.79 (m, 1H).

Enantiomer 2:
Yield: 320 mg (41.0% of theory)
[α]$_D^{20}$=+42.2°, c=0.53, CHCl$_3$
LC-MS (Method 3): $R_t$=1.59 min.; m/z=475 (M+H)$^+$
$^1$H-NMR (400 MHz, DMSO-$d_6$): δ=8.62 (s, 1H), 8.08 (d, 2H), 7.64-7.51 (m, 3H), 5.38-5.30 (m, 1H), 3.53 (s, 3H), 2.94-2.88 (m, 1H), 2.47-2.40 (m, 1H), 2.38-2.29 (m, 4H), 2.25-2.19 (m, 1H), 2.10-2.00 (m, 1H), 1.90-1.80 (m, 1H), 1.70-1.52 (m, 4H), 0.90-0.79 (m, 1H).

Example 83A cis/trans-3-[(5-Bromo-6-phenylfuro[2,3-d]pyrimidin-4-yl)oxy]cyclohexanol

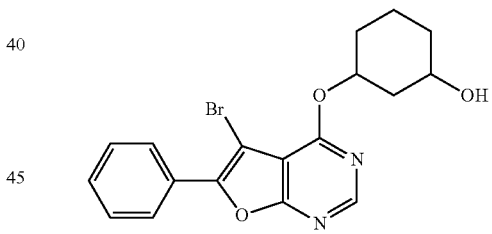

Dissolve 1.1 g (8.88 mmol) of cis/trans-cyclohexanediol at 70° C. in 10 ml of toluene and 5 ml of 1,2-dimethoxyethane and add 2.84 g of 50% sodium hydroxide solution (35.5 mmol). Add water until a biphasic reaction mixture forms. Add 120.6 mg (3.55 mmol) of tetra-n-butylammonium hydrogen sulphate and 1.10 g (3.55 mmol) of 5-bromo-4-chloro-6-phenylfuro[2,3-d]pyrimidine, and stir the mixture vigorously at 70° C. for 1 h. After cooling, add the reaction mixture to water and neutralize with conc. hydrochloric acid. Extract the aqueous phase three times with ethyl acetate. Combine the organic phases, wash with satd. sodium hydrogen sulphate solution, dry over magnesium sulphate and concentrate under reduced pressure. Purify the residue by chromatography on silica gel (eluent: cyclohexane/ethyl acetate 5:1→3:1). 0.63 g of the title compound is obtained (45.6% of theory).

LC-MS (Method 3): $R_t$=2.47 min; m/z=389 (M+H)$^+$
$^1$H-NMR (400 MHz, DMSO-$d_6$): δ=8.61 (s, 1H), 8.03 (d, 2H), 7.63-7.51 (m, 3H), 5.30-5.20 (m, 1H), 4.79 (d, 1H), 3.62-3.52 (m, 1H), 2.46-2.38 (m, 1H), 2.20-2.10 (m, 1H), 1.90-1.66 (m, 3H), 1.47-1.29 (m, 2H), 1.20-1.09 (m, 1H).

Example 84A cis/trans-({3-[(5-Bromo-6-phenylfuro[2,3-d]pyrimidin-4-yl)oxy]cyclohexyl}oxy)acetic acid tert-butyl ester

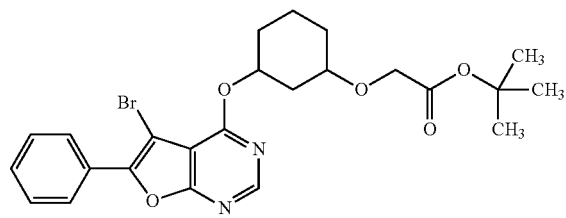

Add a solution of 625 mg (1.606 mmol) of cis/trans-3-[(5-bromo-6-phenylfuro[2,3-d]pyrimidin-4-yl)oxy]cyclohexanol in 3 ml of toluene to a mixture of 2 ml of toluene and 1.28 g of 50% sodium hydroxide solution (16.05 mmol). Then add 54.5 mg (0.16 mmol) of tetra-n-butylammonium hydrogen sulphate and 626 mg (3.21 mmol) of bromoacetic acid tert-butyl ester to the biphasic mixture, and stir the reaction mixture vigorously at 60° C. for 3 h. Then add to water and neutralize with conc. hydrochloric acid. Extract the aqueous phase three times with ethyl acetate, combine the organic phases and dry over magnesium sulphate. The residue is purified by chromatography on silica gel (eluent: cyclohexane/ethyl acetate 10:1→8:1). 592 mg of the target compound are obtained (73.2% of theory).

LC-MS (Method 8): $R_t$=3.36 min; m/z=503 (M+H)$^+$ $^1$H-NMR (400 MHz, DMSO-d$_6$): δ=8.61 (s, 1H), 8.10-8.04 (m, 2H), 7.63-7.51 (m, 3H), 5.30-5.20 (m, 1H), 4.00 (s, 2H), 3.52-3.42 (m, 1H), 2.20-2.10 (m, 1H), 2.06-1.98 (m, 1H), 1.88-1.78 (m, 1H), 1.50-1.12 (m, 14H).

Example 85A and Example 86A (+)-({3-[(5-Bromo-6-phenylfuro[2,3-d]pyrimidin-4-yl)oxy]cyclohexyloxy}acetic acid tert-butyl ester (Enantiomer 1)

and (−)-({3-[(5-Bromo-6-phenylfuro[2,3-d]pyrimidin-4-yl)oxy]cyclohexyl}oxy)acetic acid tert-butyl ester (Enantiomer 2)

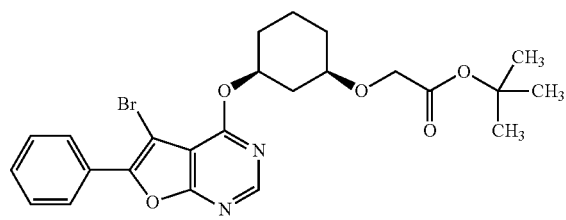

-continued

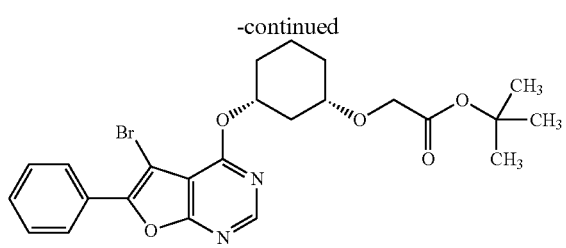

Separate 780 mg (1.64 mmol) of (+/−)-({3-[(5-bromo-6-phenylfuro[2,3-d]pyrimidin-4-yl)oxy]-cyclohexyl}oxy)acetic acid tert-butyl ester into the enantiomers by chromatography on chiral phase [column: Daicel Chiralpak AS-H, 5 μm, 250 mm×20 mm; flow rate: 15 ml/min; temperature: 28° C.; eluent: isohexane/2-propanol (+0.2% diethylamine) 80:20].

Enantiomer 1:
Yield: 159 mg (20.4% of theory)
$[\alpha]_D^{20}$=+64.5°, c=0.495, CHCl$_3$
LC-MS (Method 8): $R_t$=3.37 min; m/z=503 (M+H)$^+$
$^1$H-NMR (400 MHz, DMSO-d$_6$): δ=8.61 (s, 1H), 8.10 (d, 2H), 7.65-7.50 (m, 3H), 5.30-5.20 (m, 1H), 4.01 (s, 2H), 3.53-3.42 (m, 1H), 2.20-2.10 (m, 1H), 2.06-1.98 (m, 1H), 1.88-1.80 (m, 1H), 1.41 (s, 9H), 1.50-1.23 (m, 5H).

Enantiomer 2:
Yield: 320 mg (41.0% of theory)
$[\alpha]_D^{20}$=−68.9°, c=0.54, CHCl$_3$
LC-MS (Method 8): $R^t$=3.37 min; m/z=503 (M+H)$^+$
$^1$H-NMR (400 MHz, DMSO-d$_6$): δ=8.61 (s, 1H), 8.10 (d, 2H), 7.65-7.50 (m, 3H), 5.30-5.20 (m, 1H), 4.01 (s, 2H), 3.53-3.42 (m, 1H), 2.20-2.10 (m, 1H), 2.06-1.98 (m, 1H), 1.88-1.80 (m, 1H), 1.41 (s, 9H), 1.50-1.23 (m, 5H).

Example 87A (+/−)-cis/trans-3-{[5-(4-Methoxyphenyl)-6-phenylfuro[2,3-d]pyrimidin-4-yl]oxy}cyclopentanol

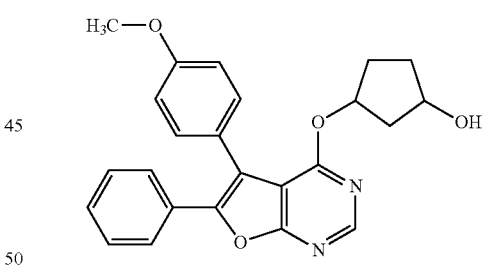

Add 1,2-dimethoxyethane to 10 g (29.7 mmol) of 4-chloro-5-(4-methoxyphenyl)-6-phenylfuro[2,3-d]pyrimidine in 150 ml of toluene at 70° C. until a homogeneous solution forms. Then add 23.75 g (296.9 mmol) of 50% sodium hydroxide solution and 2.5 ml of water, and, with vigorous stirring, 1.0 g (2.97 mmol) of tetra-n-butylammonium hydrogen sulphate and 4.55 g (44.54 mmol) of (+/−)-cis/trans-1,3-cyclopentanediol, and stir the reaction mixture at 70° C. for 4 h. After cooling, add the mixture to water and neutralize with conc. hydrochloric acid. Extract three times with dichloromethane, wash the combined organic phases with satd. sodium chloride solution, dry over magnesium sulphate and concentrate under reduced pressure. From the residue, chromatography on silica gel (eluent: cyclohexane/ethyl acetate 4:1→2:1) affords contaminated product. Crystallize this crude product by stirring with methanol. Filter off and dry the resulting crystals (Yield:

690 mg). Concentrate the mother liquor under reduced pressure and purify by preparative RP-HPLC. In this way, a further 1230 mg of the target product are obtained. In total, 1920 mg of the target compound are obtained (16.1% of theory).

LC-MS (Method 8): $R_t$=2.64 min; m/z=403 (M+H)$^+$ $^1$H-NMR (400 MHz, DMSO-d$_6$): δ=8.59 (s, 1H), 7.57 (d, 2H), 7.42-7.33 (m, 5H), 7.00 (d, 2H), 5.64-5.59 (m, 1H), 4.60 (d, 1H), 4.15-4.09 (m, 1H), 3.82 (s, 3H), 2.15-2.03 (m, 1H), 1.92-1.84 (m, 1H), 1.83-1.74 (m, 1H), 1.73-1.62 (m, 1H), 1.61-1.51 (m, 1H), 1.50-0.91 (m, 1H).

Example 88A (+/−)-cis/trans-[(3-Hydroxycyclopentyl)oxy]acetic acid tert-butyl ester

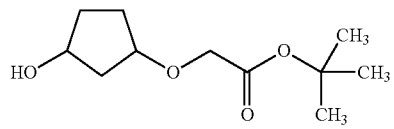

Dissolve 2.5 g (24.5 mmol) of cis/trans-cyclopentanediol in 5 ml of THF and, at 0° C., add 16.3 ml (16.3 mmol) of phosphazene base P4-t-Bu (approx. 1M solution in hexane). After 10 min, add the resulting solution dropwise to an ice-cooled solution of 4.77 g (24.5 mmol) of bromoacetic acid tert-butyl ester. After the end of the addition, warm to RT and stir the mixture overnight. Remove fractions of the THF under reduced pressure, dilute with ethyl acetate and wash successively with 1N hydrochloric acid, pH 7 buffer solution and satd. sodium chloride solution, dry over sodium sulphate and concentrate under reduced pressure. From the residue, isolate the product by chromatography on silica gel (eluent: cyclohexane/ethyl acetate 10:1→2:1). 631.4 mg (10.7% of theory) of the target compound are obtained as a cis/trans mixture.

GC-MS (Method 10): $R_t$=7.35 min (cis), 7.21 min (trans); m/z=217 (M+H)$^+$ $^1$H-NMR (400 MHz, DMSO-d$_6$): δ=4.52 (d, 0.25H, trans), 4.48 (d, 0.75H, cis), 4.20-4.13 (m, 1H), 4.07-3.98 (m, 1H), 3.90 (d, 2H), 2.14-1.49 (m, 5H), 1.41 (s, 9H).

Example 89A (+/−)-cis/trans-[(3-Aminocyclopentyl)oxy]acetic acid tert-butyl ester

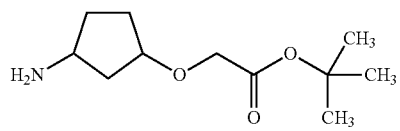

Stage a):

Dissolve 620 mg (2.87 mmol) of (+/−)-cis/trans-[(3-hydroxycyclopentyl)oxy]acetic acid tert-butyl ester and 1.2 ml (8.6 mmol) of triethylamine in 6.5 ml of dichloromethane and cool to 0° C. Add 0.28 ml (3.58 mmol) of methanesulphonyl chloride dropwise. Warm the mixture to RT over 2 h and then dilute with dichloromethane. Wash the organic phase successively with water, 1N hydrochloric acid, satd. sodium hydrogencarbonate solution and satd. sodium chloride solution, dry over magnesium sulphate and concentrate under reduced pressure. 849 mg of the mesylate are obtained, which are reacted further directly.

Stage b):

Dissolve 849 mg of the mesylate obtained above at RT in 10 ml of DMF and add 1125 mg (17.3 mmol) of sodium azide. Stir the suspension vigorously at 70° C. overnight and then, after cooling, add to water. Extract three times with ethyl acetate, wash the combined organic phases with saturated sodium chloride solution, dry over magnesium sulphate and concentrate under reduced pressure. 695 mg of the azide are obtained, which are reacted further directly.

Stage c):

Dissolve 695 mg of the azide obtained above in 3 ml of ethanol and 0.3 ml of water, add 70 mg of palladium on activated carbon and stir under a hydrogen atmosphere (standard pressure) at RT for 4 h. Remove the catalyst by filtration through kieselguhr, concentrate the filtrate under reduced pressure and dry the residue under high vacuum. 560 mg of the title compound are obtained, which are used without further purification.

Example 90A cis-(+/−)-{[(4-Hydroxycyclopent-2-en-1-yl]oxy}acetic acid tert-butyl ester

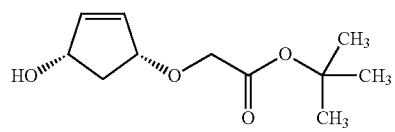

Dissolve 2.0 g (20 mmol) of cis-4-cyclopentene-1,3-diol in 1.5 ml of DMF and 15 ml of THF and, at 0° C., add 799 mg (60% strength, approx. 20 mmol) of sodium hydride in portions. After the end of the addition, warm the mixture to RT and stir at RT for a further 1 h, before adding 2.7 ml (18.2 mmol) of bromoacetic acid tert-butyl ester. Then stir the mixture at RT overnight. Then add water, extract with dichloromethane, wash the organic phase with satd. sodium chloride solution, concentrate under reduced pressure and dry the residue under high vacuum. Isolate the product by chromatography on silica gel (eluent: cyclohexane/ethyl acetate 5:1→2:1). 1.10 g (25.6% of theory) of the target compound are obtained.

GC-MS (Method 11): $R_t$=7.19 min; m/z=233 (M+H)$^+$ $^1$H-NMR (400 MHz, DMSO-d$_6$): δ=5.90 (dt, 2H), 5.00 (d, 1H), 4.44 (q, 1H), 4.35 (t, 1H), 3.99 (s, 2H), 2.60 (dd, 1H), 1.62 (s, 9H), 1.37 (dd, 1H).

Example 91A cis-(−)-{[(1R,4S)-4-Acetoxycyclopent-2-en-1-yl]oxy}acetic acid tert-butyl ester

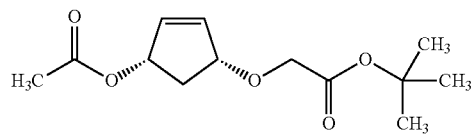

Initially charge 1.0 g (7.04 mmol) of (1R,4S)-cis-4-acetoxy-2-cyclopenten-1-ol in 5 ml of dichloromethane and, under argon, add 155 mg (0.25 mmol) of rhodium(II) acetate (as a dimer). Then add, at RT, 1.56 g (90% strength, approx. 9.84 mmol) of tert-butyl diazoacetate dropwise to the vigorously stirred suspension. After 30 min, add a further 0.3 eq. of tert-butyl diazoacetate dropwise and stir the reaction mixture at RT for a further 30 min. Then dilute with dichloromethane and wash three times with water and satd. sodium chloride solution. Dry over magnesium sulphate and concentrate under reduced pressure. Isolate the product from the residue by chromatography on silica gel (eluent: cyclohexane/ethyl acetate 8:1). 1.33 g of the target compound are obtained (73.7% of theory).

$[\alpha]_D^{20}$=−23°, c=0.55, CHCl$_3$

GC-MS (Method 9): R$_t$=5.49 min; m/z=257 (M+H)$^+$ $^1$H-NMR (400 MHz, DMSO-d$_6$): δ=6.18 (dd, 1H), 5.97 (dd, 1H), 5.41-5.36 (m, 1H), 4.48-4.41 (m, 1H), 4.01 (s, 2H), 2.72 (dt, 1H), 2.10-1.98 (m, 3H), 1.55 (td, 1H), 1.43 (s, 9H).

Example 92A cis-(+)-{[(4-Hydroxycyclopent-2-en-1-yl]oxy}acetic acid tert-butyl ester

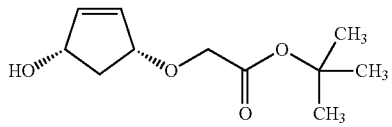

Dissolve 1.30 g (5.07 mmol) of cis-(−)-{[(1R,4S)-4-acetoxycyclopent-2-en-1-yl]oxy}acetic acid tert-butyl ester in 3 ml of THF and 2 ml of methanol and, at RT, add 5.6 ml of 1N sodium hydroxide solution dropwise. After 10 min, dilute the mixture with water and extract three times with dichloromethane. Combine the organic phases, wash with satd. sodium hydrogencarbonate solution and satd. sodium chloride solution, dry over magnesium sulphate and concentrate under reduced pressure. 780 mg of the target compound are obtained (71.8% of theory).

$[\alpha]_D^{20}$=+6.5°, c=0.515, CHCl$_3$

GC-MS (Method 9): R$_t$=4.93 min; m/z=232 (M+NH$_4$)$^+$ $^1$H-NMR (400 MHz, DMSO-d$_6$): δ=5.93-5.89 (m, 2H), 5.00 (d, 1H), 4.45 (q, 1H), 4.36 (t, 1H), 3.99 (s, 2H), 2.65-2.56 (m, 1H), 1.42 (s, 9H), 1.40-1.31 (m, 1H).

Example 93A cis-(+)-{[(1S,3R)-3-Hydroxycyclopentyl]oxy}acetic acid tert-butyl ester

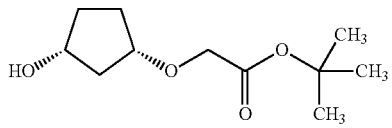

Dissolve 350 mg (1.63 mmol) of cis-(+)-{[(4-hydroxycyclopent-2-en-1-yl)oxy}acetic acid tert-butyl ester in 7 ml of ethanol and add 35 mg (0.163 mmol) of platinum(IV) oxide. Stir the suspension vigorously under a hydrogen atmosphere (standard pressure) at RT for 4 h. Then filter the reaction mixture through kieselguhr. Wash with ethanol, combine all filtrates and concentrate under reduced pressure. 278.8 mg of the target compound are obtained (81.5% of theory).

$[\alpha]_D^{20}$=+6.8°, c=0.51, CHCl$_3$

GC-MS (Method 9): R$_t$=4.93 min; m/z=234 (M+NH$_4$)$^+$ $^1$H-NMR (400 MHz, DMSO-d$_6$): δ=4.50 (d, 1H), 4.01-3.96 (m, 1H), 3.90 (s, 2H), 3.88-3.81 (m, 1H), 2.14-2.05 (m, 2H), 1.71-0.96 (m, 4H), 1.40 (s, 9H).

Example 94A cis-(+)-{[(1S,4R)-4-Acetoxycyclopent-2-en-1-yl]oxy}acetic acid tert-butyl ester

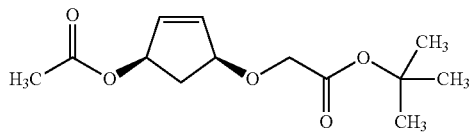

Add 248.7 mg (0.56 mmol) of rhodium(II) acetate (as a dimer) to a solution of 1.6 g (11.26 mmol) of (1R,3S)-(+)-cis-4-cyclopentene-1,3-diol 1-acetate in 9.6 ml of dichloromethane. Stir the resulting suspension vigorously and add 2.49 g (90% strength, approx. 15.8 mmol) of tert-butyl diazoacetate dropwise. After the addition has ended, stir at RT for 2 h. Then add a further 0.5 eq. of tert-butyl diazoacetate and stir the mixture at RT for a further hour. After concentrating under reduced pressure, purify the residue by chromatography on silica gel (eluent: cyclohexane/ethyl acetate 10:1). 1.96 g of the target compound are obtained (68% of theory).

$[\alpha]_D^{20}$=+27.2°, c=0.59, CHCl$_3$

LC-MS (Method 12): R$_t$=2.06 min; m/z=257 (M+H)$^+$ $^1$H-NMR (400 MHz, DMSO-d$_6$): δ=6.20-6.15 (m, 1H), 6.00-5.94 (m, 1H), 5.41-5.37 (m, 1H), 4.47-4.41 (m, 1H), 4.00 (s, 2H), 2.79-2.70 (m, 1H), 2.00 (s, 3H), 1.58-1.50 (td, 1H), 1.42 (s, 9H).

Example 95A cis-(−)-{[(1S,4R)-4-Hydroxycyclopent-2-en-1-yl]oxy}acetic acid tert-butyl ester

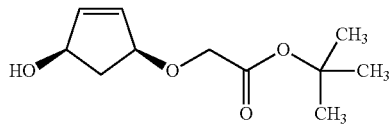

Dissolve 1000 mg (3.9 mmol) of cis-(+)-{[(1S,4R)-4-acetoxycyclopent-2-en-1-yl]oxy}acetic acid tert-butyl ester in 3 ml of THF and 2 ml of methanol and, at RT, add 4.7 ml of 1N sodium hydroxide solution dropwise. After 10 min, dilute the mixture with water and extract three times with dichloromethane. Combine the organic phases, wash with satd. sodium hydrogencarbonate solution and satd. sodium chloride solution, dry over magnesium sulphate and concentrate under reduced pressure. 570 mg of the target compound are obtained (68.2% of theory).

$[\alpha]_D^{20}$=−9.3°, c=0.515, CHCl$_3$

GC-MS (Method 9): R$_t$=4.93 min; m/z=232 (M+NH$_4$)$^+$

¹H-NMR (400 MHz, DMSO-d₆): δ=6.39-5.92 (m, 2H), 5.00 (d, 1H), 4.45 (q, 1H), 4.35 (t, 1H), 3.99 (s, 2H), 2.64-2.56 (m, 1H), 1.42 (s, 9H), 1.40-1.31 (m, 1H).

Example 96A cis-(−)-{[(1R,3S)-3-Hydroxycyclopentyl]oxy}acetic acid tert-butyl ester

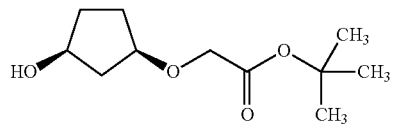

Dissolve 1170 mg (5.46 mmol) of cis-(−)-{[(1S,4R)-4-hydroxycyclopent-2-en-1-yl]oxy}acetic acid tert-butyl ester in 10 ml of ethanol and add 25 mg of platinum(IV) oxide. Stir the suspension vigorously under a hydrogen atmosphere (standard pressure) at RT for 4 h. Then filter the reaction mixture through kieselguhr. Wash twice with a mixture of ethanol and water; combine all filtrates and concentrate under reduced pressure. 940 mg of the target compound are obtained (79.9% of theory).

$[\alpha]_D^{20}$=−7.4°, c=0.475, CHCl₃

GC-MS (Method 9): R$^t$=3.88 min; m/z=234 (M+NH₄)⁺

¹H-NMR (400 MHz, DMSO-d₆): δ=4.50 (d, 1H), 4.00-3.91 (m, 2H), 3.90 (s, 2H), 3.89-3.80 (m, 2H), 1.71-1.45 (m, 6H), 1.40 (s, 9H).

Example 97A trans-(−)-4-(2-tert-Butoxy-2-oxoethoxy)cyclopent-2-en-1-yl 4-nitrobenzoate

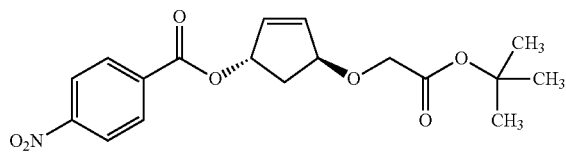

Successively add 881.4 mg (3.36 mmol) of triphenylphosphine, 561.6 mg (3.36 mmol) of 4-nitrobenzoic acid and, dropwise, 1.46 g (approx. 3.36 mmol) of a 40% solution of diethyl azodicarboxylate in toluene at RT under argon to a solution of 400 mg (1.87 mmol) of cis-(−)-{[(1R,3S)-3-hydroxycyclopentyl]oxy}acetic acid tert-butyl ester in 1.8 ml of THF. After 3 h, add a further 0.5 eq. of triphenylphosphine and 0.5 eq. of diethyl azodicarboxylate in toluene and stir the reaction mixture at RT for a further 2 h. Then add the reaction mixture to water and extract three times with dichloromethane. Dry the combined organic phases over magnesium sulphate and concentrate under reduced pressure. From the residue, isolate the product by chromatography on silica gel (eluent: cyclohexane/ethyl acetate 8:1→3:1). 555 mg (81.8% of theory) of the target compound are obtained.

$[\alpha]_D^{20}$=−169.8°, c=0.48, CHCl₃

LC-MS (Method 12): R$^t$=2.71 min; m/z=381 (M+NH₄)⁺

¹H-NMR (400 MHz, DMSO-d₆): δ=8.35 (d, 2H), 8.19 (d, 2H), 6.39-6.34 (m, 1H), 6.20-6.17 (m, 1H), 6.00-5.95 (m, 1H), 4.88-4.81 (m, 1H), 4.04 (s, 2H), 2.32-2.19 (m, 2H), 1.43 (s, 9H).

Example 98A trans-(−)-{[(4-Hydroxycyclopent-2-en-1-yl]oxy}acetic acid tert-butyl ester

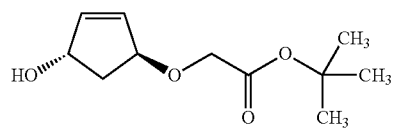

Dissolve 300 mg (0.83 mmol) of trans-(−)-4-(2-tert-butoxy-2-oxoethoxy)cyclopent-2-en-1-yl 4-nitrobenzoate in 2.4 ml of THF and 0.6 ml of methanol, and, at RT, add 0.9 ml of 1N sodium hydroxide solution. After 30 min, add the reaction mixture to water and extract three times with dichloromethane. Combine the organic phases and wash successively with satd. sodium carbonate, sodium hydrogencarbonate and sodium chloride solution. Dry over magnesium sulphate and concentrate under reduced pressure. 137.3 mg (77.6% of theory) of the target compound are obtained.

$[\alpha]_D^{20}$=−83.1°, c=0.525, CHCl₃

GC-MS (Method 9): R$_t$=5.03 min; m/z=157 (M-C₄H₉)⁺

¹H-NMR (400 MHz, DMSO-d₆): δ=5.97 (s, 2H), 4.81 (d, 1H), 4.79-4.71 (m, 1H), 4.68-4.62 (m, 1H), 3.93 (s, 2H), 2.00-1.93 (m, 1H), 1.80-1.73 (m, 1H), 1.40 (s, 9H).

Example 99A trans-{[4-(1,3-Dioxo-1,3-dihydro-2H-isoindol-2-yl)cyclopent-2-en-1-yl]oxy}acetic acid tert-butyl ester

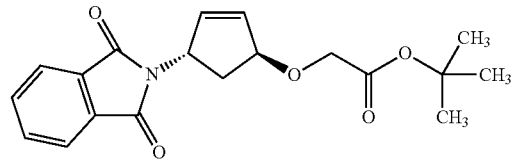

Dissolve 250 mg (1.17 mmol) of cis-(−)-{[(4-hydroxycyclopent-2-en-1-yl]oxy}acetic acid tert-butyl ester in 1.25 ml of THF and, under argon, successively add 309 mg (2.1 mmol) of phthalimide, 550.9 mg (2.1 mmol) of triphenylphosphine and, dropwise, 914 mg (approx. 2.1 mmol) of a 40% solution of diethyl azodicarboxylate in toluene. After 3 h, add a further 0.5 eq. of triphenylphosphine and 0.5 eq. of diethyl azodicarboxylate in toluene, and stir the reaction mixture at RT for a further 2 h. Then add the mixture to water and extract three times with dichloromethane. Dry the combined organic phases over magnesium sulphate and concentrate under reduced pressure. Isolate the product from the residue by chromatography on silica gel (eluent: cyclohexane/ethyl acetate 8:1→3:1). 255 mg (63.7% of theory) of the target compound are obtained.

$[\alpha]_D^{20}$=−256.6°, c=0.545, CHCl₃

LC-MS (Method 3): R$^t$=2.29 min; m/z=361 (M+NH₄)⁺

$^1$H-NMR (400 MHz, DMSO-d$_6$): δ=7.83 (s, 4H), 6.20-6.15 (m, 1H), 5.97-5.90 (m, 1H), 5.38-5.30 (m, 1H), 4.92-4.88 (m, 1H), 4.03 (s, 2H), 2.40-2.30 (m, 1H), 2.19-2.19 (m, 1H), 1.46 (s, 9H).

Example 100A trans-{[(4-Aminocyclopent-2-en-1-yl]oxy}acetic acid tert-butyl ester

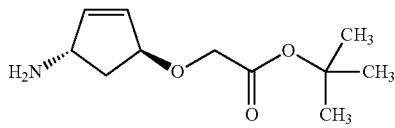

Add 22 µl (0.545 mmol) of hydrazine monohydrate to 120 mg (0.349 mmol) of trans-{[4-(1,3-dioxo-1,3-dihydro-2H-isoindol-2-yl)cyclopent-2-en-1-yl]oxy}acetic acid tert-butyl ester in 0.3 ml of ethanol. Heat the mixture under reflux for 15 min. This forms a voluminous precipitate. After cooling, remove it by filtration and wash it with a little ethanol. Concentrate the filtrate under reduced pressure and use the resulting product (74 mg) without further purification.

GC-MS (Method 9): R$_t$=4.93 min; m/z=214 (M+H)$^+$ $^1$H-NMR (400 MHz, DMSO-d$_6$): δ=5.96-5.90 (m, 1H), 5.89-5.83 (m, 1H), 4.68-4.60 (m, 1H), 4.04-3.85 (m, 4H), 2.07-1.98 (m, 1H), 1.97-1.79 (m, 1H), 1.68-1.57 (m, 1H), 1.41 (s, 9H).

Example 101A 2-(2-Fluorophenyl)-2-hydroxy-1-(4-methoxyphenyl) ethanone

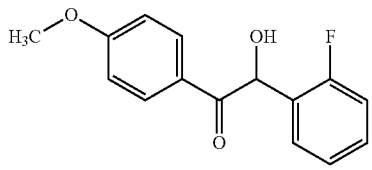

Add 441 ml (1.10 mol) of a 2.5 M n-butyllithium solution in n-hexane dropwise at –78° C. to a solution of 156 ml (1.11 mol) N,N-diisopropylamine in 1937 ml 1,2-dimethoxyethane in such a way that a temperature of –60° C. is not exceeded. After stirring for 15 min at this temperature, add a solution of 236 g (1.00 mol) (4-methoxyphenyl)[(trimethylsilyl)oxy]acetonitrile [N. Kurono, J. Org. Chem. 2005, 16, 6530-6532] in 753 ml 1,2-dimethoxyethane dropwise in the space of 30 min. Next, after stirring for 30 min at this temperature, add a solution of 128 g (1.00 mol) 2-fluorobenzaldehyde in 753 ml 1,2-dimethoxyethane dropwise in the space of 20 min. Leave the reaction mixture to warm to room temperature in 4 h. After adding 3800 ml satd. aqueous ammonium chloride solution, extract with ethyl acetate. Wash the organic phase with satd. ammonium chloride solution, dry over sodium sulphate, filter, and concentrate the filtrate by vacuum evaporation. Add 3800 ml dioxan, 2700 ml methanol and 3120 ml 1 M hydrochloric acid to the residue and stir for 16 h at room temperature. After adding 8000 ml satd. aqueous sodium chloride solution, extract with 4000 ml ethyl acetate. Re-extract the aqueous phase with 2000 ml ethyl acetate. Combine the organic phases and wash with 2000 ml water and 2000 ml satd. sodium chloride solution, dry over sodium sulphate, filter, and concentrate the filtrate by vacuum evaporation. Mix the residue with 600 ml diisopropyl ether and filter. Concentrate the mother liquor by vacuum evaporation. Take up the residue in dichloromethane and purify by flash chromatography on silica gel (solvent: cyclohexane/ethyl acetate 4:1). Mix the product fraction thus obtained with diisopropyl ether/petroleum ether (1:1), filter, and dry under vacuum. 94 g (80% purity, 29% of theor.) of the title compound is obtained.

LC-MS (Method 7): R$_t$=4.59 min; m/z=261 (M+H)$^+$ $^1$H-NMR (400 MHz, CDCl$_3$): δ=7.93-7.91 (m, 2H), 7.28-7.18 (m, 2H), 7.10-7.04 (m, 2H), 6.89-6.86 (m, 2H), 6.19 (d, 1H), 4.69 (s, 1H), 3.82 (s, 3H).

Example 102A

2-Amino-5-(2-fluorophenyl)-4-(4-methoxyphenyl)-3-furonitrile

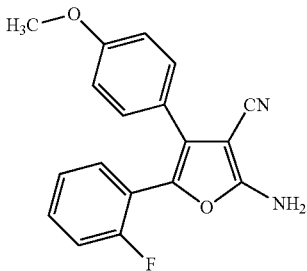

Put 84 g (0.32 mol) 2-(2-fluorophenyl)-2-hydroxy-1-(4-methoxyphenyl)ethanone and 32 g (0.48 mol) malononitrile in 153 ml THF. After stirring for five minutes, add 49 ml (36 g, 0.36 mol) triethylamine, with ice cooling. Stir the reaction mixture for 1 h with ice cooling. Then leave the reaction mixture to warm to room temperature and stir for 4 h at this temperature. After adding 1000 ml ethyl acetate, wash the organic phase five times with 300 ml water, dry over sodium sulphate and filter. Concentrate the filtrate by vacuum evaporation. Take up the residue in dichloromethane and purify by flash chromatography on silica gel (solvent: dichloromethane/methanol 70:1, then cyclohexane/ethyl acetate 2:1). 37 g (0.11 mol) of 2-(2-fluorophenyl)-2-hydroxy-1-(4-methoxyphenyl)ethanone thus recovered is again reacted with 14 g (0.03 mol) malononitrile and 21 ml (15 g, 0.15 mol) triethylamine in 67 ml THF in accordance with the above procedure. A total of 70 g (52% purity, 36% of theor.) of the target compound is obtained.

$^1$H-NMR (400 MHz, CDCl$_3$): δ=7.23-7.11 (m, 4H), 7.03-6.95 (m, 2H), 6.82-6.79 (m, 2H), 4.86 (s, NH$_2$), 3.74 (s, 3H).

Example 103A 6-(2-Fluorophenyl)-5-(4-methoxyphenyl)furo[2,3-d]pyrimidin-4(3H)-one

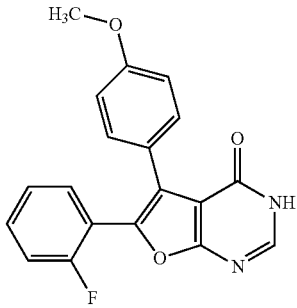

Add 268 ml formic acid dropwise to 436 ml acetic anhydride at 0° C. and stir for 30 min at this temperature. Then add a solution of 70 g (0.12 mol) 2-amino-5-(2-fluorophenyl)-4-(4-methoxyphenyl)-3-furonitrile in 100 ml acetic anhydride and stir the mixture for 24 h at 130° C. After cooling to room temperature, concentrate the mixture by evaporation in an oil-pump vacuum at 50° C. Mix the residue with 250 ml diisopropyl ether for 30 min with ice cooling, filter, wash with 70 ml diisopropyl ether and dry under vacuum. 23.7 g (60% of theor.) of the title compound is obtained.

HPLC (Method 1): $R_t$=4.27 min
MS (DCI): m/z=354 (M+NH$_4$)$^+$
$^1$H-NMR (400 MHz, CDCl$_3$): δ=12.68 (br. s, NH), 8.19 (d, 1H), 7.53-7.45 (m, 2H), 7.34-7.25 (m, 4H), 6.91-6.88 (m, 2H), 3.76 (s, 3H).

Example 104A

4-Chloro-6-(2-fluorophenyl)-5-(4-methoxyphenyl)furo[2,3-d]pyrimidine

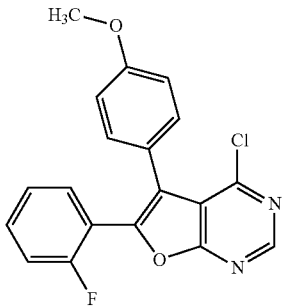

Stir a mixture of 20 g (0.06 mol) 6-(2-fluorophenyl)-5-(4-methoxyphenyl)furo[2,3-d]pyrimidin-4(3H)-one in 78 ml sulpholane and 11 ml (18 g, 0.12 mol) phosphoryl chloride for 1 h at 120° C. After cooling to room temperature, add the reaction solution dropwise to a mixture of 1000 ml water and 100 ml 25% aqueous ammonia solution, stirring vigorously and cooling with ice. Filter off the solid that is precipitated at 10° C. and wash several times with water. Dissolve the solid in 700 ml ethyl acetate again and wash the solution twice with 500 ml water each time. Dry the organic phase over sodium sulphate, filter, and concentrate the filtrate by vacuum evaporation. Mix the residue with 60 ml diisopropyl ether, filter, and dry under vacuum. 18 g (81% of theor.) of the title compound is obtained.

HPLC (Method 1): $R_t$=5.03 min
$^1$H-NMR (400 MHz, DMSO-d$_6$): δ=8.90 (s, 1H), 7.58-7.50 (m, 2H), 7.36-7.27 (m, 4H), 7.01-6.97 (m, 2H), 3.79 (s, 3H).

Example 105A 1-(4-Ethylphenyl)-2-(2-fluorophenyl)-2-hydroxyethanone

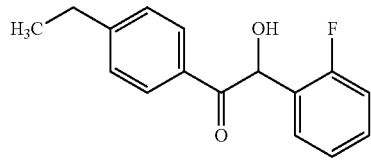

Add 217 ml (0.54 mol) of a 2.5 M n-butyllithium solution in hexane dropwise at −78° C. to a solution of 77 ml (56 g, 0.55 mol) N,N-diisopropylamine in 960 ml 1,2-dimethoxyethane in such a way that the temperature does not exceed −60° C. After stirring for 15 min at this temperature, add a solution of 116 g (0.50 mol) (4-ethylphenyl)[(trimethylsilyl)oxy]acetonitrile [D. S. Dhanoa, J. Med. Chem. 1993, 36 (23), 3738-3742] in 373 ml 1,2-dimethoxyethane dropwise in the space of 30 min. Next, after stirring for 30 min at this temperature, add a solution of 64 g (0.50 mol) 2-fluorobenzaldehyde in 373 ml 1,2-dimethoxyethane dropwise in the space of 20 min. Leave the reaction mixture to warm to room temperature in 4 h. After adding 1900 ml satd. aqueous ammonium chloride solution, extract with ethyl acetate. Wash the organic phase with satd. ammonium chloride solution, dry over sodium sulphate and filter. Concentrate the filtrate by vacuum evaporation. Add 1900 ml dioxan, 1350 ml methanol and 1560 ml 1 M hydrochloric acid to the residue and stir for 16 h at room temperature. After adding 4000 ml satd. aqueous sodium chloride solution, extract with 2000 ml ethyl acetate. Wash the organic phase with 1000 ml water and 1000 ml satd. sodium chloride solution, dry over sodium sulphate and filter. Concentrate the filtrate by vacuum evaporation. Purify the residue by flash chromatography on silica gel (solvent: cyclohexane/ethyl acetate 5:1). Mix the product fraction thus obtained in 80 ml diisopropyl ether and 240 ml petroleum ether, filter, wash with petroleum ether and dry under vacuum. 50 g (85% purity, 33% of theor.) of the title compound is obtained.

HPLC (Method 1): $R_t$=4.50 min
MS (DCI): m/z=276 (M+NH$_4$)$^+$
$^1$H-NMR (400 MHz, CDCl$_3$): δ=7.87-7.85 (m, 2H), 7.28-7.19 (m, 4H), 7.11-7.04 (m, 2H), 6.22 (d, 1H), 4.64 (d, 1H), 2.65 (q, 2H), 1.21 (t, 3H).

Example 106A

2-Amino-4-(4-ethylphenyl)-5-(2-fluorophenyl)-3-furonitrile

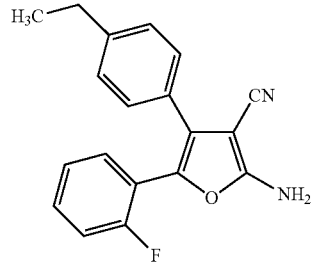

Put 50 g (0.19 mol) 1-(4-ethylphenyl)-2-(2-fluorophenyl)-2-hydroxyethanone and 17 g (0.25 mol) malononitrile in 93 ml DMF. After stirring for five minutes, add 17 ml (12 g, 0.12 mol) diethylamine, cooling with ice. Stir the reaction mixture for 1 h with ice cooling. Then leave to warm to room temperature and stir for 4 h at this temperature. After adding 500 ml water and stirring for 30 min, decant the aqueous phase. Add 500 ml water again and decant again, obtaining an oily residue, which is dissolved in ethyl acetate, dried over sodium sulphate and filtered. Concentrate the filtrate by vacuum evaporation. According to DC analysis (solvent: cyclohexane/ethyl acetate 4:1), the residue still contains 1-(4-ethylphenyl)-2-(2-fluorophenyl)-2-hydroxyethanone. Therefore, the residue is again reacted in 90 ml DMF with 5.5 g (0.08 mol) malononitrile and 10 ml (7 g, 0.10 mol) diethylamine in accordance with the above procedure. Add the reaction mixture to 500 ml ethyl acetate and wash three times with 300 ml water each time and once with 300 ml satd. sodium chloride solution. Dry the organic phase over sodium sulphate, and filter. Concentrate the filtrate by vacuum evaporation. Purify the residue by flash chromatography on silica gel (solvent: cyclohexane/ethyl acetate 3:1). 36 g (61% of theor.) of the title compound is obtained, and is reacted without further characterization.

Example 107A 5-(4-Ethylphenyl)-6-(2-fluorophenyl)furo[2,3-d]pyrimidin-4(3H)-one

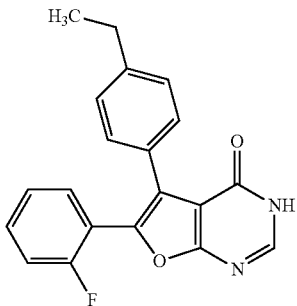

Add 140 ml (3.71 mol) formic acid dropwise to 280 ml (2.97 mol) acetic anhydride at 0° C. and stir for 30 min at this temperature. Then add 36.0 g (0.12 mol) 2-amino-4-(4-ethylphenyl)-5-(2-fluorophenyl)-3-furonitrile and stir the mixture for 24 h at 130° C. After cooling to room temperature, concentrate the mixture by evaporation under oil-pump vacuum at 50° C. Mix the residue in 150 ml diisopropyl ether at −10° C. for 30 min, filter, wash with 50 ml ice-cooled diisopropyl ether and dry under vacuum. 20.6 g (86% purity, 45% of theor.) of the title compound is obtained.

HPLC (Method 1): $R^t$=4.65 min

MS (ESIpos): m/z=335 (M+H)$^+$ $^1$H-NMR (400 MHz, DMSO-d$_6$): δ=12.68 (br. s, NH), 8.20 (s, 1H), 7.53-7.45 (m, 2H), 7.36-7.25 (m, 4H), 7.21-7.16 (m, 2H), 2.61 (q, 2H), 1.19 (t, 3H).

Example 108A

4-Chloro-5-(4-ethylphenyl)-6-(2-fluorophenyl)furo[2,3-d]pyrimidine

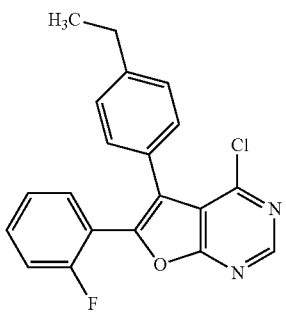

Stir a suspension of 20.0 g (0.06 mol) 5-(4-ethylphenyl)-6-(2-fluorophenyl)furo[2,3-d]pyrimidin-4(3H)-one in 100 ml (165 g, 1.07 mol) phosphoryl chloride for 1 h at 120° C. After cooling to room temperature, add the reaction solution dropwise to a mixture of 330 ml water and 610 ml 25% aqueous ammonia solution, stirring vigorously; a temperature rise to 55-65° C. is observed. Leave the reaction mixture to cool to room temperature. After extracting twice with 500 ml dichloromethane each time, wash the organic phase with satd. aqueous sodium chloride solution, dry over sodium sulphate and filter. Concentrate the filtrate by vacuum evaporation. Mix the residue with 150 ml petroleum ether, filter, wash with ice-cooled petroleum ether and dry under vacuum. 18.7 g (90% purity, 80% of theor.) of the title compound is obtained.

LC-MS (Method 6): $R_t$=3.14 min; m/z=353 (M+H)$^+$ $^1$H-NMR (400 MHz, DMSO-d$_6$): δ=8.91 (s, 1H), 7.58-7.49 (m, 2H), 7.36-7.24 (m, 6H), 2.66 (q, 2H), 1.21 (t, 3H).

Example 109A

1-[(Z)-2-Chloro-2-nitrovinyl]-4-ethylbenzene

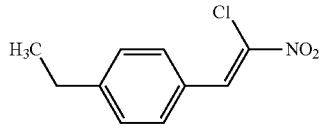

Analogously to the literature method [D. Dauzonne, Synthesis, 1990, 66-70], stir a mixture of 10.0 g (74.5 mmol) of 4-ethylbenzaldehyde, 6.8 ml (13.7 g, 97.6 mmol) of bromonitromethane, 54.7 g (670.7 mmol) of dimethylammonium chloride and 0.6 g (11.2 mmol) of potassium fluoride in 150 ml of xylene on a water separator at 160° C. for 15 hours and then at 175° C. for seven hours. After adding 25 ml of water and 100 ml of dichloromethane, remove the organic phase and extract the aqueous phase three times with 100 ml of dichloromethane each time. Dry the combined organic extracts over sodium sulphate, filter and concentrate under reduced pressure. Chromatograph the residue on silica gel (eluent: cyclohexane/dichloromethane 1:1). 11.9 g (85% purity, 64% of theory) of the target compound are obtained.

LC-MS (Method 8): $R_t$=2.84 min.

$^1$H-NMR (400 MHz, DMSO-d$_6$): δ=8.60 (s, 1H), 7.94 (d, 2H), 7.42 (d, 2H), 2.68 (q, 2H), 1.21 (t, 3H).

Example 110A 5-(4-Ethylphenyl)furo[2,3-d]pyrimidin-4(3H)-one

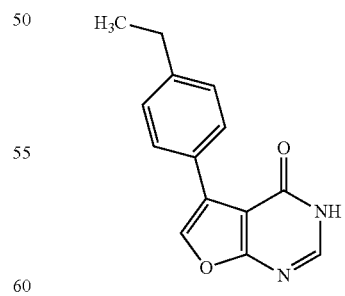

Analogously to the literature method [D. Dauzonne, Tetrahedron, 1992, 3069-3080], stir a suspension of 11.9 g (85% purity, 47.6 mmol) of 1-[(Z)-2-chloro-2-nitrovinyl]-4-ethylbenzene and 5.9 g (52.3 mmol) of 4,6-dihydroxypyrimidine in 200 ml of ethanol at 60-70° C. for 30 minutes. Then slowly add 14.4 ml (14.6 g, 96.1 mmol) of 1,8-diazabicyclo[5.4.0]

undec-7-ene. Stir the resulting reaction solution under reflux for six hours and then at 60° C. for 15 hours. After concentration under reduced pressure, take up the residue in dichloromethane and chromatograph it on silica gel (eluent: cyclohexane/ethyl acetate 1:1→1:5). Stir the resulting solid in diethyl ether and filter. 5.0 g (44% of theory) of the target compound are obtained.

LC-MS (Method 8): $R_t$=2.14 min; m/z=241 (M+H)$^+$ $^1$H-NMR (400 MHz, DMSO-d$_6$): δ=12.68 (br. s, NH), 8.18 (d, 2H), 7.87 (d, 2H), 7.26 (d, 2H), 2.63 (q, 2H), 1.20 (t, 3H).

Example 111A 5-(4-Ethylphenyl)-6-iodofuro[2,3-d]pyrimidin-4(3H)-one

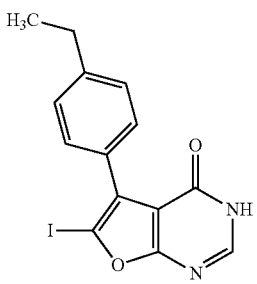

Add 7.0 g (31.3 mmol) of N-iodosuccinimide to a solution of 5.0 g (20.9 mmol) of 5-(4-ethylphenyl)furo[2,3-d]pyrimidin-4(3H)-one in 250 ml of acetonitrile/tetrachloromethane (1:1). Stir the resulting suspension under reflux for two hours. After cooling to room temperature, concentrate the reaction mixture under reduced pressure. Stir the residue in ethyl acetate and filter. Add water to the filtrate. After removal of the organic phase, extract the aqueous phase repeatedly with ethyl acetate. Concentrate the combined organic phases under reduced pressure. Take up the residue in ethyl acetate and chromatograph it on silica gel (eluent: cyclohexane/ethyl acetate 1:1→1:2). Stir the resulting solid in diethyl ether/n-pentane and filter. 1.4 g (85% purity, 16% of theory) of the target compound are obtained.

LC-MS (Method 8): $R_t$=2.34 min; m/z=367 (M+H)$^+$ $^1$H-NMR (400 MHz, DMSO-d$_6$): δ=12.68 (br. s, NH), 8.10 (s, 1H), 7.48 (d, 2H), 7.29 (d, 2H), 2.66 (q, 2H), 1.23 (t, 3H).

Example 112A

4-Chloro-5-(4-ethylphenyl)-6-iodofuro[2,3-d]pyrimidine

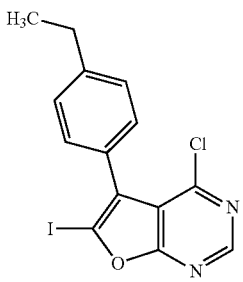

Stir a suspension of 1.4 g (85% purity, 3.3 mmol) of 5-(4-ethylphenyl)-6-iodofuro[2,3-d]pyrimidin-4(3H)-one in 20 ml (32.9 g, 214.6 mmol) of phosphoryl chloride under reflux for one hour. After concentrating under reduced pressure, add ice-cold water and dichloromethane to the residue. Dry the organic phase over sodium sulphate and filter. Concentrate the filtrate under reduced pressure and dry. 1.0 g (70% purity, 57% of theory) of the target compound is obtained.

LC-MS (Method 6): $R_t$=2.97 min; m/z=385 (M+H)$^+$ $^1$H-NMR (400 MHz, DMSO-d$_6$): δ=8.80 (s, 1H), 7.43-7.36 (m, 4H), 2.70 (q, 2H), 1.26 (t, 3H).

Example 113A

4-{[(3R)-1-Benzylpiperidin-3-yl]oxy}-5-(4-ethylphenyl)-6-iodofuro[2,3-d]pyrimidine

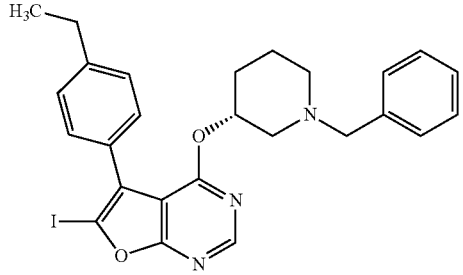

Add 106 mg (2.65 mmol) of sodium hydride (60% dispersion in mineral oil) to a solution of 483 mg (2.53 mmol) of (3R)-1-benzylpiperidin-3-ol [H. Tomori, Bull. Chem. Soc. Jpn. 69, 1, 207-216 (1996)] in 5 ml of THF. After stirring for ten minutes, add a solution of 1020 mg (70% purity, 1.86 mmol) of 4-chloro-5-(4-ethylphenyl)-6-iodofuro[2,3-d]pyrimidine in 5 ml of THF and 47 mg (0.13 mmol) of tetra-n-butylammonium iodide. Stir the reaction mixture at room temperature for five hours. After adding water and ethyl acetate, wash the removed organic phase with 1N hydrochloric acid and satd. sodium chloride solution and then concentrate under reduced pressure. Take up the residue in acetonitrile and purify by means of preparative RP-HPLC (gradient: water/acetonitrile). 266 mg (20% of theory) of the desired product are obtained.

LC-MS (Method 8): $R_t$=1.93 min; m/z=540 (M+H)$^+$ $^1$H-NMR (400 MHz, DMSO-d$_6$): δ=8.46 (s, 1H), 7.58-7.56 (m, 2H), 7.32-7.29 (m, 2H), 7.24-7.17 (m, 5H), 5.34-5.29 (m, 1H), 3.45 (d, 2H), 2.71-2.63 (m, 3H), 2.39-2.33 (m, 2H), 2.30-2.24 (m, 1H), 1.89-1.84 (m, 1H), 1.66-1.60 (m, 1H), 1.47-1.39 (m, 2H), 1.21 (t, 3H).

Example 114A

4-{[(3R)-1-Benzylpiperidin-3-yl]oxy}-5-(4-ethylphenyl)-6-(2-fluorophenyl)furo[2,3-d]pyrimidine

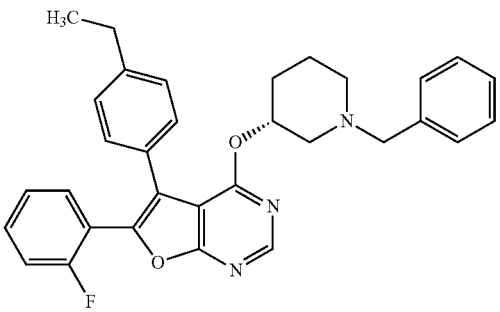

Add 0.68 ml of a 2 M aqueous sodium carbonate solution to a mixture of 365 mg (0.68 mmol) of 4-{[(3R)-1-benzylpiperidin-3-yl]oxy}-5-(4-ethylphenyl)-6-iodofuro[2,3-d]pyrimidine and 24 mg (0.03 mmol) of bis(triphenylphosphine)palladium(II) chloride in 15 ml of DMSO. Then add 118 mg (0.85 mmol) of (2-fluorophenyl)boronic acid and stir the mixture at 80° C. for 15 hours. Then filter the reaction mixture and purify directly by means of preparative RP-HPLC (gradient: water/acetonitrile). 291 mg (84% of theory) of the target compound are obtained.

LC-MS (Method 12): $R_t$=2.18 min; m/z=508 (M+H)$^+$ $^1$-NMR (400 MHz, DMSO-d$_6$): δ=8.57 (s, 1H), 7.57-7.53 (m, 2H), 7.39-7.29 (m, 4H), 7.24-7.18 (m, 7H), 5.40-5.34 (m, 1H), 3.49-3.46 (m, 2H), 2.74-2.69 (m, 1H), 2.62 (q, 2H), 2.43-2.35 (m, 2H), 2.32-2.25 (m, 1H), 1.94-1.87 (m, 1H), 1.71-1.64 (m, 1H), 1.50-1.44 (m, 2H), 1.17 (t, 3H).

Example 115A (3R)-3-{[5-(4-Ethylphenyl)-6-(2-fluorophenyl)furo[2,3-d]pyrimidin-4-yl]oxy}piperidinium formate

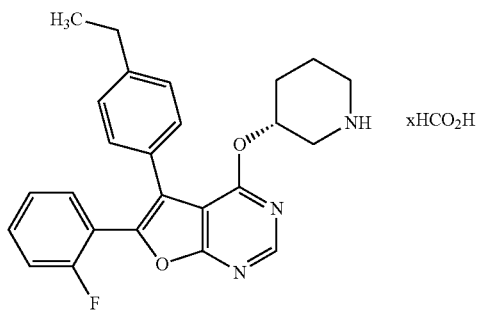

Add 30 mg of 10% palladium on activated carbon to an argon-blanketed solution of 275 mg (0.54 mmol) of 4-{[(3R)-1-benzylpiperidin-3-yl]oxy}-5-(4-ethylphenyl)-6-(2-fluorophenyl)furo-[2,3-d]pyrimidine in 5 ml of methanol/ethanol (1:2), and stir at room temperature under a hydrogen atmosphere (standard pressure) for three hours. After adding a further 70 mg of 10% palladium on activated carbon, stir the reaction mixture for another 19 hours under a hydrogen atmosphere (standard pressure) at room temperature. Add a further 175 mg of 10% palladium on activated carbon and 0.2 ml of formic acid, and stir the reaction mixture once again at room temperature under a hydrogen atmosphere (standard pressure) for 15 hours. After filtering off the catalyst, wash the catalyst residue with methanol/water. Concentrate the filtrate under reduced pressure, take up the residue in acetonitrile/DMSO and purify by means of preparative RP-HPLC (gradient: water/acetonitrile/formic acid). 137 mg (54% of theory) of the desired product are obtained.

LC-MS (Method 8): $R_t$=1.74 min; m/z=418 (M−HCO$_2$H+H)$^+$ $^1$H-NMR (400 MHz, DMSO-d$_6$): δ=8.57 (s, 1H), 7.57-7.53 (m, 2H), 7.39-7.29 (m, 4H), 7.24-7.18 (m, 7H), 5.40-5.34 (m, 1H), 3.49-3.46 (m, 2H), 2.74-2.69 (m, 1H), 2.62 (q, 2H), 2.43-2.35 (m, 2H), 2.32-2.25 (m, 1H), 1.94-1.87 (m, 1H), 1.71-1.64 (m, 1H), 1.50-1.44 (m, 2H), 1.17 (t, 3H).

Example 116A

3-{[5-(4-Ethylphenyl)-6-(2-fluorophenyl)furo[2,3-d]pyrimidin-4-yl]oxy}cyclohexanol

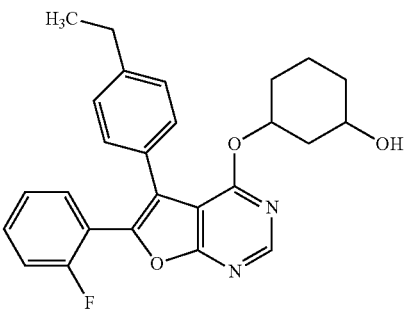

Add 4.5 ml of 12.5N sodium hydroxide solution at 70° C. to a mixture of 1.65 g (14.17 mmol) of cyclohexane-1,3-diol in 45 ml of toluene, 15 ml of 1,2-dimethoxyethane and 15 ml of water. After adding 0.19 g (0.57 mmol) of tetra-n-butylammonium hydrogen sulfate and 2.0 g (5.67 mmol) of 4-chloro-5-(4-ethylphenyl)-6-(2-fluorophenyl)furo[2,3-d]pyrimidine, stir the reaction mixture at 70° C. for 17 hours. After cooling to room temperature, adjust to pH 7 with conc. hydrochloric acid. Extract with dichloromethane. Wash the organic phase with satd. sodium chloride solution, dry over sodium sulphate, filter and concentrate under reduced pressure. Chromatograph the residue on silica gel (eluent: cyclohexane/ethyl acetate 2:1). 0.60 g (24% of theory) of the desired product are obtained as a racemic diastereomer mixture.

LC-MS (Method 8): $R_t$=2.96 min; m/z=433 (M+H)$^+$ $^1$H-NMR (400 MHz, DMSO-d$_6$): [minor stereoisomer in brackets] δ=8.62 (s, 1H), [8.61, s, 1H], 7.57-7.52 (m, 2H), 7.34-7.28 (m, 4H), 7.20-7.18 (m, 2H), [5.68-5.64, m, 1H], 5.21-5.14 (m, 1H), 4.75 (d, OH), [4.45, d, OH], 3.57-3.48 (m, 1H), 2.63 (q, 2H), 2.37-2.31 (m, 1H), 2.08-2.03 (m, 1H), 1.82-1.77 (m, 1H), 1.74-1.69 (m, 1H), 1.34-1.02 (m, 4H), 1.20 (t, 3H).

Example 117A

4-{[(3R)-1-Benzylpiperidin-3-yl]oxy}-6-(2-fluorophenyl)-5-(4-methoxyphenyl)furo[2,3-d]pyrimidine

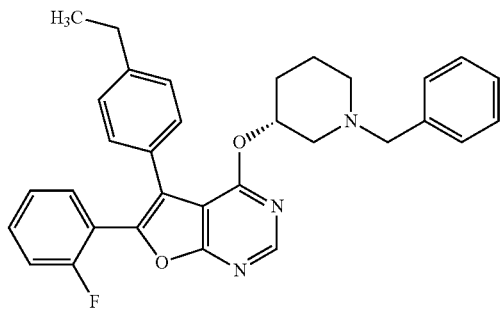

Dissolve 1037 mg (5.37 mmol) of (3R)-1-benzylpiperidin-3-ol [H. Tomori, *Bull. Chem. Soc. Jpn.* 69, 1, 207-216 (1996)] in 10 ml of THF and add 268 mg (6.71 mmol) of sodium hydride (60% in mineral oil). After 10 minutes, add a solution of 2000 mg (5.64 mmol) of 4-chloro-6-(2-fluorophenyl)-5-(4-methoxyphenyl)furo[2,3-d]pyrimidine in 10 ml of THF and 99 mg (0.27 mmol) of tetra-n-butylammonium iodide. Heat the reaction mixture under reflux for 16 hours. Then add 100 ml of water and 100 ml of ethyl acetate. Remove the organic phase and wash with 50 ml of 1N hydrochloric acid and 100 ml of satd. sodium chloride solution. Re-extract the aqueous phase with 50 ml of ethyl acetate, dry the combined organic extracts over sodium sulphate, filter and concentrate under reduced pressure. 2645 mg (89% of theory, 92% purity) of the desired product are obtained.

LC-MS (Method 8): $R_t$=1.92 min; m/z=510 (M+H)$^+$ $^1$-NMR (400 MHz, DMSO-d$_6$): δ=8.63 (s, 1H), 7.58-7.51 (m, 2H), 7.51-7.43 (m, 5H), 7.34-7.25 (m, 4H), 6.93-6.88 (m, 2H), 5.62-5.58 (m, 1H), 3.77 (s, 3H), 3.68-3.66 (m, 1H), 2.89-2.83 (m, 1H), 2.36-2.27 (m, 2H), 1.91-1.81 (m, 3H), 1.51-1.45 (m, 1H).

Example 118A 6-(2-Fluorophenyl)-5-(4-methoxyphenyl)-4-[(3R)-piperidin-3-yloxy]furo[2,3-d]pyrimidine formate

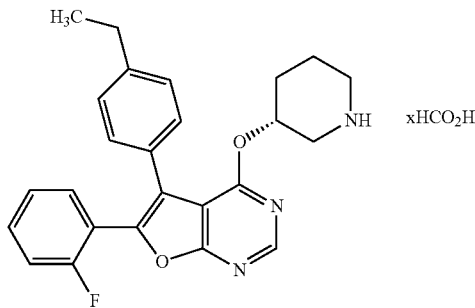

Add 400 mg of palladium black to an argon-blanketed solution of 510 mg (1.00 mmol) of 4-{[(3R)-1-benzylpiperidin-3-yl]oxy}-6-(2-fluorophenyl)-5-(4-methoxyphenyl)furo[2,3-d]pyrimidine in 5 ml of a 4.4% solution of formic acid in methanol, and stir at room temperature for two days. After filtering off the catalyst, wash the catalyst residue with methanol/water. Concentrate the filtrate under reduced pressure and purify the residue by means of preparative RP-HPLC (eluent: water/acetonitrile gradient with 0.1% formic acid). 70 mg (12% of theory, 80% purity) of the desired product are obtained.

LC-MS (Method 8): $R_t$=1.66 min; m/z=420 (M−HCO$_2$H+H)$^+$.

Example 119A 6-(2-Fluorophenyl)-5-(4-methoxyphenyl)-4-[(3R)-piperidin-3-yloxy]furo[2,3-d]pyrimidine

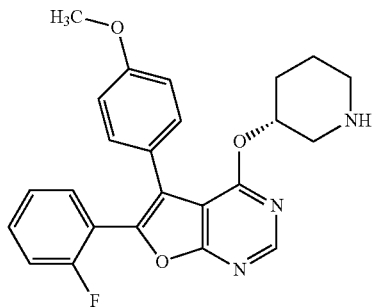

Add 300 mg of palladium black to an argon-blanketed solution of 2600 mg (4.69 mmol) of 4-{[(3R)-1-benzylpiperidin-3-yl]oxy}-6-(2-fluorophenyl)-5-(4-methoxyphenyl)furo[2,3-d]-pyrimidine in 25 ml of a 4.4% solution of formic acid in methanol and stir at room temperature for five hours. Then add another 300 mg of palladium black and 0.9 ml of formic acid and stir at room temperature for a further 16 hours. After filtering off the catalyst, wash the catalyst residue with methanol/water. Concentrate the filtrate under reduced pressure, stir the residue in acetonitrile, filter off and dry under reduced pressure. 1376 mg (68% of theory) of the desired product are obtained.

LC-MS (Method 8): $R_t$=1.62 min; m/z=420 (M+H)$^+$ $^1$H-NMR (400 MHz, DMSO-d$_6$): δ=8.66 (s, 1H), 7.58-7.52 (m, 2H), 7.42 (d, 2H), 7.35-7.30 (m, 2H), 6.93 (d, 2H), 5.45-5.40 (m, 1H), 3.77 (s, 3H), 3.47-3.30 (m, 2H), 3.10-3.04 (m, 2H), 2.07-2.02 (m, 1H), 1.78-1.71 (m, 3H).

Example 120A

3-[(2R,4R)-1-(tert-Butoxycarbonyl)-4-{[5-(4-methoxyphenyl)-6-phenylfuro[2,3-d]pyrimidin-4-yl]oxy}piperidin-2-yl]propanoic acid methyl ester

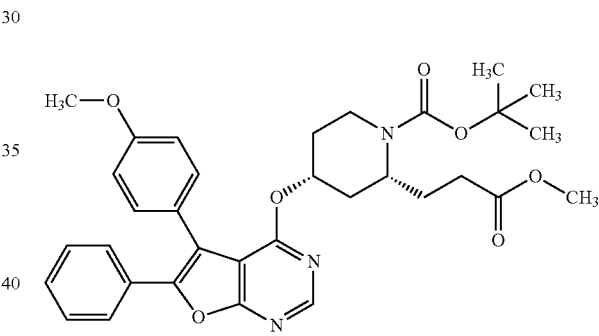

Dissolve 631.7 mg (1.87 mmol) of 4-chloro-5-(4-methoxyphenyl)-6-phenylfuro[2,3-d]pyrimidine and 490 mg (1.71 mmol) of tert-butyl(2R,4R)-4-hydroxy-2-(3-methoxy-3-oxopropyl)piperidine-1-carboxylate in 1 ml of DMF, cool to −10° C. and add 1.02 ml (2.05 mmol) of phosphazene base P2-t-Bu (approx. 2 M solution in THF). Stir the reaction mixture at 0° C. for 1 h and then add to water. Extract three times with dichloromethane, combine the organic phases, wash with satd. sodium chloride solution and dry over magnesium sulphate. After concentrating under reduced pressure, purify the product by chromatography on silica gel (eluent: cyclohexane/ethyl acetate 20:1→3:1). 420 mg (38.1% of theory) of the target compound are obtained.

LC-MS (Method 8): $R_t$=3.26 min; m/z=588 (M+H)$^+$ $^1$H-NMR (400 MHz, DMSO-d$_6$): δ=8.60 (s, 1H), 7.55 (d, 2H), 7.43-7.32 (m, 5H), 7.02 (d, 2H), 5.58 (s, 1H), 4.02-3.93 (m, 1H), 3.82 (s, 3H), 3.70-3.60 (m, 1H), 3.51 (s, 3H), 1.91-1.60 (m, 6H), 1.47-1.39 (m, 1H), 1.36 (s, 9H), 1.16-1.05 (m, 2H).

Example 121A

3-[(2R,4R)-1-(tert-Butoxycarbonyl)-4-{[5-(4-methoxyphenyl)-6-phenylfuro[2,3-d]pyrimidin-4-yl]oxy}piperidin-2-yl]propanoic acid

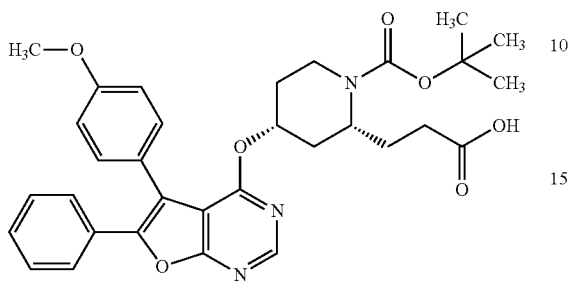

Dissolve 35 mg (0.06 mmol) of 3-[(2R,4R)-1-(tert-butoxycarbonyl)-4-{[5-(4-methoxyphenyl)-6-phenylfuro[2,3-d]pyrimidin-4-yl]oxy}piperidin-2-yl]propanoic acid methyl ester in 0.1 ml of methanol, cool to 0° C. and add approx. 240 mg of 10% sodium hydroxide solution. Stir the mixture at approx. 40° C. for several hours, then at RT overnight. Then slightly acidify the reaction mixture with 1N hydrochloric acid (pH approx. 3) and extract repeatedly with dichloromethane. Wash the combined organic phases with satd. sodium chloride solution, dry over magnesium sulphate and concentrate under reduced pressure. The target compound is obtained in quantitative yield (34 mg) and is not purified further.

Example 122A

[1-(({[5-(4-Methoxyphenyl)-6-phenylfuro[2,3-d]pyrimidin-4-yl]oxy}methyl)cyclobutyl]methanol

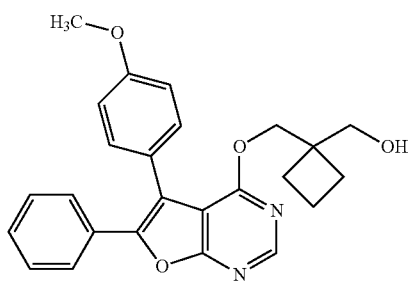

Add 2.6 ml of an 11.25N sodium hydroxide solution at 70° C. to a solution of 1.72 g (14.85 mmol) of cyclobutane-1,1-diyldimethanol [F. X. Tavares, *J. Med. Chem.* 2004, 47 (21), 5057-5068] in 20 ml of toluene, 8 ml of 1,2-dimethoxyethane and 8 ml of water. After adding 0.10 g (0.30 mmol) of tetra-n-butylammonium hydrogen sulphate and 1.00 g (2.97 mmol) of 4-chloro-5-(4-methoxyphenyl)-6-phenylfuro[2,3-d]pyrimidine, stir the reaction mixture at 70° C. for 17 h. After cooling to room temperature, adjust to pH 7 with concentrated hydrochloric acid. Extract three times with 50 ml of dichloromethane each time. Wash the combined organic extracts with satd. sodium chloride solution, dry over sodium sulphate and filter. Concentrate the filtrate under reduced pressure. Stir the residue in acetonitrile, filter and purify the filtrate by means of preparative RP-HPLC (gradient: water/acetonitrile). 0.30 g (24% of theory) of the desired product are obtained.

LC-MS (Method 3): $R_t$=2.67 min; m/z=417 (M+H)$^+$
$^1$H-NMR (400 MHz, DMSO-$d_6$): δ=8.58 (s, 1H), 7.56-7.54 (m, 2H), 7.42-7.37 (m, 5H), 7.04-6.99 (m, 2H), 4.56 (t, 1H), 4.30 (s, 2H), 3.81 (s, 3H), 3.21 (d, 2H), 1.77-1.58 (m, 6H).

Working Examples

Example 1

3-{[6-(4-Bromophenyl)-5-phenylfuro[2,3-d]pyrimidin-4-yl]amino}phenoxyacetic acid methyl ester

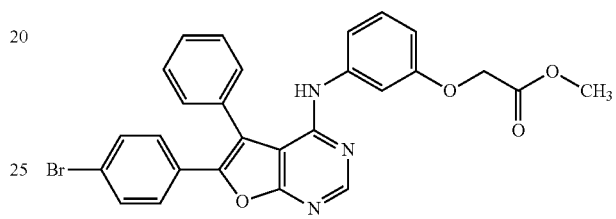

Heat 400 mg (1.04 mmol) of 6-(4-bromophenyl)-4-chloro-5-phenylfuro[2,3-d]pyrimidine (preparation according to WO 03/018589) and 225.5 mg (1.25 mmol) of 3-aminophenoxyacetic acid methyl ester to 150° C. in an oil bath for 1.5 h. After cooling, take up the residue in DMSO and filter through silica gel (eluent: cyclohexane/ethyl acetate 2:1). 140 mg (25.5% of theory) of the target compound are obtained as a yellowish solid.

LC-MS (Method 5): $R_t$=3.30 min; m/z=530, 532 (M+H)$^+$
$^1$H-NMR (400 MHz, DMSO-$d_6$): δ=8.57 (s, 1H), 7.19 (s, 5H), 7.61 (d, 2H), 7.44 (d, 2H), 7.22-7.18 (m, 2H), 6.82 (s, 1H), 6.86 (dd, 1H), 6.61 (dd, 1H), 4.77 (s, 2H), 3.71 (s, 3H).

Example 2

3-[(5,6-Diphenylfuro[2,3-d]pyrimidin-4-yl)amino]phenoxyacetic acid methyl ester

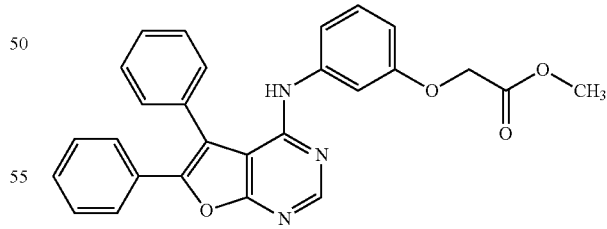

Dissolve 200 mg (0.377 mmol) of 3-{[6-(4-bromophenyl)-5-phenylfuro[2,3-d]pyrimidin-4-yl]amino}phenoxyacetic acid methyl ester in 5 ml of dichloromethane and 2 ml of THF and, under argon, add 40 mg of 10% palladium on activated carbon. Stir the mixture under a hydrogen atmosphere of 3 bar gauge at RT for 3 h, before filtering off the catalyst. Wash the catalyst residue with dichloromethane and methanol, concentrate the combined filtrates under reduced pressure and chromatograph the residue on silica gel (eluent: dichloromethane/ ethyl acetate 10:1). 79.1 mg (45.5% of theory) of the target compound are obtained as a colourless solid.

LC-MS (Method 3): $R_t$=2.87 min; m/z=452 (M+H)$^+$ $^1$H-NMR (300 MHz, DMSO-d$_6$): δ=8.58 (s, 1H), 7.70 (s, 5H), 7.56-7.51 (m, 2H), 7.44-7.38 (m, 3H), 7.25-7.18 (m, 2H), 6.80 (s, 1H), 6.78 (dd, 1H), 6.61 (dd, 1H), 4.78 (s, 2H), 3.72 (s, 3H).

Example 3

3-[(5,6-Diphenylfuro[2,3-d]pyrimidin-4-yl)amino]phenoxyacetic acid

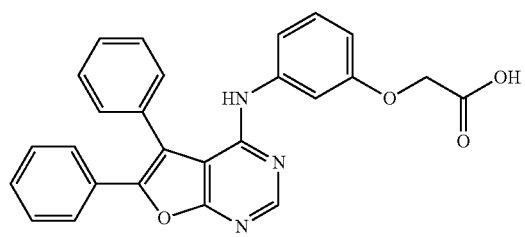

Dissolve 50 mg (0.111 mmol) of 3-[(5,6-diphenylfuro[2,3-d]pyrimidin-4-yl)amino]phenoxyacetic acid methyl ester in 2 ml of THF, add 0.33 ml of 1N sodium hydroxide solution at RT and stir at 50° C. for 1 h. Cool to RT and remove the THF under reduced pressure. Add water to the residue and then, with ice cooling, 1N hydrochloric acid. Filter off the precipitated solid, wash repeatedly with water and dry under reduced pressure. 39.4 mg (81.3% of theory) of the target compound are obtained as a white solid.

LC-MS (Method 3): $R_t$=2.52 min; m/z=438 (M+H)$^+$ $^1$H-NMR (300 MHz, DMSO-d$_6$): δ=13.04 (br. s, 1H), 8.58 (s, 1H), 7.19 (s, 5H), 7.55-7.50 (m, 2H), 7.44-7.36 (m, 3H), 7.24-7.14 (m, 2H), 6.82-6.77 (m, 2H), 6.60 (dd, 1H), 4.62 (s, 2H).

Example 4

3-{[6-(4-Bromophenyl)-5-(4-fluorophenyl)furo[2,3-d]pyrimidin-4-yl]amino}phenoxyacetic acid methyl ester

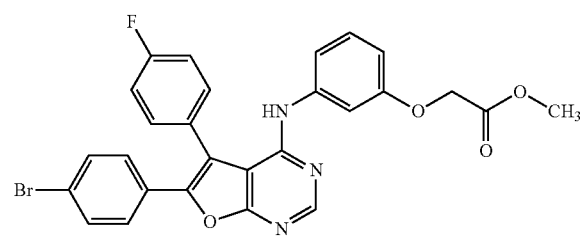

Heat 400 mg (0.991 mmol) of 6-(4-bromophenyl)-4-chloro-5-(4-fluorophenyl)furo[2,3-d]pyrimidine (for preparation see WO 03/018589) and 215.5 mg (1.19 mmol) of 3-aminophenoxyacetic acid methyl ester to 150° C. in an oil bath for 1.5 h. After cooling, take up the residue in DMSO and filter through silica gel (eluent: dichloromethane/ethyl acetate 10:1). 242 mg of a mixture are isolated, which is purified by preparative HPLC. 120 mg (15% of theory) of the target compound are obtained as a colourless solid.

LC-MS (Method 6): $R_t$=3.2 min; m/z=548, 550 (M+H)$^+$.

Example 5

3-{[5-(4-Fluorophenyl)-6-phenylfuro[2,3-d]pyrimidin-4-yl]amino}phenoxyacetic acid methyl ester

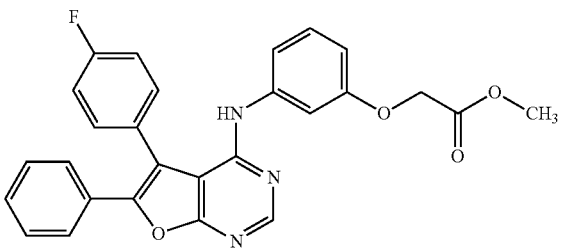

Dissolve 115 mg (0.21 mmol) of 3-{[6-(4-bromophenyl)-5-(4-fluorophenyl)furo[2,3-d]pyrimidin-4-yl]amino}phenoxy acetic acid methyl ester in 5 ml of dichloromethane and 5 ml of ethyl acetate, and add 22 mg of 10% palladium on activated carbon under argon. Stir the mixture under a hydrogen atmosphere of 3 bar gauge at RT until the starting material has been converted completely. Filter off the catalyst, concentrate the resulting filtrate under reduced pressure and chromatograph the residue on silica gel (eluent: dichloromethane/ethyl acetate 10:1). 27.9 mg (28.3% of theory) of the target compound are obtained as a colourless solid.

LC-MS (Method 6): $R_t$=3.02 min; m/z=470 (M+H)$^+$ $^1$H-NMR (300 MHz, DMSO-d$_6$): δ=8.55 (s, 1H), 7.74-7.68 (m, 2H), 7.55-7.39 (m, 6H), 7.26-7.20 (m, 2H), 7.02 (s, 1H), 6.86 (d, 1H), 6.63 (dd, 1H), 4.78 (s, 2H), 3.71 (s, 3H).

Example 6

3-{[5-(4-Fluorophenyl)-6-phenylfuro[2,3-d]pyrimidin-4-yl]amino}phenoxyacetic acid

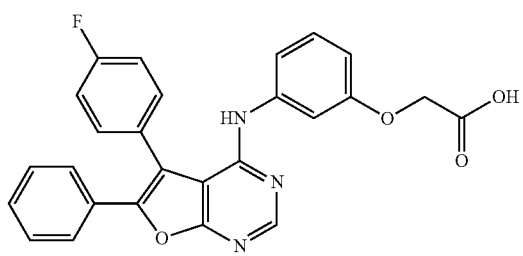

Dissolve 21.1 mg (0.045 mmol) of 3-{[5-(4-fluorophenyl)-6-phenylfuro[2,3-d]pyrimidin-4-yl]amino}phenoxyacetic acid methyl ester in 1 ml of THF, add 0.135 ml of 1N sodium hydroxide solution at RT and stir at 50° C. for 1 h. Cool to RT and remove the THF under reduced pressure. Add water to the residue, and then, with ice cooling, 1N hydrochloric acid. Filter off the precipitated solid, wash repeatedly with water and dry at 40° C. under reduced pressure. 11.5 mg (56.2% of theory) of the target compound are obtained as a white solid.

LC-MS (Method 3): $R_t$=2.51 min; m/z=456 (M+H)$^+$ $^1$H-NMR (300 MHz, DMSO-d$_6$): δ=13.03 (br. s, 1H), 8.55 (s, 1H), 7.75-7.69 (m, 2H), 7.55-7.38 (m, 7H), 7.8-7.19 (m, 2H), 6.98 (s, 1H), 6.83 (dd, 1H), 6.61 (dd, 1H), 4.65 (s, 3 H).

Example 7

3-{[5,6-Bis(4-methoxyphenyl)furo[2,3-d]pyrimidin-4-yl]amino}phenoxyacetic acid methyl ester

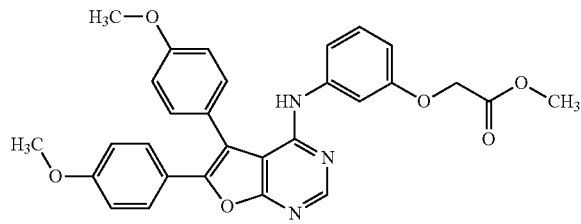

Heat 400 mg (1.091 mmol) of 4-chloro-5,6-bis(4-methoxyphenyl)furo[2,3-d]pyrimidine (for preparation see WO 03/018589) and 237.1 mg (1.309 mmol) of 3-aminophenoxyacetic acid methyl ester to 150° C. in an oil bath for 1.5 h. After cooling, add dichloromethane to the residue and purify by means of silica gel (eluent: dichloromethane/ethyl acetate 10:1). 139.3 mg (25% of theory) of the target compound are obtained as a light yellowish solid.

LC-MS (Method 6): R$_t$=3.02 min; m/z=512 (M+H)$^+$ $^1$H-NMR (400 MHz, DMSO-d$_6$): δ=8.51 (s, 1H), 7.58 (d, 2H), 7.48 (d, 2H), 7.28-7.18 (m, 4H), 6.99 (d, 2H), 6.87 (s, 1H), 6.80 (d, 1H), 6.61 (dd, 1H), 4.78 (s, 2H), 3.89 (s, 3H), 3.28 (s, 3H), 3.21 (s, 3H).

Example 8

3-{[5,6-Bis(4-methoxyphenyl)furo[2,3-d]pyrimidin-4-yl]amino}phenoxyacetic acid

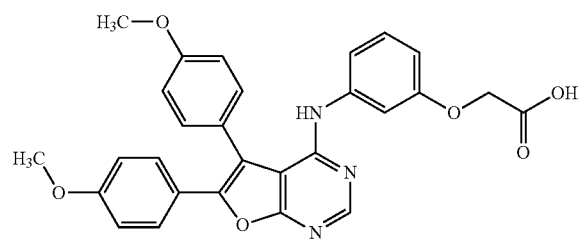

Dissolve 107 mg (0.209 mmol) of 3-{[5,6-bis(4-methoxyphenyl)furo[2,3-d]pyrimidin-4-yl]amino}-phenoxyacetic acid methyl ester in 2 ml of THF, add 0.628 ml of 1N sodium hydroxide solution at RT and stir at 50° C. for 1 h. Cool to RT and remove the THF under reduced pressure. Add water to the residue and then, with ice cooling, 1N hydrochloric acid. Filter off the precipitated solid, wash repeatedly with water and dry at 40° C. under reduced pressure. 92.5 mg (88.9% of theory) of the target compound are obtained as white solid.

LC-MS (Method 5): R$_t$=2.74 min; m/z=498 (M+H)$^+$ $^1$H-NMR (300 MHz, DMSO-d$_6$): δ=13.04 (br. s, 1H), 8.51 (s, 1H), 7.61 (d, 2H), 7.46 (d, 2H), 7.28-7.18 (m, 4H), 6.98 (d, 2H), 6.85 (s, 1H), 6.77 (d, 1H), 6.59 (dd, 1H), 4.65 (s, 2H), 3.90 (s, 3H), 3.78 (s, 3H).

Example 9

3-{[5-(4-Methoxyphenyl)-6-phenylfuro[2,3-d]pyrimidin-4-yl]amino}phenoxyacetic acid methyl ester

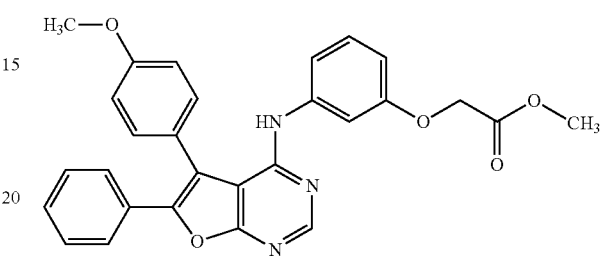

Heat 4.7 g (14 mmol) of 4-chloro-5-(4-methoxyphenyl)-6-phenylfuro[2,3-d]pyrimidine and 3.03 g (16.7 mmol) of 3-aminophenoxyacetic acid methyl ester to 150° C. in an oil bath for 1.5 h. After cooling, add dichloromethane to the residue and purify by means of silica gel (eluent: cyclohexane/ethyl acetate 2:1). 2.29 g (34.1% of theory) of the target compound are obtained as a pale yellowish solid.

LC-MS (Method 5): R$^t$=3.08 min; m/z=482 (M+H)$^+$ $^1$H-NMR (300 MHz, DMSO-d$_6$): δ=8.56 (s, 1H), 7.60 (d, 2H), 7.56-7.50 (m, 2H), 7.44-7.35 (m, 3H), 7.28-7.20 (m, 4H), 6.91 (s, 1H), 6.81 (dd, 1H), 6.64 (dd, 1H), 4.78 (s, 2H), 3.90 (s, 3H), 3.71 (s, 3H).

Example 10

3-{[5-(4-Methoxyphenyl)-6-phenylfuro[2,3-d]pyrimidin-4-yl]amino}phenoxyacetic acid

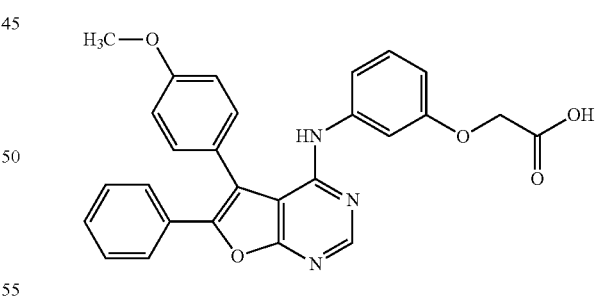

Dissolve 1000 mg (2.08 mmol) of 3-{[5-(4-methoxyphenyl)-6-phenylfuro[2,3-d]pyrimidin-4-yl]amino}phenoxyacetic acid methyl ester in 10 ml of THF, add 4.2 ml of 1N sodium hydroxide solution at RT and stir at 50° C. for 1 h. Cool to RT and remove the THF under reduced pressure. Add water to the residue and then, with ice cooling, 1N hydrochloric acid. Filter off the precipitated solid, wash repeatedly with water and dry at 40° C. under reduced pressure. 913.7 mg (92.5% of theory) of the target compound are obtained as a white solid.

LC-MS (Method 5): R$_t$=2.75 min; m/z=468 (M+H)$^+$

¹H-NMR (300 MHz, DMSO-d₆): δ=12.90 (br. s, 1H), 8.54 (s, 1H), 7.59 (d, 2H), 7.57-7.51 (m, 2H), 7.44-7.35 (m, 3H), 7.26-7.18 (m, 4H), 6.89 (s, 1H), 6.78 (d, 1H), 6.59 (dd, 1H), 4.60 (s, 2H), 3.91 (s, 3H).

Example 11

3-{[5-(4-Methoxyphenyl)-6-phenylfuro[2,3-d]pyrimidin-4-yl]amino}phenoxyacetic acid trisethanolamine salt

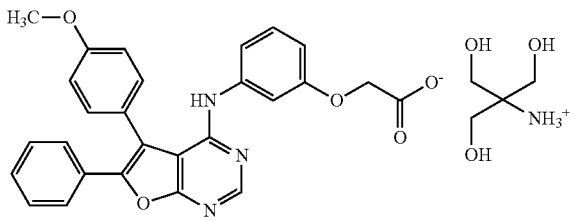

Initially charge 50 mg (0.107 mmol) of 3-{[5-(4-methoxyphenyl)-6-phenylfuro[2,3-d]pyrimidin-4-yl]amino}phenoxyacetic acid in 2 ml of a 1:1 mixture of methanol and dichloromethane, add 13 mg (0.107 mmol) of 2-amino-2-hydroxymethyl-1,3-propanediol(trisethanolamine) and stir at RT overnight. Then concentrate the mixture under reduced pressure. 60.3 mg of the target compound are obtained as a colourless glass.

LC-MS (Method 5): $R^t$=2.53 min; m/z=468 $(C_{27}H_{21}N_3O_5)^+$

¹H-NMR (300 MHz, CD₃OD): δ=8.45 (s, 1H), 7.60-7.51 (m, 4H), 7.36-7.11 (m, 7H), 6.81 (dd, 1H), 6.63 (dd, 1H), 4.38 (s, 2H), 3.94 (s, 3H), 3:65 (s, 6H).

Example 12

3-{[5-(4-Methoxyphenyl)-6-phenylfuro[2,3-d]pyrimidin-4-yl]amino}phenoxyacetic acid sodium salt

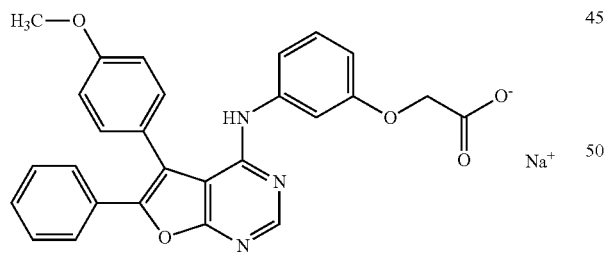

Suspend 2.52 g (5.39 mmol) of 3-{[5-(4-methoxyphenyl)-6-phenylfuro[2,3-d]pyrimidin-4-yl]amino}phenoxyacetic acid in a mixture of 10 ml of THF, 10 ml of methanol and 1 ml of water at RT, add 5.39 ml of 1N sodium hydroxide solution dropwise and stir the resulting solution at RT for 10 min, before filtering off with suction through a fine frit (removal of suspended particles). Concentrate the solution under reduced pressure and treat the residue with ethanol. Filter off the insoluble solid with suction, wash with a little ethanol and dry under reduced pressure, then under high vacuum. Concentrate the filtrate, stir the residue again with a little ethanol and thus obtain a second product batch after filtering off with suction. After combining the two fractions, a total of 2.32 g (87.9% of theory) of the target compound are obtained as a colourless solid.

LC-MS (Method 5): $R_t$=2.83 min; m/z=467 (M-Na+2H)⁺

¹H-NMR (400 MHz, DMSO-d₆): δ=8.54 (s, 1H), 7.62-7.51 (m, 4H), 7.43-7.36 (m, 3H), 7.27 (d, 2H), 7.11 (t, 1H), 7.01 (s, 1H), 6.82-6.79 (m, 2H), 6.50 (d, 1H), 4.03 (s, 2H), 3.91 (s, 3H).

Example 13

3-{[5-(4-Methoxyphenyl)-6-phenylfuro[2,3-d]pyrimidin-4-yl]oxy}phenoxy)acetic acid ethyl ester

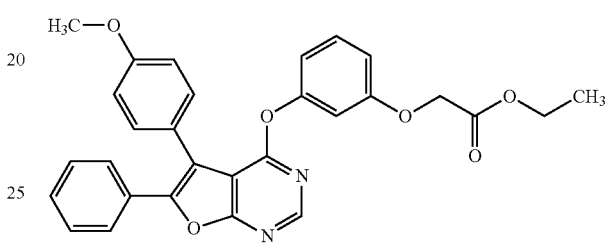

Stir 300 mg (0.731 mmol) of 3-{[5-(4-methoxyphenyl)-6-phenylfuro[2,3-d]pyrimidin-4-yl]oxy}phenol, 159 mg (0.95 mmol) of bromoacetic acid ethyl ester and 357 mg (1.1 mmol) of caesium carbonate under reflux for 1.5 h. After cooling, concentrate, take up the residue in ethyl acetate and wash the mixture repeatedly with water. Dry the organic phase over magnesium sulphate and concentrate under reduced pressure. 331.4 mg (91.3% of theory) of the target compound are obtained as a yellowish solid.

LC-MS (Method 3): $R_t$=2.92 min; m/z=497 (M+H)⁺

¹H-NMR (300 MHz, DMSO-d₆): δ=8.51 (s, 1H), 7.60-7.51 (m, 4H), 7.46-7.41 (m, 3H), 7.33 (t, 1H), 7.02 (d, 2H), 6.88-6.81 (m, 3H), 4.78 (s, 2H), 4.17 (q, 2H), 3.80 (s, 3H), 1.19 (t, 3H).

Example 14

3-{[5-(4-Methoxyphenyl)-6-phenylfuro[2,3-d]pyrimidin-4-yl]oxy}phenoxy)acetic acid methyl ester

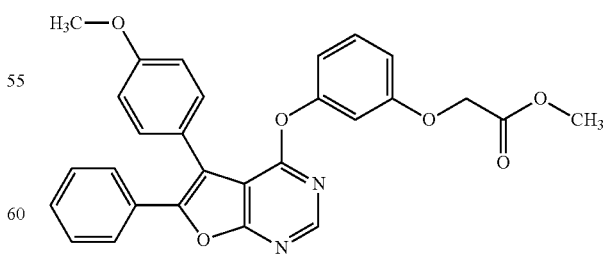

Stir 500 mg (01.22 mmol) of 3-{[5-(4-methoxyphenyl)-6-phenylfuro[2,3-d]pyrimidin-4-yl]oxy}phenol, 242 mg (1.58 mmol) of bromoacetic acid methyl ester and 595 mg (1.83 mmol) of caesium carbonate under reflux for 45 min. After cooling, concentrate and convert the crude product in the next reaction without further purification.

Example 15

3-{[5-(4-Methoxyphenyl)-6-phenylfuro[2,3-d]pyrimidin-4-yl]oxy}phenoxy)acetic acid

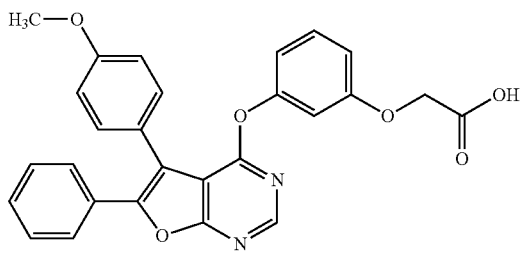

Stir 587 mg (approx. 1.217 mmol) of 3-{[5-(4-methoxyphenyl)-6-phenylfuro[2,3-d]pyrimidin-4-yl]oxy}phenoxy) acetic acid methyl ester (crude product from Example 14), 2.43 ml of 1N sodium hydroxide solution and 4 ml of dioxane at 50° C. overnight. After cooling, acidify with 1N hydrochloric acid and filter off the precipitated solid with suction, wash with water and dry at 40° C. under reduced pressure. Take up the solid in dichloromethane and THF and concentrate the solution again to dryness. 477.1 mg (81.2% of theory) of the target compound are obtained as a yellowish solid.

LC-MS (Method 3): $R_t$=2.49 min; m/z=469 (M+H)$^+$ $^1$H-NMR (400 MHz, DMSO-d$_6$): δ=13.00 (br. s, 1H), 8.54 (s, 1H), 7.61-7.51 (m, 4H), 7.47-7.40 (m, 3H), 7.32 (t, 1H), 7.03 (d, 2H), 6.88-6.78 (m, 3H), 4.68 (s, 2H), 3.80 (s, 3H).

Example 16

N-(3-{[5-(4-Methoxyphenyl)-6-phenylfuro[2,3-d]pyrimidin-4-yl]oxy}phenyl)glycine methyl ester

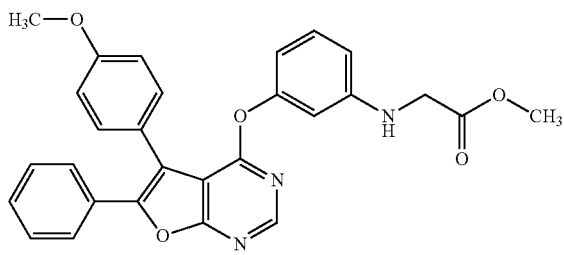

Stir 450 mg (1.1 mmol) of 3-{[5-(4-methoxyphenyl)-6-phenylfuro[2,3-d]pyrimidin-4-yl]-oxy}aniline, 202 mg (1.32 mmol) of bromoacetic acid methyl ester and 465.5 mg (1.43 mmol) of caesium carbonate in 10 ml of acetone under reflux overnight. Remove the acetone under reduced pressure and take up the residue in water and extract repeatedly with dichloromethane/ethyl acetate (1:1). Dry the combined organic phases over magnesium sulphate and concentrate. Chromatograph the residue twice on silica gel (eluent: dichloromethane/ethyl acetate 1:1). 75.4 mg (13.8% of theory) of the target compound are obtained as a white foam.

LC-MS (Method 6): $R_t$=2.92 min; m/z=482 (M+H)$^+$ $^1$H-NMR (400 MHz, DMSO-d$_6$): δ=8.53 (s, 1H), 7.59-7.40 (m, 7H), 7.09 (t, 1H), 7.02 (d, 2H), 6.45-6.39 (m, 3H), 6.20 (t, 1H), 3.91 (d, 2H), 3.70 (s, 3H), 3.65 (s, 3H).

Example 17

N-(3-{[5-(4-Methoxyphenyl)-6-phenylfuro[2,3-d]pyrimidin-4-yl]oxy}phenyl)glycine

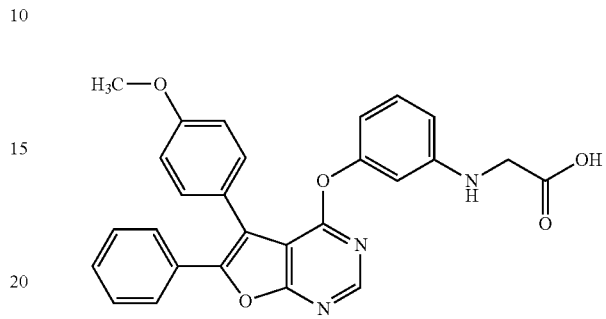

Stir 65 mg (0.135 mmol) of N-(3-{[5-(4-methoxyphenyl)-6-phenylfuro[2,3-d]pyrimidin-4-yl]oxy}-phenyl)glycine methyl ester, 0.27 ml of 1N sodium hydroxide solution and 2 ml of dioxane at RT overnight. Acidify the mixture with 1N hydrochloric acid and extract repeatedly with ethyl acetate/dichloromethane (1:1). Dry the combined organic phases over magnesium sulphate and concentrate. Chromatograph the residue on silica gel (eluent: dichloromethane/methanol 100:1→50:1). 16.8 mg (13.8% of theory) of the target compound are obtained as a yellowish hard oil.

LC-MS (Method 6): $R_t$=2.63 min; m/z=468 (M+H)$^+$ $^1$H-NMR (300 MHz, DMSO-d$_6$): δ=12.30 (br. s, 1H), 8.52 (s, 1H), 7.59-7.40 (m, 8H), 7.09 (t, 1H), 7.04-7.00 (m, 2H), 6.93 (d, 1H), 6.40-6.35 (m, 2H), 3.80 (s, 3H), 3.78 (s, 2H).

Example 18

5-(4-Methoxyphenyl)-6-phenyl-N-[3-(1H-tetrazol-5-ylmethoxy)phenyl]furo[2,3-d]pyrimidin-4-amine

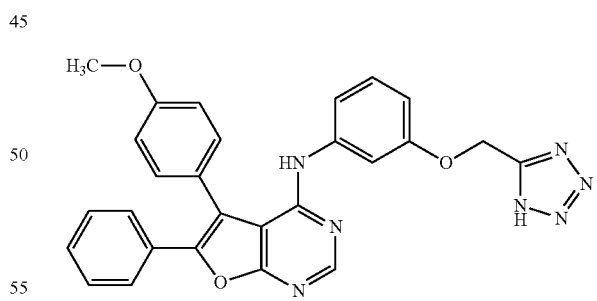

Stir a mixture of 100 mg (0.223 mmol) of (3-{[5-(4-methoxyphenyl)-6-phenylfuro[2,3-d]-pyrimidin-4-yl]amino}phenoxy)acetonitrile, 383 mg (3.345 mmol) of trimethylsilyl azide and 83.32 mg (0.334 mmol) of di-n-butyltin oxide in 5 ml of toluene at 80° C. overnight. After cooling, filter off the precipitated solid with suction, wash with toluene and dry at 50° C. under high vacuum overnight. 80.1 mg (73.1% of theory) of the target compound are obtained as a whitish solid.

LC-MS (Method 6): $R_t$=2.70 min; m/z=492 (M+H)$^+$ $^1$H-NMR (300 MHz, DMSO-d$_6$): δ=8.55 (s, 1H), 7.62-7.50 (m, 4H), 7.45-7.35 (m, 4H), 7.29-7.21 (m, 3H), 6.93 (s, 1H), 6.81-6.73 (m, 2H).

Example 19

(3-{[5-(4-Hydroxyphenyl)-6-phenylfuro[2,3-d]pyrimidin-4-yl]amino}phenoxy)acetic acid

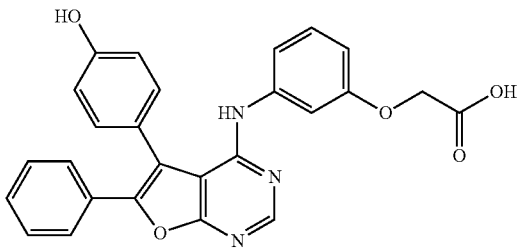

Add 109 mg (0.435 mmol) of boron tribromide at RT to a mixture of 170 mg (0.364 mmol) of 3-{[5-(4-methoxyphenyl)-6-phenylfuro[2,3-d]pyrimidin-4-yl]amino}phenoxyacetic acid and 4.5 ml of dichloromethane. Stir the mixture at RT overnight and then hydrolyse with 1N hydrochloric acid. After adding dichloromethane, filter off the insoluble solid and dry overnight under high vacuum. 128.6 mg of the target compound are obtained, which can be purified further by recrystallization from isopropanol.

LC-MS (Method 6): R$_t$=2.41 min; m/z=454 (M+H)$^+$.

Example 20

(2E)-3-(3-{[5-(4-Methoxyphenyl)-6-phenylfuro[2,3-d]pyrimidin-4-yl]amino}phenyl)acrylic acid ethyl ester

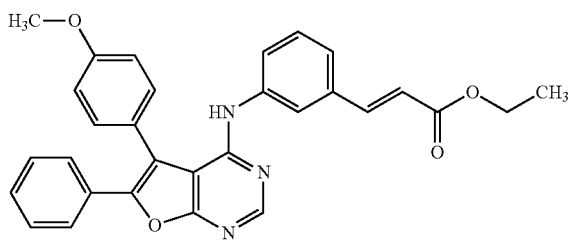

Heat 500 mg (1.85 mmol) of 4-chloro-5-(4-methoxyphenyl)-6-phenylfuro[2,3-d]pyrimidine and 369 mg (1.93 mmol) of ethyl 3-amino-trans-cinnamate to 150° C. for 1.5 h. After cooling, add dichloromethane and purify the crude product by chromatography on silica gel (eluent: dichloromethane/ethyl acetate 20:1). 539.5 mg (73.9% of theory) of the target product are obtained as a yellowish solid.

LC-MS (Method 6): R$_t$=3.34 min; m/z=492 (M+H)$^+$ $^1$H-NMR (300 MHz, DMSO-d$_6$): δ=8.53 (s, 1H), 7.71 (s, 1H), 7.62-7.51 (m, 5H), 7.46-7.35 (m, 6H), 7.23 (d, 2H), 7.05 (s, 1H), 6.54 (d, 1H), 4.21 (q, 2H), 3.90 (s, 3H), 1.27 (t, 3H).

Example 21

(2E)-3-(3-{[5-(4-Methoxyphenyl)-6-phenylfuro[2,3-d]pyrimidin-4-yl]amino}phenyl)acrylic acid

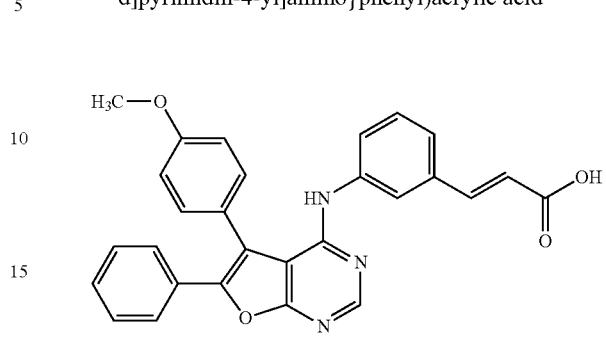

Add 0.73 ml of 1N sodium hydroxide solution dropwise to a mixture of 120 mg (0.244 mmol) of (2E)-3-(3-{[5-(4-methoxyphenyl)-6-phenylfuro[2,3-d]pyrimidin-4-yl]amino}phenyl)acrylic acid ethyl ester in 2 ml of THF. Stir the mixture at 50° C. overnight, then cool and acidify with 1N hydrochloric acid. Filter off the precipitated solid with suction, wash repeatedly with water and dry at 50° C. under high vacuum. 106 mg (93.7% of theory) of the target compound are obtained as a colourless solid.

LC-MS (Method 7): R$_t$=5.09 min; m/z=464 (M+H)$^+$ $^1$H-NMR (400 MHz, DMSO-d$_6$): δ=12.47 (br. s, 1H), 8.55 (s, 1H), 7.71 (s, 1H), 7.62-7.50 (m, 5H), 7.45-7.31 (m, 6H), 7.23 (d, 2H), 7.04 (s, 1H), 6.44 (d, 1H), 3.39 (s, 3H).

Example 22

(2E)-3-(3-{[5-(4-Methoxyphenyl)-6-phenylfuro[2,3-d]pyrimidin-4-yl]amino}phenyl)acrylic acid sodium salt

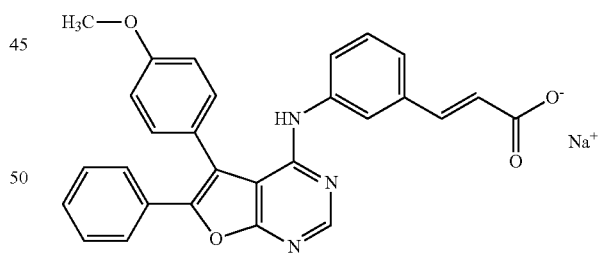

Initially charge 76 mg (0.164 mmol) of (2E)-3-(3-{[5-(4-methoxyphenyl)-6-phenylfuro[2,3-d]-pyrimidin-4-yl]amino}phenyl)acrylic acid in 1.5 ml of a 1:1 mixture of methanol and THF and add 0.164 ml of 1N sodium hydroxide solution at RT. Stir the mixture at RT for 2 h, then concentrate under reduced pressure and dry the residue under high vacuum overnight. 79.6 mg (99.9% of theory) of the target compound are obtained as a yellowish solid.

LC-MS (Method 5): R$_t$=3.01 min; m/z=464 (M-Na+2H)$^+$ $^1$H-NMR (400 MHz, DMSO-d$_6$): δ=8.54 (s, 1H), 7.65-7.48 (m, 5H), 7.43-7.34 (m, 3H), 7.31-7.21 (m, 4H), 7.15 (br. s, 1H), 6.97 (d, 1H), 6.92 (s, 1H), 6.71 (d, 1H), 3.91 (s, 3H).

Example 23

3-(4-{[5-(4-Methoxyphenyl)-6-phenylfuro[2,3-d]pyrimidin-4-yl]oxy}phenyl)propanoic acid methyl ester

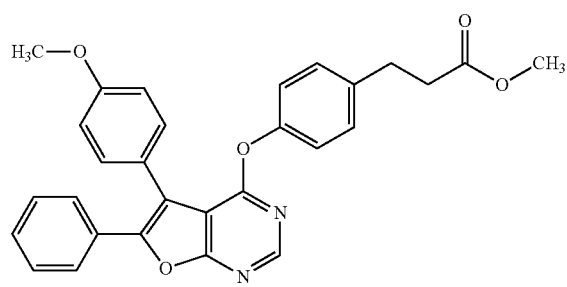

Heat 300 mg (0.891 mmol) of 4-chloro-5-(4-methoxyphenyl)-6-phenylfuro[2,3-d]pyrimidine, 642 mg (3.65 mmol) of 3-(4-hydroxyphenyl)propanoic acid methyl ester and 435.4 mg (1.34 mmol) of caesium carbonate to 120° C. for 2 h. After cooling, add water and filter off the precipitated crude product. Dissolve the solid in ethyl acetate and wash the solution twice with buffer solution (pH 7), dry over magnesium sulphate and concentrate again. After treating the residue with methanol, a solid precipitates out. Filter it off, wash with a little methanol and dry under reduced pressure. 160 mg (36.3% of theory) of the target compound are obtained as a colourless solid.

LC-MS (Method 3): $R_t$=2.93 min; m/z=481 (M+H)$^+$ $^1$H-NMR (300 MHz, DMSO-d$_6$): δ=8.52 (s, 1H), 7.60-7.50 (m, 4H), 7.45-7.38 (m, 3H), 7.28 (d, 2H), 7.12 (d, 2H), 7.02 (d, 2H), 3.80 (s, 3H), 3.60 (s, 3H), 2.87 (t, 2H), 2.67 (t, 2H).

Example 24

3-(4-{[5-(4-Methoxyphenyl)-6-phenylfuro[2,3-d]pyrimidin-4-yl]oxy}phenyl)propanoic acid

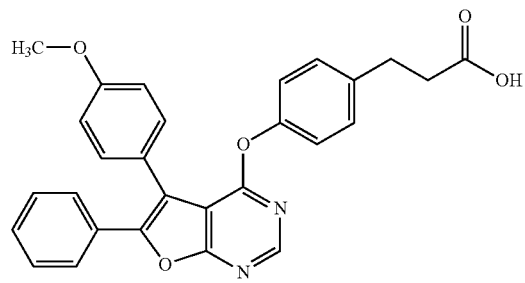

Initially charge 137 mg (0.285 mmol) of 3-(4-{[5-(4-methoxyphenyl)-6-phenylfuro[2,3-d]-pyrimidin-4-yl]oxy}phenyl)propanoic acid methyl ester in 4.5 ml of THF, and add 0.855 ml of 1N sodium hydroxide solution at RT. Stir the mixture at 50° C. for 1 h. After cooling, acidify with 1N hydrochloric acid and filter off the precipitated solid with suction, wash with water and dry under high vacuum. 125.9 mg (94.7% of theory) of the target compound are obtained.

LC-MS (Method 6): $R^t$=2.76 min; m/z=467 (M+H)$^+$ $^1$H-NMR (400 MHz, DMSO-d$_6$): δ=12.16 (s, 1H), 8.52 (s, 1H), 7.61-7.51 (m, 4H), 7.48-7.40 (m, 3H), 7.29 (d, 2H), 7.12 (d, 2H), 7.02 (d, 2H), 3.79 (s, 3H), 2.85 (t, 2H), 2.56 (t, 2H).

Example 25

3-(3-{[5-(4-Methoxyphenyl)-6-phenylfuro[2,3-d]pyrimidin-4-yl]amino}phenyl)propanoic acid methyl ester

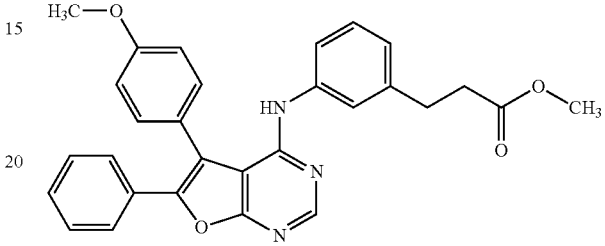

Heat 2100 mg (6.34 mmol) of 4-chloro-5-(4-methoxyphenyl)-6-phenylfuro[2,3-d]pyrimidine and 1453 mg (8.11 mmol) of 3-(3-aminophenyl)propanoic acid methyl ester to 150° C. for 1.5 h. After cooling, add dichloromethane and purify the crude product by chromatography on silica gel (eluent: dichloromethane/ethyl acetate 20:1). Stir the product thus obtained with diisopropyl ether and filter off the resulting solid with suction and wash with a little diisopropyl ether. 1367 mg (45.7% of theory) of the target product are obtained as a colourless solid.

LC-MS (Method 5): $R_t$=3.19 min; m/z=480 (M+H)$^+$.

Example 26

3-(3-{[5-(4-Methoxyphenyl)-6-phenylfuro[2,3-d]pyrimidin-4-yl]amino}phenyl)propanoic acid

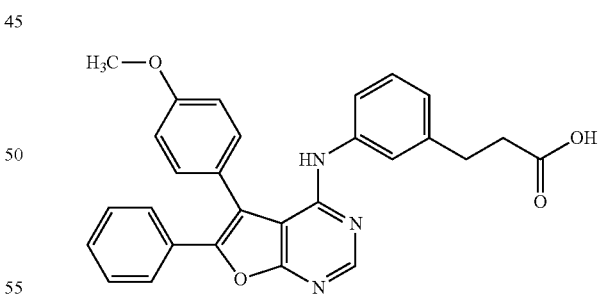

Initially charge 1000 mg (2.085 mmol) of 3-(3-{[5-(4-methoxyphenyl)-6-phenylfuro[2,3-d]-pyrimidin-4-yl]amino}phenyl)propanoic acid methyl ester in 30 ml of THF and add 6.3 ml of 1N sodium hydroxide solution at RT. Stir the mixture at 50° C. for 1 h and then, after cooling, acidify slightly with 1N hydrochloric acid. Filter off the precipitated solid with suction, wash repeatedly with water and dry at 40° C. under high vacuum overnight. 934.5 mg (96.3% of theory) of the target product are obtained as a colourless solid.

LC-MS (Method 3): δ=2.62 min; m/z=465 (M+H)$^+$ $^1$H-NMR (300 MHz, DMSO-d$_6$): δ=12.15 (br. s, 1H), 8.52 (s, 1H), 7.62-7.51 (m, 4H), 7.45-7.36 (m, 3H), 7.27-7.20 (m, 5H), 6.95-6.90 (m, 1H), 6.88 (s, 1H), 3.89 (s, 3H), 2.78 (t, 2H), 2.51 (t, 2H).

Example 27

3-(3-{[5-(4-Methoxyphenyl)-6-phenylfuro[2,3-d]pyrimidin-4-yl]amino}phenyl)propanoic acid sodium salt

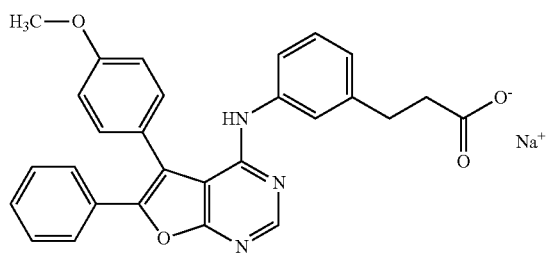

Dissolve 150 mg (0.322 mmol) of 3-(3-{[5-(4-methoxyphenyl)-6-phenylfuro[2,3-d]pyrimidin-4-yl]amino}phenyl)propanoic acid in 5 ml of THF and add 0.322 ml of 1N sodium hydroxide solution. Stir the mixture at RT for 1 h, then concentrate under reduced pressure and dry the residue under high vacuum overnight. 155.7 mg (99.1% of theory) of the target product are obtained as a colourless solid.

LC-MS (Method 5): R$_t$=2.95 min; m/z=466 (M-Na+2H)$^+$ $^1$H-NMR (400 MHz, DMSO-d$_6$): δ=8.52 (s, 2H), 7.63-7.51 (m, 4H), 7.45-7.33 (m, 3H), 7.39-7.12 (m, 5H), 6.89 (d, 1H), 6.80 (s, 1H), 3.90 (s, 3H), 2.68 (br. s, 2H), 2.08 (br. s, 2H).

Example 28

3-{[5-(4-Methoxyphenyl)-6-phenylfuro[2,3-d]pyrimidin-4-yl]amino}phenylacetic acid methyl ester

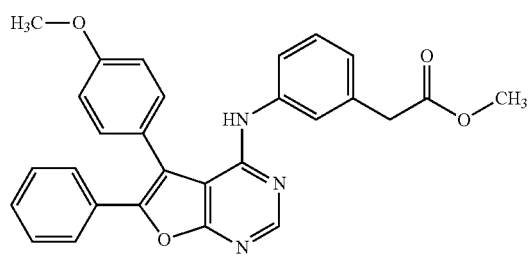

Heat 300 mg (0.89 mmol) of 4-chloro-5-(4-methoxyphenyl)-6-phenylfuro[2,3-d]pyrimidine and 191.3 mg (1.16 mmol) of 3-aminophenylacetic acid methyl ester to 150° C. for 1.5 h. After cooling, add dichloromethane and filter off the resulting solid with suction, wash with dichloromethane and dry at 50° C. under high vacuum overnight. Purify the crude product by chromatography on silica gel (eluent: dichloromethane/ethyl acetate 10:1). 273.2 mg (65.9% of theory) of the target product are obtained as a yellowish solid.

LC-MS (Method 3): R$_t$=2.88 min; m/z=466 (M+H)$^+$ $^1$H-NMR (400 MHz, DMSO-d$_6$): δ=8.52 (s, 1H), 7.59 (d, 2H), 7.53 (d, 2H), 7.44-7.37 (m, 3H), 7.32-7.21 (m, 5H), 6.95 (d, 1H), 6.90 (s, 1H), 3.90 (s, 3H), 3.65 (s, 2H), 3.61 (s, 3H).

Example 29

3-{[5-(4-Methoxyphenyl)-6-phenylfuro[2,3-d]pyrimidin-4-yl]amino}phenylacetic acid

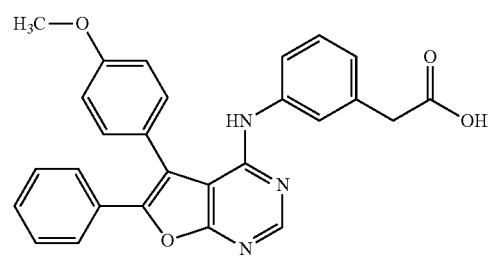

Dissolve 50 mg (0.107 mmol) of 3-{[5-(4-methoxyphenyl)-6-phenylfuro[2,3-d]pyrimidin-4-yl]amino}phenylacetic acid methyl ester in 2 ml of THF, add 0.322 ml of 1N sodium hydroxide solution at RT and stir at 50° C. for 4 h. Cool to RT and remove the THF under reduced pressure. Add water to the residue, and then 1N hydrochloric acid. Filter off the precipitated solid, wash with water and dry at 50° C. under reduced pressure. 41.7 mg (86% of theory) of the target compound are obtained as a white solid.

LC-MS (Method 5): R$_t$=2.85 min; m/z=452 (M+H)$^+$ $^1$H-NMR (400 MHz, DMSO-d$_6$): δ=8.51 (s, 1H), 7.60 (d, 2H), 7.53 (d, 2H), 7.44-7.37 (m, 3H), 7.32-7.20 (m, 5H), 6.96 (d, 1H), 6.91 (s, 1H), 3.91 (s, 3H), 3.53 (s, 2H).

Example 30

4-(4-{[5-(4-Methoxyphenyl)-6-phenylfuro[2,3-d]pyrimidin-4-yl]amino}phenyl)butanoic acid methyl ester

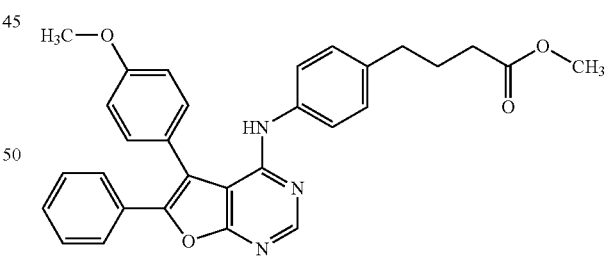

Heat 200.8 mg (0.596 mmol) of 4-chloro-5-(4-methoxyphenyl)-6-phenylfuro[2,3-d]pyrimidine and 149.8 mg (0.775 mmol) of 4-(4-aminophenyl)butanoic acid methyl ester to 150° C. for 1.5 h. After cooling, concentrate under reduced pressure, add dichloromethane to the residue and purify the crude product by chromatography on silica gel (eluent: dichloromethane/ethyl acetate 20:1). The product thus obtained is stirred with diisopropyl ether and the solid obtained is filtered off with suction and washed with a little diisopropyl ether. 236.7 mg (80.4% of theory) of the target product are obtained as a pale pink solid.

LC-MS (Method 3): R$_t$=3.08 min; m/z=494 (M+H)$^+$

¹H-NMR (400 MHz, DMSO-d₆): δ=8.49 (s, 1H), 7.60 (d, 2H), 7.53 (d, 2H), 7.43-7.37 (m, 3H), 7.32 (d, 2H), 7.23 (d, 2H), 7.13 (d, 2H), 6.84 (s, 1H), 3.88 (s, 3H), 3.59 (s, 3H), 2.58-2.50 (m, 2H), 2.29 (t, 2H), 1.84-1.77 (m, 2H).

Example 31

4-(4-{[5-(4-Methoxyphenyl)-6-phenylfuro[2,3-d]pyrimidin-4-yl]amino}phenyl)butanoic acid

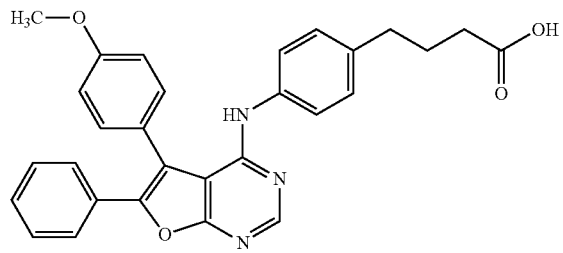

Dissolve 175.6 mg (0.356 mmol) of 4-(4-{[5-(4-methoxyphenyl)-6-phenylfuro[2,3-d]pyrimidin-4-yl]amino}phenyl)butanoic acid methyl ester in 3.5 ml of THF, add 1.07 ml of 1N sodium hydroxide solution at RT and stir at 50° C. for 1 h. Cool to RT and remove the THF under reduced pressure. Add water to the residue, and then 1N hydrochloric acid. Filter off the precipitated solid, wash repeatedly with water and dry at 40° C. under reduced pressure overnight. 130 mg (76.2% of theory) of the target compound are obtained as a white solid.

LC-MS (Method 5): $R_t$=3.03 min; m/z=480 (M+H)⁺

¹H-NMR (400 MHz, CDCl₃): δ=8.54 (s, 1H), 7.59 (d, 2H), 7.49 (d, 2H), 7.38-7.25 (m, 5H), 7.18-7.10 (m, 4H), 6.60 (s, 1H), 2.68-2.61 (m, 2H), 2.40-2.33 (m, 2H), 1.98-1.90 (m, 2H).

Example 32

4-(2-{[5-(4-Methoxyphenyl)-6-phenylfuro[2,3-d]pyrimidin-4-yl]amino}phenyl)butanoic acid methyl ester

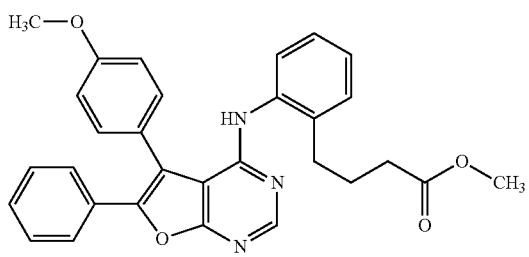

Heat 259.8 mg (0.771 mmol) of 4-chloro-5-(4-methoxyphenyl)-6-phenylfuro[2,3-d]pyrimidine and 228 mg of 4-(2-aminophenyl)butanoic acid methyl ester (85% strength, approx. 1.0 mmol) to 150° C. overnight. After cooling, concentrate under reduced pressure, add dichloromethane to the residue and purify the crude product by chromatography on silica gel (eluent: dichloromethane/ethyl acetate 50:1→10:1). The product thus obtained is purified further by preparative RP-HPLC. 33.1 mg (8.7% of theory) of the target product are obtained.

LC-MS (Method 3): $R_t$=3.08 min; m/z=494 (M+H)⁺

¹H-NMR (400 MHz, DMSO-d₆): δ=8.48 (s, 1H), 7.61 (d, 2H), 7.53 (d, 2H), 7.42-7.12 (m, 9H), 6.83 (s, 1H), 6.39 (s, 3H), 3.58 (s, 3H), 2.59-2.50 (m, 2H), 2.33-2.28 (m, 2H), 1.83-1.75 (m, 2H).

Example 33

4-(2-{[5-(4-Methoxyphenyl)-6-phenylfuro[2,3-d]pyrimidin-4-yl]amino}phenyl)butanoic acid

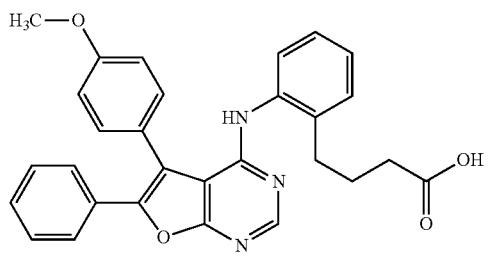

Dissolve 28.9 mg (0.059 mmol) of 4-(2-{[5-(4-methoxyphenyl)-6-phenylfuro[2,3-d]pyrimidin-4-yl]amino}phenyl)butanoic acid methyl ester in 1 ml of THF, add 0.176 ml of 1N sodium hydroxide solution at RT and stir at 50° C. for 1 h. Cool to RT and remove the THF under reduced pressure. Add water to the residue, and then 1N hydrochloric acid. Filter off the precipitated solid, wash repeatedly with water and dry at 40° C. under reduced pressure overnight. 16.9 mg (60.2% of theory) of the target compound are obtained as a white solid.

LC-MS (Method 6): $R_t$=2.89 min; m/z=480 (M+H)⁺

¹H-NMR (400 MHz, DMSO-d₆): δ=12.02 (br. s, 1H), 8.50 (s, 1H), 7.60 (d, 2H), 7.52 (d, 2H), 7.43-7.12 (m, 9H), 6.84 (s, 1H), 3.89 (s, 3H), 2.58-2.49 (m, 2H), 2.20 (t, 2H), 1.27 (t, 2H).

Example 34

5-(3-{[5-(4-Methoxyphenyl)-6-phenylfuro[2,3-d]pyrimidin-4-yl]amino}benzyl)-1,3,4-oxadiazol-2(3H)-one

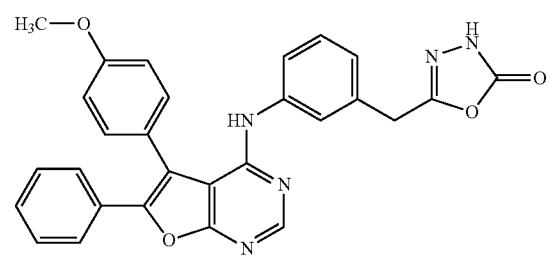

Heat 0.85 mg (0.183 mmol) of 2-(3-{[5-(4-methoxyphenyl)-6-phenylfuro[2,3-d]pyrimidin-4-yl]amino}phenyl)acetic hydrazide and 35.5 mg (0.219 mmol) of N,N'-carbonyldiimidazole under reflux in 3 ml of THF for 2 h. After cooling to RT, add to water and extract repeatedly with dichloromethane. Dry the combined organic phases over magnesium sulphate and concentrate under reduced pressure. 79.9 mg (89% of theory) of the target product are obtained as a beige solid.

LC-MS (Method 3): δ=2.55 min; m/z=492 (M+H)⁺

¹H-NMR (400 MHz, DMSO-d₆): δ=8.51 (s, 1H), 7.68 (s, 1H), 7.58 (d, 2H), 7.54 (d, 2H), 7.44-7.38 (m, 3H), 7.30-7.27 (m, 2H), 7.21 (d, 2H), 7.06-6.97 (m, 3H), 3.90 (s, 2H), 3.88 (s, 3H).

Example 35 and Example 36

(+/−)-cis-N-(3-{[5-(4-Methoxyphenyl)-6-phenylfuro [2,3-d]pyrimidin-4-yl]amino}cyclohexyl)-glycine methyl ester and (+/−)-trans-N-(3-{[5-(4-Methoxyphenyl)-6-phenyl-furo[2,3-d]pyrimidin-4-yl]amino}cyclohexyl)-gly-cine methyl ester

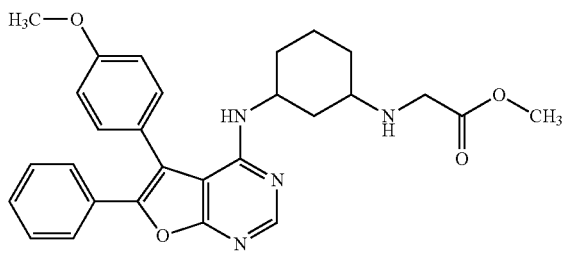

Dissolve 132 mg (0.318 mmol) of ⁻(+/−)-cis/trans-N-[5-(4-methoxyphenyl)-6-phenylfuro[2,3-d]pyrimidin-4-yl]-cyclohexane-1,3-diamine (Example 36A) in 1.5 ml of dichloromethane and add 18.7 μl of acetic acid at RT. Add 28 mg (0.318 mmol) of oxoacetic acid methyl ester and, after 5 min, 101 mg (0.478 mmol) of sodium triacetoxyborohydride. Stir the mixture at RT for 2 h and then dilute with water and dichloromethane. Wash the organic phase with saturated sodium carbonate solution, dry over sodium sulphate and concentrate under reduced pressure. Purify the crude product by preparative RP-HPLC (eluent: acetonitrile/water gradient) and separate the cis/trans isomers:

(+/−)-cis-N-(3-{[5-(4-Methoxyphenyl)-6-phenylfuro [2,3-d]pyrimidin-4-yl]amino}cyclohexyl)-glycine methyl ester (Example 35)

Yield: 26.5 mg (17.1% of theory)
LC-MS (Method 3): $R_t$=1.70 min; m/z=487 (M+H)$^+$;

(+/−)-trans-N-(3-{[5-(4-Methoxyphenyl)-6-phenyl-furo[2,3-d]pyrimidin-4-yl]amino}cyclohexyl)-gly-cine methyl ester (Example 36)

Yield: 22.1 mg (14.3% of theory)
LC-MS (Method 3): $R_t$=1.61 min; m/z=487 (M+H)$^+$.

Example 37

(+/−)-cis-[(3-{[5-(4-Methoxyphenyl)-6-phenylfuro [2,3-d]pyrimidin-4-yl]oxy}cyclohexyl)oxy]-acetic acid tert-butyl ester

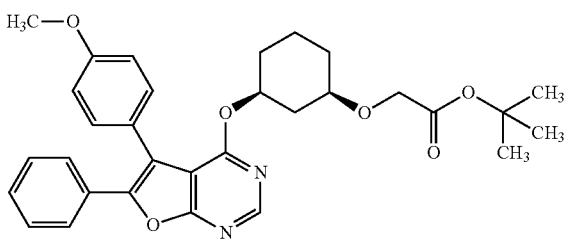

Dissolve 350 mg (0.84 mmol) of (+/−)-cis-3-{[5-(4-methoxyphenyl)-6-phenylfuro[2,3-d]pyrimidin-4-yl] oxy}cyclohexanol in 1 ml of absolute THF, cool to 0° C. and add 0.48 ml (approx. 0.97 mmol) of phosphazene base P2-t-Bu (2 M solution in THF). Remove the cooling and stir the solution at RT for 10 min, and then add dropwise at RT to a solution of 295 mg (1.51 mmol) of bromoacetic acid tert-butyl ester in 2 ml of THF. After 2 h at RT, the reaction mixture is concentrated under reduced pressure and purified directly by chromatography on silica gel (Biotage, eluent: cyclohexane/ethyl acetate 10:1→1:1). As well as 180 mg of starting material, 207 mg (46.4% of theory) of the target product are obtained.

LC-MS (Method 6): $R_t$=3.38 min; m/z=531 (M+H)$^+$
$^1$H-NMR (400 MHz, DMSO-d$_6$): δ=8.58 (s, 1H), 7.54 (dd, 2H), 7.43-7.39 (m, 5H), 7.0 (d, 2H), 5.13 (m, 1H), 3.98 (s, 2H), 3.82 (s, 3H), 3.42 (m, 1H), 2.41 (br. d, 1H), 2.05-1.93 (m, 2H), 1.78-1.70 (m, 1H), 1.40 (s, 9H), 1.30-1.05 (m, 4H).

Separation of the Enantiomers:
Dissolve 0.2 g of (+/−)-cis-[(3-{[5-(4-Methoxyphenyl)-6-phenylfuro[2,3-d]pyrimidin-4-yl]oxy}-cyclohexyl)oxy]acetic acid tert-butyl ester in 4 ml of ethanol and 16 ml of isohexane. Separate the racemate into the enantiomers by preparative HPLC on chiral phase (see Example 38 and 39) [column: Daicel Chiralcel OJ-H, 5 μm, 250 mm×20 mm; flow rate: 15 ml/min; detection: 220 nm; injection volume 0.5 ml; temperature: 45° C.; eluent: t=0 min 90% isohexane/10% ethanol→t=7 min 90% isohexane/10% ethanol].

Example 38 cis-[(3-{[5-(4-Methoxyphenyl)-6-phenylfuro[2,3-d] pyrimidin-4-yl]oxy}cyclohexyl)oxy]acetic acid tert-butyl ester (Enantiomer 1)

LC-MS (Method 3): $R_t$=3.22 min; m/z=531 (M+H)$^+$
$[α]_D^{20}$=−59°, c=0.525, CHCl$_3$.

Example 39 cis-[(3-{[5-(4-Methoxyphenyl)-6-phenylfuro[2,3-d] pyrimidin-4-yl]oxy}cyclohexyl)oxy]acetic acid tert-butyl ester (Enantiomer 2)

LC-MS (Method 3): $R_t$=3.22 min; m/z=531 (M+H)$^+$
$[α]_D^{20}$=+55.5°, c=0.51, CHCl$_3$.

Example 40

(+/−)-trans-[(3-{[5-(4-Methoxyphenyl)-6-phenylfuro [2,3-d]pyrimidin-4-yl]oxy}cyclohexyl)oxy]-acetic acid tert-butyl ester

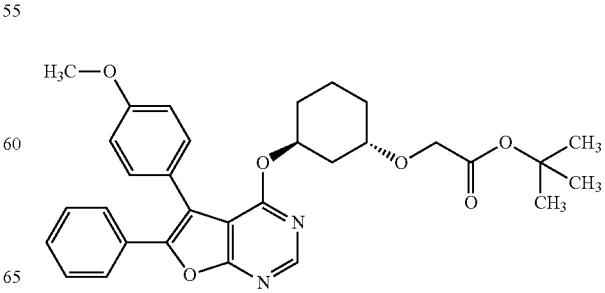

Heat 920 mg (11.53 mmol) of 50% sodium hydroxide solution and approx. 5 ml of toluene to 40° C. and add 65.2 mg (0.192 mmol) of tetrabutylammonium hydrogensulphate and 800 mg (1.91 mmol) of (+/−)-trans-3-{[5-(4-methoxyphenyl)-6-phenylfuro[2,3-d]pyrimidin-4-yl]oxy}cyclohexanol. Dilute the suspension with a little THF, which starts to dissolve the solid. After adding 749 mg (3.84 mmol) of bromoacetic acid tert-butyl ester, heat the suspension to 60° C. with very vigorous stirring. After a total of 3 h at 60° C., in the course of which a further 920 mg of 50% sodium hydroxide solution and approx. 1500 mg of bromoacetic acid tert-butyl ester are added, cool the reaction mixture and add to water. Extract three times with dichloromethane. Dry the combined organic phases over magnesium sulphate and concentrate under reduced pressure. Separate the crude product by chromatography on silica gel (eluent: cyclohexane/ethyl acetate 10:1→1:1). As well as 473 mg of starting material, 286 mg (28.1% of theory) of the target compound are isolated.

LC-MS (Method 6): $R_t$=3.36 min; m/z=531 (M+H)$^+$ $^1$H-NMR (400 MHz, DMSO-$d_6$): δ=8.58 (s, 1H), 7.54 (d, 2H), 7.43-7.39 (m, 5H), 7.05 (d, 2H), 5.58 (m, 1H), 3.88 (d, 2H), 3.82 (s, 3H), 3.21 (m, 1H), 1.99-1.92 (m, 1H), 1.78-1.70 (m, 1H), 1.61-1.53 (m, 3H), 1.49-1.40 (m, 1H), 1.38 (s, 9H), 1.27-1.17 (m, 2H).

Separation of the Enantiomers:

Dissolve 0.3 g of (+/−)-trans-[(3-{[5-(4-methoxyphenyl)-6-phenylfuro[2,3-d]pyrimidin-4-yl]oxy}-cyclohexyl)oxy] acetic acid tert-butyl ester in 2 ml of ethanol and 8 ml of isohexane. Separate the racemate into the enantiomers by preparative HPLC on chiral phase (see Example 41 and 42) [column: Daicel Chiralcel OJ-H, 5 μm, 250 mm×20 mm; flow rate: 15 ml/min; detection: 220 nm; injection volume 0.5 ml; temperature: 40° C.; eluent: t=0 min 90% isohexane/10% ethanol→t=10 min 90% isohexane/10% ethanol].

Example 41

(+)-trans-[(3-{[5-(4-Methoxyphenyl)-6-phenylfuro [2,3-d]pyrimidin-4-yl]oxy}cyclohexyl)oxy]-acetic acid tert-butyl ester (Enantiomer 1)

$[α]_D^{20}$=+60.6°, c=0.50, CHCl$_3$ $^1$H-NMR (400 MHz, DMSO-$d_6$): δ=8.58 (s, 1H), 7.54 (d, 2H), 7.43-7.39 (m, 5H), 7.05 (d, 2H), 5.58 (br. s, 1H), 3.88 (d, 2H), 3.82 (s, 3H), 3.21 (m, 1H), 1.99-1.92 (m, 1H), 1.78-1.70 (m, 1H), 1.61-1.53 (m, 3H), 1.49-1.40 (m, 1H), 1.38 (s, 9H), 1.27-1.17 (m, 2H).

Example 42

(−)-trans-[(3-{[5-(4-Methoxyphenyl)-6-phenylfuro [2,3-d]pyrimidin-4-yl]oxy}cyclohexyl)oxy]-acetic acid-tert-butyl ester (Enantiomer 2)

$[α]_D^{20}$=−70.4°, c=0.525, CHCl$_3$ $^1$H-NMR (400 MHz, DMSO-$d_6$): δ=8.58 (s, 1H), 7.54 (d, 2H), 7.43-7.39 (m, 5H), 7.05 (d, 2H), 5.58 (br. s, 1H), 3.88 (d, 2H), 3.82 (s, 3H), 3.21 (m, 1H), 1.99-1.92 (m, 1H), 1.78-1.70 (m, 1H), 1.61-1.53 (m, 3H), 1.49-1.40 (m, 1H), 1.38 (s, 9H), 1.27-1.17 (m, 2H).

Example 43

(+/−)-all-cis-[(3-Hydroxy-5-{[5-(4-methoxyphenyl)-6-phenylfuro[2,3-d]pyrimidin-4-yl]oxy}cyclohexyl) oxy]acetic acid tert-butyl ester

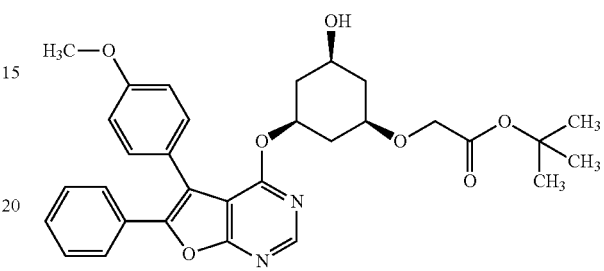

Add 0.69 ml (approx. 1.39 mmol) of phosphazene base P2-t-Bu (approx. 2 M solution in THF) to a solution, cooled to 0° C., of 600 mg (1.39 mmol) of (+/−)-all-cis-5-{[5-(4-methoxyphenyl)-6-phenylfuro[2,3-d]pyrimidin-4-yl] oxy}cyclohexane-1,3-diol in 1.2 ml of DMF. Stir the resulting solution at 0° C. for 5 min and then add 0.25 ml (1.67 mmol) of tert-butyl bromoacetate. Remove the cooling and stir the mixture at RT for 15 min. Then add to water and extract three times with ethyl acetate. Dry the combined organic phases over magnesium sulphate and concentrate under reduced pressure. After purification by preparative RP-HPLC (eluent: acetonitrile/water gradient), 207 mg (27.3% of theory) of the target product are obtained.

LC-MS (Method 6): $R_t$=2.90 min; m/z=547 (M+H)$^+$ $^1$H-NMR (400 MHz, DMSO-$d_6$): δ=8.60 (s, 1H), 7.56 (dd, 2H), 7.43-7.38 (m, 5H), 7.02 (d, 2H), 5.13 (m, 1H), 4.85 (d, 1H), 3.98 (s, 2H), 3.83 (s, 3H), 3.59-3.49 (m, 2H), 2.96-2.90 (m, 1H), 2.30-2.18 (m, 2H), 1.42 (s, 9H), 1.13-1.02 (m, 3H).

Example 44

(+/−)-3-(3-{[5-(4-Methoxyphenyl)-6-phenylfuro[2,3-d]pyrimidin-4-yl]oxy}piperidin-1-yl)-propanoic acid methyl ester

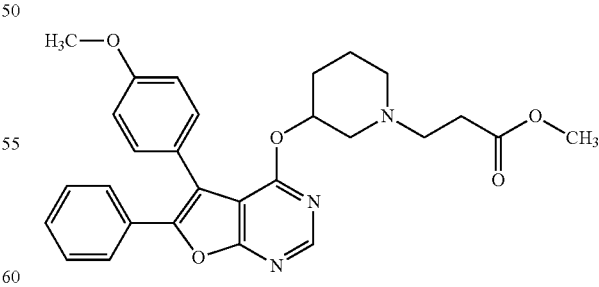

Dissolve 200 mg (0.5 mmol) of (+/−)-5-(4-methoxyphenyl)-6-phenyl-4-(piperidin-3-yloxy)furo-[2,3-d]pyrimidine (Example 37A) in 1 ml of THF and add 69 μl (0.5 mmol) of triethylamine. After adding 54 μl (0.5 mmol) of 3-bromopropionic acid methyl ester, stir the mixture at 20-40° C. for approx. 8 h. In the meantime, add triethylamine (total of approx. 1.2 mmol) and 3-bromopropionic acid methyl ester (total of approx. 1.2 mmol) twice more. After diluting with dichloromethane, wash the mixture with saturated sodium hydrogencarbonate solution and concentrate under reduced pressure. Purify the crude product by means of preparative RP-HPLC (eluent: acetonitrile/water gradient). 118 mg (45.7% of theory) of the target product are obtained.

LC-MS (Method 5): $R^t$=1.91 min; m/z=488 (M+H)$^+$ $^1$H-NMR (400 MHz, DMSO-d$_6$): δ=8.59 (s, 1H), 7.58-7.52 (m, 2H), 7.43-7.39 (m, 5H), 7.01 (d, 2H), 5.26 (m, 1H), 3.82 (s, 3H), 3.50 (s, 3H), 2.80-2.75 (m, 1H), 2.60-2.50 (m, 2H), 2.46-2.22 (m, 5H), 1.89-1.81 (m, 1H), 1.68-1.59 (m, 1H), 1.45-1.32 (m, 2H).

Example 45

(+/−)-4-(3-{[5-(4-Methoxyphenyl)-6-phenylfuro[2,3-d]pyrimidin-4-yl]oxy}piperidin-1-yl)butanoic acid methyl ester

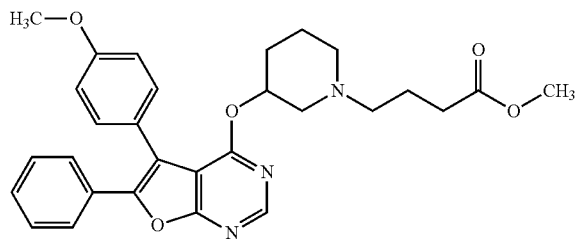

Add 0.65 ml (3.74 mmol) of DIEA, 20.6 mg (0.125 mmol) of potassium iodide and 450 mg (2.5 mmol) of 4-bromobutyric acid methyl ester successively to 500 mg (1.25 mmol) of (+/−)-5-(4-methoxyphenyl)-6-phenyl-4-(piperidin-3-yloxy)furo[2,3-d]pyrimidine (Example 37A) in 1 ml of THF. Heat the mixture under reflux for 4 h, then cool, dilute with dichloromethane, wash with saturated sodium hydrogencarbonate solution and concentrate under reduced pressure. Purify the crude product by chromatography on silica gel (eluent: cyclohexane/ethyl acetate 4:1→1:1). 662 mg (100% of theory) of the target compound are obtained.

LC-MS (Method 5): $R_t$=1.89 min; m/z=502 (M+H)$^+$ $^1$H-NMR (400 MHz, DMSO-d$_6$): δ=8.58 (s, 1H), 7.54 (d, 2H), 7.43-7.39 (m, 5H), 7.00 (d, 2H), 5.24 (m, 1H), 3.81 (s, 3H), 3.52 (s, 3H), 2.79-2.74 (m, 1H), 2.48-2.41 (m, 1H), 2.28-2.21 (m, 5H), 2.14 (m, 1H), 1.92-1.85 (m, 1H), 1.68-1.58 (m, 3H), 1.47-1.30 (m, 2H).

Separation of the Enantiomers:

Dissolve racemic (+/−)-4-(3-{[5-(4-methoxyphenyl)-6-phenylfuro[2,3-d]pyrimidin-4-yl]oxy}-piperidin-1-yl)butanoic acid methyl ester in a 1:4 mixture of ethanol and isohexane and separate it into the enantiomers by preparative HPLC on chiral phase (see Example 46 and 47) [column: Daicel Chiralpak AS-H, 5 μm, 250 mm×20 mm; flow rate: 15 ml/min; detection: 220 nm; injection volume 0.5 ml; temperature: 28° C.; eluent: t=0 min 90% isohexane/10% ethanol→t=8 min 90% isohexane/10% ethanol].

Example 46

4-(3-{[5-(4-Methoxyphenyl)-6-phenylfuro[2,3-d]pyrimidin-4-yl]oxy}piperidin-1-yl)butanoic acid methyl ester (Enantiomer 1)

LC-MS (Method 6): $R_t$=1.84 min; m/z=502 (M+H)$^+$ $R^t$=7.26 min [column: Daicel Chiralpak AS-H, 5 μm, 250 mm×4.6 mm; flow rate: 1.0 ml/min; detection: 230 nm; temperature: 25° C.; eluent: 90% isohexane/10% ethanol with 0.2% diethylamine];

$^1$H-NMR (400 MHz, DMSO-d$_6$): δ=8.58 (s, 1H), 7.54 (d, 2H), 7.43-7.39 (m, 5H), 7.00 (d, 2H), 5.24 (m, 1H), 3.81 (s, 3H), 3.52 (s, 3H), 2.79-2.74 (m, 1H), 2.48-2.41 (m, 1H), 2.28-2.21 (m, 5H), 2.18-2.12 (m, 1H), 1.92-1.85 (m, 1H), 1.68-1.58 (m, 3H), 1.47-1.30 (m, 2H).

Example 47

4-(3-{[5-(4-Methoxyphenyl)-6-phenylfuro[2,3-d]pyrimidin-4-yl]oxy}piperidin-1-yl)butanoic acid methyl ester (Enantiomer 2)

LC-MS (Method 3): $R_t$=1.67 min; m/z=502 (M+H)$^+$ $R_t$=7.63 min [column: Daicel Chiralpak AS-H, 5 μm, 250 mm×4.6 mm; flow rate: 1.0 ml/min; detection: 230 nm; temperature: 25° C.; eluent: 90% isohexane/10% ethanol with 0.2% diethylamine];

$^1$H-NMR (400 MHz, DMSO-d$_6$): δ=8.58 (s, 1H), 7.54 (d, 2H), 7.43-7.39 (m, 5H), 7.00 (d, 2H), 5.24 (m, 1H), 3.81 (s, 3H), 3.52 (s, 3H), 2.79-2.74 (m, 1H), 2.48-2.41 (m, 1H), 2.28-2.21 (m, 5H), 2.19-2.12 (m, 1H), 1.92-1.85 (m, 1H), 1.68-1.58 (m, 3H), 1.47-1.30 (m, 2H).

Example 48

(+/−)-3-[2-({[5-(4-Methoxyphenyl)-6-phenylfuro[2,3-d]pyrimidin-4-yl]oxy}methyl)pyrrolidin-1-yl]propanoic acid methyl ester

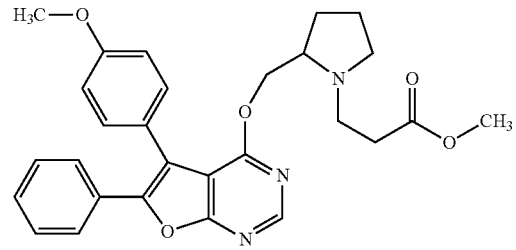

Dissolve 160 mg (0.4 mmol) of (+/−)-5-(4-methoxyphenyl)-6-phenyl-4-(pyrrolidin-2-ylmethoxy)-furo[2,3-d]pyrimidine (Example 38A) in 0.8 ml of THF and add 110 μl (0.8 mmol) of triethylamine and 87 μl (0.8 mmol) of 3-bromopropionic acid methyl ester. Stir the mixture at 20-40° C. overnight, then dilute with dichloromethane and wash with saturated sodium hydrogencarbonate solution. Concentrate the solution under reduced pressure and purify the resulting oil by preparative RP-HPLC (eluent: acetonitrile/water gradient). 90 mg (44% of theory) of the target product are obtained.

LC-MS (Method 6): $R_t$=1.79 min; m/z=488 (M+H)$^+$ $^1$H-NMR (400 MHz, DMSO-d$_6$): δ=8.58 (s, 1H), 7.53 (d, 2H), 7.42-7.36 (m, 5H), 7.01 (d, 2H), 4.39 (dd, 1H), 4.18 (dd, 1H), 3.81 (s, 3H), 3.51 (s, 3H), 2.96-2.89 (m, 2H), 2.64 (m, 1H), 2.41-2.30 (m, 3H), 2.12 (q, 1H), 1.75-1.35 (m, 4H).

The following enantiomerically pure compounds are prepared in an analogous manner (4 h of reaction time at approx. 40° C., greater excesses of DMA and 3-bromopropionic acid methyl ester overall) proceeding from the enantiomerically pure pyrrolidine derivatives Example 40A or 41A:

| Example | Structure | Analytical data |
|---|---|---|
| 49 | 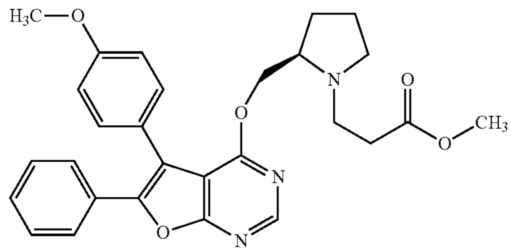 | LC-MS (Method 5): $R_t$ = 1.91 min; m/z = 488 (M + H)$^+$<br>$^1$H-NMR (400 MHz, DMSO-$d_6$): δ = 8.58 (s, 1H), 7.52 (d, 2H), 7.42-7.36 (m, 5H), 7.01 (d, 2H), 4.38 (dd, 1H), 4.18 (dd, 1H), 3.81 (s, 3H), 3.52 (s, 3H), 2.97-2.89 (m, 2H), 2.69-2.61 (m, 1H), 2.41-2.30 (m, 3H), 2.12 (q, 1H), 1.75-1.35 (m, 4H). |
| 50 | 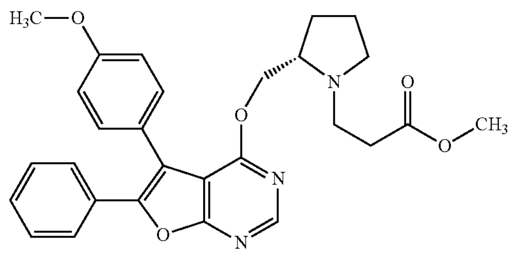 | LC-MS (Method 6): $R_t$ = 1.80 min; m/z = 488 (M + H)$^+$<br>$^1$H-NMR (400 MHz, DMSO-$d_6$): δ = 8.58 (s, 1H), 7.52 (d, 2H), 7.42-7.36 (m, 5H), 7.01 (d, 2H), 4.39 (dd, 1H), 4.18 (dd, 1H), 3.81 (s, 3H), 3.52 (s, 3H), 2.97-2.89 (m, 2H), 2.69-2.61 (m, 1H), 2.41-2.30 (m, 3H), 2.12 (q, 1H), 1.75-1.35 (m, 4H). |

Example 51

(+/−)-(3-{[5-(4-Methoxyphenyl)-6-phenylfuro[2,3-d]pyrimidin-4-yl]amino}piperidin-1-yl)propanoic acid methyl ester

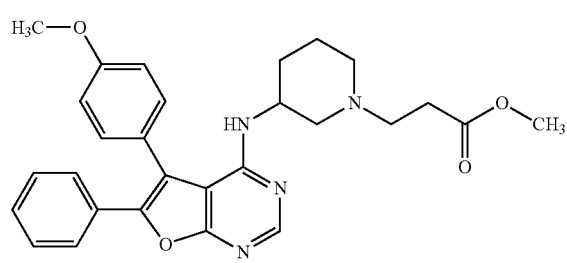

Add 82 µl (0.749 mmol) of 3-bromopropanoic acid methyl ester and 104 µl (0.749 mmol) of triethylamine to a solution of 150 mg (0.375 mmol) of (+/−)-5-(4-methoxyphenyl)-6-phenyl-N-piperidin-3-ylfuro[2,3-d]pyrimidin-4-amine (Example 39A) in 0.75 ml of THF, and stir at 20-40° C. overnight. Dilute the mixture with dichloromethane and wash with saturated sodium hydrogencarbonate solution. After concentration under reduced pressure, stir the residue with methanol, filter off the precipitated product with suction and dry under high vacuum. Isolate a second product batch from the filtrate after concentration by preparative RP-HPLC (eluent: acetonitrile/water gradient). A total of 124 mg (67.1% of theory) of the target product are obtained.

LC-MS (Method 5): $R_t$=1.83 min; m/z=487 (M+H)$^+$ $^1$H-NMR (400 MHz, DMSO-$d_6$): δ=8.31 (s, 1H), 7.49-7.44 (m, 4H), 7.39-7.30 (m, 3H), 7.14 (d, 2H), 5.59 (d, 1H), 4.24 (m, 1H), 3.83 (s, 3H), 3.59 (s, 3H), 2.42-2.35 (m, 2H), 2.28-2.18 (m, 2H), 2.05-1.97 (m, 1H), 1.62-1.55 (m, 1H), 1.40 (br. s, 2H).

Example 52

(+/−)-4-[2-({[5-(4-Methoxyphenyl)-6-phenylfuro[2,3-d]pyrimidin-4-yl]oxy}methyl)pyrrolidin-1-yl]butanoic acid methyl ester

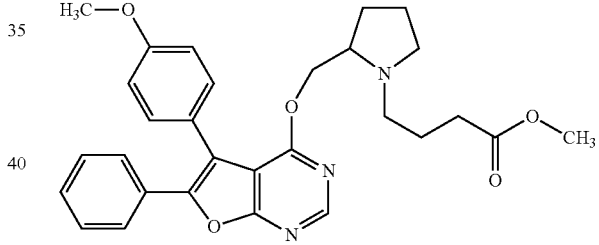

Dissolve 100 mg (0.25 mmol) of (+/−)-5-(4-methoxyphenyl)-6-phenyl-4-(pyrrolidin-2-ylmethoxy)furo[2,3-d]-pyrimidine (Example 38A) in 2 ml of THF and successively add 65 µl (0.374 mmol) of DIEA, 4.1 mg (0.025 mmol) of potassium iodide and 45 mg (0.25 mmol) of 4-bromobutyric acid methyl ester. Heat the mixture under reflux for 1 h and then add to water with cooling. Extract three times with ethyl acetate and wash the combined organic phases twice with buffer solution (pH 7) and with saturated sodium chloride solution. Dry the solution over magnesium sulphate and concentrate under reduced pressure. Purify the crude product by preparative RP-HPLC (eluent: acetonitrile/water gradient). 47 mg (37.6% of theory) of the target product are obtained.

LC-MS (Method 3): $R_t$=1.73 min; m/z=502 (M+H)$^+$ $^1$H-NMR (400 MHz, DMSO-$d_6$): δ=8.60 (s, 1H), 7.55-7.52 (m, 2H), 7.42-7.37 (m, 5H), 7.01 (d, 2H), 4.32 (dd, 1H), 4.19 (dd, 1H), 3.80 (s, 3H), 3.49 (s, 3H), 2.93 (t, 1H), 2.62-2.50 (m, 2H), 2.20-2.02 (m, 4H), 1.74-1.67 (m, 1H), 1.60-1.37 (m, 5H).

The following enantiomerically pure compounds are prepared in an analogous manner proceeding from the enantiomerically pure pyrrolidine derivatives Example 40A or 41A:

| Example | Structure | Analytical data |
|---|---|---|
| 53 | 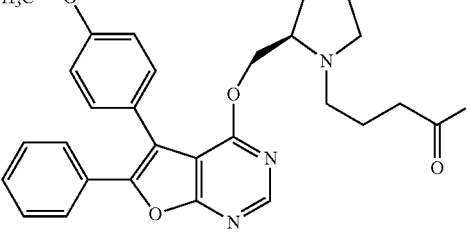 | LC-MS (Method 3): $R_t$ = 1.72 min; m/z = 502 (M + H)$^+$<br>$^1$H-NMR (400 MHz, DMSO-d$_6$): δ = 8.60 (s, 1H), 7.55-7.52 (m, 2H), 7.42-7.37 (m, 5H), 7.01 (d, 2H), 4.32 (dd, 1H), 4.19 (dd, 1H), 3.80 (s, 3H), 3.49 (s, 3H), 2.93 (t, 1H), 2.62-2.50 (m, 2H), 2.20-2.02 (m, 4H), 1.74-1.67 (m, 1H), 1.60-1.37 (m, 5H). |
| 54 | 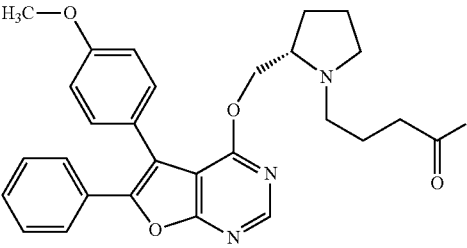 | LC-MS (Method 3): $R_t$ = 1.70 min; m/z = 502 (M + H)$^+$<br>$^1$H-NMR (400 MHz, DMSO-d$_6$): δ = 8.60 (s, 1H), 7.55-7.52 (m, 2H), 7.42-7.37 (m, 5H), 7.01 (d, 2H), 4.32 (dd, 1H), 4.19 (dd, 1H), 3.80 (s, 3H), 3.49 (s, 3H), 2.93 (t, 1H), 2.62-2.50 (m, 2H), 2.20-2.02 (m, 4H), 1.74-1.67 (m, 1H), 1.60-1.37 (m, 5H). |

Example 55

(+/−)-4-(3-{[5-(4-Methoxyphenyl)-6-phenylfuro[2,3-d]pyrimidin-4-yl]amino}piperidin-1-yl)-butanoic acid methyl ester

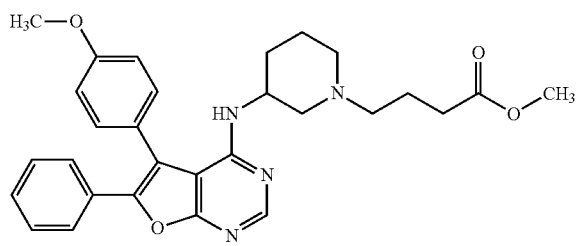

Heat a mixture of 100 mg (0.25 mmol) of (+/−)-5-(4-methoxyphenyl)-6-phenyl-N-piperidin-3-yl-furo[2,3-d]pyrimidin-4-amine (Example 39A), 65 µl (0.375 mmol) of DIEA, 4.1 mg (0.025 mmol) of potassium iodide and 45 mg (0.25 mmol) of 4-bromobutyric acid methyl ester in 2 ml of THF under reflux for 1 h. After cooling, add the reaction mixture to water and extract three times with ethyl acetate. Wash the combined organic phases twice with buffer solution (pH 7) and saturated sodium chloride solution, dry over magnesium sulphate and concentrate under reduced pressure. Purify the crude product by preparative RP-HPLC (eluent: acetonitrile/water gradient), followed by chromatography on silica gel (eluent: dichloromethane→dichloromethane/methanol 50:1). After stirring the resulting product with methanol, the precipitate is filtered off with suction, washed with a little methanol and dried under high vacuum. 58 mg (46.4% of theory) of the target product are isolated.

LC-MS (Method 6): δ=1.85 min; m/z=501 (M+H)$^+$ $^1$H-NMR (400 MHz, DMSO-d$_6$): δ=8.31 (s, 1H), 7.48-7.42 (m, 4H), 7.39-7.30 (m, 3H), 7.13 (d, 2H), 5.58 (br. d, 1H), 4.28 (br. s, 1H), 3.83 (s, 3H), 3.59 (s, 3H), 2.50-2.42 (m, 1H), 2.38-2.31 (m, 1H), 2.22-2.15 (m, 3H), 2.12 (t, 1H), 2.02 (br. s, 1H), 1.58-1.40 (m, 6H).

Example 56

(+/−)-trans-[(3-{[5-(4-Methoxyphenyl)-6-phenylfuro[2,3-d]pyrimidin-4-yl]amino}cyclohexyl)-oxy]acetic acid tert-butyl ester

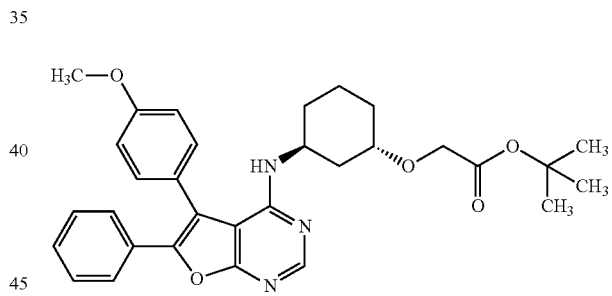

Stir a mixture of 549 mg (1.63 mmol) of 4-chloro-5-(4-methoxyphenyl)-6-phenylfuro[2,3-d]-pyrimidine, 0.43 ml (2.45 mmol) of DIEA and 456 mg of (+/−)-trans-{[3-aminocyclohexyl]oxy}acetic acid tert-butyl ester (Example 43A/crude product, approx. 1.63 mmol) in 1.5 ml of DMF at 120° C. for 2 h. After cooling, add the mixture to water and extract three times with ethyl acetate. Wash the combined organic phases with saturated sodium chloride solution and concentrate under reduced pressure. Purify the crude product by preparative RP-HPLC (eluent: acetonitrile/water gradient). 434 mg (50.3% of theory) of the target product are obtained.

LC-MS (Method 5): $R_t$=3.29 min; m/z=530 (M+H)$^+$ $^1$H-NMR (400 MHz, DMSO-d$_6$): δ=8.35 (s, 1H), 7.50-7.45 (m, 4H), 7.40-7.31 (m, 3H), 7.18 (d, 2H), 4.71 (d, 1H), 4.31 (m, 1H), 3.92 (s, 2H), 3.87 (s, 3H), 3.38-3.30 (m, 1H), 1.77-1.67 (m, 2H), 1.55-1.42 (m, 4H), 1.38 (s, 9H), 1.18-1.10 (m, 2H).

Separation of the Enantiomers:

Dissolve 0.39 g of (+/−)-trans-[(3-{[5-(4-methoxyphenyl)-6-phenylfuro[2,3-d]pyrimidin-4-yl]-amino}cyclohexyl)oxy]

acetic acid tert-butyl ester in 4 ml of 2-propanol and 13 ml of isohexane. Separate the racemate into the enantiomers by preparative HPLC on chiral phase (see Example 57 and 58) [column: Daicel Chiralpak AD-H, 5 μm, 250 mm×20 mm; flow rate: 15 ml/min; detection: 215 nm; injection volume 1.0 ml; temperature: 30° C.; eluent: t=0 min 80% isohexane/20% 2-propanol→t=9.5 min 80% isohexane/20% 2-propanol].

Example 57

(+)-trans-[(3-{[5-(4-Methoxyphenyl)-6-phenylfuro[2,3-d]pyrimidin-4-yl]amino}cyclohexyl)oxy]-acetic acid tert-butyl ester (Enantiomer 1)

$[\alpha]_D^{20}$=43.3°, c=0.51, CHCl$_3$
$^1$H-NMR (400 MHz, DMSO-d$_6$): δ=8.34 (s, 1H), 7.50-7.45 (m, 4H), 7.40-7.31 (m, 3H), 7.18 (d, 2H), 4.72 (d, 1H), 4.36-4.28 (m, 1H), 3.93 (s, 2H), 3.87 (s, 3H), 3.38-3.30 (m, 1H), 1.77-1.67 (m, 2H), 1.55-1.42 (m, 4H), 1.40 (s, 9H), 1.18-1.10 (m, 2H).

Example 58

(−)-trans-[(3-{[5-(4-Methoxyphenyl)-6-phenylfuro[2,3-d]pyrimidin-4-yl]amino}cyclohexyl)oxy]-acetic acid tert-butyl ester (Enantiomer 2)

$[\alpha]_D^{20}$=−49.1°, c=0.49, CHCl$_3$
$^1$H-NMR (400 MHz, DMSO-d$_6$): δ=8.35 (s, 1H), 7.50-7.45 (m, 4H), 7.40-7.31 (m, 3H), 7.18 (d, 2H), 4.72 (d, 1H), 4.36-4.28 (m, 1H), 3.93 (s, 2H), 3.87 (s, 3H), 3.38-3.30 (m, 1H), 1.77-1.67 (m, 2H), 1.55-1.42 (m, 4H), 1.40 (s, 9H), 1.19-1.10 (m, 2H).

Example 59

(+/−)-cis-[(-3-{[5-(4-Methoxyphenyl)-6-phenylfuro[2,3-d]pyrimidin-4-yl]amino}cyclohexyl)oxy]-acetic acid tert-butyl ester

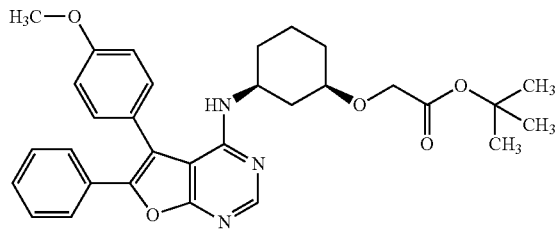

Add 1.05 g (2.53 mmol) of (+/−)-cis/trans-3-{[5-(4-methoxyphenyl)-6-phenylfuro[2,3-d]pyrimidin-4-yl]amino}cyclohexanol (Example 44A) as a solution in 2.5 ml of toluene and 0.75 ml (5.05 mmol) of bromoacetic acid tert-butyl ester at 40° C. to a mixture of 2.02 g of 50% sodium hydroxide solution (25.3 mmol), 2.5 ml of toluene and 85.8 mg (0.25 mmol) of tetrabutylammonium hydrogensulphate. Stir the heterogeneous mixture very vigorously at 70° C. for 2 h. After cooling, add the mixture to water and extract three times with dichloromethane. Wash the combined organic phases with saturated ammonium chloride solution, dry over magnesium sulphate and concentrate under reduced pressure. From the crude product, chromatography on silica gel (Biotage, eluent: dichloromethane/methanol 500:1→100:1) affords 671 mg (50.2% of theory) of the target compound.

LC-MS (Method 5): R$_t$=3.33 min; m/z=530 (M+H)$^+$
$^1$H-NMR (400 MHz, DMSO-d$_6$): δ=8.34 (s, 1H), 7.48-7.41 (m, 4H), 7.39-7.30 (m, 3H), 7.14 (d, 2H), 5.13 (br. d, 1H), 4.14-4.08 (m, 1H), 3.85 (s, 3H), 3.82 (d, 2H), 3.43-3.35 (m, 1H), 2.09 (br. d, 1H), 1.81-1.60 (m, 3H), 1.41 (s, 9H), 1.30-1.04 (m, 4H).

Separation of the Enantiomers:
Dissolve (+/−)-cis-[(3-{[5-(4-methoxyphenyl)-6-phenylfuro[2,3-d]pyrimidin-4-yl]amino}cyclohexyl)oxy]acetic acid tert-butyl ester in equal amounts of ethanol and isohexane. Separate the racemate into the enantiomers by preparative HPLC on chiral phase (see Example 60 and 61) [column: Daicel Chiralcel OJ-H, 5 μm, 250 mm×20 mm; flow rate: 15 ml/min; detection: 220 nm; injection volume 0.5 ml; temperature: 29° C.; eluent: t=0 min 80% isohexane/20% ethanol→t=12 min 80% isohexane/20% ethanol].

Example 60

(+)-cis-[(-3-{[5-(4-Methoxyphenyl)-6-phenylfuro[2,3-d]pyrimidin-4-yl]amino}cyclohexyl)oxy]acetic acid tert-butyl ester (Enantiomer 1)

$[\alpha]_D^{20}$=+77.4°, c=0.53, CHCl$_3$
LC-MS (Method 3): R$_t$=3.10 min; m/z=530 (M+H)$^+$
$^1$H-NMR (400 MHz, DMSO-d$_6$): δ=8.34 (s, 1H), 7.48-7.41 (m, 4H), 7.39-7.30 (m, 3H), 7.14 (d, 2H), 5.13 (br. d, 1H), 4.14-4.08 (m, 1H), 3.85 (s, 3H), 3.82 (d, 2H), 3.43-3.35 (m, 1H), 2.09 (br. d, 1H), 1.81-1.71 (m, 2H), 1.68-1.60 (m, 1H), 1.41 (s, 9H), 1.30-1.04 (m, 4H).

Example 61

(−)-trans-[(-3-{[5-(4-Methoxyphenyl)-6-phenylfuro[2,3-d]pyrimidin-4-yl]amino}cyclohexyl)-oxy]acetic acid tert-butyl ester (Enantiomer 2)

$[\alpha]_D^{20}$=−71.4°, c=0.54, CHCl$_3$
LC-MS (Method 3): R$_t$=3.09 min; m/z=530 (M+H)$^+$
$^1$H-NMR (400 MHz, DMSO-d$_6$): δ=8.34 (s, 1H), 7.48-7.41 (m, 4H), 7.39-7.30 (m, 3H), 7.14 (d, 2H), 5.13 (br. d, 1H), 4.14-4.08 (m, 1H), 3.85 (s, 3H), 3.82 (d, 2H), 3.43-3.35 (m, 1H), 2.09 (br. d, 1H), 1.81-1.71 (m, 2H), 1.68-1.60 (m, 1H), 1.41 (s, 9H), 1.30-1.04 (m, 4H).

Example 62

(+/−)-cis-({-[(5,6-Diphenylfuro[2,3-d]pyrimidin-4-yl)amino]cyclohexyl}oxy)acetic acid tert-butyl ester

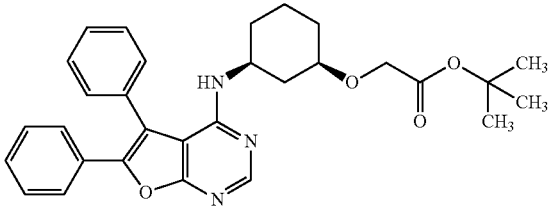

Dissolve 50 mg (0.10 mmol) of (+/−)-cis-({[(5-bromo-6-phenylfuro[2,3-d]pyrimidin-4-yl)amino]cyclohexyl}oxy)acetic acid tert-butyl ester (Example 47A) in 0.33 ml of DMSO and add 3.5 mg of bis(triphenylphosphine)palladium (II) chloride. Under argon, add 0.1 ml of 2N sodium carbonate solution and 15.2 mg (0.124 mmol) of phenylboronic acid successively at RT. Stir the heterogeneous mixture vigorously at 80° C. for 4 h. After cooling, isolate the product directly by preparative RP-HPLC (eluent: acetonitrile/water gradient). 43.9 mg (88.3% of theory) of the target compound are obtained.

LC-MS (Method 5): $R_t$=3.38 min; m/z=500 (M+H)$^+$ $^1$H-NMR (400 MHz, DMSO-d$_6$): δ=8.35 (s, 1H), 7.64-7.53 (m, 5H), 7.46-7.40 (m, 2H), 7.38-7.31 (m, 3H), 5.03 (d, 1H), 4.07 (br. d, 1H), 3.71 (s, 2H), 3.41-3.35 (m, 1H), 2.08 (d, 1H), 1.70-1.60 (m, 2H), 1.65-1.55 (m, 1H), 1.41 (s, 9H), 1.30-1.12 (m, 2H), 1.08-0.95 (m, 2H).

Example 63

(+/−)-cis-({3-[(5,6-Diphenylfuro[2,3-d]pyrimidin-4-yl)oxy]cyclohexyl}oxy)acetic acid tert-butyl ester

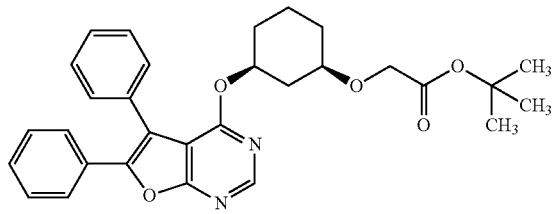

Dissolve 36 mg (0.072 mmol) of (+/−)-cis-({[(6-bromo-5-phenylfuro[2,3-d]pyrimidin-4-yl)oxy]-cyclohexyl}oxy)acetic acid tert-butyl ester (Example 49A) in 0.15 ml of DMSO and add 2.5 mg of bis(triphenylphosphine)palladium(II) chloride. Under argon, add 0.07 ml of 2N sodium carbonate solution and 10.9 mg (0.089 mmol) of phenylboronic acid successively at RT. Stir the heterogeneous mixture vigorously at 80° C. for 4 h. After cooling, isolate the product directly by preparative RP-HPLC (eluent: acetonitrile/water gradient). 19.8 mg (55.3% of theory) of the target compound are obtained.

LC-MS (Method 6): $R_t$=3.41 min; m/z=501 (M+H)$^+$ $^1$H-NMR (400 MHz, DMSO-d$_6$): δ=8.59 (s, 1H), 7.56-7.39 (m, 10H), 5.11 (m, 1H), 3.98 (s, 2H), 3.40 (m, 1H), 2.39 (br. d, 1H), 2.03-1.92 (m, 2H), 1.75-1.67 (m, 1H), 1.40 (s, 9H), 1.28-1.02 (m, 4H).

General Method D: Hydrolysis of methyl or ethyl esters to the Corresponding carboxylic acid Derivatives Add 1.5 to 10 eq. of sodium hydroxide as a 1N aqueous solution at RT to a solution of the methyl or ethyl ester in THF or THF/methanol (1:1) (concentration approx. 0.05 to 0.5 mol/l). Stir the mixture at RT for a period of 0.5-18 h and then neutralize or slightly acidify with 1N hydrochloric acid. If a solid precipitates out, the product can be isolated by filtration, washing with water and drying under high vacuum. Alternatively, the target compound is isolated directly from the crude product, if appropriate after extractive workup with dichloromethane, by preparative RP-HPLC (eluent: water/acetonitrile gradient).

General Method E: Cleavage of tert-butyl esters to the Corresponding carboxylic acid Derivatives Add TFA dropwise at 0° C. to RT to a solution of the tert-butyl ester in dichloromethane (concentration 0.05 to 1.0 mol/l; additionally one drop of water) until a dichloromethane/TFA ratio of approx. 2:1 to 1:1 has been attained. Stir the mixture at RT for 1-18 h and then concentrate under reduced pressure. Purify the residue by preparative RP-HPLC (eluent: acetonitrile/water gradient).

The examples which follow are prepared according to general method D or E from the compounds described above:

| Example | Starting material (method) | Structure | Analytical data |
|---|---|---|---|
| 64 | Example 36 (D) | (structure shown; (+/−)-cis/trans) | LC-MS (Method 6): $R_t$ = 1.90 min; m/z = 473 (M + H)$^+$ |
| 65 | Example 35 (D) | (structure shown; (+/−)-cis) | LC-MS (Method 6): $R_t$ = 1.94 min; m/z = 473 (M + H)$^+$ |

-continued

| Example | Starting material (method) | Structure | Analytical data |
|---|---|---|---|
| 66 | Example 37 (E) | 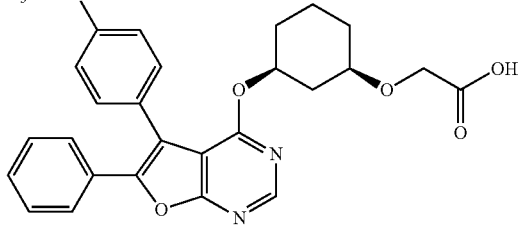<br>(+/−)-cis | LC-MS (Method 3): $R_t$ = 2.57 min; m/z = 475 (M + H)$^+$<br>$^1$H-NMR (400 MHz, DMSO-d$_6$): δ = 8.59 (s, 1H), 7.58-7.53 (m, 2H), 7.44-7.39 (m, 5H), 7.01 (d, 2H), 5.13 (m, 1H), 4.03 (s, 2H), 3.83 (s, 3H), 3.49-3.35 (m, 2H), 2.46-2.40 (m, 1H), 2.06-1.93 (m, 2H), 1.78-1.70 (m, 1H), 1.37-1.05 (m, 4H). |
| 67 | Example 38 (E) | 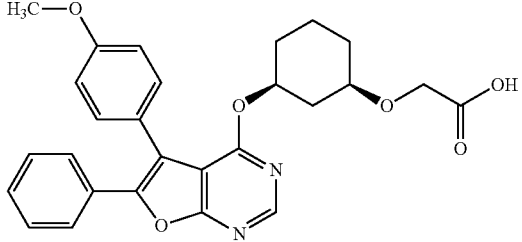<br>(−)-Enantiomer | LC-MS (Method 5): $R_t$ = 2.84 min; m/z = 475 (M + H)$^+$<br>$[α]_D^{20}$ = −64.2°, c = 0.55, CHCl$_3$<br>$^1$H-NMR (400 MHz, DMSO-d$_6$): δ = 8.59 (s, 1H), 7.58-7.53 (m, 2H), 7.44-7.39 (m, 5H), 7.01 (d, 2H), 5.15-5.08 (m, 1H), 4.03 (s, 2H), 3.83 (s, 3H), 3.49-3.35 (m, 1H), 2.46-2.40 (m, 1H), 2.06-1.93 (m, 2H), 1.78-1.70 (m, 1H), 1.37-1.05 (m, 4H). |
| 68 | Example 39 (E) | 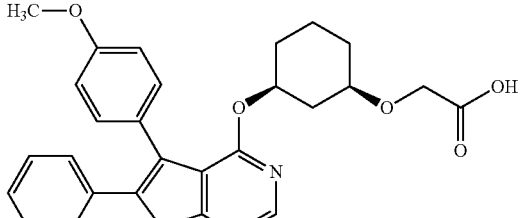<br>(+)-Enantiomer | LC-MS (Method 5): $R_t$ = 2.84 min; m/z = 475 (M + H)$^+$<br>$[α]_D^{20}$ = +62.8°, c = 0.55, CHCl$_3$<br>$^1$H-NMR (400 MHz, DMSO-d$_6$): δ = 8.59 (s, 1H), 7.58-7.53 (m, 2H), 7.44-7.39 (m, 5H), 7.01 (d, 2H), 5.17-5.08 (m, 1H), 4.03 (s, 2H), 3.83 (s, 3H), 3.49-3.35 (m, 1H), 2.46-2.40 (m, 1H), 2.06-1.93 (m, 2H), 1.78-1.70 (m, 1H), 1.37-1.05 (m, 4H). |
| 69 | Example 40 (E) | 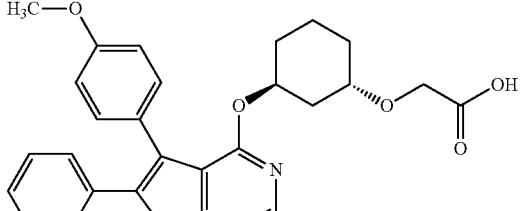<br>(+/−)-trans | LC-MS (Method 3): $R_t$ = 2.53 min; m/z = 475 (M + H)$^+$<br>$^1$H-NMR (400 MHz, DMSO-d$_6$): δ = 12.54 (br. s, 1H), 8.56 (s, 1H), 7.54 (d, 2H), 7.43-7.35 (m, 5H), 7.05 (d, 2H), 5.63-5.59 (m, 1H), 3.90 (d, 2H), 3.81 (s, 3H), 3.30-3.20 (m, 1H), 1.96-1.90 (m, 1H), 1.79-1.43 (m, 5H), 1.30-1.13 (m, 2H). |
| 70 | Example 41 (E) | 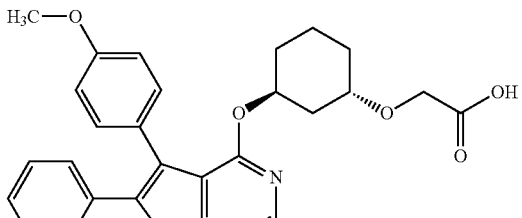<br>(+)-Enantiomer | LC-MS (Method 3): $R_t$ = 2.53 min; m/z = 475 (M + H)$^+$<br>$^1$H-NMR (400 MHz, DMSO-d$_6$): δ = 12.55 (br. s, 1H), 8.56 (s, 1H), 7.54 (d, 2H), 7.43-7.35 (m, 5H), 7.05 (d, 2H), 5.63-5.59 (m, 1H), 3.90 (d, 2H), 3.81 (s, 3H), 3.30-3.20 (m, 1H), 1.96-1.90 (m, 1H), 1.76-1.69 (m, 1H), 1.65-1.54 (m, 3H), 1.5-1.43 (m, 1H), 1.30-1.13 (m, 2H).<br>$[α]_D^{20}$ = +62.4°, c = 0.48, CHCl$_3$ |

| Example | Starting material (method) | Structure | Analytical data |
|---|---|---|---|
| 71 | Example 42 (E) | 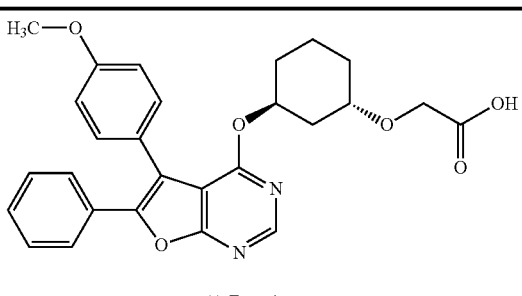<br>(−)-Enantiomer | LC-MS (Method 5): $R_t$ = 2.80 min; m/z = 475 (M + H)$^+$<br>$^1$H-NMR (400 MHz, DMSO-$d_6$): δ = 12.54 (br. s, 1H), 8.56 (s, 1H), 7.54 (d, 2H), 7.43-7.35 (m, 5H), 7.05 (d, 2H), 5.63-5.59 (m, 1H), 3.90 (d, 2H), 3.81 (s, 3H), 3.30-3.20 (m, 1H), 1.96-1.90 (m, 1H), 1.76-1.69 (m, 1H), 1.65-1.54 (m, 3H), 1.51-1.43 (m, 1H), 1.30-1.13 (m, 2H). $[α]_D^{20}$ = −74.0°, c = 0.50, CHCl$_3$ |
| 72 | Example 43 (E) | 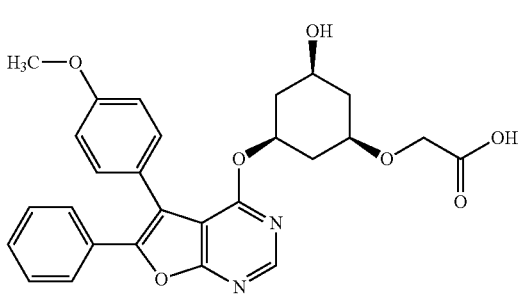<br>(+/−)-cis | LC-MS (Method 5): $R_t$ = 2.42 min; m/z = 491 (M + H)$^+$<br>$^1$H-NMR (400 MHz, DMSO-$d_6$): δ = 8.60 (s, 1H), 7.57 (d, 2H), 7.45-7.38 (m, 5H), 7.02 (d, 2H), 5.15 (m, 1H), 4.80 (br. s, 1H), 4.02 (s, 2H), 3.82 (s, 3H), 3.58-3.35 (m, 2H), 2.45-2.38 (m, 1H), 2.20-2.10 (m, 2H), 1.18-1.02 (m, 3H). |
| 73 | Example 44 (D) | 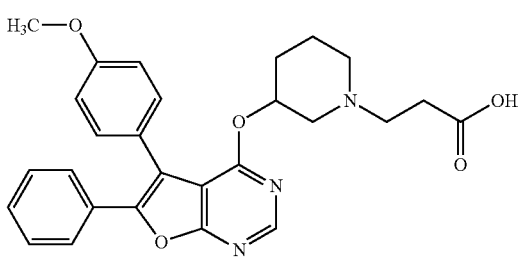<br>(rac.) | LC-MS (Method 3): $R_t$ = 1.68 min; m/z = 474 (M + H)$^+$<br>$^1$H-NMR (400 MHz, DMSO-$d_6$): δ = 8.59 (s, 1H), 7.55 (d, 2H), 7.45-7.40 (m, 5H), 7.01 (d, 2H), 5.26 (m, 1H), 3.82 (s, 3H), 3.45-3.25 (m, 2H), 2.83 (d, 1H), 2.60-2.45 (m, 2H), 2.39-2.27 (m, 4H), 1.90-1.82 (m, 1H), 1.65-1.55 (m, 1H), 1.48-1.31 (m, 2H). |
| 74 | Example 48 (D) | 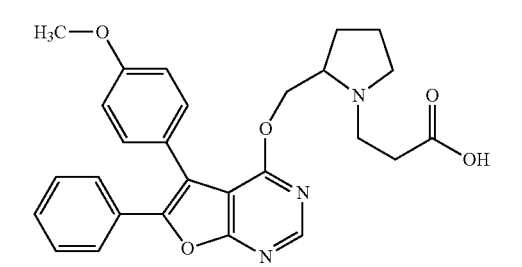<br>(rac.) | LC-MS (Method 6): $R_t$ = 1.76 min; m/z = 464 (M + H)$^+$<br>$^1$H-NMR (400 MHz, DMSO-$d_6$): δ = 8.59 (s, 1H), 7.54 (dd, 2H), 7.43-7.35 (m, 5H), 7.02 (d, 2H), 4.41 (dd, 1H), 4.22 (dd, 1H), 3.82 (s, 3H), 2.99-2.88 (m, 2H), 2.72-2.65 (m, 1H), 2.42-2.38 (m, 1H), 2.30-2.22 (m, 2H), 2.22-2.12 (m, 1H), 1.76-1.68 (m, 1H), 1.65-1.55 (m, 1H), 1.50-1.40 (m, 2H). |
| 75 | Example 49 (D) | 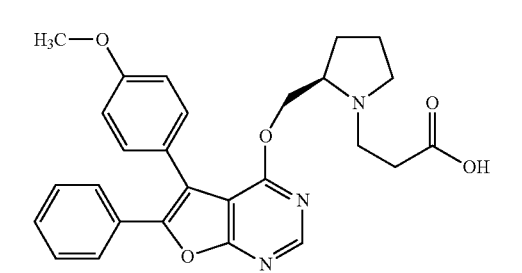<br>(R-Enantiomer) | LC-MS (Method 5): $R_t$ = 1.85 min; m/z = 474 (M + H)$^+$<br>$^1$H-NMR (400 MHz, DMSO-$d_6$): δ = 8.56 (s, 1H), 7.53 (d, 2H), 7.43-7.36 (m, 5H), 7.01 (d, 2H), 4.42 (dd, 1H), 4.15 (dd, 1H), 3.81 (s, 3H), 2.96-2.88 (m, 2H), 2.67-2.60 (m, 1H), 2.42-2.35 (m, 1H), 2.21-2.10 (m, 3H), 1.73-1.35 (m, 4H). |

-continued

| Example | Starting material (method) | Structure | Analytical data |
|---|---|---|---|
| 76 | Example 50 (D) | (S-Enantiomer) | LC-MS (Method 5): $R_t$ = 1.83 min; m/z = 474 (M + H)$^+$ $^1$H-NMR (400 MHz, DMSO-$d_6$): δ = 8.56 (s, 1H), 7.53 (d, 2H), 7.43-7.36 (m, 5H), 7.01 (d, 2H), 4.42 (dd, 1H), 4.15 (dd, 1H), 3.81 (s, 3H), 2.96-2.88 (m, 2H), 2.67-2.60 (m, 1H), 2.42-2.35 (m, 1H), 2.21-2.10 (m, 3H), 1.73-1.35 (m, 4H). |
| 77 | Example 51 (D) | (rac.) | LC-MS (Method 6): $R_t$ = 1.80 min; m/z = 473 (M + H)$^+$ $^1$H-NMR (400 MHz, DMSO-$d_6$): δ = 8.32 (s, 1H), 7.50-7.45 (m, 4H), 7.40-7.30 (m, 3H), 7.14 (d, 2H), 5.59 (br. d, 1H), 4.25 (br. s, 1H), 3.84 (s, 2H), 2.48-2.35 (m, 2H), 2.27-1.98 (m, 3H), 1.55 (br. s, 1H), 1.48 (br. s, 2H). |
| 78 | Example 55 (D) | (rac.) | LC-MS (Method 5): $R_t$ = 1.87 min; m/z = 487 (M + H)$^+$ $^1$H-NMR (400 MHz, DMSO-$d_6$): δ = 8.32 (s, 1H), 7.49-7.45 (m, 4H), 7.39-7.30 (m, 3H), 7.14 (d, 2H), 5.58 (br. d, 1H), 4.27 (br. s, 1H), 3.85 (s, 3H), 2.50-2.42 (m, 1H), 2.39-2.32 (m, 1H), 2.27-2.19 (m, 1H), 2.16-2.02 (m, 4H), 1.55-1.26 (m, 5H). |
| 79 | Example 52 (D) | (rac.) | LC-MS (Method 3): $R_t$ = 1.61 min; m/z = 488 (M + H)$^+$ $^1$H-NMR (400 MHz, DMSO-$d_6$): δ = 8.58 (s, 1H), 7.53 (dd, 2H), 7.42-7.37 (m, 5H), 7.02 (d, 2H), 4.38 (dd, 1H), 4.16 (dd, 1H), 3.81 (s, 3H), 2.95 (br. t, 1H), 2.62-2.50 (m, 1H), 2.18-1.92 (m, 4H), 1.74-1.65 (m, 1H), 1.60-1.37 (m, 6H). |
| 80 | Example 53 (D) | (R-Enantiomer) | LC-MS (Method 3): $R_t$ = 1.59 min; m/z = 488 (M + H)$^+$ $^1$H-NMR (400 MHz, DMSO-$d_6$): δ = 8.58 (s, 1H), 7.53 (dd, 2H), 7.42-7.37 (m, 5H), 7.02 (d, 2H), 4.38 (dd, 1H), 4.16 (dd, 1H), 3.81 (s, 3H), 2.95 (br. t, 1H), 2.62-2.50 (m, 1H), 2.18-1.92 (m, 4H), 1.74-1.65 (m, 1H), 1.60-1.37 (m, 6H). $[\alpha]_D^{20}$ = −124.4°, c = 0.50, CHCl$_3$ |

-continued

| Example | Starting material (method) | Structure | Analytical data |
|---|---|---|---|
| 81 | Example 54 (D) | 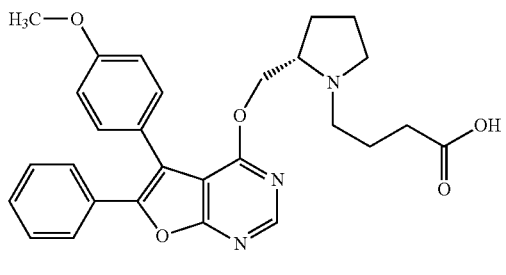<br>(S-Enantiomer) | LC-MS (Method 5): $R_t$ = 1.86 min; m/z = 488 (M + H)$^+$<br>$^1$H-NMR (400 MHz, DMSO-d$_6$): δ = 8.58 (s, 1H), 7.53 (dd, 2H), 7.42-7.37 (m, 5H), 7.02 (d, 2H), 4.38 (dd, 1H), 4.16 (dd, 1H), 3.81 (s, 3H), 2.95 (br. t, 1H), 2.62-2.50 (m, 1H), 2.18-1.92 (m, 4H), 1.74-1.65 (m, 1H), 1.60-1.37 (m, 6H).<br>$[α]_D^{20}$ = +81.0°, c = 0.50, CHCl$_3$ |
| 82 | Example 45 (D) | 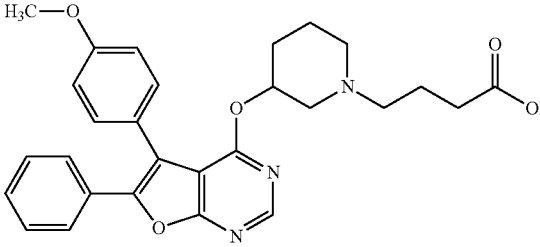<br>(rac.) | LC-MS (Method 5): $R_t$ = 1.88 min; m/z = 488 (M + H)$^+$<br>$^1$H-NMR (400 MHz, DMSO-d$_6$): δ = 8.57 (s, 1H), 7.54 (dd, 2H), 7.45-7.38 (m, 5H), 7.00 (d, 2H), 5.24 (m, 1H), 3.82 (s, 3H), 2.84 (br. d, 1H), 2.53-2.45 (m, 1H), 2.29-2.22 (m, 2H), 2.18-1.99 (m, 4H), 1.93-1.86 (m, 1H), 1.64-1.52 (m, 2H), 1.49-1.36 (m, 1H), 1.34-1.25 (m, 1H). |
| 83 | Example 48 (D) | 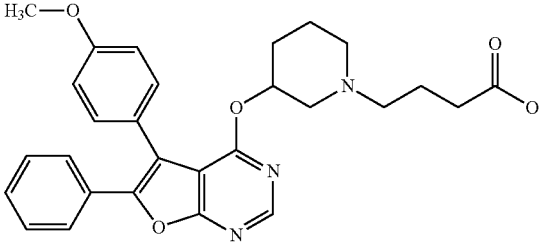<br>(+)-Enantiomer | LC-MS (Method 5): $R_t$ = 1.87 min; m/z = 488 (M + H)$^+$<br>$[α]_D^{20}$ = +84.0°, c = 0.50, CHCl$_3$ |
| 84 | Example 47 (D) | 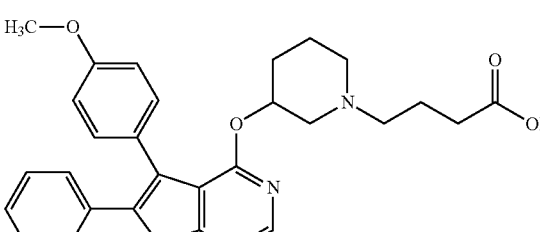<br>(-)-Enantiomer | LC-MS (Method 5): $R_t$ = 1.88 min; m/z = 488 (M + H)$^+$<br>$[α]_D^{20}$ = −85.7°, c = 0.50, CHCl$_3$ |
| 85 | Example 56 (E) | 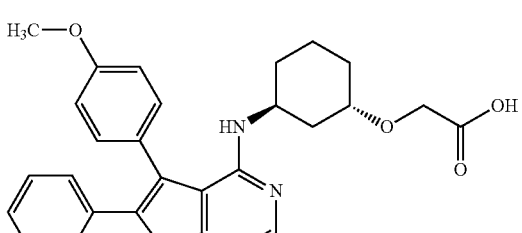<br>(+/−)-trans | LC-MS (Method 3): $R_t$ = 2.39 min; m/z = 474 (M + H)$^+$<br>$^1$H-NMR (400 MHz, DMSO-d$_6$): δ = 8.35 (s, 1H), 7.52-7.47 (m, 2H), 7.39-7.30 (m, 3H), 7.18 (d, 2H), 4.73 (d, 1H), 4.34 (br. s, 1H), 3.95 (br. s, 2H), 3.87 (s, 3H), 3.40-3.25 (m, 1H), 1.80-1.63 (m, 2H), 1.60-1.40 (m, 4H), 1.20-1.10 (m, 2H). |

-continued

| Example | Starting material (method) | Structure | Analytical data |
|---|---|---|---|
| 86 | Example 58 (E) | (−)-Enantiomer | LC-MS (Method 6): $R_t$ = 2.55 min; m/z = 474 (M + H)$^+$ $[\alpha]_D^{20}$ = −72.2°, c = 0.50, CHCl$_3$ $^1$H-NMR (400 MHz, DMSO-d$_6$): δ = 12.66 (br. s, 1H), 8.35 (s, 1H), 7.52-7.45 (m, 5H), 7.39-7.30 (m, 3H), 7.18 (d, 2H), 4.74 (d, 1H), 4.40-4.30 (m, 1H), 3.96 (s, 2H), 3.88 (s, 3H), 3.40-3.25 (m, 1H), 1.80-1.62 (m, 2H), 1.60-1.40 (m, 4H), 1.20-1.08 (m, 2H). |
| 87 | Example 57 (E) | (+)-Enantiomer | LC-MS (Method 6): $R_t$ = 2.55 min; m/z = 474 (M + H)$^+$ $[\alpha]_D^{20}$ = +63°, c = 0.50, CHCl$_3$ $^1$H-NMR (400 MHz, DMSO-d$_6$): δ = 12.66 (br. s, 1H), 8.35 (s, 1H), 7.52-7.45 (m, 5H), 7.39-7.30 (m, 3H), 7.18 (d, 2H), 4.74 (d, 1H), 4.40-4.30 (m ,1H), 3.96 (s, 2H), 3.88 (s, 3H), 3.40-3.25 (m, 1H), 1.80-1.62 (m, 2H), 1.60-1.40 (m, 4H), 1.20-1.08 (m, 2H). |
| 88 | Example 59 (E) | (+/−)-cis | LC-MS (Method 3): $R_t$ = 2.39 min; m/z = 474 (M + H)$^+$ $^1$H-NMR (400 MHz, DMSO-d$_6$): δ = 12.40 (br. s, 1H), 8.35 (s, 1H), 7.48-7.42 (m, 4H), 7.39-7.30 (m, 3H), 7.14 (d, 2H), 5.15 (br. d, 1H), 4.15-4.07 (m, 1H), 3.35 (2 s, 5H), 3.45-3.38 (m, 1H), 2.10 (br. d, 1H), 1.82-1.72 (m, 2H), 1.66-1.55 (m, 1H), 1.28-1.18 (m, 2H), 1.12-1.02 (m, 2H). |
| 89 | Example 60 (E) | (+)-Enantiomer | LC-MS (Method 6): $R_t$ = 2.54 min; m/z = 474 (M + H)$^+$ $[\alpha]_D^{20}$ = +69.5°, c = 0.5, CHCl$_3$ $^1$H-NMR (400 MHz, DMSO-d$_6$): δ = 12.57 (br. s, 1H), 8.35 (s, 1H), 7.48-7.42 (m, 4H), 7.39-7.30 (m, 3H), 7.14 (d, 2H), 5.18-5.11 (m, 1H), 4.15-4.07 (m, 1H), 3.35 (2 s, 5H), 3.45-3.36 (m, 1H), 2.10 (br. d, 1H), 1.82-1.72 (m, 2H), 1.66-1.55 (m, 1H), 1.28-1.18 (m, 2H), 1.12-1.02 (m, 2H). |

| Example | Starting material (method) | Structure | Analytical data |
|---|---|---|---|
| 90 | Example 61 (E) | 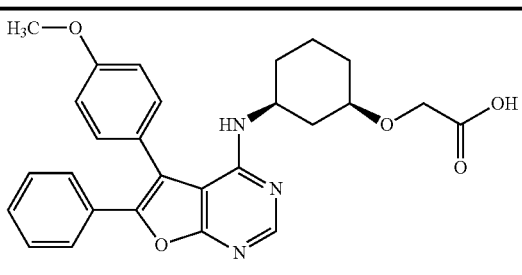 (-)-Enantiomer | LC-MS (Method 6): $R_f$ = 2.54 min; m/z = 474 (M + H)$^+$ [α]$_D^{20}$ = −85.4°, c = 0.54, CHCl$_3$ $^1$H-NMR (400 MHz, DMSO-d$_6$): δ = 12.57 (br. s, 1H), 8.35 (s, 1H), 7.48-7.42 (m, 4H), 7.39-7.30 (m, 3H), 7.14 (d, 2H), 5.18-5.11 (m, 1H), 4.15-4.07 (m, 1H), 3.35 (2 s, 5H), 3.45-3.36 (m, 1H), 2.10 (br. d, 1H), 1.82-1.72 (m, 2H), 1.66-1.55 (m, 1H), 1.28-1.18 (m, 2H), 1.12-1.02 (m, 2H). |
| 91 | Example 63 (E) | 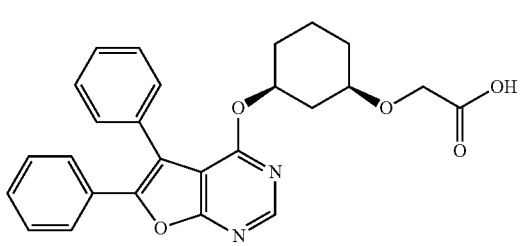 (+/−)-cis | LC-MS (Method 3): $R_f$ = 2.59 min; m/z = 445 (M + H)$^+$ $^1$H-NMR (400 MHz, DMSO-d$_6$): δ = 12.35 (br. s, 1H), 8.61 (s, 1H), 7.56-7.37 (m, 10H), 5.15-5.06 (m, 1H), 4.00 (s, 2H), 3.46-3.25 (m, 1H), 2.41 (br. d, 1H), 2.05-1.95 (m, 2H), 1.71 (br. d, 1H), 1.30-1.02 (m, 4H). |
| 92 | Example 62 (E) | 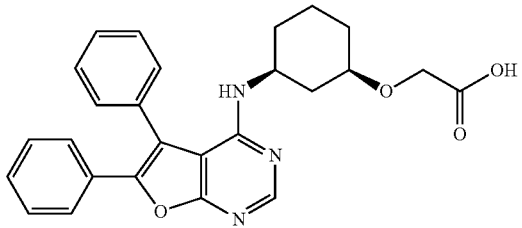 (+/−)-cis | LC-MS (Method 5): $R_f$ = 2.70 min; m/z = 444 (M + H)$^+$. |

Example 93

(+/−)-(5-cis,3-trans)-[(3-Fluoro-5-{[5-(4-methoxyphenyl)-6-phenylfuro[2,3-d]pyrimidin-4-yl]oxy}-cyclohexyl)oxy]acetic acid

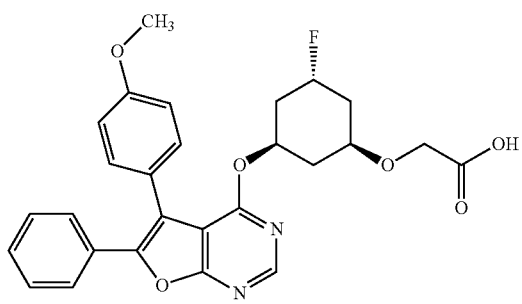

Initially charge 150 mg (0.27 mmol) of (+/−)-all-cis-[(3-hydroxy-5-{[5-(4-methoxyphenyl)-6-phenylfuro[2,3-d]pyrimidin-4-yl]oxy}cyclohexyl)oxy]acetic acid tert-butyl ester in 2.5 ml of dichloromethane and cool to 0° C. Add 53 mg (0.33 mmol) of diethylaminosulphur trifluoride (DAST) and then allow the mixture to come to RT. Then dilute with water and dichloromethane and separate the phases. Extract the aqueous phase twice with dichloromethane, wash the combined organic phases once with satd. sodium chloride solution, dry over magnesium sulphate and concentrate. Dissolve the residue in 5 ml of dichloromethane, add 1 ml of trifluoroacetic acid and stir at RT for 30 min. Then add satd. sodium hydrogencarbonate solution, remove the aqueous phase and wash the aqueous phase once with diethyl ether. Then acidify with 1N hydrochloric acid and extract the aqueous phase twice with ethyl acetate. Wash the combined organic phases once with satd. sodium chloride solution, dry over magnesium sulphate and concentrate. Purify the residue by chromatography using a silica gel thick-layer plate (eluent: dichloromethane/methanol 9:1). Extract the product zone with dichloromethane/methanol 9:1. Then purify once again by means of preparative RP-HPLC (eluent: aacetonitrile/water gradient) to obtain 46 mg (34.0% of theory) of the target compound.

LC-MS (Method 8): $R_f$=2.76 min; m/z=493 (M+H)$^+$
$^1$H-NMR (400 MHz, DMSO-d$_6$): δ=12.55 (s, 1H), 8.61 (s, 1H), 7.55 (d, 2H), 7.44-7.35 (m, 5H), 7.01 (d, 2H), 5.45-5.35 (m, 1H), 5.15-4.96 (d, 1H), 4.05 (s, 2H), 3.81 (s, 3H), 3.78-3.69 (m, 1H), 2.52-2.42 (m, 1H), 2.42-2.21 (m, 2H), 1.65-1.33 (m, 3H).

General Method F: Reaction of Nitriles with Trimethylsilyl Azide to give the Corresponding Tetrazole Derivatives Add approx. 15 eq. of trimethylsilyl azide and approx. 1.5 eq. of di-n-butyltin oxide at RT to a solution of the nitrile in toluene (concentration approx. 100 mg/ml). Stir the mixture within a temperature range of 70° C. up to reflux for several hours, preferably overnight. After the end of the reaction, add a relatively high excess of ethylene glycol and stir the mixture under reflux for approx. 1 h. After cooling, dilute with ethyl acetate, wash with satd. sodium hydrogencarbonate solution, 1N hydrochloric acid and satd. sodium chloride solution, and concentrate under reduced pressure. The product is obtained after purification by preparative RP-HPLC (eluent:water/acetonitrile gradient) or by chromatography on silica gel.

The following examples are obtained according to general method F:

| Example | Structure | Analytical data |
|---|---|---|
| 94 | 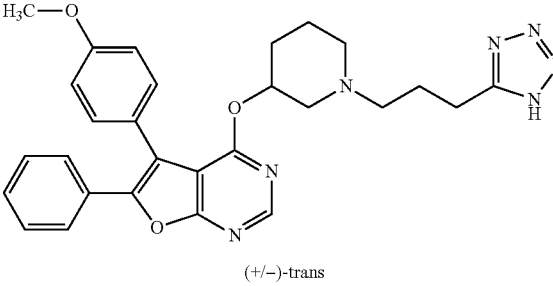 (+/−)-trans | LC-MS (Method 5): $R_t$ = 1.88 min; m/z = 512 (M + H)$^+$ $^1$H-NMR (400 MHz, DMSO-d$_6$): δ = 8.59 (s, 1H), 7.53 (d, 2H), 7.46-7.35 (m, 5H), 7.00 (d, 2H), 5.78 (s, 0.3H), 5.79-5.71 (m, 1H), 3.81 (s, 3H), 2.90-2.85 (m, 1H), 2.61-2.56 (m, 1H), 2.30 (t, 2H), 2.19-2.04 (m, 2H), 1.95-1.86 (m, 1H), 1.79-1.65 (m, 2H), 1.69-1.57 (m, 1H), 1.50-1.40 (m, 1H), 1.32-1.21 (m, 1H). |
| 95 | 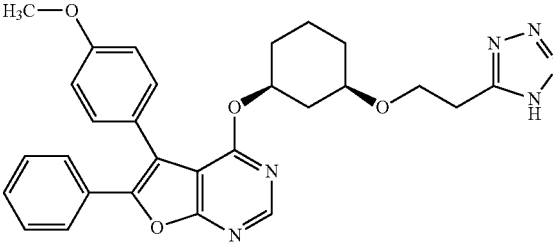 (+/−)-cis | LC-MS (Method 6): $R_t$ = 2.69 min; m/z = 513 (M + H)$^+$ $^1$H-NMR (400 MHz, DMSO-d$_6$): δ = 8.60 (s, 1H), 8.00-7.71 (m, 1H), 7.59-7.50 (m, 2H), 7.44-7.38 (m, 5H), 7.01 (d, 2H), 5.19-5.09 (m, 1H), 3.81 (s, 3H), 3.71-3.62 (m, 2H), 2.82 (t, 2H), 2.47-2.39 (m, 1H), 2.07-1.90 (m, 2H), 1.79-1.68 (m, 1H), 1.32-1.00 (m, 5H). |
| 96 | 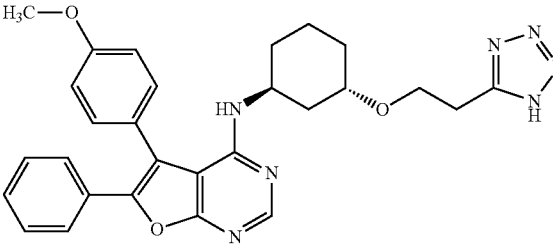 (+/−)-trans | LC-MS (Method 3): $R_t$ = 2.42 min; m/z = 512 (M + H)$^+$ $^1$H-NMR (400 MHz, DMSO-d$_6$): δ = 8.60 (s, 1H), 7.60-7.52 (m, 2H), 7.41 (d, 2H), 7.31-7.22 (m, 4H), 7.09 (d, 2H), 4.71 (d, 1H), 4.35-4.23 (m, 1H), 3.90 (s, 3H), 3.82-3.78 (m, 1H), 3.70 (s, 1H), 3.40-3.29 (m, 2H), 2.50-2.41 (m, 1H), 1.85-0.81 (m, 9H). |
| 97 | 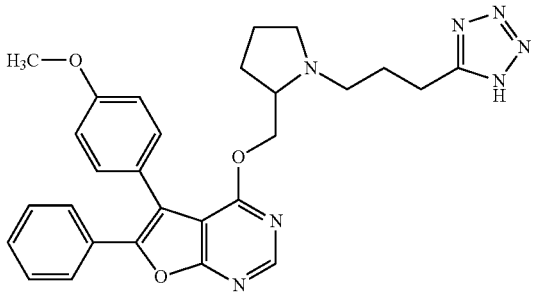 (+/−) | LC-MS (Method 8): $R_t$ = 1.82 min; m/z = 512 (M + H)$^+$ $^1$H-NMR (400 MHz, DMSO-d$_6$): δ = 8.60 (s, 1H), 7.52 (d, 2H), 7.44-7.32 (m, 5H), 7.00 (d, 2H), 4.43-4.35 (m, 1H), 4.23-4.15 (m, 1H), 3.81 (s, 3H), 3.01-2.94 (m, 1H), 2.72-2.45 (m, 7H), 2.28-2.19 (m, 1H), 2.18-2.07 (m, 1H), 1.79-1.39 (m, 4H). |

| Example | Structure | Analytical data |
|---|---|---|
| 98 | (+/−) | LC-MS (Method 3): $R_t$ = 1.70 min; m/z = 498 (M + H)$^+$<br>$^1$H-NMR (400 MHz, DMSO-d$_6$): δ = 8.59 (s, 1H), 7.54 (d, 2H), 7.45-7.32 (m, 5H), 6.98 (d, 2H), 5.76 (s, 0.3H), 5.30-5.21 (m, 1H), 3.80 (s, 3H), 3.01 (t, 2H), 2.88 (d, 1H), 2.73 (t, 2H), 2.42-2.28 (m, 2H), 1.90-1.82 (m, 1H), 1.64-1.53 (m, 1H), 1.50-1.20 (m, 3H). |
| 99 | (−)-Enantiomer | LC-MS (Method 3): $R_t$ = 1.71 min; m/z = 498 (M + H)$^+$<br>$^1$H-NMR (400 MHz, DMSO-d$_6$): δ = 8.59 (s, 1H), 7.53 (d, 2H), 7.45-7.32 (m, 5H), 6.98 (d, 2H), 5.31-5.22 (m, 1H), 3.81 (s, 3H), 3.08 (s, 2H), 2.93 (d, 1H), 2.80 (t, 2H), 2.65-2.36 (m, 4H), 1.92-1.82 (m, 1H), 1.68-1.55 (m, 1H), 1.51-1.30 (m, 2H). |
| 100 | (+)-Enantiomer | LC-MS (Method 6): $R_t$ = 1.81 min; m/z = 498 (M + H)$^+$<br>$^1$H-NMR (400 MHz, DMSO-d$_6$): δ = 8.59 (s, 1H), 7.53 (d, 2H), 7.45-7.32 (m, 5H), 6.98 (d, 2H), 5.31-5.22 (m, 1H), 3.81 (s, 3H), 3.08 (s, 2H), 2.93 (d, 1H), 2.80 (t, 2H), 2.65-2.36 (m, 4H), 1.92-1.82 (m, 1H), 1.68-1.55 (m, 1H), 1.51-1.30 (m, 2H). |

Example 101

(+)-3-[(3S)-3-{[5-(4-Methoxyphenyl)-6-phenylfuro[2,3-d]pyrimidin-4-yl]oxy}piperidin-1-yl]-propanoic acid

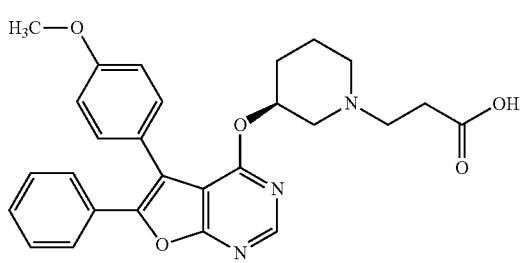

Suspend 50 mg (0.10 mmol) of (+)-3-(3-{[5-(4-methoxyphenyl)-6-phenylfuro[2,3-d]pyrimidin-4-yl]oxy}piperidin-1-yl)propanenitrile in 0.5 ml of conc. hydrochloric acid and heat under reflux for 30 min. After cooling, concentrate under high vacuum and adjust the residue to pH 7 with 1N sodium hydroxide solution. Purify the mixture by preparative RP-HPLC (eluent: acetonitrile/water gradient). 29.8 mg (57.2% of theory) of the target compound are obtained.

$[α]_D^{20}$=+76.1°, c=0.49, CHCl$_3$

LC-MS (Method 8): $R_t$=1.94 min; m/z=474 (M+H)$^+$
$^1$H-NMR (400 MHz, DMSO-d$_6$): δ=8.59 (s, 1H), 7.55 (d, 2H), 7.45-7.34 (m, 5H), 7.00 (d, 2H), 5.28-5.19 (m, 1H), 3.80 (s, 3H), 3.60-3.00 (br, 4H), 2.84 (d, 1H), 2.28-2.09 (m, 4H), 1.92-1.81 (m, 1H), 1.64-1.51 (m, 1H), 1.49-1.37 (m, 1H), 1.36-1.21 (m, 1H).

Example 102

(−)-3-[(3R)-3-{[5-(4-Methoxyphenyl)-6-phenylfuro[2,3-d]pyrimidin-4-yl]oxy}piperidin-1-yl]-propanoic acid

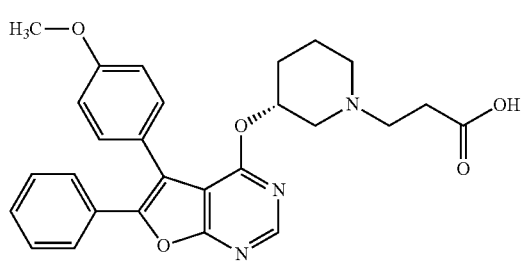

Suspend 55 mg (0.121 mmol) of (−)-3-(3-{[5-(4-methoxyphenyl)-6-phenylfuro[2,3-d]pyrimidin-4-yl]oxy}piperidin- 1-yl)propanenitrile in 0.55 ml of conc. hydrochloric acid and heat under reflux for 30 min. After cooling, concentrate under high vacuum and adjust the residue to pH 7 with 1N sodium hydroxide solution. Purify the mixture by preparative RP-HPLC (eluent: acetonitrile/water gradient). 38.4 mg (67.0% of theory) of the target compound are obtained.

$[\alpha]_D^{20}=-87.9°$, c=0.565, $CHCl_3$

LC-MS (Method 3): $R_t$=1.68 min; m/z=474 (M+H)$^+$ $^1$H-NMR (400 MHz, DMSO-d$_6$): δ=12.60 (br, 1H), 8.60 (s, 1H), 7.55 (d, 2H), 7.46-7.35 (m, 5H), 7.00 (d, 2H), 5.29-5.20 (m, 1H), 3.80 (s, 3H), 2.82 (d, 1H), 2.61-2.54 (m, 1H), 2.40-2.21 (m, 4H), 2.19 (s, 2H), 1.91-1.81 (m, 1H), 1.65-1.52 (m, 1H), 1.49-1.29 (m, 2H).

Example 103

3-[(2R,4R)-4-{[5-(4-Methoxyphenyl)-6-phenylfuro[2,3-d]pyrimidin-4-yl]oxy}piperidin-2-yl]-propanoic acid

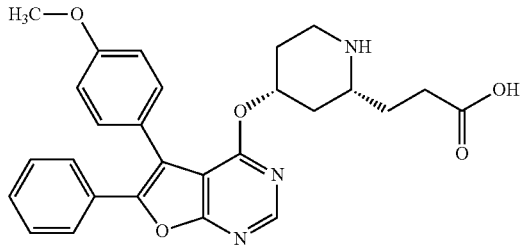

Stir 34 mg of 3-[(2R,4R)-1-(tert-butoxycarbonyl)-4-{[5-(4-methoxyphenyl)-6-phenylfuro[2,3-d]pyrimidin-4-yl]oxy}piperidin-2-yl]propanoic acid in approx. 0.1 ml of a 3:2 mixture of trifluoroacetic acid and dichloromethane at RT for 30 min. Then remove the volatile components under reduced pressure and dry the residue under high vacuum. Take up the residue in acetonitrile/water and neutralize with 1N sodium hydroxide solution (pH approx. 7). Filter off the precipitated colourless solid with suction, wash twice with water and twice with acetonitrile and dry under high vacuum. 20 mg (71.3% of theory) of the target compound are obtained.

LC-MS (Method 4): $R_t$=3.12 min; m/z=474 (M+H)$^+$ $^1$H-NMR (400 MHz, DMSO-d$_6$): δ=8.59 (s, 1H), 7.55 (d, 2H), 7.45-7.38 (m, 5H), 7.00 (d, 2H), 5.30-5.20 (m, 1H), 3.81 (s, 3H), 3.05-2.99 (m, 1H), 2.31-2.23 (m, 1H), 2.10 (s, 7H), 2.02-1.95 (m, 1H).

Example 104

3-[(2R,4R)-4-{[5-(4-Methoxyphenyl)-6-phenylfuro[2,3-d]pyrimidin-4-yl]oxy}-1-methylpiperidin-2-yl] propanoic acid

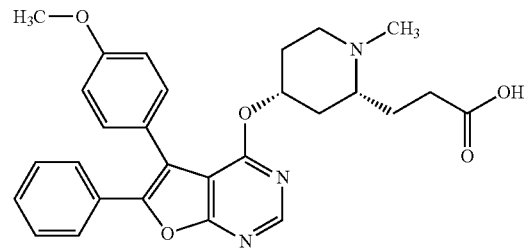

Dissolve 8 mg (17 μmol) of 3-[(2R,4R)-4-{[5-(4-methoxyphenyl)-6-phenylfuro[2,3-d]pyridimidin-4-yl]oxy}piperidin-2-yl]propanoic acid in 50 μl of acetic acid and successively add 13 μl of conc. (approx. 37%) formalin solution and 53.7 μg (253 μmol) of sodium triacetoxyborohydride. Stir the mixture at RT for 4 h. Then add another 13 μl of conc. formalin solution and 53.7 μg (253 μmol) of sodium triacetoxyborohydride, and continue to stir the mixture overnight. Then purify the mixture directly by preparative RP-HPLC (eluent: acetonitrile/water gradient). 5 mg of the target product are obtained (60.7% of theory).

LC-MS (Method 8): $R_t$=1.69 min; m/z=488 (M+H)$^+$ $^1$H-NMR (400 MHz, DMSO-d$_6$): δ=8.59 (s, 1H), 7.55 (d, 2H), 7.43-7.36 (m, 5H), 7.01 (d, 2H), 5.19-5.10 (m, 1H), 3.81 (s, 3H), 2.84-2.79 (m, 1H), 2.66-2.57 (m, 6H), 2.13-1.93 (m, 2H), 1.72-1.58 (m, 2H), 1.48-1.38 (m, 1H), 1.21 (s, 3H).

General Method G: Palladium-Catalysed Arylation of 5-bromo-6-phenylfuro[2,3-d]pyrimidine derivatives Add 1.2 to 1.5 eq. of the appropriate arylboronic acid and, as a base, either approx. 2.0 eq. of sodium carbonate (as a 2 M aqueous solution) or approx. 1.5 to 2.5 eq. of solid potassium carbonate and methanol (approx. 10% by volume) successively at RT to a solution of 1.0 eq. of 5-bromo-6-phenylfuro[2,3-d]pyrimidine derivative in DMSO (approx. 0.1 to 0.5 mol/l). Then add approx. 5 mol % of bis(triphenylphosphine)palladium(II) chloride under argon. Stir the mixture at temperatures of 70-100° C. for a period of 3-18 h. After cooling, isolate the target product directly from the reaction solution by RP-HPLC (eluent: acetonitrile/water gradient). If necessary, a further purification can be effected by chromatography on silica gel (eluent: dichloromethane/methanol or cyclohexane/ethyl acetate mixtures).

The following examples are obtained according to general method G:

| Example | Structure | Analytical data |
| --- | --- | --- |
| 105 | (structure shown; (+/−)-trans) | LC-MS (Method 6): $R_t$ = 3.16 min; m/z = 548 (M + H)$^+$<br>$^1$H-NMR (400 MHz, CDCl$_3$):<br>δ = 8.41 (s, 1H), 7.58-7.51 (m, 2H), 7.32-7.19 (m, 5H), 7.18-7.10 (m, 1H), 4.59 (d, 1H), 4.50-4.40 (m, 1H), 4.01 (s, 3H), 3.98 (d, 1H), 3.50 (br. s, 1H), 2.01-1.91 (m, 1H), 1.89-1.60 (m, 3H), 1.59 (s, 2H), 1.47 (s, 9H), 1.30-1.17 (m, 3H). |

| Example | Structure | Analytical data |
|---|---|---|
| 106 | 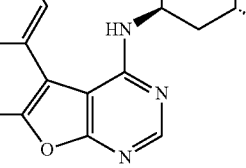<br>(+/−)-trans | LC-MS (Method 8): $R_t$ = 3.40 min; m/z = 534 (M + H)$^+$<br>$^1$H-NMR (400 MHz, CDCl$_3$):<br>δ = 8.40 (s, 1H), 7.58-7.49 (m, 4H), 7.44 (d, 2H), 7.31-7.24 (m, 3H), 4.50-4.40 (m, 2H), 3.99 (d, 2H), 3.48 (br. s, 1H), 2.01-1.91 (m, 1H), 1.88-1.60 (m, 2H), 1.49 (s, 9H), 1.26 (s, 4H), 0.91-0.85 (m, 1H). |
| 107 | 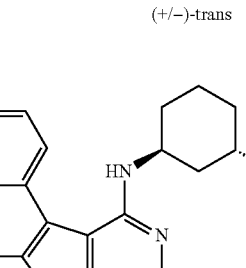<br>(+/−)-trans | LC-MS (Method 8): $R_t$ = 3.01 min; m/z = 515 (M + H)$^+$<br>$^1$H-NMR (400 MHz, CDCl$_3$):<br>δ = 8.39 (s, 1H), 7.60 (d, 2H), 7.30-7.20 (m, 5H), 6.85 (d, 2H), 4.78 (d, 1H), 4.50-4.40 (m, 1H), 4.05-3.88 (m, 3H), 3.40 (br. s, 1H), 1.93-1.82 (m, 1H), 1.80-1.67 (m, 2H), 1.65-1.50 (m, 3H), 1.48 (s, 9H), 1.31-1.19 (m, 3H). |
| 108 | 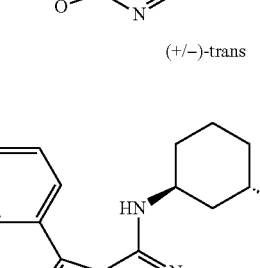<br>(+/−)-trans | LC-MS (Method 8): $R_t$ = 3.38 min; m/z = 568 (M + H)$^+$<br>$^1$H-NMR (400 MHz, CDCl$_3$):<br>δ = 8.43 (s, 1H), 7.72 (d, 2H), 7.68 (d, 2H), 7.53-6.97 (m, 2H), 7.37-7.29 (m, 3H), 4.50-4.40 (m, 1H), 4.38 (d, 1H), 3.97 (s, 2H), 3.46 (br. s, 1H), 2.00-1.90 (m, 1H), 1.88-1.69 (m, 3H), 1.68-1.51 (m, 2H), 1.48 (s, 9H), 1.20-1.09 (m, 2H). |
| 109 | 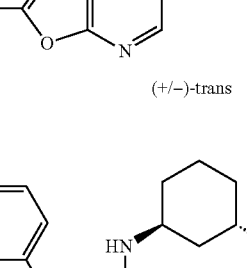<br>(+/−)-trans | LC-MS (Method 3): $R_t$ = 3.27 min; m/z = 528 (M + H)$^+$<br>$^1$H-NMR (400 MHz, CDCl$_3$):<br>δ = 8.39 (s, 1H), 7.59 (d, 2H), 7.42-7.35 (m, 3H), 7.30-7.21 (m, 4H), 4.61 (d, 1H), 4.50-4.40 (m, 1H), 3.95 (d, 2H), 3.42-3.34 (m, 1H), 2.79 (q, 2H), 1.88-1.79 (m, 1H), 1.78-1.62 (m, 2H), 1.60-1.51 (m, 2H), 1.48 (s, 9H), 1.32 (t, 3H), 1.22-1.03 (m, 3H). |
| 110 | 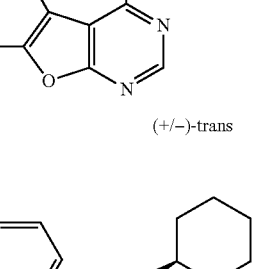<br>(+/−)-trans | LC-MS (Method 6): $R_t$ = 3.31 min; m/z = 544 (M + H)$^+$<br>$^1$H-NMR (400 MHz, CDCl$_3$):<br>δ = 8.40 (s, 1H), 7.58 (d, 2H), 7.39 (d, 2H), 7.30-7.22 (m, 3H), 7.05 (d, 2H), 4.65 (d, 1H), 4.49-4.39 (m, 1H), 4.13 (q, 2H), 3.97 (d, 2H), 3.40 (br. s, 1H), 2.19 (s, 1H), 1.94-1.87 (m, 1H), 1.82-1.66 (m, 2H), 1.62-1.53 (m, 4H), 1.48 (s, 9H), 1.29-1.13 (m, 3H). |

| Example | Structure | Analytical data |
|---|---|---|
| 111 | 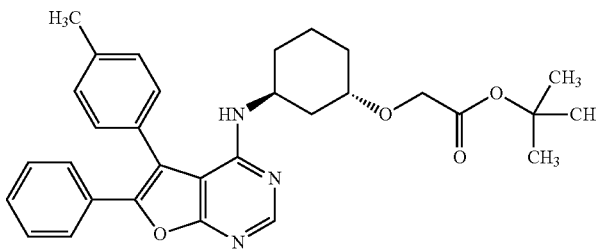<br>(+/−)-trans | LC-MS (Method 3): $R_t$ = 3.19 min; m/z = 514 (M + H)$^+$<br>$^1$H-NMR (400 MHz, CDCl$_3$): δ = 8.40 (s, 1H), 7.60-7.52 (m, 3H), 7.40-7.32 (m, 4H), 7.30-7.21 (m, 2H), 4.61 (d, 1H), 4.48-4.39 (m, 1H), 3.94 (d, 2H), 3.39 (br. s, 1H), 2.50 (s, 3H), 1.90-1.81 (m, 1H), 1.80-1.64 (m, 2H), 1.59 (s, 1H), 1.48 (s, 9H), 1.30-1.11 (m, 4H). |
| 112 | 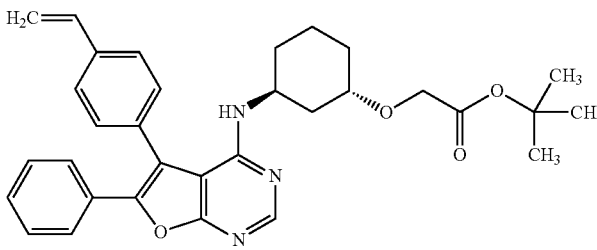<br>(+/−)-trans | LC-MS (Method 6): $R_t$ = 3.35 min; m/z = 526 (M + H)$^+$<br>$^1$H-NMR (400 MHz, CDCl$_3$): δ = 8.43 (s, 1H), 7.88-7.78 (m, 2H), 7.50-7.40 (m, 3H), 7.40-7.30 (m, 1H), 6.97-6.86 (m, 3H), 5.70 (br. s, 1H), 5.52 (d, 1H), 4.64-4.53 (m, 1H), 3.90 (s, 2H), 3.60 (br. s, 1H), 2.12-2.03 (m, 1H), 1.98-1.88 (m, 1H), 1.82-1.71 (m, 1H), 1.64 (s, 4H), 1.50 (s, 9H), 1.26 (s, 2H), 0.91-0.80 (m, 1H). |
| 113 | 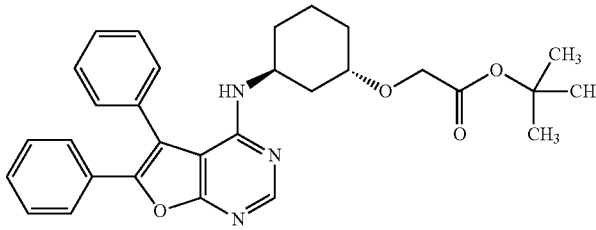<br>(+/−)-trans | LC-MS (Method 3): $R_t$ = 3.11 min; m/z = 500 (M + H)$^+$<br>$^1$H-NMR (400 MHz, CDCl$_3$): δ = 8.40 (s, 1H), 7.60-7.48 (m, 7H), 7.31-7.22 (m, 3H), 4.54 (d, 1H), 4.48-4.39 (m, 1H), 3.96 (d, 2H), 3.40 (br. s, 1H), 1.92-1.83 (m, 1H), 1.80-1.64 (m, 2H), 1.58 (s, 3H), 1.47 (s, 9H), 1.23-1.10 (m, 2H). |
| 114 | 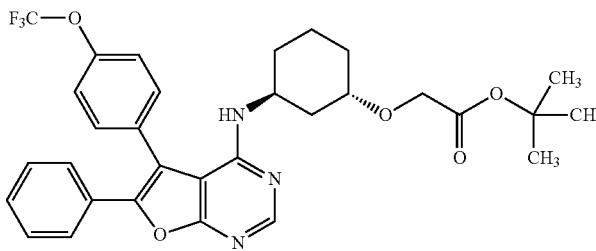<br>(+/−)-trans | LC-MS (Method 6): $R_t$ = 3.35 min; m/z = 584 (M + H)$^+$<br>$^1$H-NMR (400 MHz, CDCl$_3$): δ = 8.41 (s, 1H), 7.58-7.49 (m, 4H), 7.42 (d, 2H), 7.31-7.29 (m, 3H), 4.50-4.38 (m, 2H), 3.96 (d, 2H), 3.49 (br. s, 1H), 1.98-1.90 (m, 1H), 1.86-1.69 (m, 2H), 1.68-1.60 (m, 1H), 1.55 (s, 2H), 1.48 (s, 9H), 1.21-1.09 (m, 2H). |
| 115 | 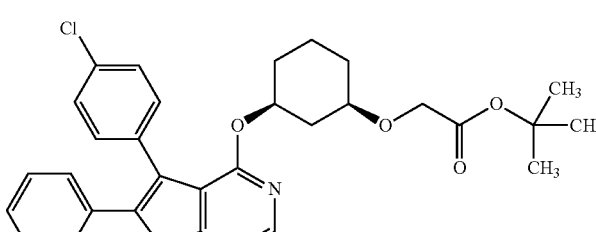 | LC-MS (Method 3): $R_t$ = 3.35 min; m/z = 535 (M + H)$^+$<br>$^1$H-NMR (400 MHz, DMSO-d$_6$): δ = 8.61 (s, 1H), 7.55-7.49 (m, 6H), 7.48-7.40 (m, 3H), 5.18-5.08 (m, 1H), 3.99 (s, 2H), 3.48-3.38 (m, 1H), 2.45-2.38 (m, 1H), 2.04-1.90 (m, 2H), 1.78-1.69 (m, 1H), 1.40 (s, 9H), 1.29-1.04 (m, 4H). |

-continued

| Example | Structure | Analytical data |
|---|---|---|
| 116 | 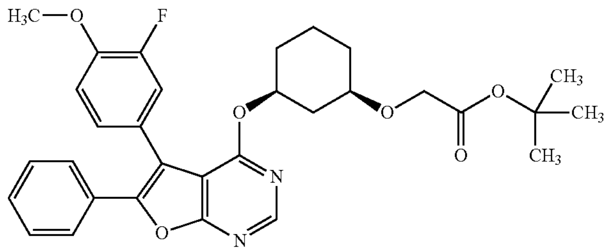 | LC-MS (Method 3): $R_t$ = 3.40 min; m/z = 547 (M + H)$^+$<br>$^1$H-NMR (400 MHz, DMSO-d$_6$): δ = 8.61 (s, 1H), 7.59-7.51 (m, 2H), 7.48-7.40 (m, 3H), 7.39-7.29 (m, 2H), 7.22-7.19 (m, 1H), 5.18-5.07 (m, 1H), 3.98 (s, 2H), 3.47-3.38 (m, 1H), 2.71 (q, 2H), 2.45-2.37 (m, 1H), 2.06-1.89 (m, 2H), 1.78-1.69 (m, 1H), 1.39 (s, 9H), 1.29-1.01 (m, 7H). |
| 117 | 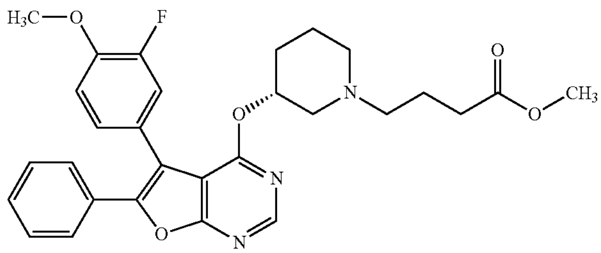 | LC-MS (Method 8): $R_t$ = 1.86 min; m/z = 520 (M + H)$^+$<br>$^1$H-NMR (400 MHz, DMSO-d$_6$): δ = 8.60 (s, 1H), 7.59-7.51 (m, 2H), 7.47-7.39 (m, 5H), 7.24-7.18 (m, 2H), 7.30-7.20 (m, 1H), 3.90 (s, 3H), 3.52 (s, 2H), 2.80-2.70 (m, 1H), 2.31-2.20 (m, 5H), 2.19-2.11 (m, 1H), 1.93-1.81 (m, 1H), 1.68-1.53 (m, 2H), 1.50-1.30 (m, 2H). |
| 118 | 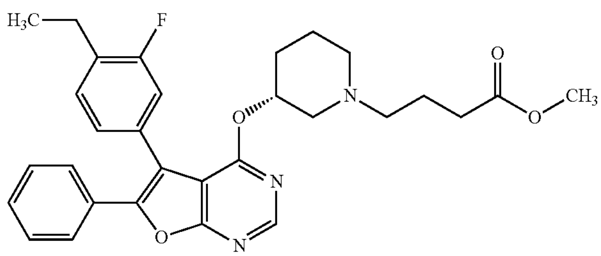 | LC-MS (Method 8): $R_t$ = 2.01 min; m/z = 518 (M + H)$^+$<br>$^1$H-NMR (400 MHz, DMSO-d$_6$): δ = 8.60 (s, 1H), 7.59-7.51 (m, 2H), 7.48-7.39 (m, 3H), 7.38-7.30 (m, 2H), 7.20 (d, 1H), 5.29-5.20 (m, 1H), 3.50 (s, 3H), 2.75-2.61 (m, 3H), 2.42-2.35 (m, 1H), 2.35-2.12 (m, 5H), 1.90-1.80 (m, 1H), 1.66-1.49 (m, 3H), 1.48-1.30 (m, 2H), 1.29-1.15 (m, 4H). |
| 119 | 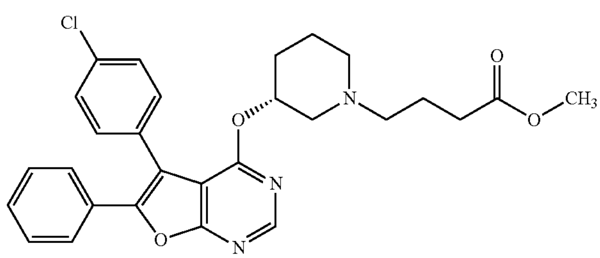 | LC-MS (Method 8): $R_t$ = 1.88 min; m/z = 506 (M + H)$^+$<br>$^1$H-NMR (400 MHz, DMSO-d$_6$): δ = 8.60 (s, 1H), 7.56-7.47 (m, 6H), 7.48-7.39 (m, 3H), 5.30-5.20 (m, 1H), 3.52 (s, 3H), 2.78-2.69 (m, 1H), 2.48-2.39 (m, 1H), 2.30-2.20 (m, 5H), 2.20-2.11 (m, 1H), 1.90-1.81 (m, 1H), 1.66-1.50 (m, 3H), 1.49-1.29 (m, 2H). |

Example 120

(−)-{[(3-{[5-(4-Ethylphenyl)-6-phenylfuro[2,3-d]pyrimidin-4-yl]oxy}cyclohexyl]oxy}acetic acid tert-butyl ester

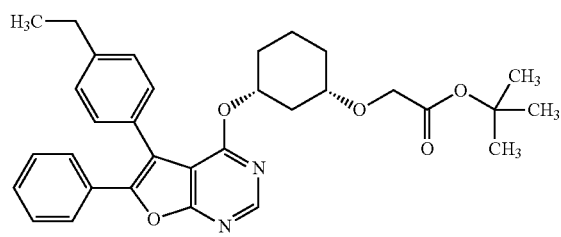

Add 0.104 ml (0.208 mmol) of phosphazene base P2-t-Bu (2 M solution in THF) with cooling to a mixture of 40 mg (0.174 mmol) of (−)-cis-{[3-hydroxycyclohexyl]oxy}acetic acid tert-butyl ester and 58.15 mg (0.174 mmol) of 4-chloro-5-(4-ethylphenyl)-6-phenylfuro[2,3-d]pyrimidine in 0.3 ml of DMF. Stir the mixture at RT for one hour. Then add water and extract with dichloromethane. Wash the organic phase with pH 7 buffer solution and with satd. sodium chloride solution, dry over sodium sulphate and concentrate under reduced pressure. From the residue, 45.6 mg (49.7% of theory) of the target compound are isolated by preparative RP-HPLC (eluent: acetonitrile/water).

$[α]_D^{20}$=−56.7°, c=0.485, CHCl$_3$

LC-MS (Method 3): $R_t$=3.41 min; m/z=529 (M+H)$^+$ $^1$H-NMR (400 MHz, DMSO-d$_6$): δ=8.60 (s, 1H), 7.58-7.50 (m, 2H), 7.43-7.35 (m, 5H), 7.29 (d, 2H), 5.18-5.07 (m, 1H), 3.90 (s, 2H), 3.46-3.36 (m, 1H), 2.70 (q, 2H), 2.44-2.36 (m, 1H), 2.05-1.90 (m, 2H), 1.78-1.69 (m, 1H), 1.41 (s, 9H), 1.25 (t, 3H), 1.20-1.01 (m, 4H).

Example 121

(+)-{[(3-{[5-(4-Ethylphenyl)-6-phenylfuro[2,3-d]pyrimidin-4-yl]oxy}cyclohexyl]oxy}acetic acid tert-butyl ester

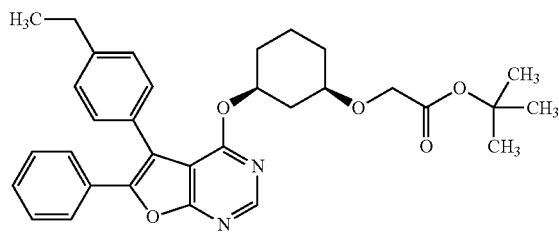

The title compound is obtained analogously to Example 120 by reacting (+)-cis-{[3-hydroxycyclo-hexyl]oxy}acetic acid tert-butyl ester with 4-chloro-5-(4-ethylphenyl)-6-phenylfuro[2,3-d]-pyrimidine.

$[\alpha]_D^{20}$=+54.7°, c=0.505, CHCl$_3$
LC-MS (Method 3): R$_t$=3.41 min; m/z=529 (M+H)$^+$
$^1$H-NMR (400 MHz, DMSO-d$_6$): δ=8.60 (s, 1H), 7.58-7.50 (m, 2H), 7.43-7.35 (m, 5H), 7.29 (d, 2H), 5.18-5.07 (m, 1H), 3.90 (s, 2H), 3.46-3.36 (m, 1H), 2.70 (q, 2H), 2.44-2.36 (m, 1H), 2.95-1.90 (m, 2H), 1.78-1.69 (m, 1H), 1.41 (s, 9H), 1.25 (t, 3H), 1.20-1.01 (m, 4H).

Example 122

(−)-4-[(3R)-3-{[5-(4-Ethylphenyl)-6-phenylfuro[2,3-d]pyrimidin-4-yl]oxy}piperidin-1-yl]butanoic acid methyl ester

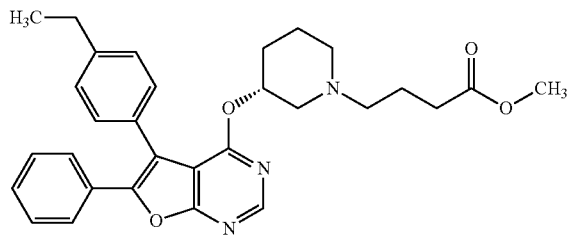

Add 1.55 ml (3.10 mmol) of phosphazene base P4-t-Bu (1 M solution in hexane) with ice cooling to a mixture of 798 mg (2.39 mmol) of 4-chloro-5-(4-ethylphenyl)-6-phenylfuro[2,3-d]pyrimidine and 600 mg (2.981 mmol) of (−)-4-[(3R)-3-hydroxypiperidin-1-yl]butanoic acid methyl ester in 2 ml of DMF. After 2 h at RT, add a further 220 mg of (−)-4-[(3R)-3-hydroxypiperidin-1-yl]-butanoic acid methyl ester and 0.57 ml of phosphazene base P4-t-Bu (1 M solution in hexane), and stir the mixture at RT for a further 2 h. For workup, dilute the mixture with dichloromethane, wash with water, dry over sodium sulphate and concentrate under reduced pressure. After purifying the residue by preparative RP-HPLC (eluent: acetonitrile/water gradient), 548.4 mg of the target product are obtained (46.0% of theory).

$[\alpha]_D^{20}$=−40.6°, c=0.505, CHCl$_3$
LC-MS (Method 8): R$_t$=1.95 min; m/z=500 (M+H)$^+$
$^1$H-NMR (400 MHz, DMSO-d$_6$): δ=8.59 (s, 1H), 7.59-7.52 (m, 2H), 7.46-7.38 (m, 5H), 7.30-7.21 (m, 2H), 5.25-5.19 (m, 1H), 3.52 (s, 3H), 2.73-2.65 (m, 3H), 2.44-2.38 (m, 1H), 2.30-2.20 (m, 5H), 2.19-2.05 (m, 1H), 1.90-1.80 (m, 1H), 1.64-1.50 (m, 3H), 1.44-1.39 (m, 2H), 1.23 (t, 3H).

Example 123

4-[(3S)-3-{[5-(4-Ethylphenyl)-6-phenylfuro[2,3-d]pyrimidin-4-yl]oxy}piperidin-1-yl]butanoic acid methyl ester

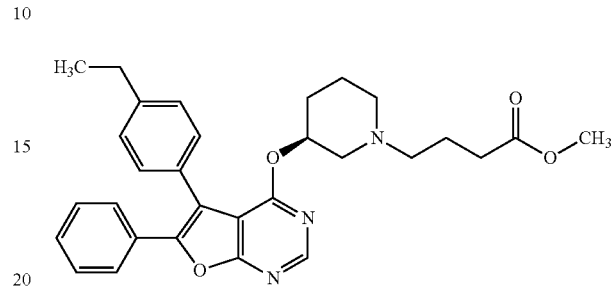

Add 5.2 mg (0.007 mmol) of bis(triphenylphosphine)palladium(II) chloride,. 30.6 mg (0.221 mmol) of potassium carbonate, 0.04 ml of methanol and 31 mg (0.207 mmol) of 4-ethylbenzeneboronic acid successively under argon to a solution of 70 mg (0.148 mmol) of (+)-4-{(3S)-3-[(5-bromo-6-phenylfuro[2,3-d]pyrimidin-4-yl)oxy]piperidin-1-yl}butanoic acid methyl ester in 0.4 ml of DMSO. Stir the mixture at 80° C. for a total of 3.5 h. After cooling, purify the reaction mixture directly by preparative RP-HPLC (eluent: acetonitrile/water gradient). 37.3 mg (50.6% of theory) of the target compound are isolated.

LC-MS (Method 8): R$_t$=1.86 min; m/z=500 (M+H)$^+$
$^1$H-NMR (400 MHz, DMSO-d$_6$): δ=8.59 (s, 1H), 7.59-7.52 (m, 2H), 7.46-7.38 (m, 5H), 7.30-7.21 (m, 2H), 5.25-5.19 (m, 1H), 3.52 (s, 3H), 2.73-2.65 (m, 3H), 2.44-2.38 (m, 1H), 2.30-2.20 (m, 5H), 2.19-2.05 (m, 1H), 1.90-1.80 (m, 1H), 1.64-1.50 (m, 3H), 1.44-1.39 (m, 2H), 1.23 (t, 3H).

Example 124 rac-(cis/trans)-{[3-{[5-(4-Methoxyphenyl)-6-phenyl-furo[2,3-d]pyrimidin-4-yl]oxy}cyclopentyl]-oxy}acetic acid tert-butyl ester

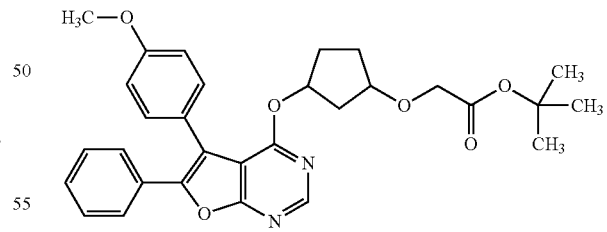

Add a solution of 2.5 g (6.2 mmol) of rac-(cis/trans)-3-{[5-(4-methoxyphenyl)-6-phenylfuro-[2,3-d]pyrimidin-4-yl]oxy}cyclopentanol in 10 ml of toluene and 10 ml of 1,2-dimethoxyethane, 210.9 mg (0.62 mmol) of tetra-n-butylammonium hydrogensulphate and 1.8 ml (12.4 mmol) of bromoacetic acid tert-butyl ester successively at 40° C. to 4.97 g (62.1 mmol) of 50% sodium hydroxide solution and 10 ml of toluene. Stir the biphasic reaction mixture vigorously at 60° C. for a total of 3 h. After cooling, add the reaction mixture to water and neutralize with conc. hydrochloric acid.

Extract three times with ethyl acetate, combine the organic phases, dry over magnesium sulphate and concentrate under reduced pressure. From the residue, 300 mg (9.4% of theory) of the target compound are isolated by chromatography on silica gel (eluent: cyclohexane/ethyl acetate 10:1→1:1).

LC-MS (Method 3): $R_f$=3.17 min; m/z=517 (M+H)$^+$ $^1$H-NMR (400 MHz, DMSO-d$_6$): δ=8.60 (s, 1H), 7.59-7.52 (m, 2H), 7.45-7.36 (m, 5H), 7.08-6.99 (m, 2H), 5.62-5.40 (m, 1H), 3.89 (d, 1H), 3.81 (s, 3H), 2.10-1.60 (m, 6H), 1.40 (d, 9H), 1.10-1.00 (m, 1H), 0.90-0.79 (m, 1H).

Separation of the cis/trans Isomers and Enantiomers:

Separate 300 mg (0.581 mmol) of rac-(cis/trans)-{[3-{[5-(4-methoxyphenyl)-6-phenylfuro[2,3-d]pyrimidin-4-yl]oxy}cyclopentyl]oxy}acetic acid tert-butyl ester into the isomers/enantiomers by chromatography on chiral phase (see Examples 125-128) [column: Daicel Chiralpak AD-H 5 μm, 250 mm×20 mm; flow rate: 15 ml/min; detection: 220 nm; temperature: 25° C.; eluent: 90:10 isohexane/2-propanol].

Example 125

(−)-cis-{[3-{[5-(4-Methoxyphenyl)-6-phenylfuro[2,3-d]pyrimidin-4-yl]oxy}cyclopentyl]oxy}acetic acid tert-butyl ester

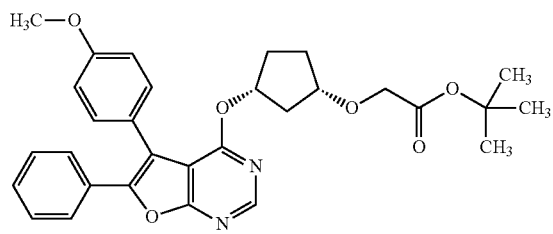

Yield: 75 mg (25.0% of theory) $[α]_D^{20}$=−24.7°, c=0.455, CHCl$_3$

LC-MS (Method 3): $R_f$=3.17 min; m/z=517 (M+H)$^+$ $^1$H-NMR (400 MHz, DMSO-d$_6$): δ=8.59 (s, 1H), 7.56 (d, 2H), 7.47-7.35 (m, 5H), 7.00 (d, 2H), 5.47-5.40 (m, 1H), 4.00-3.92 (m, 1H), 3.88 (d, 2H), 3.80 (s, 3H), 2.37-2.26 (m, 1H), 1.96-1.61 (m, 5H), 1.40 (s, 9H).

Example 126

(+)-cis-{[3-{[5-(4-Methoxyphenyl)-6-phenylfuro[2,3-d]pyrimidin-4-yl]oxy}cyclopentyl]oxy}acetic acid tert-butyl ester

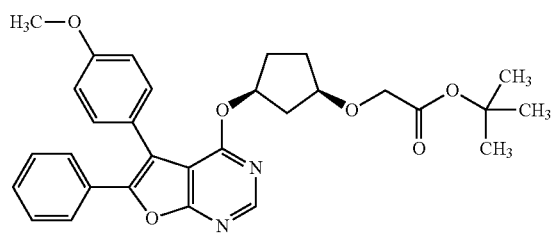

Yield: 57 mg (19.0% of theory)
$[α]_D^{20}$=+24.2°, c=0.48, CHCl$_3$.

Example 127

(+)-trans-{[3-{[5-(4-Methoxyphenyl)-6-phenylfuro[2,3-d]pyrimidin-4-yl]oxy}cyclopentyl]oxy}-acetic acid tert-butyl ester

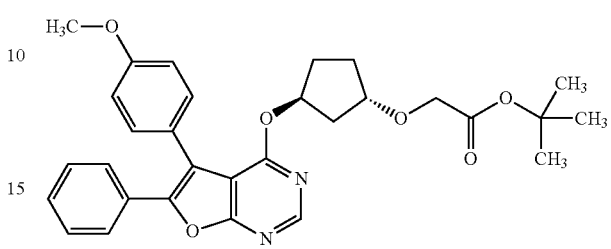

Yield: 23 mg (7.7% of theory)
$[α]_D^{20}$=+32.6°, c=0.48, CHCl$_3$

LC-MS (Method 6): $R_f$=3.31 min; m/z=517 (M+H)$^+$ $^1$H-NMR (400 MHz, DMSO-d$_6$): δ=8.59 (s, 1H), 7.56 (d, 2H), 7.45-7.36 (m, 5H), 7.01 (d, 2H), 5.63-5.58 (m, 1H), 3.97-3.90 (m, 1H), 3.89 (s, 2H), 3.82 (s, 3H), 2.10-1.84 (m, 3H), 1.76-1.57 (m, 3H), 1.42 (s, 9H).

Example 128

(−)-trans-{[3-{[5-(4-Methoxyphenyl)-6-phenylfuro[2,3-d]pyrimidin-4-yl]oxy}cyclopentyl]oxy}-acetic acid tert-butyl ester

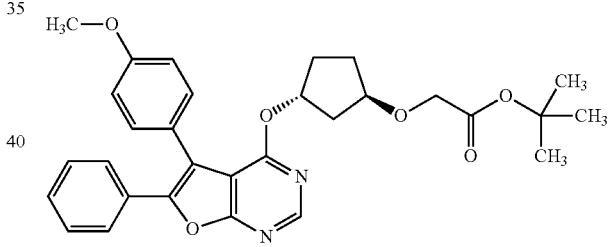

Yield: 39 mg (13.0% of theory)
$[α]_D^{20}$=−30.1°, c=0.54, CHCl$_3$.

Example 129

(+)-cis-{[(1R,3S)-3-{[5-(4-Methoxyphenyl)-6-phenylfuro[2,3-d]pyrimidin-4-yl]oxy}cyclopentyl]oxy}acetic acid tert-butyl ester

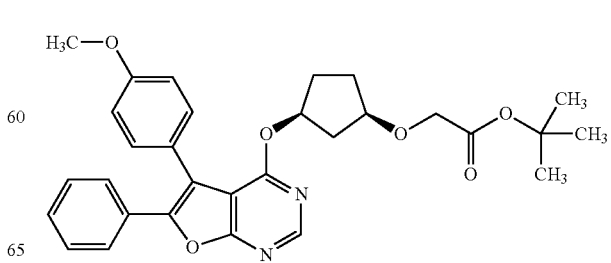

Dissolve 233.6 mg (0.694 mmol) of 4-chloro-5-(4-methoxyphenyl)-6-phenylfuro[2,3-d]pyrimidine and 150 mg (0.694 mmol) of cis-(−)-{[(1R,3S)-3-hydroxycyclopentyl]oxy}acetic acid tert-butyl ester in 0.35 ml of DMF, cool to 0° C. and add 0.69 ml (0.69 mmol) of phosphazene base P4-t-Bu (1 M solution in hexane). After stirring at RT for 1 h, add the reaction mixture to water, adjust to pH 7 with 1N hydrochloric acid and extract with dichloromethane three times. Combine the organic phases, wash with satd. sodium chloride solution, dry over magnesium sulphate and concentrate under reduced pressure. After purification by preparative RP-HPLC (eluent: acetonitrile/water gradient), 27.2 mg (7.6% of theory) of the target compound are obtained.

$[\alpha]_D^{20}$=+28.4°, c=0.48, CHCl$_3$

LC-MS (Method 3): $R_t$=3.18 min; m/z=517 (M+H)$^+$ $^1$H-NMR (400 MHz, DMSO-d$_6$): δ=8.59 (s, 1H), 7.56 (d, 2H), 7.47-7.35 (m, 5H), 7.00 (d, 2H), 5.47-5.40 (m, 1H), 4.00-3.92 (m, 1H), 3.88 (d, 2H), 3.80 (s, 3H), 2.37-2.26 (m, 1H), 196-1.61 (m, 5H), 1.40 (s, 9H).

Example 130 and Example 131 rac-trans-{[3-{[5-(4-Methoxyphenyl)-6-phenylfuro[2,3-d]pyrimidin-4-yl]amino}cyclopentyl]oxy}acetic acid tert-butyl ester and rac-cis-{[3-{[5-(4-Methoxyphenyl)-6-phenylfuro[2,3-d]pyrimidin-4-yl]amino}cyclopentyl]oxy}-acetic acid tert-butyl ester

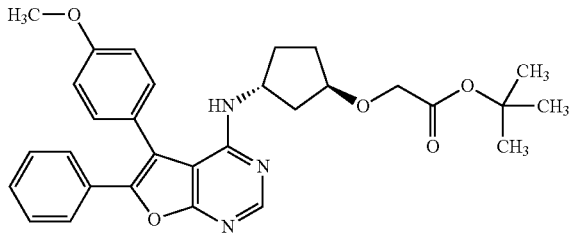

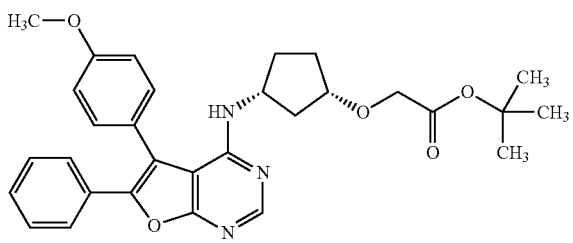

Add 0.86 ml (5 2 mmol) of diisopropylethylamine to a mixture of 560.4 mg of (+/−)-cis/trans-[(3-aminocyclopentyl)oxy]acetic acid tert-butyl ester (crude product, approx. 2.60 mmol) and 964.3 mg (2.86 mmol) of 4-chloro-5-(4-methoxyphenyl)-6-phenylfuro[2,3-d]pyrimidine in 2.0 ml of DMF. Heat the reaction mixture to 100° C. for 6 h. After cooling, add water and extract with dichloromethane. Wash the organic phase with satd. sodium hydrogencarbonate solution and satd. sodium chloride solution, dry over sodium sulphate and concentrate under reduced pressure. After drying under high vacuum, purify the product mixture by preparative RP-HPLC (eluent: acetonitrile/water gradient) and separate it into the cis/trans isomers.

rac-trans-Isomer (Example 130):

Yield: 153.7 mg (11.5% of theory)

LC-MS (Method 3): $R_t$=3.02 min; m/z=516 (M+H)$^+$ $^1$H-NMR (400 MHz, DMSO-d$_6$): δ=8.32 (s, 1H), 7.47-7.39 (m, 4H), 7.38-7.29 (m, 3), 7.10 (d, 2H), 5.31 (d, 1H), 4.61-4.52 (m, 1H), 3.92 (br. s, 1H), 3.84 (s, 3H), 3.65 (s, 2H), 2.00-1.90 (m, 2H), 1.70-1.60 (m, 2H), 1.52-1.43 (m, 2H), 1.40 (s, 9H).

rac-cis-Isomer (Example 131):

Yield: 404.1 mg (30.1% of theory)

LC-MS (Method 3): $R_t$=3.05 min; m/z=516 (M+H)$^+$ $^1$H-NMR (400 MHz, DMSO-d$_6$): δ=8.35 (s, 1H), 7.51-7.45 (m, 4H), 7.40-7.30 (m, 3H), 7.15 (d, 2H), 4.81 (d, 1H), 4.51-4.40 (m, 1H), 3.90 (br. s, 3H), 3.86 (s, 3H), 2.10-1.99 (m, 2H), 1.81-1.53 (m, 2H), 1.49-1.35 (m, 2H), 1.42 (s, 9H).

Separation of the Racemic Mixtures into the Enantiomers:

Separate 350 mg (0.679 mmol) of rac-cis-{[3-{[5-(4-methoxyphenyl)-6-phenylfuro[2,3-d]-pyrimidin-4-yl]amino}cyclopentyl]oxy}acetic acid tert-butyl ester or 119 mg (0.231 mmol) of rac-trans-{[3-{[5-(4-methoxyphenyl)-6-phenylfuro[2,3-d]pyrimidin-4-yl]amino}cyclopentyl acetic acid tert-butyl ester into the enantiomers in each case by chromatography on chiral phase (see Examples 132-135) [column: Sepapak-2 5 μm, 250 mm×20 mm; flow rate: 15 ml/min; detection: 220 nm; temperature: 40° C.; eluent: isohexane/2-propanol 50:50].

Example 132 cis-(−)-{[3-{[5-(4-Methoxyphenyl)-6-phenylfuro[2,3-d]pyrimidin-4-yl]amino}cyclopentyl]oxy}-acetic acid tert-butyl ester

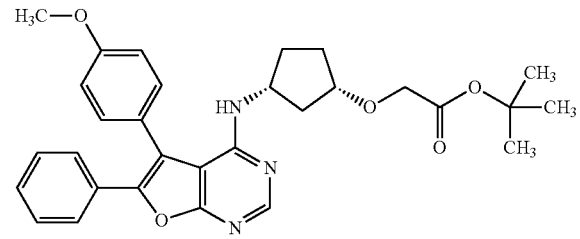

Yield: 165 mg (47.1% of theory)

$[\alpha]_D^{20}$=−12.2°, c=0.455, CHCl$_3$

LC-MS (Method 6): $R_t$=3.20 min; m/z=516 (M+H)$^+$ $^1$H-NMR (400 MHz, DMSO-d$_6$): δ=8.35 (s, 1H), 7.48-7.40 (m, 4H), 7.39-7.29 (m, 3H), 7.11 (d, 2H), 5.32 (d, 1H), 4.62-4.52 (m, 1H), 3.97-3.90 (m, 1H), 3.82 (s, 3H), 3.68 (s, 2H), 2.00-1.90 (m, 2H), 1.70-1.60 (m, 2H), 1.53-1.44 (m, 2H), 1.40 (s, 9H).

Example 133 cis-(+)-{[3-{[5-(4-Methoxyphenyl)-6-phenylfuro[2,3-d]pyrimidin-4-yl]amino}cyclopentyl]oxy}-acetic acid tert-butyl ester

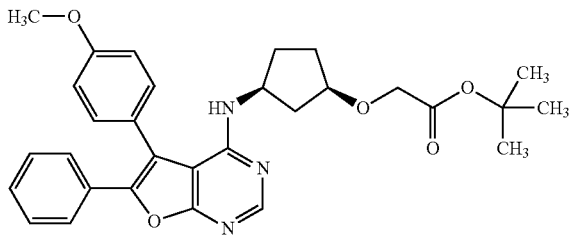

Yield: 163 mg (46.6% of theory)
$[\alpha]_D^{20}$=+8.4°, c=0.51, CHCl$_3$
LC-MS (Method 6): R$_t$=3.20 min; m/z=516 (M+H)$^+$
$^1$H-NMR (400 MHz, DMSO-d$_6$): δ=8.34 (s, 1H), 7.47-7.39 (m, 4H), 7.38-7.29 (m, 3H), 7.10 (d, 2H), 5.32 (d, 1H), 4.61-4.51 (m, 1H), 3.97-3.90 (m, 1H), 3.83. (s, 3H), 3.66 (s, 2H), 2.00-1.89 (m, 2H), 1.70-1.60 (m, 2H), 1.53-1.47 (m, 1H), 1.40 (s, 9H), 0.90-0.79 (m, 1H).

Example 134 trans-(+)-{[3-{[5-(4-Methoxyphenyl)-6-phenylfuro[2,3-d]pyrimidin-4-yl]amino}cyclopentyl]oxy}acetic acid tert-butyl ester

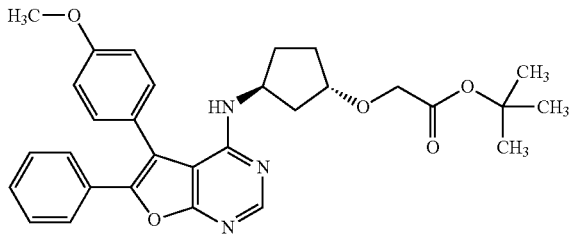

Yield: 54 mg (45.4% of theory)
$[\alpha]_D^{20}$=+29.5°, c=0.46, CHCl$_3$
$^1$H-NMR (400 MHz, DMSO-d$_6$): δ=8.35 (s, 1H), 7.50-7.45 (m, 4H), 7.40-7.30 (m, 3H), 7.16 (d, 2H), 4.80 (d, 1H), 4.50-4.40 (m, 1H), 3.95-3.39 (m, 3H), 3.86 (s, 3H), 2.08-1.98 (m, 2H), 1.81-1.71 (m, 1H), 1.63-1.54 (m, 1H), 1.42 (s, 9H), 1.40-1.32 (m, 1H), 1.21-1.10 (m, 1H).

Example 135 trans-(−)-{[3-{[5-(4-Methoxyphenyl)-6-phenylfuro[2,3-d]pyrimidin-4-yl]amino}cyclopentyl]oxy}-acetic acid tert-butyl ester

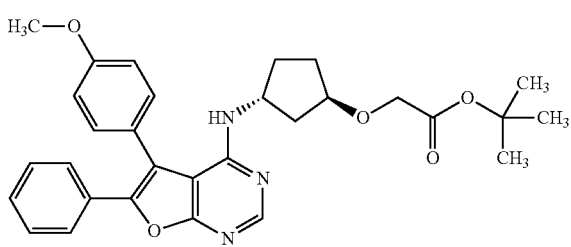

Yield: 50 mg (42.0% of theory)
$[\alpha]_D^{20}$=−30.3°, c=0.52, CHCl$_3$
$^1$H-NMR (400 MHz, DMSO-d$_6$): δ=8.36 (s, 1H), 7.51-7.44 (m, 4H), 7.40-7.30 (m, 3H), 7.17 (d, 2H), 4.81 (d, 1H), 4.51-4.40 (m, 1H), 3.95-3.89 (m, 3H), 3.85 (s, 3H), 2.10-1.99 (m, 2H), 1.81-1.71 (m, 1H), 1.65-1.54 (m, 1H), 1.42 (s, 9H), 1.40-1.35 (m, 1H), 1.21-1.11 (m, 1H).

Example 136 cis-(+/−)-{[4-{[5-(4-Ethylphenyl)-6-phenylfuro[2,3-d]pyrimidin-4-yl]oxy}cyclopent-2-en-1-yl]-oxy}acetic acid tert-butyl ester

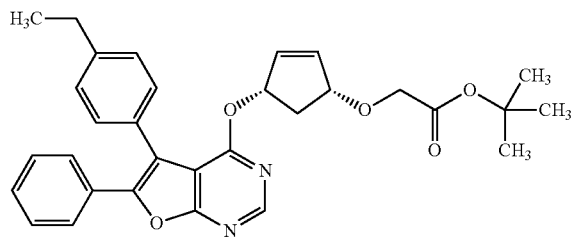

Dissolve 390.7 mg (1.17 mmol) of 4-chloro-5-(4-ethylphenyl)-6-phenylfuro[2,3-d]pyrimidine and 250 mg (1.17 mmol) of cis-(+/−)-{[(4-hydroxycyclopent-2-en-1-yl)oxy}acetic acid tert-butyl ester in 0.95 ml of DMF, cool to 0° C. and add 0.58 ml (1.17 mmol) of phosphazene base P2-t-Bu (2 M solution in THF). After the end of the addition, warm the mixture to RT and stir for a further 1 h. Then add the reaction mixture to water, adjust to pH 7 with 1N hydrochloric acid and extract three times with dichloromethane. Combine the organic phases, wash with satd. sodium chloride solution, dry over magnesium sulphate and concentrate under reduced pressure. Isolate the crude product by chromatography on silica gel (eluent: cyclohexane/ethyl acetate 20:1→5:1). 510 mg (85.3% of theory) of the target compound are obtained.
LC-MS (Method 8): R$_t$=3.47 min; m/z=513 (M+H)$^+$
$^1$H-NMR (400 MHz, DMSO-d$_6$): δ=8.61 (s, 1H), 7.49-7.51 (m, 2H), 7.44-7.35 (m, 5H), 7.28 (d, 2H), 6.13 (dd, 2H), 5.84-5.79 (m, 1H), 4.53-4.48 (m, 1H), 3.93 (s, 2H), 2.88-2.79 (m, 1H), 2.68 (q, 2H), 1.52 (td, 1H), 1.40 (s, 9H), 1.23 (t, 3H).

Example 137 cis-(−)-{[4-{[5-(4-Ethylphenyl)-6-phenylfuro[2,3-d]pyrimidin-4-yl]oxy}cyclopent-2-en-1-yl]oxy}-acetic acid tert-butyl ester

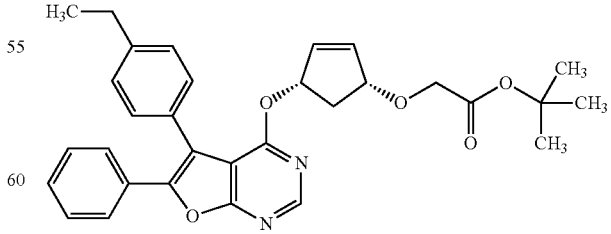

Dissolve 125 mg (0.373 mmol) of 4-chloro-5-(4-ethylphenyl)-6-phenylfuro[2,3-d]pyrimidine and 80 mg (0.373 mmol) of cis-(+)-{[(4-hydroxycyclopent-2-en-1-yl)oxy}acetic acid tert-butyl ester in 0.19 ml of DMF, cool to 0° C. and add 0.19 ml (0.373 mmol) of phosphazene base P2-t-Bu (2 M solution in THF). After the end of the addition, warm the mixture to RT and stir for a further 1 h. Then add the reaction mixture to water, adjust to pH 7 with 1N hydrochloric acid and extract three times with dichloromethane. Combine the organic phases, wash with satd. sodium chloride solution, dry over magnesium sulphate and concentrate under reduced pressure. Purify the crude product by preparative RP-HPLC (eluent: acetonitrile/water gradient). 140.5 mg (73.4% of theory) of the target compound are obtained.

$[\alpha]_D^{20}$=−92.2°, c=0.515, CHCl$_3$

LC-MS (Method 12): R$_t$=3.37 min; m/z=513 (M+H)$^+$ $^1$H-NMR (400 MHz, DMSO-d$_6$): δ=8.61 (s, 1H), 7.58-7.52 (m, 2H), 7.42-7.37 (m, 5H), 7.28 (d, 2H), 6.12 (dd, 2H), 5.85-5.79 (m, 1H), 4.53-4.49 (m, 1H), 3.92 (s, 2H), 2.88-2.79 (m, 1H), 2.69 (q, 2H), 1.53 (td, 1H), 1.40 (s, 9H), 1.23 (t, 3H).

Example 138 cis-(−)-{[4-{[5-(4-Ethylphenyl)-6-phenylfuro[2,3-d]pyrimidin-4-yl]oxy}cyclopent-2-en-1-yl]oxy}-acetic acid tert-butyl ester

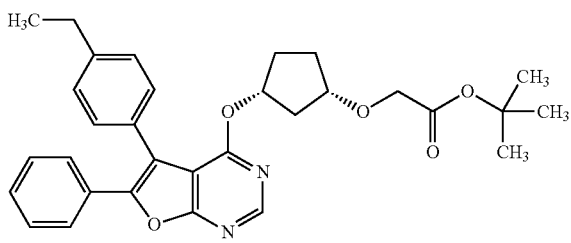

Dissolve 218 mg (0.652 mmol) of 4-chloro-5-(4-ethylphenyl)-6-phenylfuro[2,3-d]pyrimidine and 141 mg (0.652 mmol) of cis-(+)-{[(1S,3R)-3-hydroxycyclopentyl]oxy}acetic acid tert-butyl ester in 0.19 ml of DMF, cool to 0° C. and add 0.65 ml (0.65 mmol) of phosphazene base P4-t-Bu (1 M solution in hexane). After the end of the addition, warm the mixture to RT and stir for a further 1 h. Then add the reaction mixture to water, adjust to pH 7 with 1N hydrochloric acid and extract three times with dichloromethane. Combine the organic phases, wash with satd. sodium chloride solution, dry over magnesium sulphate and concentrate under reduced pressure. Purify the crude product by preparative RP-HPLC (eluent: acetonitrile/water gradient). 92.1 mg (27.5% of theory) of the target compound are obtained.

$[\alpha]_D^{20}$=−36.2°, c=0.490, CHCl$_3$

LC-MS (Method 12): R$_t$=3.40 min; m/z=515 (M+H)$^+$ $^1$H-NMR (400 MHz, DMSO-d$_6$): δ=8.60 (s, 1H), 7.54 (d, 2H), 7.45-7.37 (m, 5H), 5H), 7.29 (d, 2H), 5.45-5.39 (m, 1H), 4.00-3.94 (m, 1H), 3.81 (d, 2H), 2.69 (q, 2H), 2.34-2.22 (m, 1H), 1.94-1.83 (m, 1H), 1.81-1.71 (m, 1H), 1.70-1.56 (m, 3H), 1.40 (s, 9H), 1.22 (t, 3H).

Example 139 trans-(+)-[{4-{[5-(4-Ethylphenyl)-6-phenylfuro[2,3-d]pyrimidin-4-yl]oxy}cyclopent-2-en-1-yl]-oxy}acetic acid tert-butyl ester

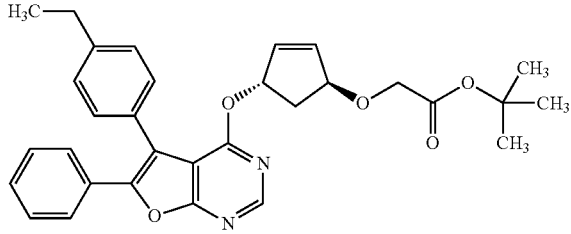

Dissolve 393.9 mg (1.18 mmol) of 4-chloro-5-(4-ethylphenyl)-6-phenylfuro[2,3-d]pyrimidine and 274 mg (80% purity, approx. 1.02 mmol) of trans-(+)-{[(4-hydroxycyclopent-2-en-1-yl)oxy}acetic acid tert-butyl ester in 0.59 ml of THF, cool to 0° C. and slowly add 1.02 ml (1.02 mmol) of phosphazene base P4-t-Bu (1 M solution in hexane). After stirring at 0° C. for 1 h, add the reaction mixture to water. Adjust to pH 7 with 1N hydrochloric acid and extract three times with dichloromethane. Combine the organic phases, wash with satd. sodium chloride solution, dry over magnesium sulphate and concentrate under reduced pressure. Purify the crude product by preparative RP-HPLC (eluent: acetonitrile/water gradient). 258.3 mg (42.8% of theory) of the target compound are obtained.

$[\alpha]_D^{20}$=−102.7°, c=0.58, CHCl$_3$

LC-MS (Method 8): R$_t$=3.49 min; m/z=513 (M+H)$^+$ $^1$H-NMR (400 MHz, DMSO-d$_6$): δ=8.61 (s, 1H), 7.59-7.51 (m, 2H), 7.47-7.31 (m, 5H), 7.30-7.21 (m, 2H), 6.28-6.22 (m, 1H), 6.19-6.09 (m, 2H), 4.67-4.60 (m, 1H), 4.00 (s, 2H), 2.69 (q, 2H), 2.65-2.57 (m, 1H), 2.20-2.10 (m, 1H), 2.05-1.95 (m, 1H), 1.46 (s, 9H), 1.29-1.20 (m, 2H).

Example 140 trans-(−)-{[4-{[5-(4-Ethylphenyl)-6-phenylfuro[2,3-d]pyrimidin-4-yl]amino}cyclopent-2-en-1-yl]-oxy}acetic acid tert-butyl ester

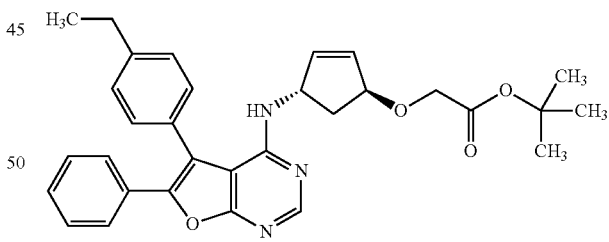

Add 87 μl (0.524 mmol) of diisopropylethylamine to a mixture of 128.6 mg (0.384 mmol) of 4-chloro-5-(4-ethylphenyl)-6-phenylfuro[2,3-d]pyrimidine and 74.5 mg of trans-{[(4-aminocyclopent-2-en-1-yl)oxy}acetic acid tert-butyl ester (crude product) in 0.5 ml of DMF. Heat the reaction to 100° C. for 4.5 h. After cooling, add water and extract with dichloromethane. Wash the organic phase with satd. sodium hydrogencarbonate solution and satd. sodium chloride solution, dry over sodium sulphate and concentrate under reduced pressure. Purify the crude product by preparative RP-HPLC (eluent: acetonitrile/water gradient). 70.5 mg (39.5% of theory) of the target compound are obtained.

$[\alpha]_D^{20}$=195.3°, c=0.50, CHCl$_3$

LC-MS (Method 3): $R_t$=3.20 min; m/z=512 (M+H)$^+$ $^1$H-NMR (400 MHz, DMSO-$d_6$): δ=8.39 (s, 1H), 7.52-7.48 (m, 2H), 7.47-7.30 (m, 7H), 6.07-6.01 (m, 1H), 5.90 (d, 1H), 5.24-5.16 (m, 1H), 4.65 (d, 1H), 4.59-4.51 (m, 1H), 3.98 (s, 2H), 2.72 (q, 2H), 2.20-2.10 (m, 1H), 1.67-1.58 (m, 1H), 1.42 (s, 9H), 1.27 (t, 3H).

Example 141 cis-(+)-{[4-{[5-(4-Ethylphenyl)-6-phenylfuro[2,3-d]pyrimidin-4-yl]oxy}cyclopent-2-en-1-yl]oxy}-acetic acid tert-butyl ester

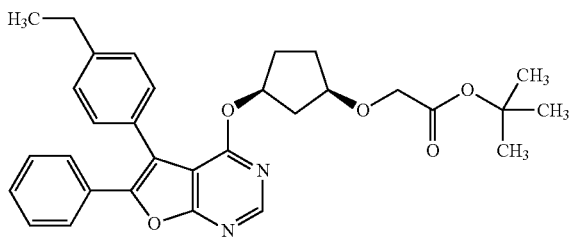

Dissolve 233.6 mg (0.698 mmol) of 4-chloro-5-(4-ethylphenyl)-6-phenylfuro[2,3-d]pyrimidine and 150.9 mg (0.698 mmol) of cis-(−)-{[(1R,3S)-3-hydroxycyclopentyl]oxy}acetic acid tert-butyl ester in 0.35 ml of DMF, cool to 0° C. and add 0.7 ml (0.7 mmol) of phosphazene base P4-t-Bu (1 M solution in hexane). After stirring at 0° C. for 2 h, add the reaction mixture to water. Adjust to pH 7 with 1N hydrochloric acid and extract three times with dichloromethane. Combine the organic phases, wash with satd. sodium chloride solution, dry over magnesium sulphate and concentrate under reduced pressure. Purify the crude product by preparative RP-HPLC (eluent: acetonitrile/water gradient). 60.9 mg (17.0% of theory) of the target compound are obtained.

$[α]_D^{20}$=+26.7°, c=0.475, CHCl$_3$

LC-MS (Method 12): $R_t$=3.39 min; m/z=515 (M+H)$^+$ $^1$H-NMR (400 MHz, DMSO-$d_6$): δ=8.60 (s, 1H), 7.56 (d, 2H), 7.44-7.38 (m, 5H), 7.29 (d, 2H), 5.45-5.40 (m, 1H), 4.00-3.92 (m, 1H), 3.82 (d, 2H), 2.69 (q, 2H), 2.32-2.25 (m, 1H), 1.92-1.85 (m, 1H), 1.81-1.74 (m, 1H), 1.70-1.58 (m, 3H), 1.40 (s, 9H), 1.22 (t, 3H).

The examples which follow are prepared according to general method D or E (see above) from the compounds described above:

| Example | Structure | Analytical data |
|---|---|---|
| 142 | (+/−)-trans | LC-MS (Method 6): $R_t$ = 2.50 min; m/z = 492 (M + H)$^+$<br>$^1$H-NMR (400 MHz, CDCl$_3$): δ = 8.40 (s, 1H), 7.59-7.50 (m, 3H), 7.34-7.10 (m, 5H), 4.60-4.53 (m, 1H), 4.49-4.39 (m, 1H), 4.18-4.05 (m, 1H), 4.00 (s, 3H), 3.64-3.50 (m, 1H), 2.11-2.00 (m, 2H), 1.88-1.53 (m, 2H), 1.28 (s, 4H), 0.93-0.80 (m, 2H). |
| 143 | (+/−)-trans | LC-MS (Method 6): $R_t$ = 2.69 min; m/z = 478 (M + H)$^+$<br>$^1$H-NMR (400 MHz, CDCl$_3$): δ = 8.40 (s, 1H), 7.59-7.49 (m, 4H), 7.46 (d, 2H), 7.33-7.29 (m, 3H), 4.50-4.38 (m, 2H), 4.20-4.05 (m, 2H), 3.55 (br. s, 1H), 2.10-2.00 (m, 1H), 1.88-1.79 (m, 1H), 1.78-1.62 (m, 2H), 1.61-1.50 (m, 1H), 1.49-1.11 (m, 4H). |
| 144 | (+/−)-trans | LC-MS (Method 6): $R_t$ = 2.19 min; m/z = 459 (M + H)$^+$<br>$^1$H-NMR (400 MHz, CDCl$_3$): δ = 8.40 (s, 1H), 7.57 (d, 2H), 7.33-7.21 (m, 5H), 6.90 (d, 2H), 4.80 (d, 1H), 4.49 (br. s, 1H), 4.10 (dd, 2H), 3.20 (br. s, 1H), 1.88-1-73 (m, 2H), 1.72-1.53 (m, 5H), 1.49-1.38 (m, 1H), 1.36-1.20 (m, 3H). |

| Example | Structure | Analytical data |
|---|---|---|
| 145 | (+/−)-trans | LC-MS (Method 6): $R_t$ = 2.74 min; m/z = 512 (M + H)+ <br> $^1$H-NMR (400 MHz, CDCl$_3$): <br> δ = 8.43 (s, 1H), 7.83 (d, 2H), 7.65 (d, 2H), 7.51-7.44 (m, 2H), 7.34-7.29 (m, 3H), 4.48-4.38 (m, 1H), 7.34 (d, 1H), 4.01 (dd, 2H), 3.58 (br. s, 1H), 2.11-2.00 (m, 1H), 1.88-1.79 (m, 1H), 1.77-1.63 (m, 2H), 1.58-1.47 (m, 1H), 1.45-1.35 (m, 1H), 1.28 (s, 2H), 1.18-1.04 (m, 1H). |
| 146 | (+/−)-trans | LC-MS (Method 6): $R_t$ = 2.81 min; m/z = 472 (M + H)+ <br> $^1$H-NMR (400 MHz, CDCl$_3$): <br> δ = 8.40 (s, 1H), 7.60-7.53 (m, 2H), 7.43-7.35 (m, 4H), 7.30-7.22 (m, 3H), 4.60 (d, 1H), 4.48-4.38 (m, 1H), 4.10 (dd, 2H), 3.50 (br. s, 1H), 2.80 (q, 2H), 2.00-1.90 (m, 1H), 1.80-1.45 (m, 5H), 1.32 (t, 3H), 1.29-1.10 (m, 3H). |
| 147 | (+/−)-trans | LC-MS (Method 8): $R_t$ = 2.87 min; m/z = 488 (M + H)+ <br> $^1$H-NMR (400 MHz, CDCl$_3$): <br> δ = 8.40 (s, 1H), 7.57 (d, 2H), 7.40 (d, 2H), 7.32-7.22 (m, 3H), 7.07 (d, 2H), 4.64 (d, 1H), 4.48-4.37 (m, 1H), 4.19-4.02 (m, 4H), 3.49 (br. s, 1H), 2.03-1.94 (m, 1H), 1.80-1.68 (m, 2H), 1.60 (br. s, 2H), 1.51 (t, 3H), 1.39-1.20 (m, 4H). |
| 148 | (+/−)-trans | LC-MS (Method 6): $R_t$ = 2.68 min; m/z = 458 (M + H)+ <br> $^1$H-NMR (400 MHz, CDCl$_3$); <br> δ = 8.40 (s, 1H), 7.59-7.50 (m, 2H), 7.40-7.34 (m, 5H), 7.31-7.21 (m, 2H), 4.60 (d, 1H), 4.48-4.36 (br. m, 1H), 4.19-4.00 (br. m, 2H), 3.50 (br. s, 1H), 2.50 (s, 3H), 2.05-1.92 (m, 1H), 1.81-1.40 (m, 5H), 1.35-1.12 (m, 3H). |
| 149 | (+/−)-trans | LC-MS (Method 3): $R_t$ = 2.57 min; m/z = 470 (M + H)+ <br> $^1$H-NMR (400 MHz, CDCl$_3$): <br> δ = 8.49 (s, 1H), 7.62 (d, 2H), 7.55 (s, 2H), 7.49 (d, 2H), 7.29 (d, 2H), 6.82 (dd, 1H), 5.91 (d, 1H), 5.42 (d, 1H), 4.90-4.78 (br. m, 1H), 4.51-4.40 (br. m, 1H), 4.09 (dt, 2H), 3.50 (s, 1H), 2.09-1.90 (m, 1H), 1.89-1.78 (m, 1H), 1.77-1.61 (m, 2H), 1.54-1.42 (m, 1H), 1.41-1.30 (m, 2H), 1.20-1.10 (m, 1H), 0.92-0.80 (m, 1H). |

-continued

| Example | Structure | Analytical data |
|---|---|---|
| 150 | (+/−)-trans | LC-MS (Method 6): $R_t$ = 2.55 min; m/z = 444 (M + H)$^+$<br>$^1$H-NMR (400 MHz, CDCl$_3$):<br>δ =8.42 (s, 1H), 7.60-7.49 (m, 7H), 7.29 (s, 1H), 5.31 (s, 2H), 4.55 (d, 1H), 4.48-4.36 (br. m, 1H), 4.10 (dd, 2H), 3.48 (br. s, 1H), 2.02-1.92 (m, 1H), 1.81-1.50 (m, 3H), 1.49-1.39 (m, 1H), 1.38-1.12 (m, 3H). |
| 151 | (+/−)-trans | LC-MS (Method 3): $R_t$ = 2.67 min; m/z = 528 (M + H)$^+$<br>$^1$H-NMR (400 MHz, CDCl$_3$):<br>δ = 8.42 (s, 1H), 7.56 (d, 2H), 7.52-7.49 (m, 2H), 7.42 (d, 2H), 7.33-7.29 (m, 3H), 4.50-4.38 (m, 2H), 4.11 (dd, 2H), 3.60 (br. s, 1H), 2.11-2.01 (m, 1H), 1.91-1.80 (m, 1H), 1.79-1.62 (m, 2H), 1.58-1.48 (m, 1H), 1.47-1.38 (m, 1H), 1.37-1.22 (m, 1H), 1.17-1.04 (m, 1H). |
| 152 | 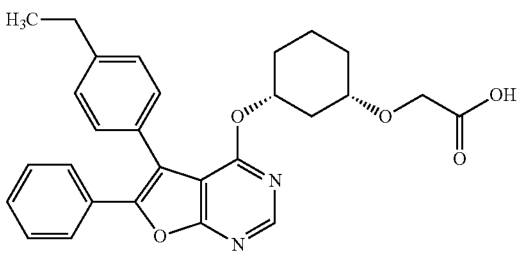 | LC-MS (Method 3): $R_t$ = 2.90 min; m/z = 473 (M + H)$^+$<br>$^1$H-NMR (400 MHz, DMSO-d$_6$):<br>δ = 12.51 (s, 1H), 8.60 (s, 1H), 7.58-7.51 (m, 2H), 7.43-7.35 (m, 5H), 7.29 (d, 2H), 5.18-5.09 (m, 1H), 4.01 (s, 2H), 3.15-3.08 (m, 1H), 2.74-2.65 (m, 3H), 2.05-1.92 (m, 2H), 1.79-1.69 (m, 1H), 1.24 (t, 3H), 1.20-1.00 (m, 4H). |
| 153 | 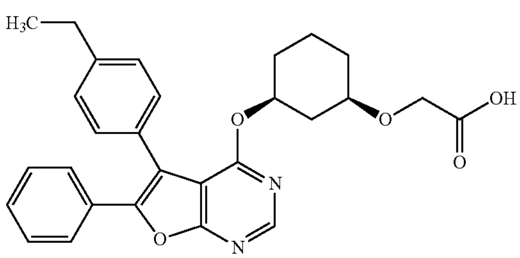 | LC-MS (Method 3): $R_t$ = 2.89 min; m/z = 473 (M + H)$^+$<br>$^1$H-NMR (400 MHz, DMSO-d$_6$):<br>δ = 12.51 (s, 1H), 8.60 (s, 1H), 7.59-7.51 (m, 2H), 7.43-7.36 (m, 5H), 7.29 (d, 2H), 5.18-5.08 (m, 1H), 4.01 (s, 2H), 3.49-3.39 (m, 1H), 2.70 (q, 2H), 2.05-1.91 (m, 2H), 1.79-1.69 (m, 1H), 1.24 (t, 3H), 1.20-1.00 (m, 5H). |
| 154 | (−)-Enantiomer | LC-MS (Method 6): $R_t$ = 1.99 min; m/z = 486 (M + H)$^+$<br>$^1$H-NMR (400 MHz, DMSO-d$_6$):<br>δ = 8.60 (s, 1H), 7.59-7.51 (m, 2H), 7.43-7.38 (m, 5H), 7.28 (d, 2H), 5.25-5.18 (m, 1H), 3.63-3.59 (m, 1H), 2.80 (d, 1H), 2.70 (q, 2H), 2.25-2.18 (m, 2H), 2.14-2.02 (m, 2H), 1.92-1.72 (m, 4H), 1.61-1.49 (m, 3H), 1.48-1.35 (m, 2H), 1.25 (t, 3H). |

| Example | Structure | Analytical data |
|---|---|---|
| 155 | (+)-Enantiomer | LC-MS (Method 8): $R_t$ = 1.87 min; m/z = 486 (M + H)$^+$<br>$^1$H-NMR (400 MHz, DMSO-d$_6$):<br>δ = 8.60 (s, 1H), 7.59-7.51 (m, 2H), 7.43-7.38 (m, 5H), 7.28 (d, 2H), 5.25-5.18 (m, 1H), 3.63-3.59 (m, 1H), 2.80 (d, 1H), 2.70 (q, 2H), 2.25-2.18 (m, 2H), 2.14-2.02 (m, 2H), 1.92-1.72 (m, 4H), 1.61-1.49 (m, 3H), 1.48-1.35 (m, 2H), 1.25 (t, 3H). |
| 156 | 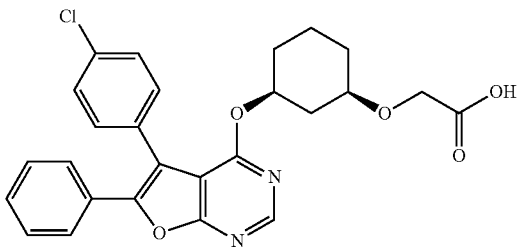 | LC-MS (Method 3): $R_t$ = 2.78 min; m/z = 479 (M + H)$^+$<br>$^1$H-NMR (400 MHz, DMSO-d$_6$):<br>δ = 8.60 (s, 1H), 7.55-7.49 (m, 6H), 7.56-7.39 (m, 3H), 5.15-5.04 (m, 1H), 3.55 (s, 2H), 2.14 (d, 1H), 2.02-1.90 (m, 2H), 1.75-1.67 (m, 1H), 1.30-1.15 (m, 4H), 1.14-0.95 (m, 2H). |
| 157 | 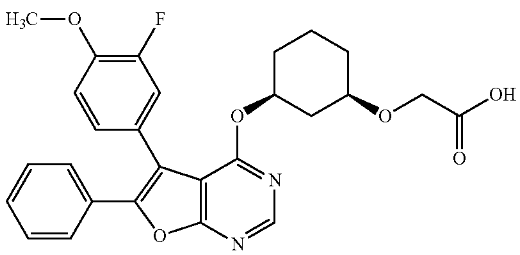 | LC-MS (Method 8): $R_t$ = 3.19 min; m/z = 491 (M + H)$^+$. |
| 158 | Enantiomer 1 | LC-MS (Method 3): $R_t$ = 1.68 min; m/z = 506 (M + H)$^+$<br>$^1$H-NMR (400 MHz, DMSO-d$_6$):<br>δ = 8.60 (s, 1H), 7.71-7.68 (m, 1H), 7.66-7.60 (m, 1H), 7.59-7.51 (m, 1H), 7.50-7.35 (m, 4H), 7.23-7.17 (m, 1H), 5.95-5.86 (m, 1H), 5.32-5.21 (m, 1H), 4.70-4.67 (m, 1H), 3.90 (s, 2H), 2.86-2.78 (m, 1H), 2.30-2.07 (m, 3H), 2.00 (s, 1H), 1.95-1.86 (m, 1H), 1.65-1.51 (m, 2H), 1.50-1.40 (m, 1H), 1.40-1.29 (m, 2H). |
| 159 | Enantiomer 1 | LC-MS (Method 8): $R_t$ = 1.88 min; m/z = 504 (M + H)$^+$<br>$^1$H-NMR (400 MHz, CDCl$_3$):<br>δ = 8.51 (s, 1H), 7.65-7.59 (m, 2H), 7.36-7.31 (m, 3H), 7.30-7.18 (m, 3H), 5.40-5.31 (m, 1H), 3.12 (br. s, 1H), 2.86-2.73 (m, 1H), 2.77 (q, 2H), 2.68-2.53 (m, 3H), 2.47 (br. s, 1H), 2.09 (br. s, 1H), 1.83-1.68 (m, 4H), 1.51-1.40 (m, 2H), 1.30 (t, 3H), 1.25 (s, 1H), 0.90-0.81 (m, 1H). |

| Example | Structure | Analytical data |
|---|---|---|
| 160 | 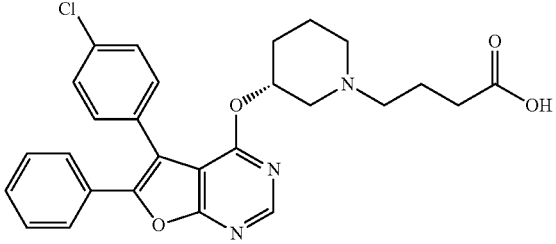<br>Enantiomer 1 | LC-MS (Method 8): $R_t$ = 1.81 min; m/z = 492 (M + H)$^+$<br>$^1$H-NMR (400 MHz, CDCl$_3$): δ = 8.54 (s, 1H), 7.61-7.53 (m, 2H), 7.48 (d, 2H), 7.40 (d, 2H), 7.37-7.30 (m, 3H), 5.41-5.32 (m, 1H), 3.08 (br. s, 1H), 2.76 (br. s, 1H), 2.70-2.48 (m, 6H), 2.01 (br. s, 1H), 1.85-1.68 (m, 4H), 1.46 (br. s, 1H), 1.26 (s, 1H). |
| 161 | 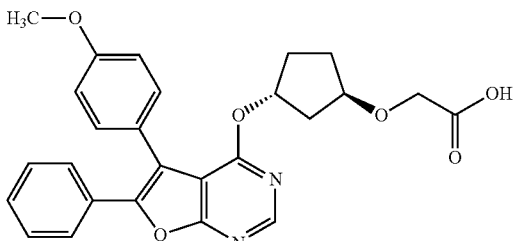 | LC-MS (Method 8): $R_t$ = 2.74 min; m/z = 461 (M + H)$^+$<br>$^1$H-NMR (400 MHz, DMSO-d$_6$): δ = 8.59 (s, 1H), 7.59-7.51 (m, 2H), 7.44-7.32 (m, 5H), 7.05-6.98 (m, 2H), 5.62-5.55 (m, 1H), 4.11 (s, 1H), 3.71 (d, 2H), 2.14 (d, 1H), 2.05-1.55 (m, 2H). |
| 162 | 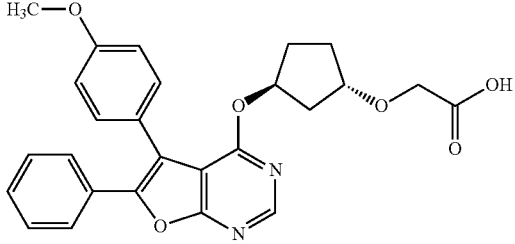 | LC-MS (Method 8): $R_t$ = 2.71 min; m/z = 461 (M + H)$^+$<br>$^1$H-NMR (400 MHz, CDCl$_3$): δ = 8.50 (s, 1H), 7.67-7.60 (m, 2H), 7.40-7.33 (m, 2H), 7.32-7.28 (m, 3H), 6.99-6.81 (m, 2H), 5.72-5.65 (m, 2H), 5.31 (s, 2H), 4.16 (br. s, 1H), 3.90 (s, 3H), 2.40-2.21 (m, 2H), 2.21-2.10 (m, 1H), 2.06-1.98 (m, 1H), 1.88-1.63 (m, 2H). |
| 163 | 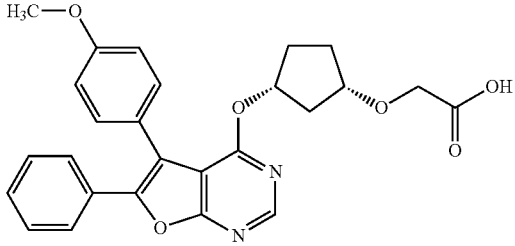 | LC-MS (Method 8): $R_t$ = 2.72 min; m/z = 461 (M + H)$^+$<br>$^1$H-NMR (400 MHz, DMSO-d$_6$): δ = 8.58 (s, 1H), 7.59-7.51 (m, 2H), 7.45-7.33 (m, 5H), 7.04-6.95 (m, 2H), 5.45-5.38 (m, 1H), 4.06-3.96 (m, 2H), 3.82 (s, 3H), 3.62 (s, 1H), 2.15 (d, 1H), 1.79-1.60 (m, 2H), 1.28 (s, 4H). |
| 164 | 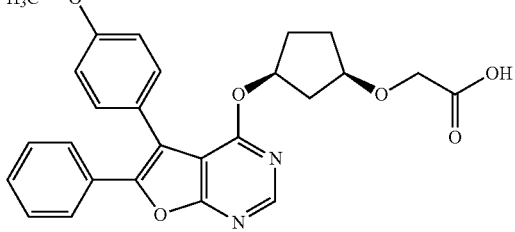 | LC-MS (Method 3): $R_t$ = 2.45 min; m/z = 461 (M + H)$^+$<br>$^1$H-NMR (400 MHz, DMSO-d$_6$): δ = 8.59 (s, 1H), 7.59-7.52 (m, 2H), 7.46-7.35 (m, 5H), 7.00 (d, 2H), 5.48-5.40 (m, 1H), 4.04-3.97 (m, 1H), 3.91 (s, 2H), 3.82 (s, 2H), 2.39-2.28 (m, 2H), 1.98-1.89 (m, 2H), 1.84-1.76 (m, 1H), 1.75-1.62 (m, 3H). |
| 165 | 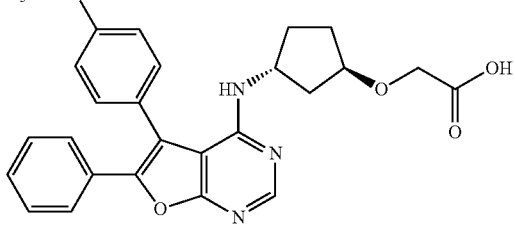<br>(+/−)-trans | LC-MS (Method 3): $R_t$ = 2.27 min; m/z = 460 (M + H)$^+$<br>$^1$H-NMR (400 MHz, CDCl$_3$): δ = 8.42 (s, 1H), 7.55 (d, 2H), 7.40 (d, 2H), 7.31-7.26 (m, 3H), 7.08 (d, 2H), 4.66 (d, 1H), 4.61-4.53 (m, 1H), 4.10-4.00 (m, 3H), 3.91 (s, 3H), 2.29-2.17 (m, 2H), 1.95-1.85 (m, 1H), 1.81-1.71 (m, 1H), 1.50-1.41 (m, 1H), 1.30-1.18 (m, 2H). |

-continued

| Example | Structure | Analytical data |
|---|---|---|
| 166 | 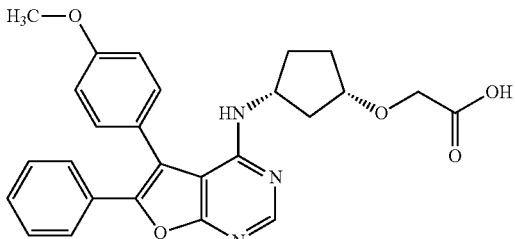<br>(+/−)-cis | LC-MS (Method 3): R$_t$ = 2.25 min; m/z = 460 (M + H)$^+$<br>$^1$H-NMR (400 MHz, DMSO-d$_6$): δ = 8.41 (s, 1H), 7.52 (d, 2H), 7.39 (d, 2H), 7.30-7.24 (m, 3H), 7.05 (d, 2H), 5.07 (d, 1H), 4.69-4.60 (m, 1H), 4.09-4.03 (m, 1H), 3.90 (s, 3H), 3.88 (d, 2H), 2.20-2.04 (m, 2H), 1.81-1.74 (m, 2H), 1.62-1.48 (m, 3H). |
| 167 | 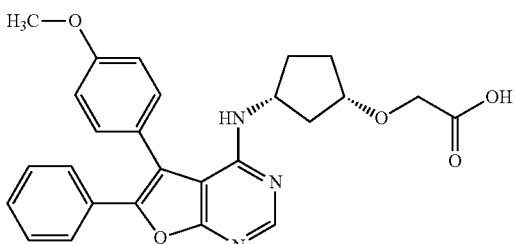<br>(−)-Enantiomer | LC-MS (Method 6): R$_t$ = 2.42 min; m/z = 460 (M + H)$^+$<br>$^1$H-NMR (400 MHz, DMSO-d$_6$): δ = 12.62 (br. s, 1H), 8.32 (s, 1H), 7.48-7.40 (m, 4H), 7.39-7.29 (m, 3H), 7.11 (d, 2H), 5.31 (d, 1H), 4.61-4.52 (m, 1H), 4.00-3.94 (m, 1H), 3.83 (s, 3H), 3.69 (s, 2H), 2.00-1.88 (m, 2H), 1.70-1.61 (m, 2H), 1.54-1.35 (m, 2H). |
| 168 | 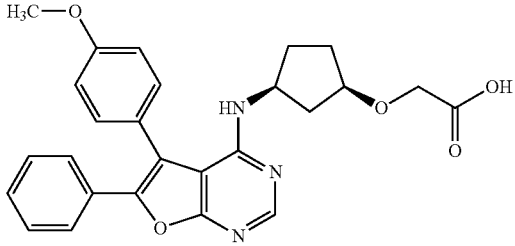<br>(+)-Enantiomer | LC-MS (Method 6): R$_t$ = 2.42 min; m/z = 460 (M + H)$^+$<br>$^1$H-NMR (400 MHz, DMSO-d$_6$): δ = 12.62 (br. s, 1H), 8.32 (s, 1H), 7.48-7.40 (m, 4H), 7.39-7.29 (m, 3H), 7.11 (d, 2H), 5.31 (d, 1H), 4.61-4.52 (m, 1H), 4.00-3.94 (m, 1H), 3.83 (s, 3H), 3.69 (s, 2H), 2.00-1.88 (m, 2H), 1.70-1.61 (m, 2H), 1.54-1.35 (m, 2H). |
| 169 | 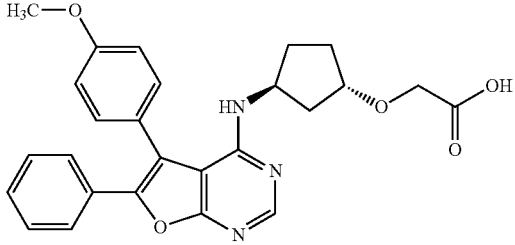<br>(+)-Enantiomer | LC-MS (Method 8): R$_t$ = 2.55 min; m/z = 460 (M + H)$^+$<br>$^1$H-NMR (400 MHz, DMSO-d$_6$): δ = 12.60 (br. s, 1H), 8.38 (s, 1H), 7.51-7.45 (m, 4H), 7.40-7.30 (m, 3H), 7.27 (d, 2H), 4.81 (d, 1H), 4.52-3.90 (m, 1H), 3.98-3.90 (m, 3H), 3.88 (s, 3H), 2.09-1.99 (m, 2H), 1.82-1.71 (m, 1H), 1.67-1.55 (m, 1H), 1.45-1.35 (m, 1H), 1.21-1.11 (m, 1H). |
| 170 | 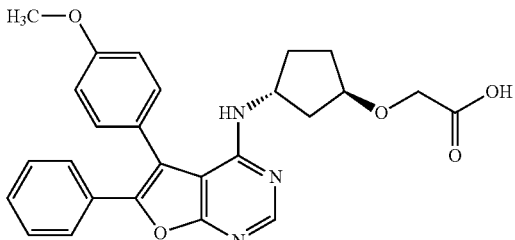<br>(−)-Enantiomer | LC-MS (Method 8): R$_t$ = 2.55 min; m/z = 460 (M + H)$^+$<br>$^1$H-NMR (400 MHz, DMSO-d$_6$): δ = 12.60 (br. s, 1H), 8.38 (s, 1H), 7.51-7.45 (m, 4H), 7.40-7.30 (m, 3H), 7.27 (d, 2H), 4.81(d, 1H), 4.52-3.90 (m, 1H), 3.98-3.90 (m, 3H), 3.88 (s, 3H), 2.09-1.99 (m, 2H), 1.82-1.71 (m, 1H), 1.67-1.55 (m, 1H), 1.45-1.35 (m, 1H), 1.21-1.11 (m, 1H). |

| Example | Structure | Analytical data |
|---|---|---|
| 171 | (+/−)-cis | LC-MS (Method 3): $R_t$ = 2.66 min; m/z = 457 (M + H)$^+$<br>$^1$H-NMR (400 MHz, DMSO-d$_6$):<br>δ = 12.65 (s, 1H), 8.62 (s, 1H), 7.56 (d, 2H), 7.48-7.31 (m, 5H), 7.28 (d, 2H), 6.14 (dd, 2H), 5.89-5.80 (m, 1H), 4.55-4.50 (m, 1H), 3.97 (s, 2H), 2.83 (q, 2H), 1.96-1.88 (m, 1H), 1.53 (td, 1H), 1.22 (t, 3H). |
| 172 | (−)-Enantiomer | LC-MS (Method 8): $R_t$ = 2.92 min; m/z = 457 (M + H)$^+$<br>$^1$H-NMR (400 MHz, DMSO-d$_6$):<br>δ = 8.60 (s, 1H), 7.54 (d, 2H), 7.43-7.38 (m, 5H), 7.28 (d, 2H), 6.20 (d, 1H), 6.00 (d, 1H), 5.82-5.78 (m, 1H), 4.59-4.51 (m, 1H), 3.51 (d, 2H), 2.82-2.71 (m, 1H), 2.69 (q, 2H), 1.52-1.44 (m, 1H), 1.22 (t, 3H), 1.06 (t, 1H). |
| 173 | (−)-Enantiomer | LC-MS (Method 3): $R_t$ = 2.72 min; m/z = 459 (M + H)$^+$<br>$^1$H-NMR (400 MHz, DMSO-d$_6$):<br>δ = 8.59 (s, 1H), 7.55 (d, 2H), 7.45-7.36 (m, 5H), 7.29 (d, 2H), 5.46-5.39 (m, 1H), 4.03-3.96 (m, 1H), 3.50 (d, 2H), 2.70 (q, 2H), 2.38-2.25 (m, 1H), 2.22-2.12 (m, 1H), 1.95-1.74 (m, 2H), 1.71-1.58 (m, 3H), 1.25 (t, 3H). |
| 174 | (+)-Enantiomer | $^1$H-NMR (400 MHz, DMSO-d$_6$):<br>δ = 12.55 (s, 1H), 8.59 (s, 1H), 7.55 (d, 2H), 7.45-7.36 (m, 5H), 7.29 (d, 2H), 5.46-5.39 (m, 1H), 4.03-3.96 (m, 1H), 3.88 (d, 2H), 2.70 (q, 2H), 2.38-2.25 (m, 1H), 1.95-1.74 (m, 2H), 1.71-1.58 (m, 3H), 1.25 (t, 3H). |
| 175 | (−)-Enantiomer | LC-MS (Method 8): $R_t$ = 3.13 min; m/z = 457 (M + H)$^+$<br>$^1$H-NMR (400 MHz, DMSO-d$_6$):<br>δ = 12.65 (s, 1H), 8.61 (s, 1H), 7.60-7.52 (m, 2H), 7.47-7.30 (m, 5H), 7.27 (d, 2H), 6.28 (d, 1H), 6.15 (d, 1H), 6.11 (d, 1H), 4.70-4.63 (m, 1H), 4.02 (s, 2H), 2.70 (q, 2H), 2.20-2.10 (m, 1H), 2.05-1.98 (m, 1H), 1.24 (t, 3H). |

| Example | Structure | Analytical data |
|---|---|---|
| 176 | 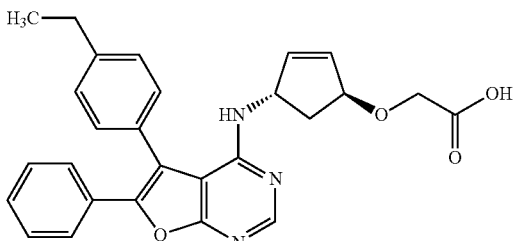<br>(−)-Enantiomer | LC-MS (Method 12): $R_t$ = 2.66 min; m/z = 456 (M + H)$^+$<br>$^1$H-NMR (400 MHz, DMSO-d$_6$):<br>δ = 12.60 (s, 1H), 8.39 (s, 1H), 7.50 (d, 2H), 7.47-7.30 (m, 7H), 6.06 (d, 1H), 5.90 (d, 1H), 5.22-5.16 (m, 1H), 4.65 (d, 1H), 4.60-4.54 (m, 1H), 4.00 (s, 2H), 2.71 (q, 2H), 2.20-2.11 (m, 1H), 1.67-1.58 (m, 1H), 1.23 (t, 3H). |

Example 177

[(3-{[5-(4-Ethylphenyl)-6-(2-fluorophenyl)furo[2,3-d]pyrimidin-4-yl]oxy}cyclohexyl)oxy]acetic acid tert-butyl ester (rac. diastereomer mixture)

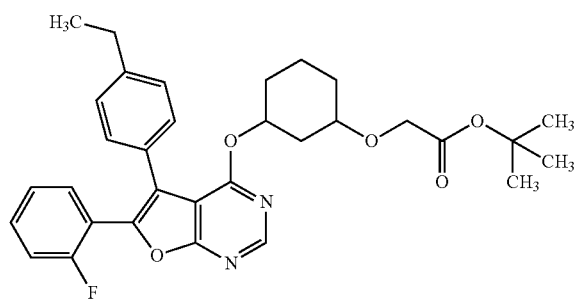

1.4 ml of an 11.25N sodium hydroxide solution is added at 70° C. to a solution of 700 mg (1.62 mmol) of 3-{[5-(4-ethylphenyl)-6-(2-fluorophenyl)furo[2,3-d]pyrimidin-4-yl]oxy}cyclohexanol in 15 ml of toluene. After adding 55 mg (0.16 mmol) of tetra-n-butylammonium hydrogensulphate and 631 mg (3.24 mmol) of bromoacetic acid tert-butyl ester, stir the reaction mixture at 70° C. for 30 hours. Then add a further 330 mg (1.69 mmol) of bromoacetic acid tert-butyl ester to the reaction mixture and stir at 70° C. for another 14 hours. After cooling to room temperature, adjust to pH 7 with conc. hydrochloric acid. Extract with dichloromethane. Wash the organic phase with satd. sodium chloride solution, dry over sodium sulphate, filter and concentrate under reduced pressure. Purify the residue by means of preparative RP-HPLC (eluent:water/acetonitrile gradient). 632 mg (69% of theory) of the desired product are obtained as a racemic diastereomer mixture.

LC-MS (Method 8): $R_t$=3.47 min; m/z=547 (M+H)$^+$ $^1$H-NMR (400 MHz, DMSO-d$_6$): [minor stereoisomer in brackets] δ=8.62 (s, 1H), 7.57-7.50 (m, 2H), 7.34-7.28 (m, 4H), 7.21-7.19 (m, 2H), [5.69-5.64, m, 1H], 5.23-5.16 (m, 1H), 3.99 (m, 2H), [3.89, d, 2H], 3.47-3.40 (m, 1H), 2.64 (q, 2H), 2.46-2.42 (m, 1H), 2.09-2.95 (m, 1H), 1.99-1.93 (m, 1H), 1.78-1.73 (m, 1H), 1.41 (s, 9H), 1.30-1.12 (m, 4H), 1.20 (t, 3H).

Example 178

[(3-{[5-(4-Ethylphenyl)-6-(2-fluorophenyl)furo[2,3-d]pyrimidin-4-yl]oxy}cyclohexyl)oxy]acetic acid tert-butyl ester (cis-enantiomer 1)

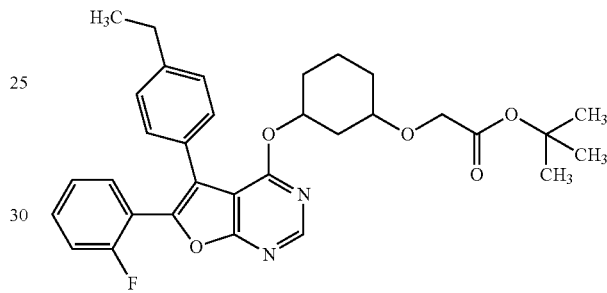

Proceeding from 600 mg. (1.10 mmol) of [(3-{[5-(4-ethylphenyl)-6-(2-fluorophenyl)furo[2,3-d]-pyrimidin-4-yl]oxy}cyclohexyl)oxy]acetic acid tert-butyl ester (rac. diastereomer mixture), after chromatographic enantiomer separation on chiral phase, 236 mg (39% of theory) of the pure cis-enantiomer 1 are obtained [column: Daicel Chiralpak AD-H, 5 μm, 250 mm×20 mm; flow rate: 15 ml/min; detection: 220 nm; temperature: 30° C.; eluent: 93% isohexane/7% ethanol].

HPLC [column: Daicel Chiralpak AD-H, 5 μm, 250 mm×4.6 mm; flow rate: 1 ml/min; detection: 215 nm; temperature: 35° C.; eluent: 93% isohexane/7% ethanol]: $R_t$=6.64 min.

$^1$H-NMR (400 MHz, DMSO-d$_6$): δ=8.62 (s, 1H), 7.56-7.52 (m, 2H), 7.34-7.28 (m, 4H), 7.21-7.19 (m, 2H), 5.23-5.16 (m, 1H), 3.98 (d, 2H), 3.47-3.40 (m, 1H), 2.64 (q, 2H), 2.48-2.44 (m, 1H), 2.09-2.05 (m, 1H), 1.98-1.94 (m, 1H), 1.78-1.73 (m, 1H), 1.41 (s, 9H), 1.30-1.10 (m, 4),1.209t, 3H).

Example 179

[(3-{[5-(4-Ethylphenyl)-6-(2-fluorophenyl)furo[2,3-d]pyrimidin-4-yl]oxy}cyclohexyl)oxy]acetic acid tert-butyl ester (cis-enantiomer 2)

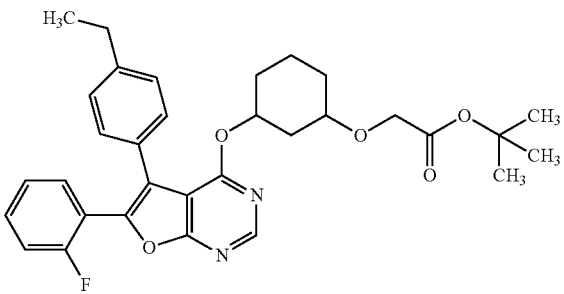

Proceeding from 600 mg (1.10 mmol) of [(3-{[5-(4-ethylphenyl)-6-(2-fluorophenyl)furo[2,3-d]-pyrimidin-4-yl]oxy}cyclohexyl)oxy]acetic acid tert-butyl ester (rac. diastereomer mixture), after chromatographic enantiomer separation on chiral phase, 263 mg (43% of theory) of the pure cis-enantiomer 2 are obtained [column: Daicel Chiralpak AD-H, 5 μm, 250 mm×20 mm; flow rate: 15 ml/min; detection: 220 nm; temperature: 30° C.; eluent: 93% isohexane/7% ethanol]

HPLC [column: Daicel Chiralpak AD-H, 5 μm, 250 mm×4.6 mm; flow rate: 1 ml/min; detection: 215 nm; temperature: 35° C.; eluent: 93% isohexane/7% ethanol]: $R_t$=8.06 min.

$^1$H-NMR (400 MHz, DMSO-$d_6$): δ=8.62 (s, 1H), 7.56-7.52 (m, 2H), 7.34-7.28 (m, 4H), 7.21-7.19 (m, 2H), 5.23-5.16 (m, 1H), 3.98 (d, 2H), 3.47-3.40 (m, 1H), 2.64 (q, 2H), 2.48-2.44 (m, 1H), 2.09-2.05 (m, 1H), 1.98-1.94 (m, 1H), 1.78-1.73 (m, 1H), 1.41 (s, 9H), 1.30-1.10 (m, 4H), 1.20 (t, 3H).

Example 180

4-[(3R)-3-{[5-(4-Ethylphenyl)-6-(2-fluorophenyl)furo[2,3-d]pyrimidin-4-yl]oxy}piperidin-1-yl]-butyric acid methyl ester

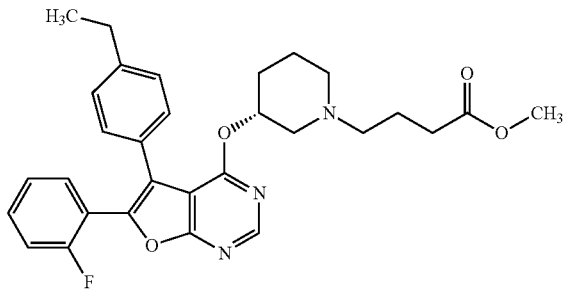

Add 1677 mg (12.1 mmol) of potassium carbonate to a solution of 2250 mg (4.9 mmol) of 5-(4-ethylphenyl)-6-(2-fluorophenyl)-4-[(3R)-piperidin-3-yloxy]furo[2,3-d]pyrimidine in 100 ml of THF and 10 ml of acetonitrile. Then add 0.74 ml (1054 mg, 5.8 mmol) of 4-brombutyric acid methyl ester and 72 mg (0.19 mmol) of tetra-n-butylammonium iodide. Stir the reaction mixture at 80° C. for 13 hours. After cooling to room temperature, filter off the residue, wash with THF, concentrate the filtrate under reduced pressure and purify the residue by column chromatography on silica gel (eluent: cyclohexane/ethyl acetate 1:2). 2005 mg (75% of theory) of the target compound are obtained.

LC-MS (Method 12): $R_t$=1.82 min; m/z=518 (M+H)$^+$ $^1$H-NMR (300 MHz, DMSO-$d_6$): δ=8.63 (s, 1H), 7.56-7.53 (m, 2H), 7.35-7.28 (m, 4H), 7.18 (d, 2H), 5.33-5.31 (m, 1H), 3.52 (s, 3H), 2.78-2.75 (m, 1H), 2.64 (q, 2H), 2.44-2.40 (m, 1H), 2.36-2.23(m, 6H), 1.93-1.89 (m, 1H), 1.67-1.59 (m, 3H), 1.44-1.42 (m, 2H), 1.19 (t, 3H).

Example 181

4-[(3R)-3-{[5-(4-Ethylphenyl)-6-(2-fluorophenyl)furo[2,3-d]pyrimidin-4-yl]oxy}piperidin-1-yl]-butyric acid

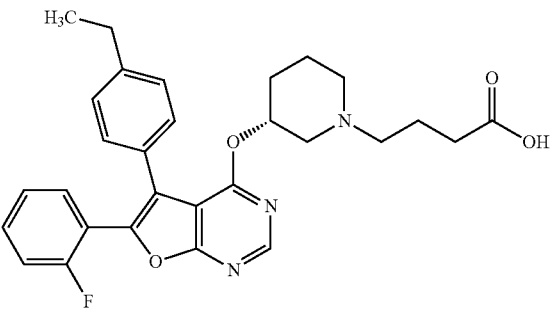

Dissolve 500 mg (0.97 mmol) of 4-[(3R)-3-{[5-(4-ethylphenyl)-6-phenylfuro[2,3-d]pyrimidin-4-yl]oxy}piperidin-1-yl]butyric acid methyl ester in 10 ml of dioxane and add 2.9 ml of 1N sodium hydroxide solution. Stir at room temperature for 16 hours. Then add 2.9 ml of 1N hydrochloric acid and extract the mixture with 20 ml of ethyl acetate. Remove the organic phase, dry over sodium sulphate, filter and concentrate. Purify the residue by preparative RP-HPLC (eluent: water/acetonitrile gradient with 0.1% formic acid). Take up the resulting product in 10 ml of ethyl acetate and wash twice with 10 ml each time of a 1 M aqueous sodium hydrogencarbonate solution. Remove the organic phase, dry over sodium sulphate, filter and concentrate. 309 mg (62% of theory) of the target compound are obtained.

LC-MS (Method 3): $R_t$=1.74 min; m/z=504 (M+H)$^+$ $^1$H-NMR (400 MHz, DMSO-$d_6$): δ=12.12 (s, 1H), 8.62 (s, 1H), 7.56-7.51 (m, 2H), 7.36-7.27 (m, 4H), 7.18 (d, 2H), 5.32 (t, 1H), 2.83-2.80 (m, 1H), 2.63 (q, 2H), 2.49-2.47 (m, 1H), 2.33-2.25 (m, 4H), 2.19 (t, 2H), 1.94-1.91 (m, 1H), 1.65-1.57 (m, 3H), 1.43-1.39 (m, 2H), 1.19 (t, 3H).

Example 182

4-[(3R)-3-{[5-(4-Ethylphenyl)-6-(2-fluorophenyl)furo[2,3-d]pyrimidin-4-yl]oxy}piperidin-1-yl]-butyric acid formate

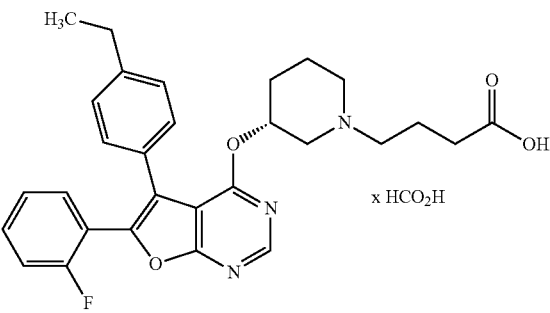

Dissolve 500 mg (0.97 mmol) of 4-[(3R)-3-{[5-(4-ethylphenyl)-6-phenylfuro[2,3-d]pyrimidin-4-yl]oxy}piperidin-1-yl]butyric acid methyl ester in 10 ml of dioxane and add 2.9 ml of 1N sodium hydroxide solution. Stir at room temperature for 16 hours. Then add 2.9 ml of 1N hydrochloric acid, and extract the mixture with 20 ml of ethyl acetate. Remove the organic phase, dry over sodium sulphate, filter and concentrate. Purify the residue by preparative RP-HPLC (eluent: water/acetonitrile gradient with 0.1% formic acid). 411 mg (77% of theory) of the target compound are obtained.

LC-MS (Method 8): $R_t$=1.88 min; m/z=504 (M-HCO$_2$H+H)$^+$ $^1$H-NMR (400 MHz, DMSO-d$_6$): δ=8.62 (s, 1H), 8.14 (s, 1H), 7.56-7.51 (m, 2H), 7.36-7.29 (m, 4H), 7.19 (d, 2H), 5.33 (t, 1H), 2.83-2.80 (m, 1H), 2.63 (q, 2H), 2.49-2.47 (m, 1H), 2.33-2.25 (m, 4H), 2.19 (t, 2H), 1.94-1.91 (m, 1H), 1.66-1.58 (m, 3H), 1.48-1.34 (m, 2H), 1.19 (t, 3H).

Example 183

4-[(3R)-3-{[6-(2-Fluorophenyl)-5-(4-methoxyphenyl)furo[2,3-d]pyrimidin-4-yl]oxy}piperidin-1-yl]butyric acid methyl ester

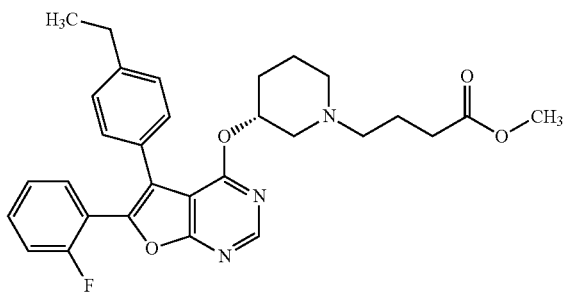

411 mg (3.0 mmol) of potassium carbonate are added to a suspension of 500 mg (1.2 mmol) of 6-(2-fluorophenyl)-5-(4-methoxyphenyl)-4-[(3R)-piperidin-3-yloxy]furo[2,3-d]pyrimidine in 10 ml of THF. Then add 0.18 ml (259 mg, 1.4 mmol) of 4-bromobutyric acid methyl ester and 17 mg (0.05 mmol) of tetra-n-butylammonium iodide. Stir the reaction mixture at 80° C. for 13 hours. Then add 10 ml of DMF and again stir the mixture at 70° C. for 13 hours. After adding 10 ml each of water, 1N hydrochloric acid and ethyl acetate, remove the organic phase, concentrate under reduced pressure and purify the residue by means of preparative RP-HPLC eluent: water/acetonitrile gradient). 146 mg (22% of theory) of the target compound are obtained.

LC-MS (Method 13): $R_t$=2.77 min; m/z=520 (M+H)$^+$ $^1$H-NMR (400 MHz, DMSO-d$_6$): δ=8.61 (s, 1H), 7.56-7.52 (m, 2H), 7.35 (d, 2H), 7.32-7.28 (m, 2H), 6.90 (d, 2H), 5.34-5.31 (m, 1H), 3.76 (s, 1H), 3.53 (s, 3H), 2.81-2.79 (m, 1H), 2.48-2.42 (m, 1H), 2.32-2.18 (m, 6H), 2.00-1.92 (m, 1H), 1.67-1.60 (m, 3H), 1.45-1.41 (m, 2H).

Example 184

4-[(3R)-3-{[6-(2-Fluorophenyl)-5-(4-methoxyphenyl)furo[2,3-d]pyrimidin-4-yl]oxy}piperiridin-1-yl]butyric acid methyl ester formate

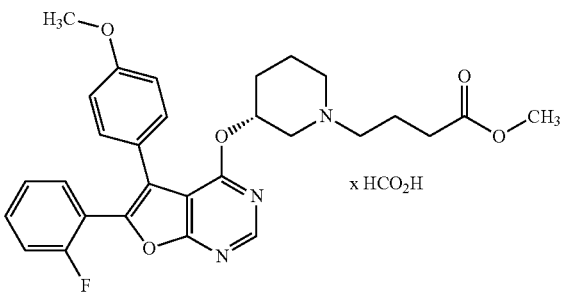

Add 52 mg (0.38 mmol) of potassium carbonate to a solution of 70 mg (0.15 mmol) of 6-(2-fluoro-phenyl)-5-(4-methoxyphenyl)-4-[(3R)-piperidin-3-yloxy]furo[2,3-d]pyrimidine formate in 1 ml of THF. Then add 0.02 ml (33 mg, 0.18 mmol) of 4-bromobutyric acid methyl ester and 2 mg (0.01 mmol) of tetra-n-butylammonium iodide. Stir the reaction mixture at 80° C. for 13 hours. After cooling to room temperature, concentrate under reduced pressure and purify the residue by means of preparative RP-HPLC (eluent:water/acetonitrile gradient with 0.1% formic acid). 40 mg (42% of theory) of the target compound are obtained.

LC-MS (Method 3): $R_t$=1.75 min; m/z=520 (M+H)$^+$ $^1$H-NMR (300 MHz, DMSO-d$_6$): δ=8.62 (s, 1H), 8.15 (s, 1H), 7.53-7.51 (m, 2H), 7.35 (d, 2H), 7.32-7.28 (m, 2H), 6.90 (d, 2H), 5.5-5.30 (m, 1H), 3.76 (s, 3H), 3.52 (s, 3H), 2.82-2.79 (m, 1H), 2.36-2.24 (m, 5H), 1.94-1.88 (m, 1H), 1.67-1.60 (m, 2H), 1.45-1.41 (m, 2H).

Example 185

4-[(3R)-3-{[6-(2-Fluorophenyl)-5-(4-methoxyphenyl)furo[2,3-d]pyrimidin-4-yl]oxy}piperidin-1-yl]butyric acid

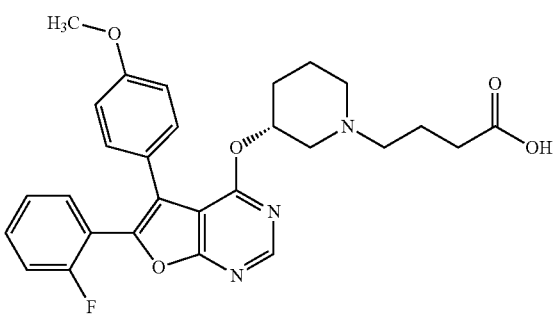

Dissolve 113 mg (0.20 mmol) of 4-[(3R)-3-{[6-(2-fluorophenyl)-5-(4-methoxyphenyl)furo[2,3-d]-pyrimidin-4-yl]oxy}piperidin-1-yl]butyric acid methyl ester in 3 ml of dioxane and add 0.8 ml of a 1 N sodium hydroxide solution. Stir at room temperature for 16 hours, then add 0.8 ml of 1 N hydrochloric acid and 10 ml of ethyl acetate. Remove the organic phase, dry over sodium sulphate, filter and concentrate. 95 mg (90% of theory) of the target compound are obtained.

LC-MS (Method 8): $R_t$=1.70 min; m/z=504 (M+H)$^+$ $^1$H-NMR (400 MHz, DMSO-$d_6$): δ=12.20 (br. s, 1H), 8.63 (s, 1H), 7.56-7.51 (m, 2H), 7.37-7.29 (m, 4H), 6.91 (d, 2H), 5.35 (t, 1H), 3.76 (s, 1H), 2.99-2.94 (m, 1H), 2.64-2.62 (m, 1H), 2.40-2.32 (m, 4H), 2.20 (t, 2H), 2.02-1.98 (m, 1H), 1.67-1.63 (m, 3H), 1.43-1.39 (m, 2H).

Example 186

[(1S,3R)-3-{[5-(4-Ethylphenyl)-6-(2-fluorophenyl) furo[2,3-d]pyrimidin-4-yl]oxy}cyclohexyl]-oxy}acetic acid

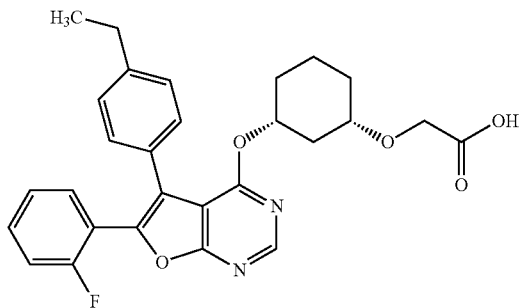

Add 10 ml of 4N hydrogen chloride in dioxane to 237 mg (0.43 mmol) of {[(1S,3R)-3-{[5-(4-ethyl-phenyl)-6-(2-fluorophenyl)furo[2,3-d]pyrimidin-4-yl]oxy}cyclohexyl] oxy}acetic acid tert-butyl ester and stir at room temperature for 16 hours. After removing the solvent under reduced pressure, purify the residue by means of preparative RP-HPLC (eluent:water/acetonitrile gradient). 132 mg (62% of theory) of the target compound are obtained.

LC-MS (Method 8): $R_t$=3.10 min; m/z=491 (M+H)$^+$ $^1$H-NMR (400 MHz, DMSO-$d_6$): δ=12.54 (s, 1H), 8.63 (s, 1H), 7.56-7.52 (m, 2H), 7.34-7.28 (m, 4H), 7.20 (d, 2H), 5.22-5.16 (m, 1H), 4.03 (s, 2H), 3.48-3.43 (m, 1H), 2.63 (q, 2H), 2.12-2.06 (m, 1H), 2.00-1.96 (m, 1H), 1.77-1.73 (m, 1H), 1.29-1.08 (m, 4H), 1.19 (t, 3H).

$[α]_D^{20}$=+62°, c=0.525, CHCl$_3$.

Example 187

{[(1R,3S)-3-{[5-(4-Ethylphenyl)-6-(2-fluorophenyl) furo[2,3-d]pyrimidin-4-yl]oxy}cyclohexyl]-oxy}acetic acid

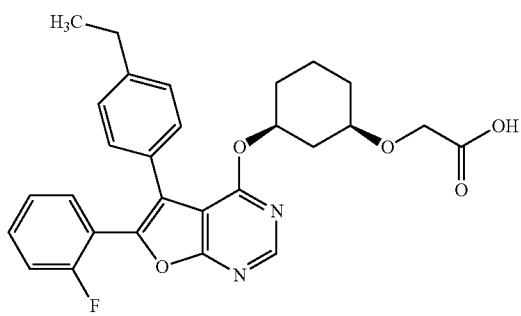

Add 10 ml of 4N hydrogen chloride in dioxane to 215 mg (0.39 mmol) of {[(1R,3S)-3-{[5-(4-ethyl-phenyl)-6-(2-fluorophenyl)furo[2,3-d]pyrimidin-4-yl]oxy}cyclohexyl] oxy}acetic acid tert-butyl ester and stir at room temperature for 16 hours. After removing the solvent under reduced pressure, purify the residue by means of preparative RP-HPLC (eluent:water/acetonitrile gradient). 128 mg (66% of theory) of the target compound are obtained.

LC-MS (Method 8): $R_t$=3.11 min; m/z=491 (M+H)$^+$ $^1$H-NMR (300 MHz, DMSO-$d_6$): δ=12.54 (s, 1H), 8.63 (s, 1H), 7.56-7.52 (m, 2H), 7.34-7.28 (m, 4H), 7.20 (d, 2H), 5.22-5.16 (m, 1H), 4.03 (s, 2H), 3.48-3.43 (m, 1H), 2.63 (q, 2H), 2.12-2.06 (m, 1H), 2.00-1.96 (m, 1H), 1.77-1.74 (m, 1H), 1.29-1.08 (m, 4H), 1.18 (t, 3H).

$[α]_D^{20}$=−57°, c=0.660, CHCl$_3$.

Example 188

{[1-({[5-(4-Methoxyphenyl)-6-phenylfuro[2,3-d] pyrimidin-4-yl]oxy}methyl)cyclobutyl]methoxy}-acetic acid tert-butyl ester

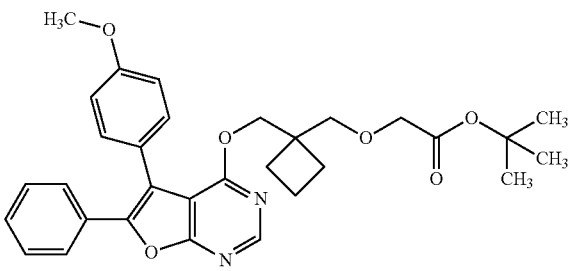

Add 0.6 ml of an 11.25N sodium hydroxide solution to a solution of 285 mg (0.68 mmol) of [1-({[5-(4-methoxyphenyl)-6-phenylfuro[2,3-d]pyrimidin-4-yl]oxy}methyl)cyclobutyl]methanol in 5 ml of toluene. After adding 23 mg (0.07 mmol) of tetra-n-butylammonium hydrogensulphate and 267 mg (1.37 mmol) of bromoacetic acid tert-butyl ester, stir the reaction mixture at 70° C. for 20 h. After cooling to room temperature, adjust to pH 7 with conc. hydrochloric acid. Extract three times with 20 ml each time of dichloromethane. Wash the combined organic extracts with satd. aqueous sodium chloride solution, dry over sodium sulphate and filter. Concentrate the filtrate under reduced pressure. Purify the crude product by means of preparative RP-HPLC (gradient: water/acetonitrile). 260 mg (72% of theory) of the desired product are obtained.

LC-MS (Method 8): $R_t$=3.38 min; m/z=531 (M+H)$^+$ $^1$H-NMR (400 MHz, DMSO-$d_6$): δ=8.58 (s, 1H), 7.56-7.54 (m, 2H), 7.42-7.37 (m, 5H), 7.04-7.00 (m, 2H), 4.34 (s, 2H), 3.85 (s, 2H), 3.81 (s, 3H), 3.22 (s, 2H), 1.78-1.65 (m, 6H), 1.38 (s, 9H).

Example 189

{[1-({[5-(4-Methoxyphenyl)-6-phenylfuro[2,3-d]pyrimidin-4-yl]oxy}methyl)cyclobutyl]methoxy}-acetic acid

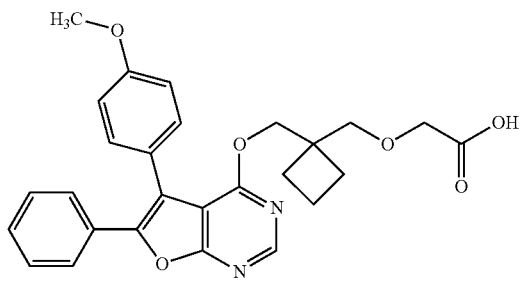

Dissolve 237 mg (0.45 mmol) of {[1-({[5-(4-methoxyphenyl)-6-phenylfuro[2,3-d]pyrimidin-4-yl]oxy}methyl)cyclobutyl]methoxy}acetic acid tert-butyl ester in 1 ml of dioxane, add 2 ml of 4 N hydrogen chloride in dioxane and stir at RT for 16 h. After concentrating the reaction solution under reduced pressure, purify the residue by means of preparative RP-HPLC (gradient: water/acetonitrile). 180 mg (85% of theory) of the desired product are obtained.

LC-MS (Method 8): $R_t$=2.84 min; m/z=475 (M+H)$^+$ $^1$H-NMR (400 MHz, DMSO-d$_6$): δ=12.49 (br. s, 1H), 8.57 (s, 1H), 7.56-7.54 (m, 2H), 7.42-7.36 (m, 5H), 7.04-7.00 (m, 2H), 4.34 (s, 2H), 3.87 (s, 2H), 3.81 (s, 3H), 3.23 (s, 2H), 1.80-1.67 (m, 6H).

B. Assessment of Pharmacological Efficacy

The pharmacological action of the compounds according to the invention can be demonstrated in the following assays:

B-1. Studies of Binding to Prostacyclin Receptors (IP Receptors) of Human Thrombocyte Membranes Thrombocyte membranes are obtained by centrifuging 50 ml human blood (Buffy coats with CDP Stabilizer, from Maco Pharma, Langen) for 20 min at 160×g. Remove the supernatant (platelet-rich plasma, PRP) and then centrifuge again at 2000×g for 10 min at room temperature. Resuspend the sediment in 50 mM tris-(hydroxymethyl)-aminomethane, which has been adjusted to a pH of 7.4 with 1 N hydrochloric acid, and store at −20° C. overnight. On the next day, centrifuge the suspension at 80000×g and 4° C. for 30 minDiscard the supernatant. Resuspend the sediment in 50 mM tris-(hydroxymethyl)-aminomethane/hydrochloric acid, 0.25 mM ethylene diamine tetraacetic acid (EDTA), pH 7.4, and then centrifuge once again at 80000×g and 4° C. for 30 min. Take up the membrane sediment in binding buffer (50 mM tris-(hydroxymethyl)-aminomethane/hydrochloric acid, 5 mM magnesium chloride, pH 7.4) and store at −70° C. until the binding test.

For the binding test, incubate 3 .nM $^3$H-Iloprost (592 GBq/mmol, from AmershamBioscience) for 60 min with 300-1000 μg/ml human thrombocyte membranes per charge (max. 0.2 ml) in the presence of the test substances at room temperature. After stopping, add cold binding buffer to the membranes and wash with 0.1% bovine serum albumin. After adding Ultima Gold Scintillator, quantify the radioactivity bound to the membranes using a scintillation counter. The nonspecific binding is defined as radioactivity in the presence of 1 μM Iloprost (from Cayman Chemical, Ann Arbor) and is as a rule <25% of the bound total radioactivity. The binding data (IC$_{50}$ values) are determined using the program GraphPad Prism Version 3.02.

Representative results for the compounds according to the invention are shown in Table 1:

TABLE 1

| Example No. | IC$_{50}$ [nM] |
| --- | --- |
| 6 | 237 |
| 9 | 43 |
| 10 | 18 |
| 21 | 11 |
| 24 | 15 |
| 67 | 388 |
| 68 | 34 |
| 69 | 8 |
| 84 | 152 |
| 87 | 17 |
| 99 | 34 |
| 146 | 20 |
| 154 | 28 |
| 156 | 293 |
| 159 | 83 |
| 162 | 37 |
| 168 | 71 |
| 170 | 6 |
| 175 | 13 |
| 176 | 24 |
| 181 | 27 |
| 183 | 218 |

B-2. IP-Receptor Stimulation on Whole Cells

The IP-agonistic action of test substances is determined by means of the human erythroleukaemia line (HEL), which expresses the IP-receptor endogenously [Murray, R., FEBS Letters 1989, 1: 172-174]. For this, the suspension cells (4×10$^7$ cells/ml) are incubated with the particular test substance for 5 minutes at 30° C. in buffer [10 mM HEPES (4-(2-hydroxyethyl)-1-piperazineethanesulphonic acid)/PBS (phosphate-buffered saline, from Oxoid, UK)], 1 mM calcium chloride, 1 mM magnesium chloride, 1 mM IBMX (3-isobutyl-1-methylxanthine), pH 7.4. Next, the reaction is stopped by addition of 4° C. cold ethanol and the charges are stored for a further 30 minutes at 4° C. Then the samples are centrifuged at 10000×g and 4° C. The resultant supernatant is discarded and the sediment is used for determination of the concentration of cyclic adenosine monophosphate (cAMP) in a commercially available cAMP-radioimmunoassay (from IBL, Hamburg). In this test, IP agonists lead to an increase in cAMP concentration, but IP antagonists have no effect. The effective concentration (EC$_{50}$ value) is determined using the program GraphPad Prism Version 3.02.

B-3. Inhibition of Thrombocyte Aggregation in vitro

Inhibition of thrombocyte aggregation is determined using blood from healthy test subjects. Mix 9 parts blood with one part 3.8% sodium citrate solution as coagulant. Centrifuge the blood at 900 rev/min for 20 minAdjust the pH value of the platelet-rich plasma obtained to pH 6.5 with ACD solution (sodium citrate/citric acid/glucose). Then remove the thrombocytes by centrifugation, take up in buffer and centrifuge again. Take up the thrombocyte deposit in buffer and additionally resuspend with 2 mmol/l calcium chloride.

For the measurements of aggregation, incubate aliquots of the thrombocyte suspension with the test substance for 10 min at 37° C. Next, aggregation is induced by adding ADP and is determined by the turbidimetric method according to Born in the Aggregometer at 37° C. [Born G. V. R., J. Physiol. (London) 168, 178-179 (1963)].

B-4. Measurement of Blood Pressure of Anaesthetized Rats

Anaesthetize male Wistar rats with a body weight of 300-350 g with thiopental (100 mg/kg i.p.). After tracheotomy, catheterize the arteria femoralis for blood pressure measurement. Administer the test substances as solution, orally by oesophageal tube or intravenously via the femoral vein in a suitable vehicle.

C. Examples of Application for Pharmaceutical Compositions

The compounds according to the invention can be converted to pharmaceutical preparations as follows:

Tablet:

Composition:

100 mg of the compound according to the invention, 50 mg lactose (monohydrate), 50 mg maize starch (native), 10 mg polyvinylpyrrolidone (PVP 25) (from BASF, Ludwigshafen, Germany) and 2 mg magnesium stearate.

Tablet weight 212 mg. Diameter 8 mm, radius of convex portion 12 mm.

Production:

The mixture of compound according to the invention, lactose and starch is granulated with a 5% solution (w/w) of PVP in water. After drying, the granules are mixed with the magnesium stearate for 5 minutes. This mixture is compressed using an ordinary tablet press (tablet format: see above). A guide value for the pressing force for compaction is 15 kN.

Suspension for Oral Application:

Composition:

1000 mg of the compound according to the invention, 1000 mg ethanol (96%), 400 mg Rhodigel® (xanthan gum from the company FMC, Pennsylvania, USA) and 99 g water.

10 ml of oral suspension corresponds to a single dose of 100 mg of the compound according to the invention.

Production:

The Rhodigel is suspended in ethanol, and the compound according to the invention is added to the suspension. The water is added while stirring. It is stirred for approx. 6 h until swelling of the Rhodigel ceases.

Solution for Oral Application:

Composition:

500 mg of the compound according to the invention, 2.5 g polysorbate and 97 g polyethylene glycol 400. 20 g of oral solution corresponds to a single dose of 100 mg of the compound according to the invention.

Production:

The compound according to the invention is suspended in the mixture of polyethylene glycol and polysorbate with stirring. Stirring continues until the compound according to the invention has dissolved completely.

i.v. solution:

The compound according to the invention is dissolved in a physiologically acceptable solvent (e.g. isotonic sodium chloride solution, glucose solution 5% and/or PEG 400 solution 30%) at a concentration below the saturation solubility. The solution is sterile-filtered and is packed in sterile, pyrogen-free injection containers.

The invention claimed is:

1. Compound of formula (I)

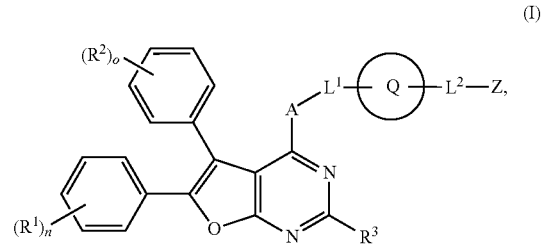

in which

A stands for O, S or N—$R^4$ where
$R^4$ denotes hydrogen, ($C_1$-$C_6$) alkyl, ($C_3$-$C_7$) cycloalkyl or ($C_4$-$C_7$) cycloalkenyl, $L^1$ stands for a bond or for ($C_1$-$C_4$) alkanediyl, the Q ring stands for ($C_3$-$C_7$) cycloalkyl, ($C_4$-$C_7$) cycloalkenyl, a 5- to 7-membered heterocycle, phenyl or 5- or 6-membered heteroaryl, each of which may be up to disubstituted, identically or differently, by fluorine, chlorine, ($C_1$-$C_4$) alkyl, trifluoromethyl, hydroxyl, ($C_1$-$C_4$) alkoxy, trifluoromethoxy, amino, mono-($C_1$-$C_4$) alkylamino and/or di-($C_1$-$C_4$) alkylamino, where ($C_1$-$C_4$) alkyl may in turn be substituted by hydroxyl, ($C_1$-$C_4$) alkoxy, amino, mono- or di-($C_1$-$C_4$) alkylamino, $L^2$ stands for ($C_1$-$C_4$) alkanediyl, which is mono- or disubstituted by fluorine and in which one methylene group may be exchanged for O or N—$R^5$ in which
$R^5$ denotes hydrogen, ($C_1$-$C_6$) alkyl or ($C_3$-$C_7$) cycloalkyl, or stands for ($C_2$-$C_4$) alkenediyl, Z stands for a group of formula

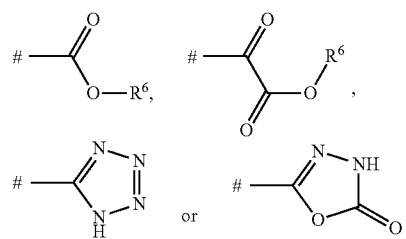

where
# denotes the point of linkage with group $L^2$ and
$R^6$ denotes hydrogen or ($C_1$-$C_4$) alkyl,
$R^1$ and $R^2$, independently of one another, stand for a substituent selected from the group comprising halogen, cyano, nitro, ($C_1$-$C_6$) alkyl, ($C_2$-$C_6$) alkenyl, ($C_2$-$C_4$) alkynyl, ($C_3$-$C_7$) cycloalkyl, ($C_4$-$C_7$) cycloalkenyl, ($C_1$-$C_6$) alkoxy, trifluoromethyl, trifluoromethoxy, ($C_1$-$C_6$) alkylthio, ($C_1$-$C_6$) acyl, amino, mono-($C_1$-$C_6$) alkylamino, di-($C_1$-$C_6$) alkylamino and ($C_1$-$C_6$) acylamino,
in which ($C_1$-$C_6$) alkyl and ($C_1$-$C_6$) alkoxy can in their turn each be substituted with cyano, hydroxy, ($C_1$-$C_4$) alkoxy, ($C_1$-$C_4$) alkylthio, amino, mono- or di-($C_1$-$C_4$) alkylamino, or
two residues $R^1$ and/or $R^2$ bound to adjacent carbon atoms of the respective phenyl ring together form a group of formula —O—$CH_2$—O—, —O—CHF—O—, —O—$CF_2$—O—, —O—$CH_2$—$CH_2$—O— or —O—$CF_2$—$CF_2$—O—, n and o, independently of one another, stand for the number 0, 1, 2 or 3, and for the case when $R^1$ or $R^2$ occurs more than once, their meanings can in each case be identical or different, and $R^3$ stands for hydrogen, $(C_1-C_4)$ alkyl or cyclopropyl, and the salts thereof.

2. Compound of formula (I) according to claim 1, in which

A stands for O, S or N—$R^4$, where $R^4$ denotes hydrogen, $(C_1-C_6)$ alkyl, $(C_3-C_7)$ cycloalkyl or $(C_4-C_7)$ cycloalkenyl, $L^1$ stands for a bond or for $(C_1-C_4)$ alkanediyl, the Q ring stands for $(C_3-C_7)$ cycloalkyl, $(C_4-C_7)$ cycloalkenyl, a 5- to 7-membered heterocycle, phenyl or 5- or 6-membered heteroaryl, each of which may be up to disubstituted, identically or differently, by fluorine, chlorine, $(C_1-C_4)$ alkyl, trifluoromethyl, hydroxyl, $(C_1-C_4)$ alkoxy, trifluoromethoxy, amino, mono-$(C_1-C_4)$ alkylamino and/or di-$(C_1-C_4)$ alkylamino, where $(C_1-C_4)$ alkyl may in turn be substituted by hydroxyl, $(C_1-C_4)$ alkoxy, amino, mono- or di-$(C_1-C_4)$ alkylamino, $L^2$ stands for $(C_1-C_4)$ alkanediyl, which is mono- or disubstituted by fluorine and in which one methylene group may be exchanged for O or N—$R^5$ in which $R^5$ denotes hydrogen, $(C_1-C_6)$ alkyl or $(C_3-C_7)$ cycloalkyl, or stands for $(C_2-C_4)$ alkenediyl, Z stands for a group of formula

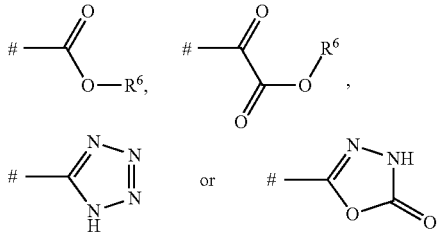

where # denotes the point of linkage with group $L^2$ and $R^2$ denotes hydrogen or $(C_1-C_4)$ alkyl, $R^1$ and $R^2$, independently of one another, stand for a substituent selected from the group comprising halogen, cyano, nitro, $(C_1-C_6)$ alkyl, $(C_2-C_6)$ alkenyl, $(C_2-C_4)$ alkenyl, $(C_3-C_7)$ cycloalkyl, $(C_4-C_7)$ cycloalkenyl, $(C_1-C_6)$ alkoxy, trifluoromethyl, trifluoromethoxy, $(C_1-C_6)$ alkylthio, $(C_1-C_6)$ acyl, amino, mono-$(C_1-C_6)$ alkylamino, di-$(C_1-C_6)$ alkylamino and $(C_1-C_6)$ acylamino, and $(C_1-C_6)$ alkyl and $(C_1-C_6)$ alkoxy in their turn can each be substituted with hydroxy, $(C_1-C_4)$ alkoxy, amino, mono- or di-$(C_1-C_4)$ alkylamino, or two residues $R^1$ and/or $R^2$ bound to adjacent carbon atoms of the respective phenyl ring together form a group of formula —O—CH$_2$—O—, —O—CHF—O—, —O—CF$_2$—O—, —O—CH$_2$—CH$_2$—O— or —O—CF$_2$—CF$_2$—O—, n and o, independently of one another, stand for the number 0, 1, 2 or 3, and for the case when $R^1$ or $R^2$ occurs more than once, their meanings can in each case be identical or different, and $R^3$ stands for hydrogen, $(C_1-C_4)$ alkyl or cyclopropyl.

3. Compound of formula (I) according to claim 1, in which

A stands for O or N—$R^4$, where $R^4$ denotes hydrogen, $(C_1-C_4)$ alkyl or $(C_3-C_6)$ cycloalkyl, $L^1$ stands for a bond or $(C_1-C_3)$ alkanediyl, the Q ring stands for $(C_3-C_6)$ cycloalkyl, $(C_4-C_6)$ cycloalkenyl, a 5- or 6-membered heterocycle, phenyl or 5- or 6-membered heteroaryl, each of which may be up to disubstituted, identically or differently, by fluorine, chlorine, $(C_1-C_3)$ alkyl, trifluoromethyl, hydroxyl, methoxy, ethoxy, trifluoromethoxy, amino, methylamino, ethylamino, dimethylamino and/or diethylamino, where $(C_1-C_3)$ alkyl may in turn be substituted by hydroxyl, methoxy, ethoxy, amino, methylamino, ethylamino, dimethylamino or diethylamino, $L^2$ stands for $(C_1-C_3)$ alkanediyl which may be mono- or disubstituted by fluorine, $(C_2-C_3)$ alkenediyl or a group of the formula *-M-CR$^7$R$^8$—, *-M-CH$_2$—CR$^7$R$^8$— or *—CH$_2$—M—CR$^7$R$^8$—, in which denotes the point of linkage with the Q ring, M is O or N—$R^5$ in which $R^5$ is hydrogen, $(C_1-C_3)$ alkyl or cyclopropyl, and $R^7$ and $R^8$, independently of one another, are hydrogen or fluorine, Z stands for a group of formula

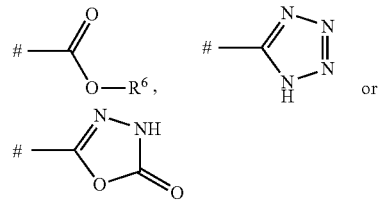

where # denotes the point of linkage with group $L^2$ and $R^6$ denotes hydrogen, methyl or ethyl, $R^1$ and $R^2$, independently of one another, stand for a substituent selected from the group comprising fluorine, chlorine, cyano, $(C_{1-5})$ alkyl, $(C_{2-5})$ alkenyl, $(C_3-C_6)$ cycloalkyl, $(C_4-C_6)$ cycloalkenyl, $(C_1-C_4)$ alkoxy, trifluoromethyl, trifluoromethoxy, $(C_1-C_4)$ alkylthio, $(C_{1-5})$ acyl, amino, mono-$(C_1-C_4)$ alkylamino, di-$(C_1-C_4)$ alkylamino and $(C_1-C_4)$ acylamino or two residues $R^1$ and/or $R^2$ bound to adjacent carbon atoms of the respective phenyl ring together form a group of formula —O—CH$_2$—O—, —O—CHF—O— or —O—CF$_2$—O—, n and o, independently of one another, stand for the number 0, 1, 2 or 3, and for the case when $R^1$ or $R^2$ occurs more than once, their meanings can in each case be identical or different, and $R^3$ stands for hydrogen or $(C_1-C_3)$ alkyl.

4. Compound of formula (I) according to claim 1, in which

A stands for O or N—$R^4$ in which $R^4$ is hydrogen or $(C_1-C_4)$ alkyl, $L^1$ stands for a bond or $(C_1-C_3)$ alkanediyl, the Q ring stands for $(C_4-C_6)$ cycloalkyl, $(C_5-C_6)$ cycloalkenyl, a 5- or 6-membered heterocycle or phenyl, each of which may be up to disubstituted, identically or differently, by fluorine, chlorine, $(C_1-C_3)$ alkyl, trifluoromethyl, hydroxyl, methoxy, ethoxy, trifluoromethoxy, amino, methylamino, ethylamino, dimethylamino and/or diethylamino, $L^2$ stands for $(C_1-C_3)$ alkanediyl which may be mono- or disubstituted by fluorine, $(C_2-C_3)$ alkenediyl or a group of the formula *-M—CR$^7$R$^8$—, *-M—CH$_2$—CR$^7$R$^8$— or *—CH$_2$—M—CR$^7$R$^8$—, in which denotes the point of linkage with the Q ring, M is O or N—$R^5$ in which
$R^5$ is hydrogen or $(C_1-C_3)$ alkyl, and
$R^7$ and $R^8$, independently of one another, denote hydrogen or fluorine,
Z stands for a group of the formula

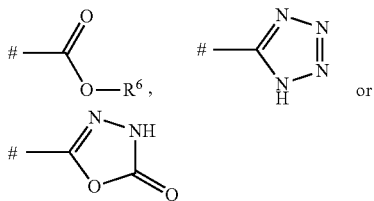

where
# denotes the point of linkage with group $L^2$ and
$R^6$ denotes hydrogen, methyl or ethyl,
$R^1$ and $R^2$, independently of one another, stand for a substituent selected from the group comprising fluorine, chlorine, cyano, $(C_1-C_5)$ alkyl, $(C_2-C_5)$ alkenyl, $(C_3-C_6)$ cycloalkyl, $(C_4-C_6)$ cycloalkenyl, $(C_1-C_4)$ alkoxy, trifluoromethyl, trifluoromethoxy, $(C_1-C_4)$ alkylthio, $(C_1-C_5)$ acyl, amino, mono-$(C_1-C_4)$ alkylamino, di-$(C_1-C_4)$ alkylamino and $(C_1-C_4)$ acylamino or
two residues $R^1$ and/or $R^2$ bound to adjacent carbon atoms of the respective phenyl ring together form a group of formula —O—$CH_2$—O—, —O—CHF—O— or —O—$CF_2$—O—,
n and o, independently of one another, stand for the number 0, 1 or 2,
and for the case when $R^1$ or $R^2$ occurs twice, their meanings can in each case be identical or different, and
$R^3$ stands for hydrogen or $(C_1-C_3)$ alkyl.

5. Compound of formula (I) according to claim 1, in which
A stands for O or NH,
$L^1$ stands for a bond, methylene, ethane-1,1-diyl or ethane-1,2-diyl,
the Q ring stands for cyclobutyl, cyclopentyl, cyclopentenyl, cyclohexyl, pyrrolidinyl, piperidinyl, tetrahydrofuranyl, tetrahydropyranyl, morpholinyl or phenyl, each of which may be up to disubstituted, identically or differently, by fluorine, methyl, ethyl, trifluoromethyl, hydroxyl, methoxy, ethoxy, amino, methylamino and/or dimethylamino,
$L^2$ stands for $(C_1-C_3)$ alkanediyl, $(C_2-C_3)$ alkenediyl or a group of the formula *-M-$CH_2$— or *-M-$CH_2$—$CH_2$—, in which
denotes the point of linkage to the Q ring and
M denotes O or N—$R^5$, in which
$R^5$ is hydrogen or $(C_1-C_3)$ alkyl,
Z stands for a group of formula

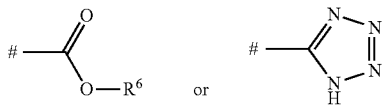

where
# denotes the point of linkage with group $L^2$ and
$R^6$ denotes hydrogen, methyl or ethyl,
$R^1$ and $R^2$, independently of one another, stand for a substituent selected from the group comprising fluorine, chlorine, cyano, $(C_1-C_5)$ alkyl, $(C_2-C_5)$ alkenyl, $(C_3-C_6)$ cycloalkyl, $(C_4-C_6)$ cycloalkenyl, $(C_1-C_4)$ alkoxy, trifluoromethyl, trifluoromethoxy, $(C_1-C_4)$ alkylthio, $(C_1-C_5)$ acyl, amino, mono-$(C_1-C_4)$ alkylamino, di-$(C_1-C_4)$ alkylamino and $(C_1-C_4)$ acylamino or
two residues $R^1$ and/or $R^2$ bound to adjacent carbon atoms of the respective phenyl ring together form a group of formula —O—$CH_2$—O—, —O—CHF—O— or —O—$CF_2$—O—,
n and o, independently of one another, stand for the number 0, 1 or 2,
and for the case when $R^1$ or $R^2$ occurs twice, their meanings can in each case be identical or different, and
$R^3$ stands for hydrogen.

6. Compound of formula (I) according to claim 1, in which
A stands for O or NH,
$L^1$ stands for a bond, methylene or ethane-1,1-diyl,
the Q ring stands for cyclobutyl, cyclopentyl, cyclopentenyl, cyclohexyl, pyrrolidinyl, piperidinyl or phenyl, each of which may be up to disubstituted, identically or differently, by fluorine, methyl, hydroxyl and/or methoxy,
$L^2$ is $(C_1-C_3)$ alkanediyl, $(C_2-C_3)$ alkenediyl or a group of the formula *-M-$CH_2$— or *-M-$CH_2$—$CH_2$—, in which
denotes the point of linkage with the Q ring, and
M denotes O or NH,
Z stands for a group of formula

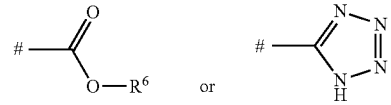

where
# denotes the point of linkage with group $L^2$ and
$R^6$ denotes hydrogen, methyl or ethyl,
$R^1$ stands for a substituent selected from the group comprising fluorine, chlorine, methyl, ethyl, vinyl, trifluoromethyl and methoxy,
$R^2$ stands for a substituent selected from the group comprising fluorine, chlorine, cyano, methyl, ethyl, n-propyl, vinyl, trifluoromethyl, methoxy, ethoxy, trifluoromethoxy, methylthio, ethylthio, amino, methylamino and ethylamino,
n and o, independently of one another, stand for the number 0, 1 or 2,
and for the case when $R^1$ or $R^2$ occurs twice, their meanings can in each case be identical or different, and
$R^3$ stands for hydrogen.

7. A method for producing compounds of formula (I), as defined in claim 1, in which Z stands for —COOH or —C(=O)—COOH, characterized in that either
[A] Compounds of formula (II)

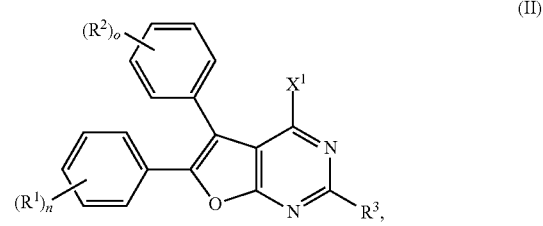

in which $R^1$, $R^2$, $R^3$, n and o have the respective meanings given in claim 1 and $X^1$ stands for a leaving group, in the presence of a base if necessary in an inert solvent with a compound of formula (III)

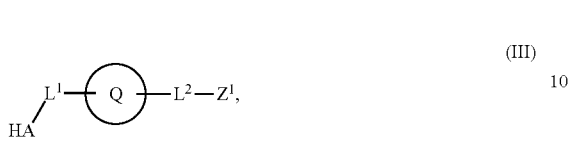
(III)

in which A, $L^1$, $L^2$ and Q have the respective meanings given in claim 1 and $Z^1$ stands for cyano or a group of formula —[C(O)]$_y$—COOR$^{6A}$, where y denotes the number 0 Or 1 and $R_{6A}$ denotes ($C_1$-$C_4$) alkyl, to form compounds of formula (IV)

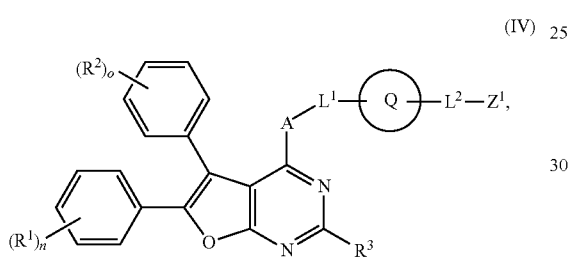
(IV)

in which A, $L^1$, $L^2$, Q, $Z^1$, $R^1$, $R^2$, $R^3$, n and o have the respective meanings given in claim 1, or

[B] Compounds of formula (V-1)

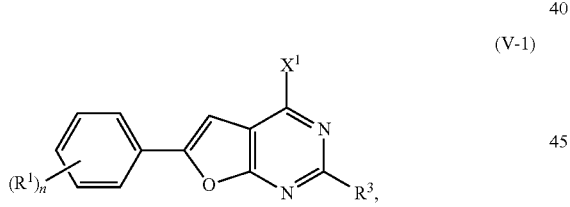
(V-1)

$R^1$, $R^3$, $X^1$ and n have the respective meanings given in claim 1, optionally, in the presence of a base, and an inert solvent are reacted with a compound of formula (III) to form compounds of formula (VI-1)

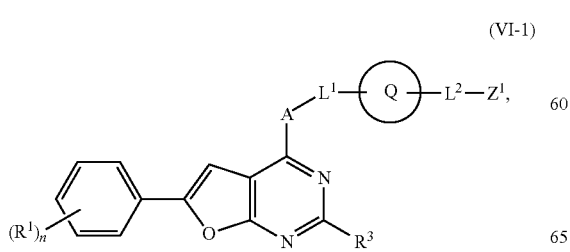
(VI-1)

in which A, $L^1$, $L^2$, Q, $Z^1$, $R^1$, $R^3$ and n have the respective meanings given in claim 1, then brominated in an inert solvent to form compounds of formula (VII-1)

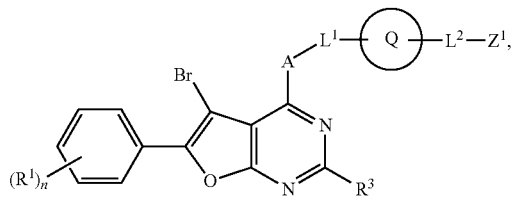
(VII-1)

A, $L^1$, $L^2$, Q, $Z^1$, $R^1$, $R^3$ and n have the respective meanings given in claim 1, and these are then coupled in an inert solvent in the presence of a base and a suitable palladium catalyst with a phenylboronic acid of formula (VIII-1)

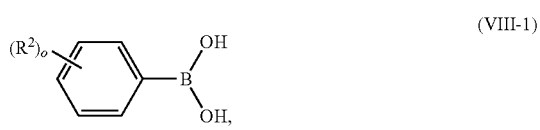
(VIII-1)

in which $R^2$ and o have the meanings given in claim 1, to form compounds of formula (IV) or

[C] Compounds of formula (V-2)

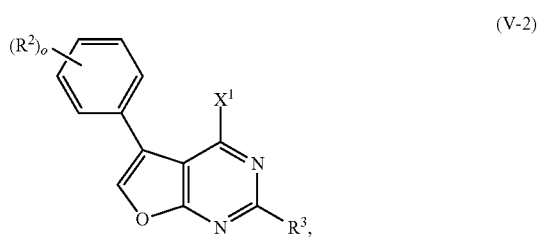
(V-2)

in which $R^2$, $R^3$, $X^1$ and o have the respective meanings given in claim 1, are reacted optionally, in the presence of a base, and an inert solvent is reacted with a compound of formula (III) to form compounds of formula (VI-2)

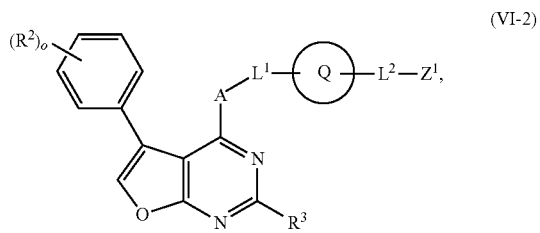
(VI-2)

in which A, $L^1$, $L^2$, Q, $Z^1$, $R^2$, $R^3$ and o have the respective meanings given in claim 1, then brominated in an inert solvent to compounds of formula (VII-2)

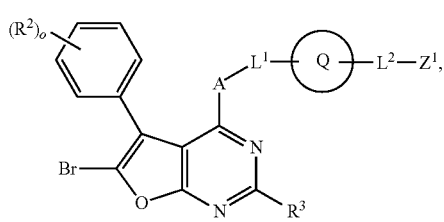

(VII-2)

in which A, $L^1$, $L^2$, Q, $Z^1$, $R^2$, $R^3$ and o have the respective meanings given in claim 1, and these are then coupled in an inert solvent in the presence of a base and a suitable palladium catalyst with a phenylboronic acid of formula (VIII-2)

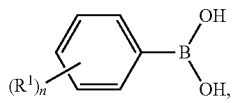

(VIII-2)

in which $R^1$ and n have the meanings given in claim 1, to form compounds of formula (IV), and in each case the resultant compounds of formula (IV) are then converted by hydrolysis of the ester or cyano group $Z^1$ to the carboxylic acids of formula (I-A)

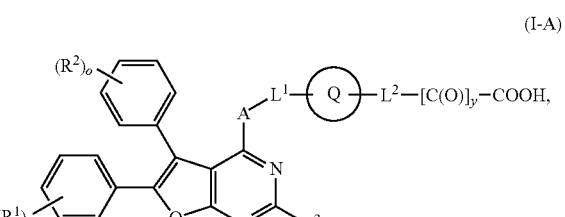

(I-A)

in which A, $L^1$, $L^2$, Q, $R^1$, $R^2$, $R^3$, n, o and y have the respective meanings given in claim 1, and these are converted if necessary with the corresponding (i) solvents and/or (ii) bases or acids to their salts.

8. A medicinal product comprising a compound of formula (I), as defined in claim 1 in combination with an inert, non-toxic, pharmaceutically acceptable excipient.

* * * * *